(12) United States Patent
Saenger et al.

(10) Patent No.: US 10,626,463 B2
(45) Date of Patent: Apr. 21, 2020

(54) BIOMARKER ASSOCIATED WITH RISK OF MELANOMA REOCCURRENCE

(71) Applicant: Icahn School of Medicine at Mount Sinai, New York, NY (US)

(72) Inventors: Yvonne Saenger, New York, NY (US); Shanthi Sivendran, Gettysburg, PA (US); Rui Chang, New York, NY (US); Analisa Difeo, Port Washington, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 21 days.

(21) Appl. No.: 14/419,409

(22) PCT Filed: Aug. 2, 2013

(86) PCT No.: PCT/US2013/053511
§ 371 (c)(1),
(2) Date: Feb. 3, 2015

(87) PCT Pub. No.: WO2014/022826
PCT Pub. Date: Feb. 6, 2014

(65) Prior Publication Data
US 2015/0218649 A1  Aug. 6, 2015

Related U.S. Application Data

(60) Provisional application No. 61/679,394, filed on Aug. 3, 2012.

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/158* (2013.01); *C12Q 2600/16* (2013.01)
(58) Field of Classification Search
None
See application file for complete search history.

(56) References Cited

U.S. PATENT DOCUMENTS

| | | |
|---|---|---|
| 2011/0023145 A1 | 1/2011 | Weinstein et al. |
| 2011/0091377 A1 | 4/2011 | Alani et al. |
| 2012/0071343 A1* | 3/2012 | Ma ........... C12Q 1/6886 506/9 |

FOREIGN PATENT DOCUMENTS

WO    WO 2012/037128 A2    3/2012

OTHER PUBLICATIONS

Journe (British Journal of Cancer (Nov. 2011) 105, 1726-1732).*
Hoshikawa et al (Physical Genomics 2003 vol. 12 pp. 209-219).*
Coleman (Drug Discovery Today. 2003. 8: 233-235).*
Agarwala (Cancer Treatment Reviews 37 (2011) 133-142).*
Notification of Transmittal of the International Search Report and the Written Opinion of the International Searching Authority, or the Declaration, including an International Search Report and Written Opinion of the International Searching Authority, dated Jan. 31, 2014 in connection with PCT International Application No. PCT/US2013/05351I, filed Aug. 2, 2013.
Examination Report No. 1 mailed for Australian Patent application No. 2013296233, dated May 4, 2018, 2 pages.
WIPO, International Preliminary Report on Patentability mailed for International Application No. PCT/US2013/053511, dated Feb. 3, 2015, 9 Pages.

* cited by examiner

*Primary Examiner* — Amanda Haney

(57) ABSTRACT

The present invention provides a method of predicting the risk of reoccurrence of melanoma in a patient from whom melanoma tissue was previously removed which comprises the following:
a. obtaining a RNA-containing sample of the previously removed melanoma tissue containing RNA from the patient;
b. treating the sample to determine from the RNA contained in the sample the level of expression of a plurality of preselected genes; and
c. comparing the level of expression of each gene of the plurality of pre-selected genes to a predetermined reference level of expression for each such gene;
wherein a higher level of expression of the plurality of pre-selected genes in the sample as compared with the predetermined reference level of expression of such genes indicates that the patient has a reduced risk of reoccurrence of melanoma.

13 Claims, 50 Drawing Sheets

Specification includes a Sequence Listing.

Figure 1

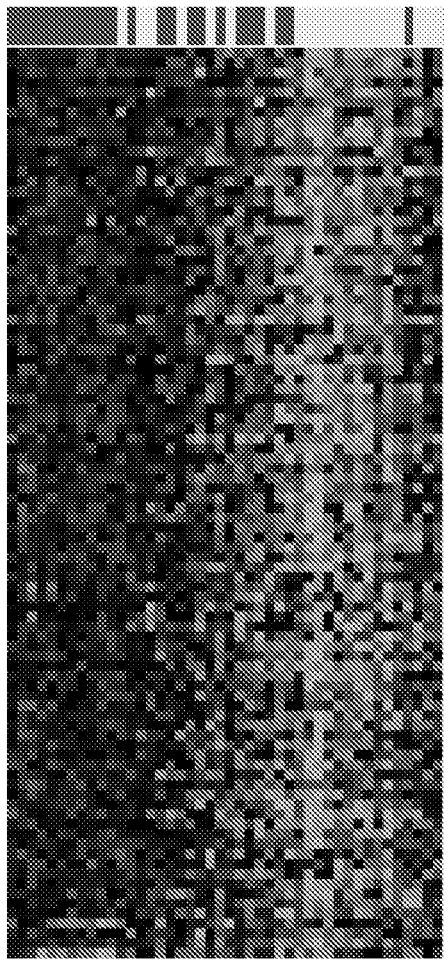

Training Gene Set

| | | |
|---|---|---|
| CD2 | CD68 | GZMK |
| KLRK1 | B2M | IRF8 |
| ITK | IRF9 | TNFRSF18 |
| HLAE | CD27 | CLECL1 |
| LCK | KLRD1 | MST1R |
| CREB1 | CD40 | TARP |
| IFNAR1 | PTPRC | IFITM1 |
| CD48 | NFATC3 | MFGE8 |
| CXCR3 | C3 | CYBB |
| CD4 | CD8A | NFKB1 |
| IFNG | IKZF1 | LY9 |
| CTSS | IL18 | STAT2 |
| CCR4 | HLADPA1 | XCR1 |
| HLADQB1 | TAP1 | MRC1 |
| TAP2 | ITGB2 | CCR5 |
| CD37 | IFI27 | CXCL9 |
| IRF2 | STAT1 | SKAP1 |
| TNFSF18 | CD3E | CD1C |
| LGMN | TBX21 | SP110 |
| CCL5 | CD5 | IFNGR2 |
| CSF2RA | PLCG2 | MAP3K7 |
| ITGAL | TNFSF13B | CEBPA |
| BTK | LAMP1 | NLRC5 |
| CD53 | IL37 | CXCL11 |
| IRF5 | GATA3 | ICOS |
| IL17RA | LTA | CTLA4 |
| HLADPB1 | CLEC2A | BIRC5 |
| CCL27 | IKZF5 | TLR6 |
| IFNGR1 | XCL2 | IL10RA |
| SYK | ZAP70 | CXCL6 |
| CD180 | PILRA | |

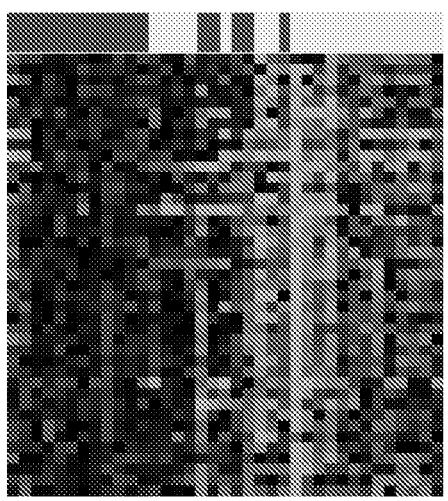

Validation Gene Set

| | | |
|---|---|---|
| IFI27 | CCL27 | TNFSF13B |
| HLADPB1 | ICOS | LCK |
| STAT1 | IRF8 | IL1F7 |
| MRC1 | IFITM1 | XCR1 |
| B2M | HLAE | C3 |
| IL18 | GATA3 | CD4 |
| IFNGR1 | TAP1 | CD48 |
| CXCL11 | CD2 | LGMN |
| TAP2 | CD37 | TNFRSF18 |
| CXCL9 | KLRK1 | IRF9 |
| CLEC2A | CD5 | SKAP1 |
| HLADPA1 | LY9 | TARP |
| XCL2 | CXCR3 | GZMK |
| CTSS | CD3E | |

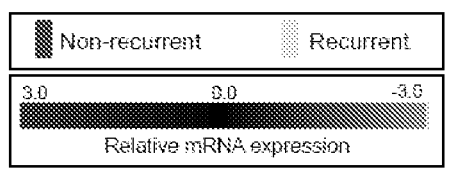

Figure 2, continued
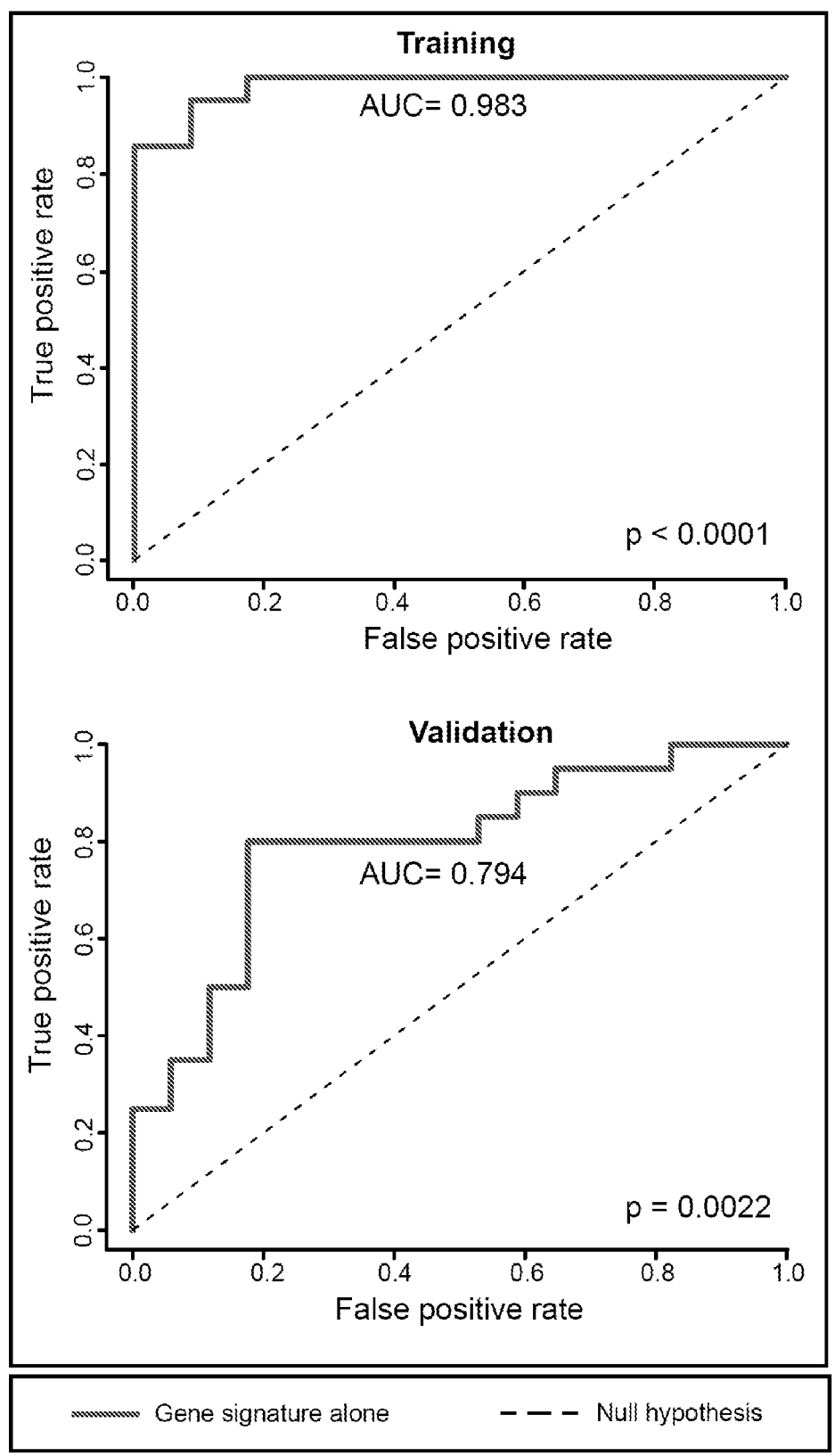

Figure 2, continued
C
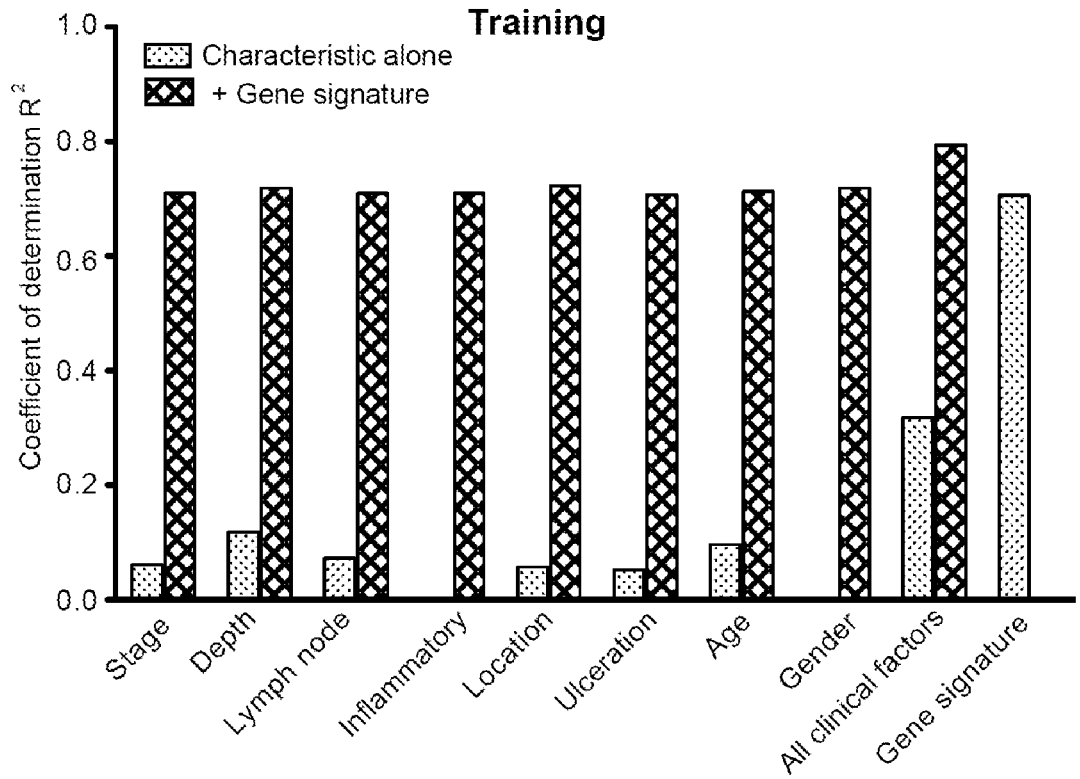
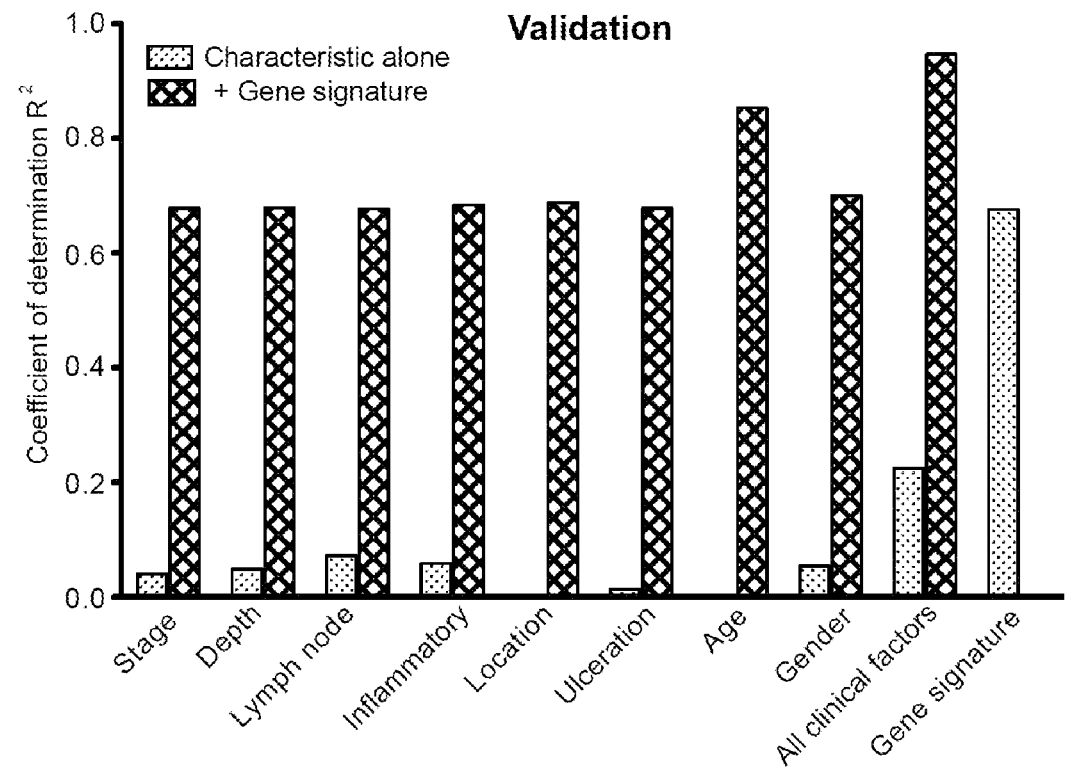

Figure 3, continued
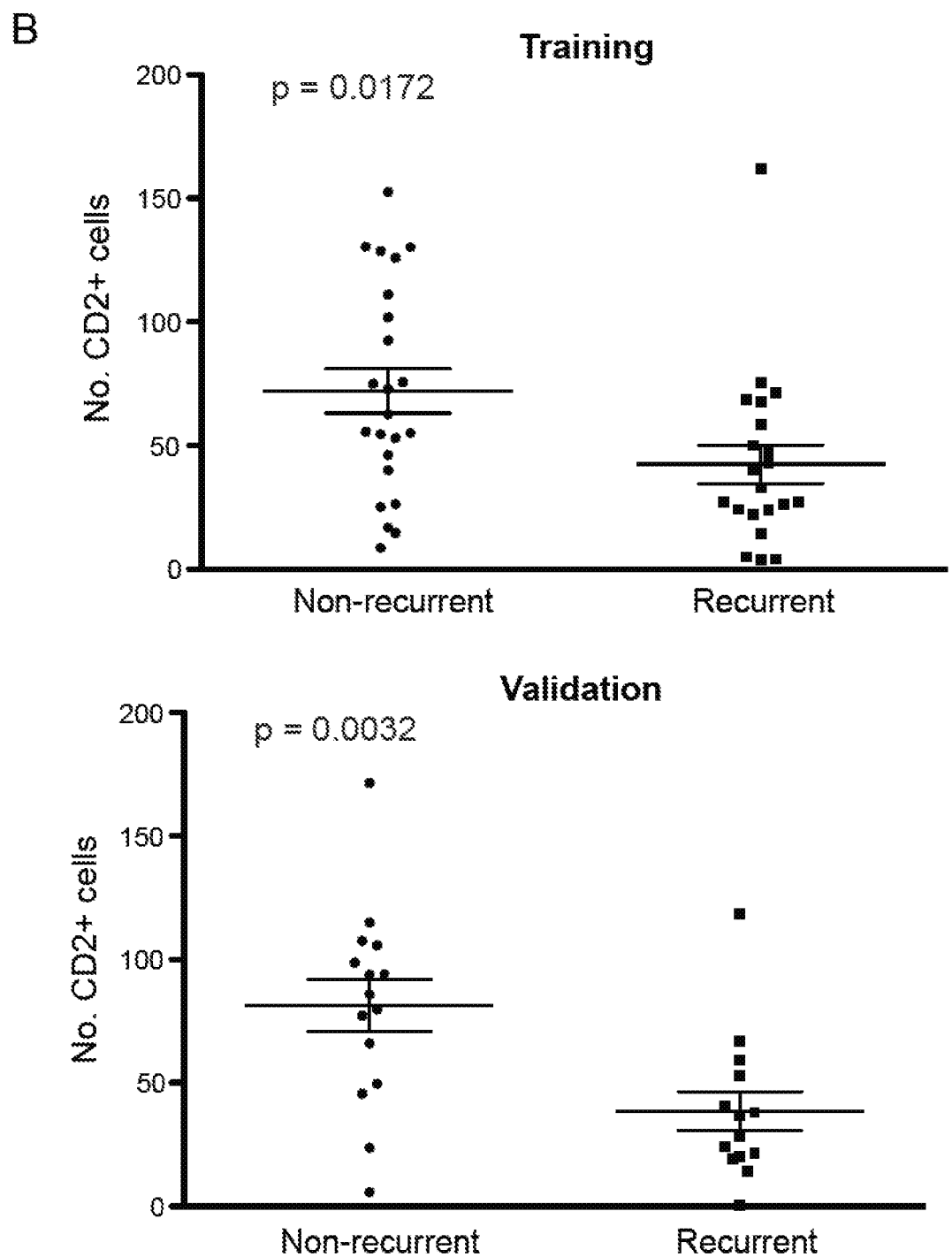

Figure 3, continued
C
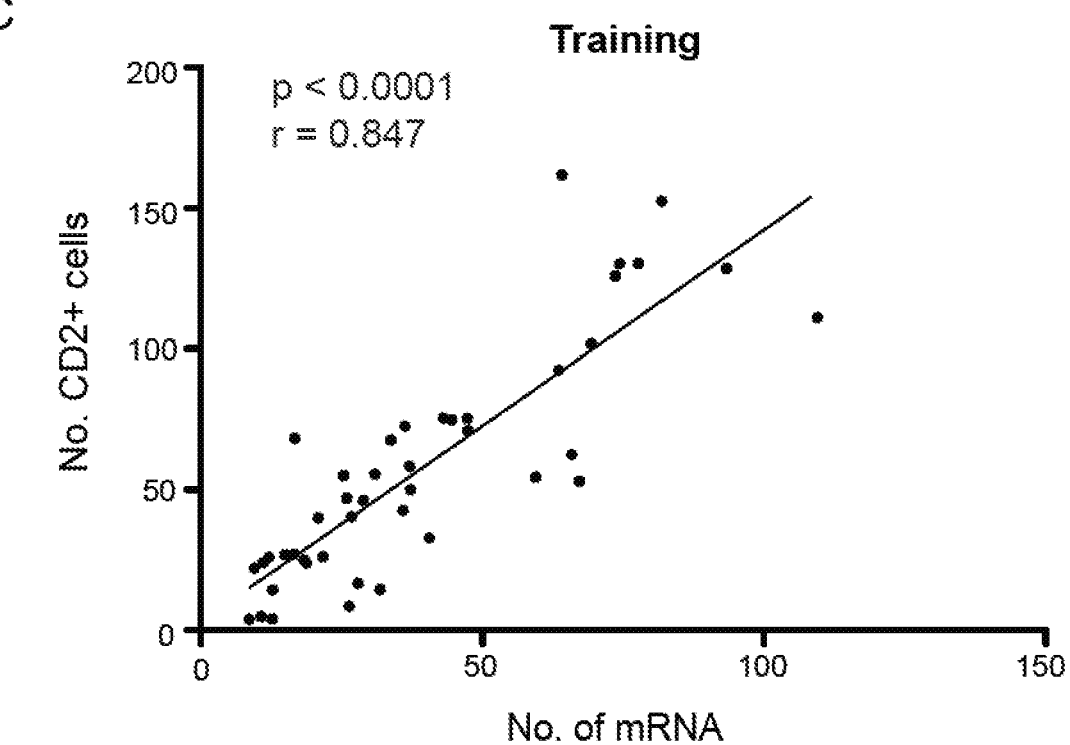
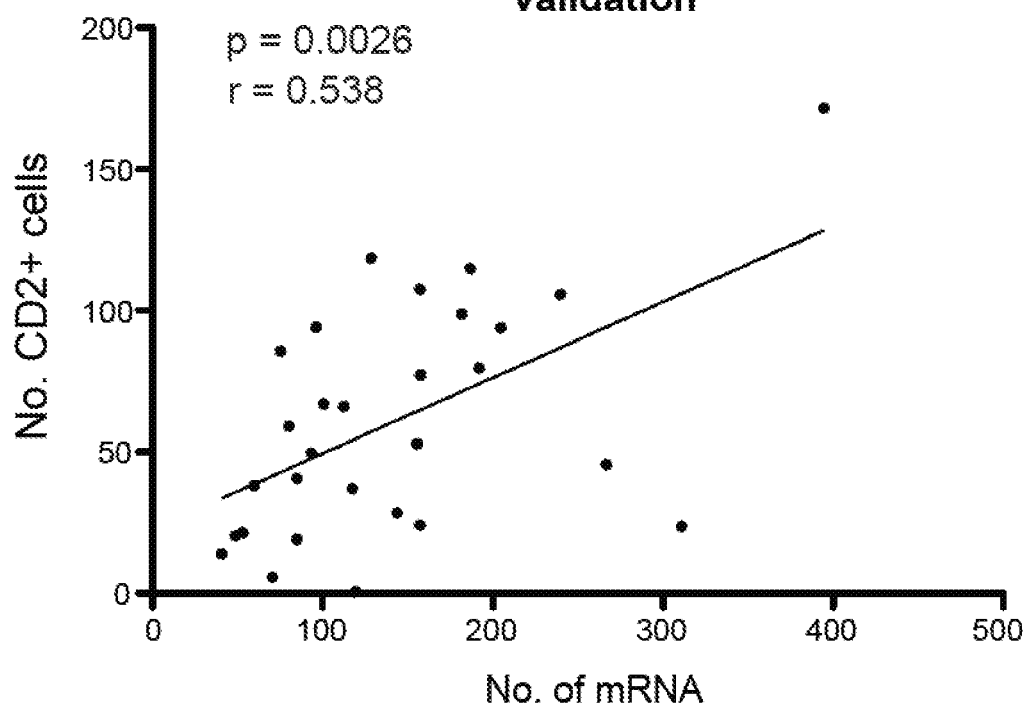

Figure 4
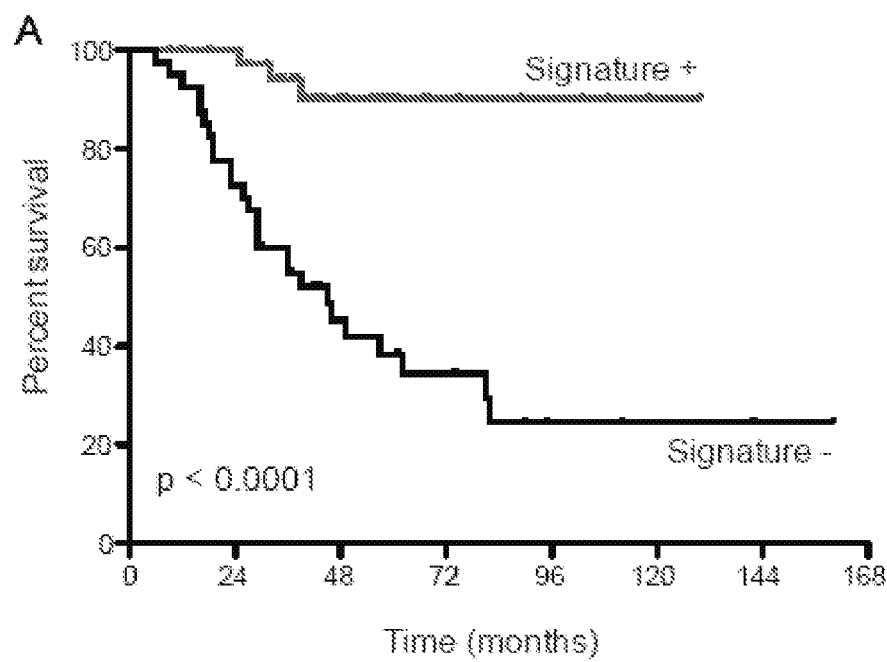
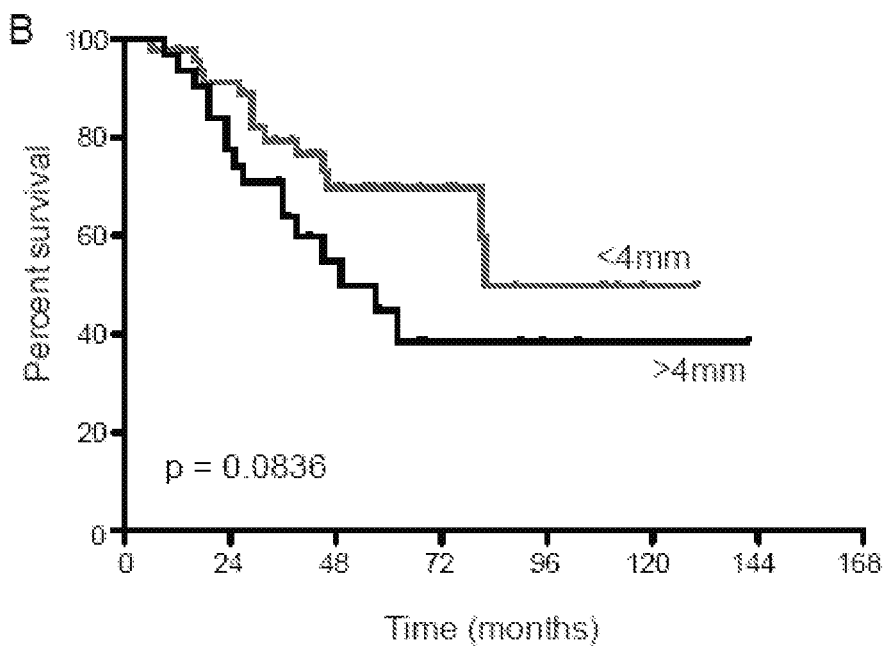

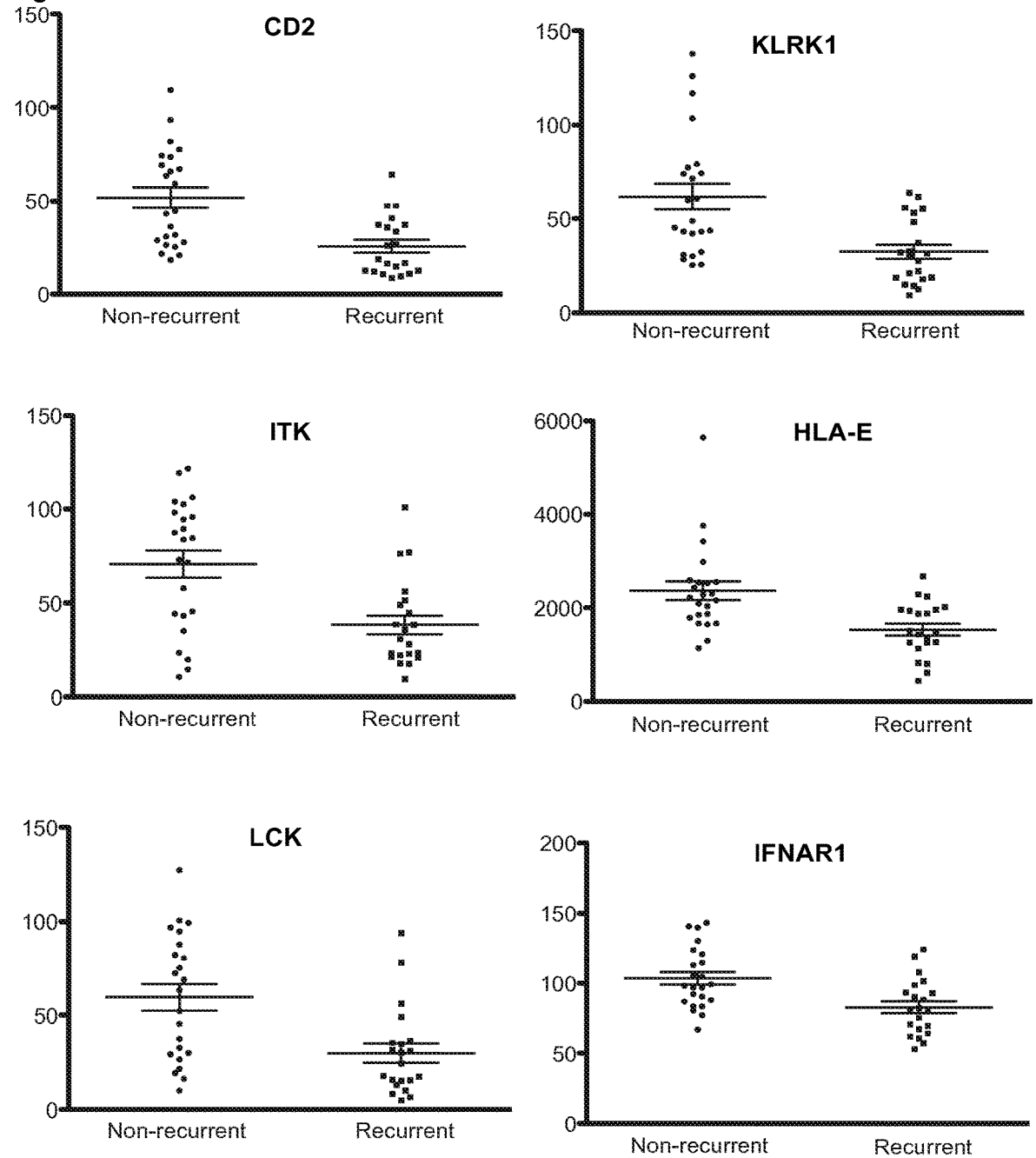
Figure 6 Panel A

Figure 6 Panel A, continued
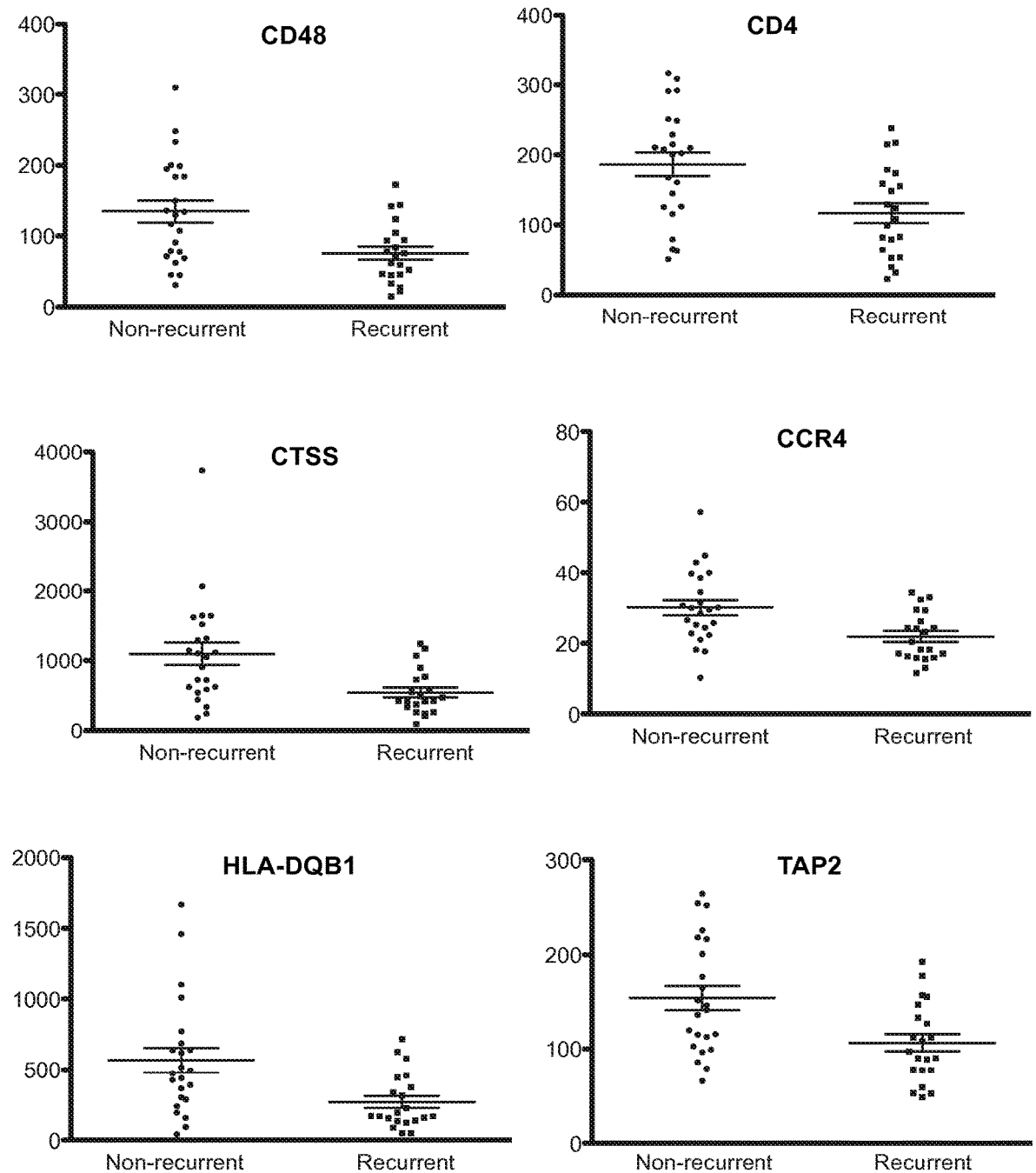

Figure 6 Panel A, continued
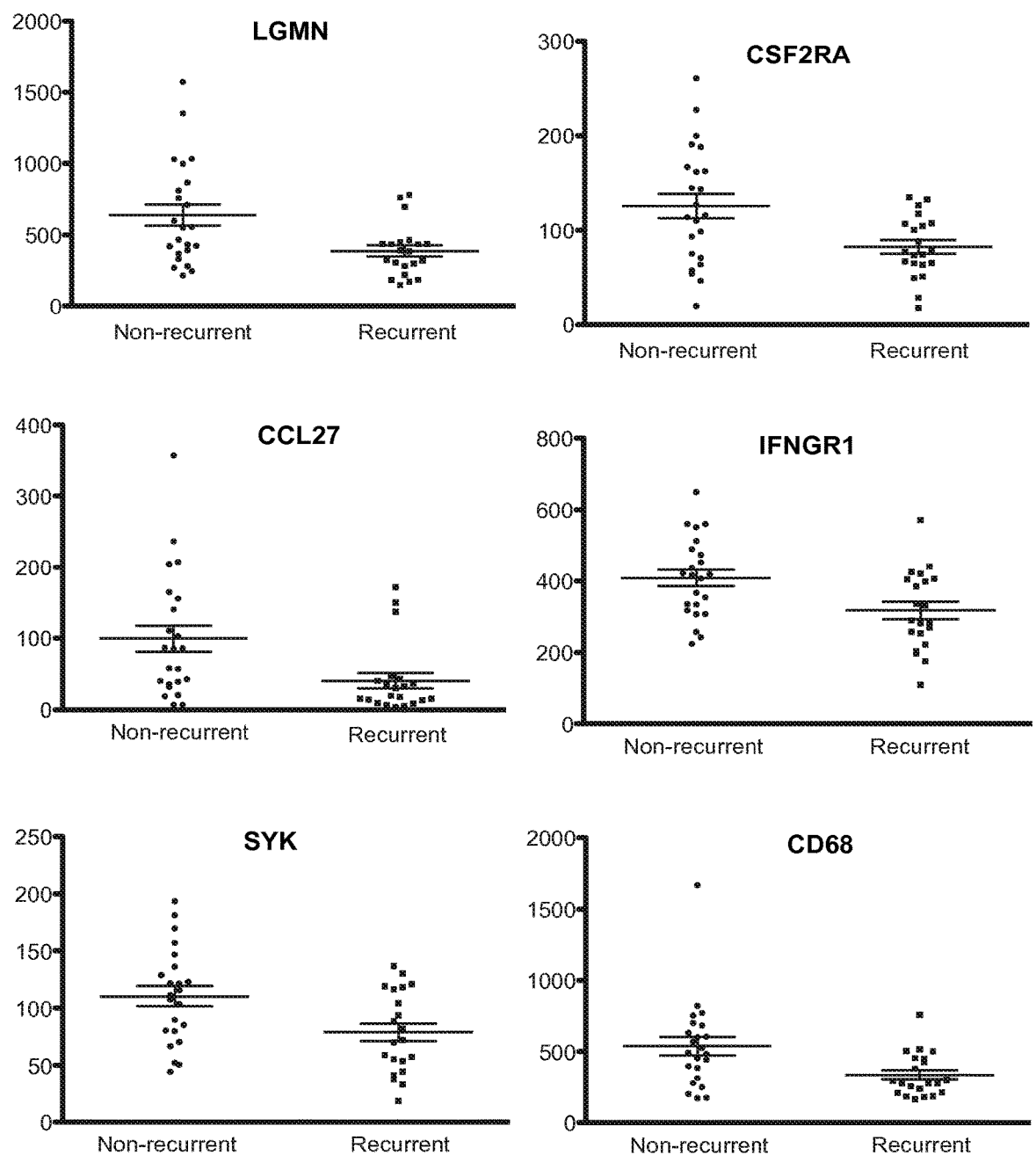

Figure 6 Panel A, continued
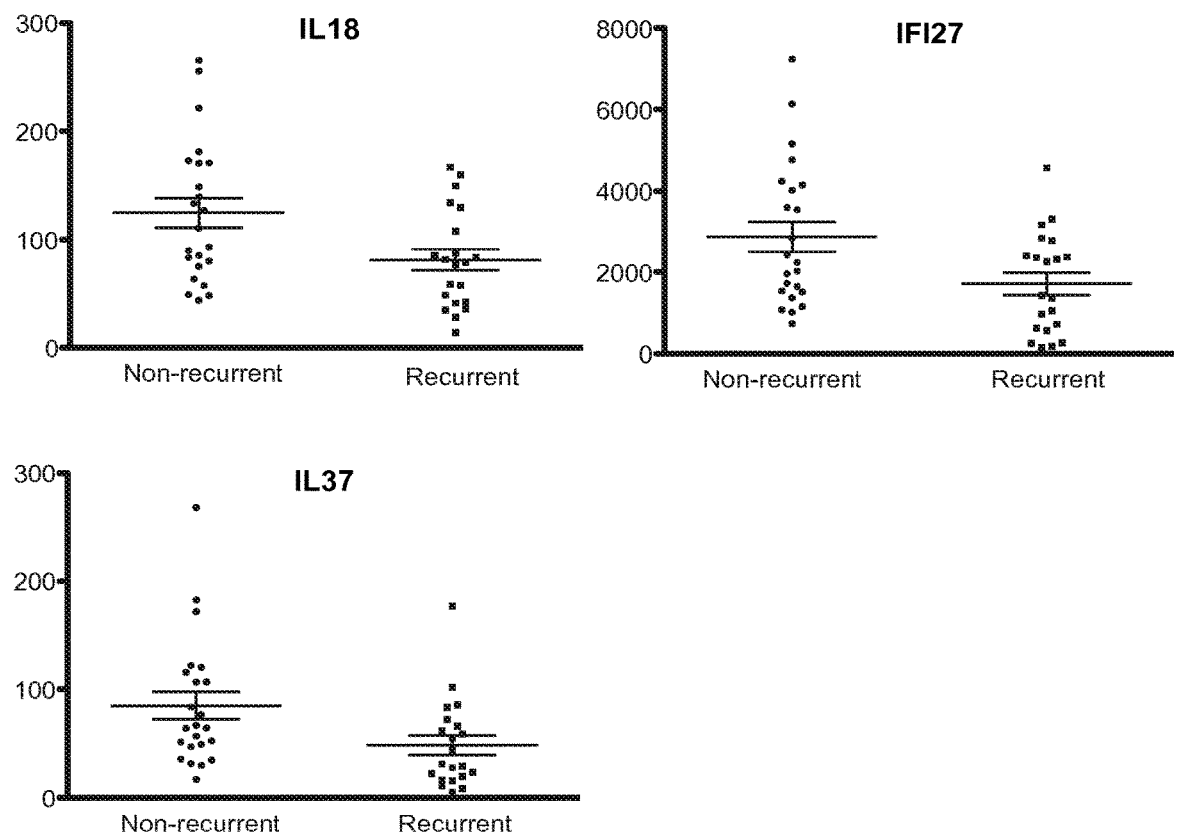

Figure 6 Panel B
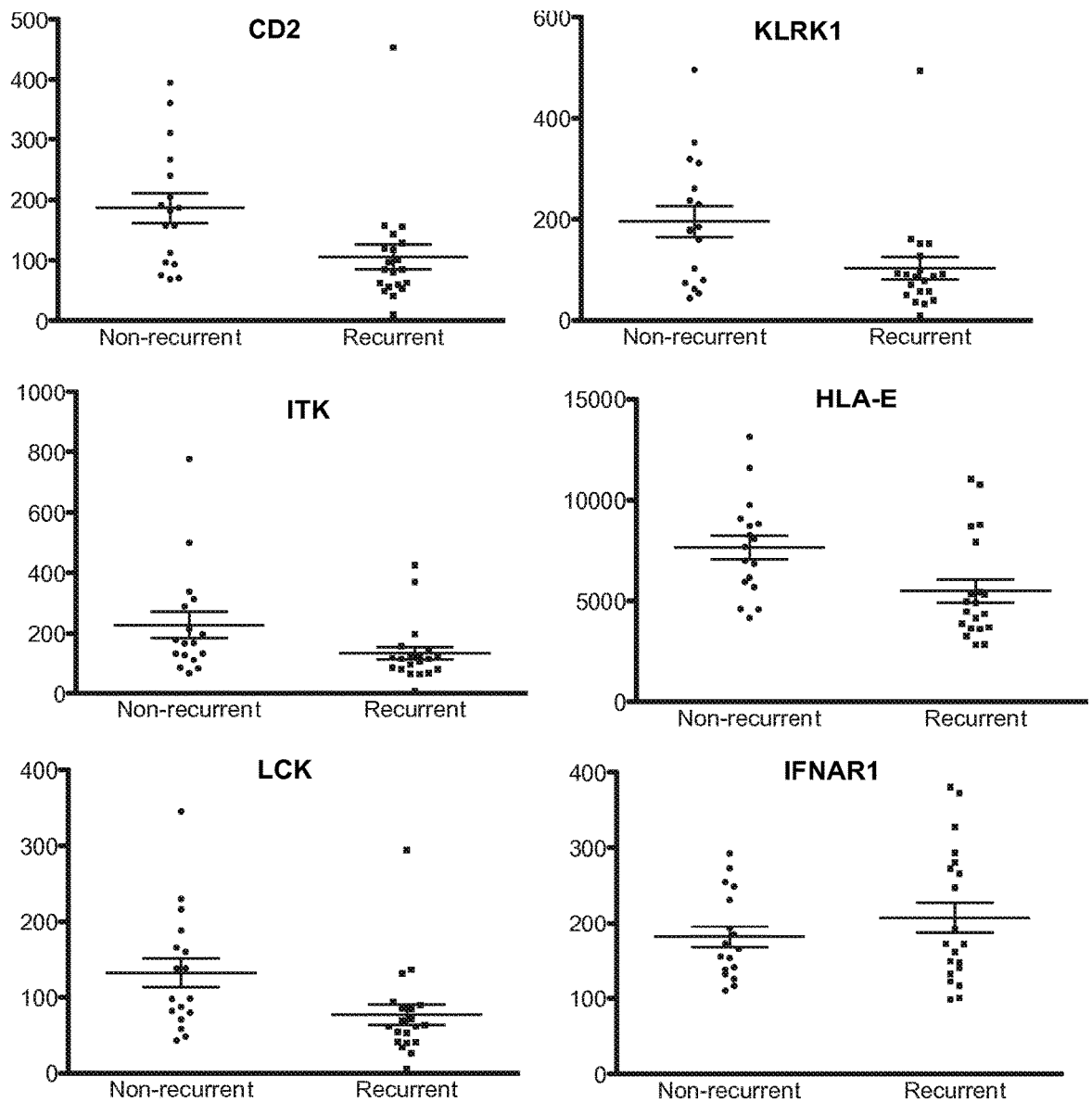

Figure 6 Panel B, continued
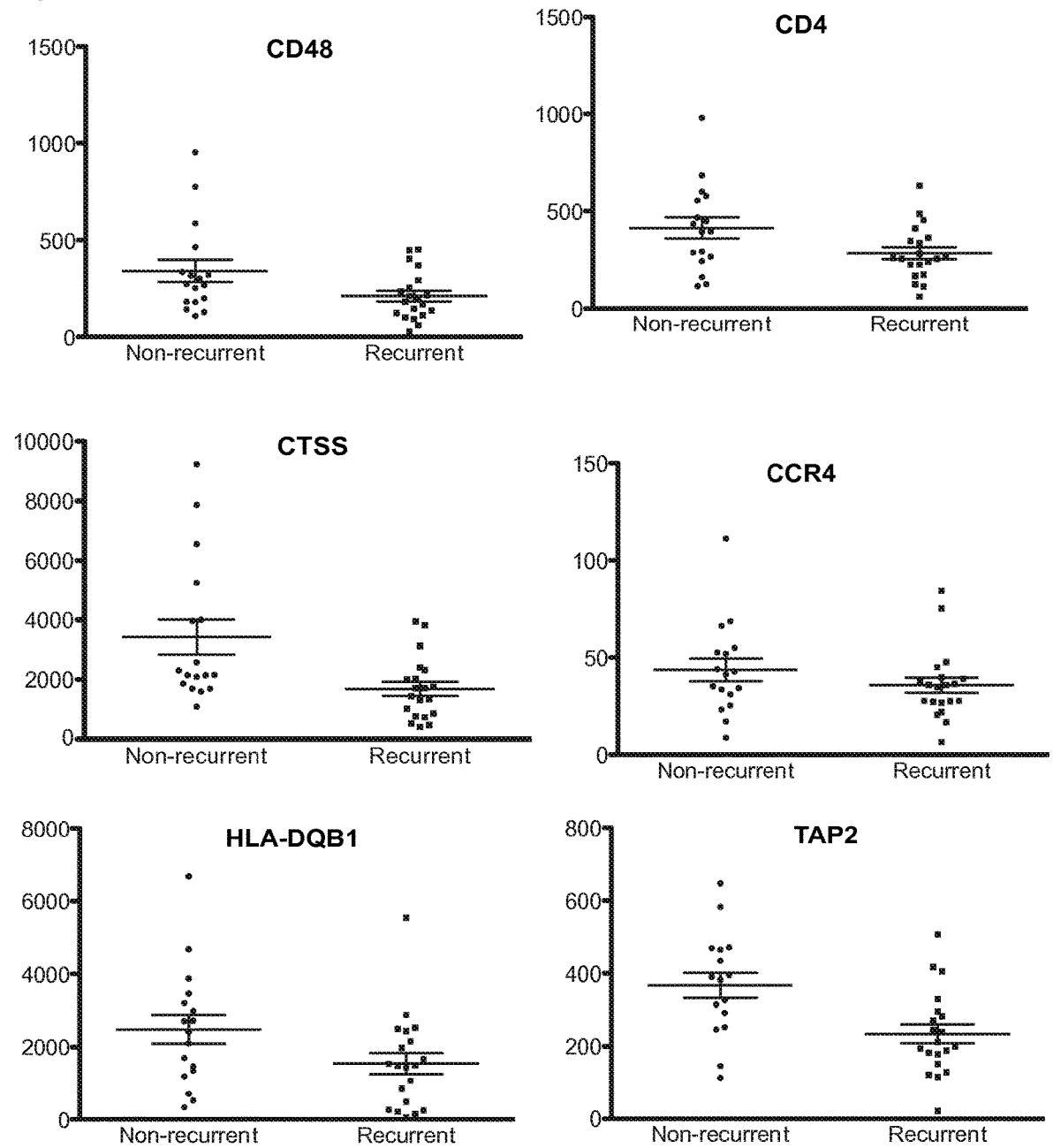

Figure 6 Panel B, continued
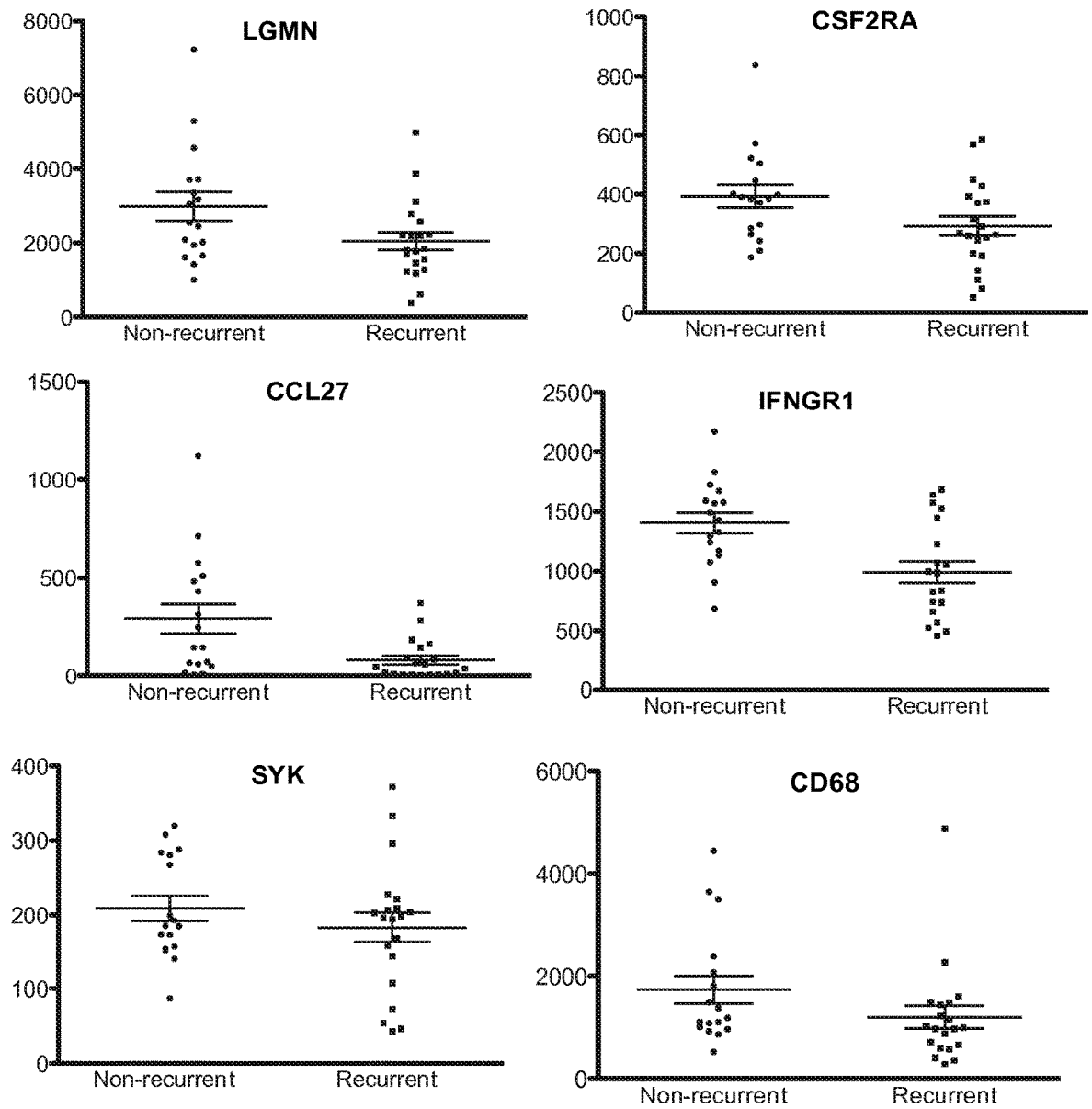

Figure 6 Panel B, continued
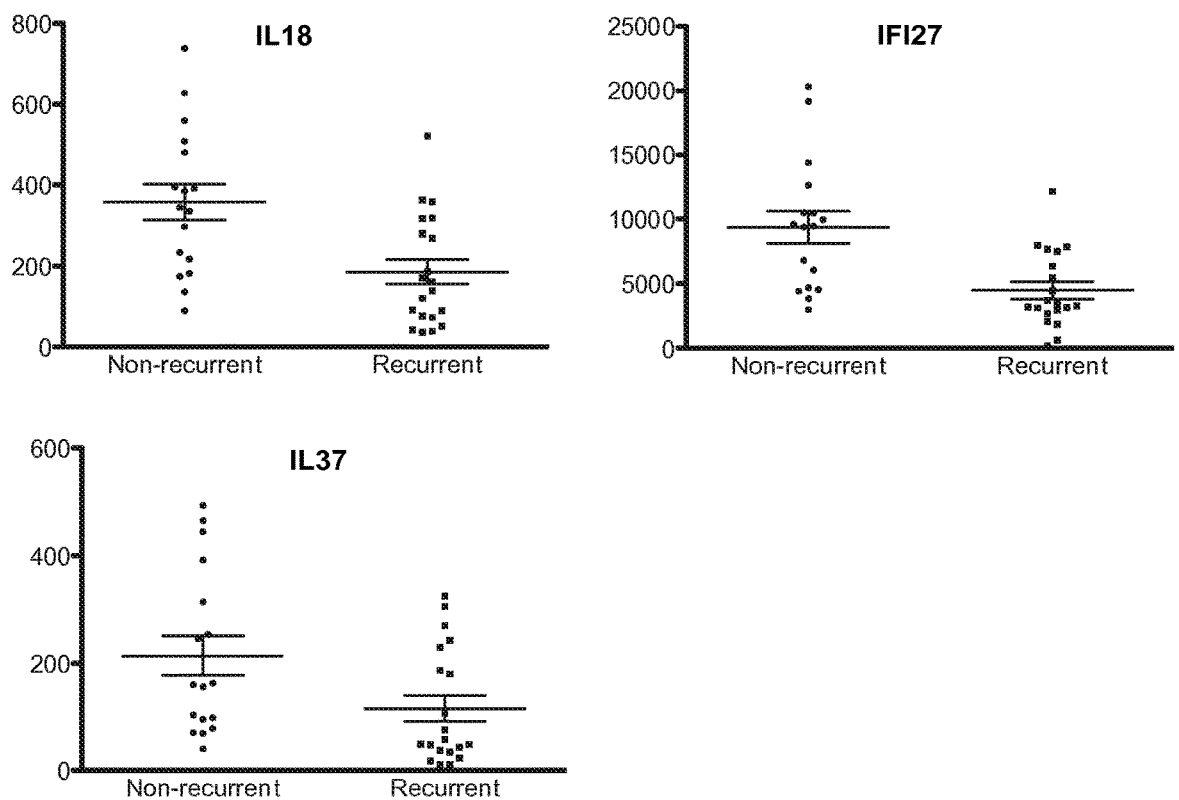

Figure 12, continued
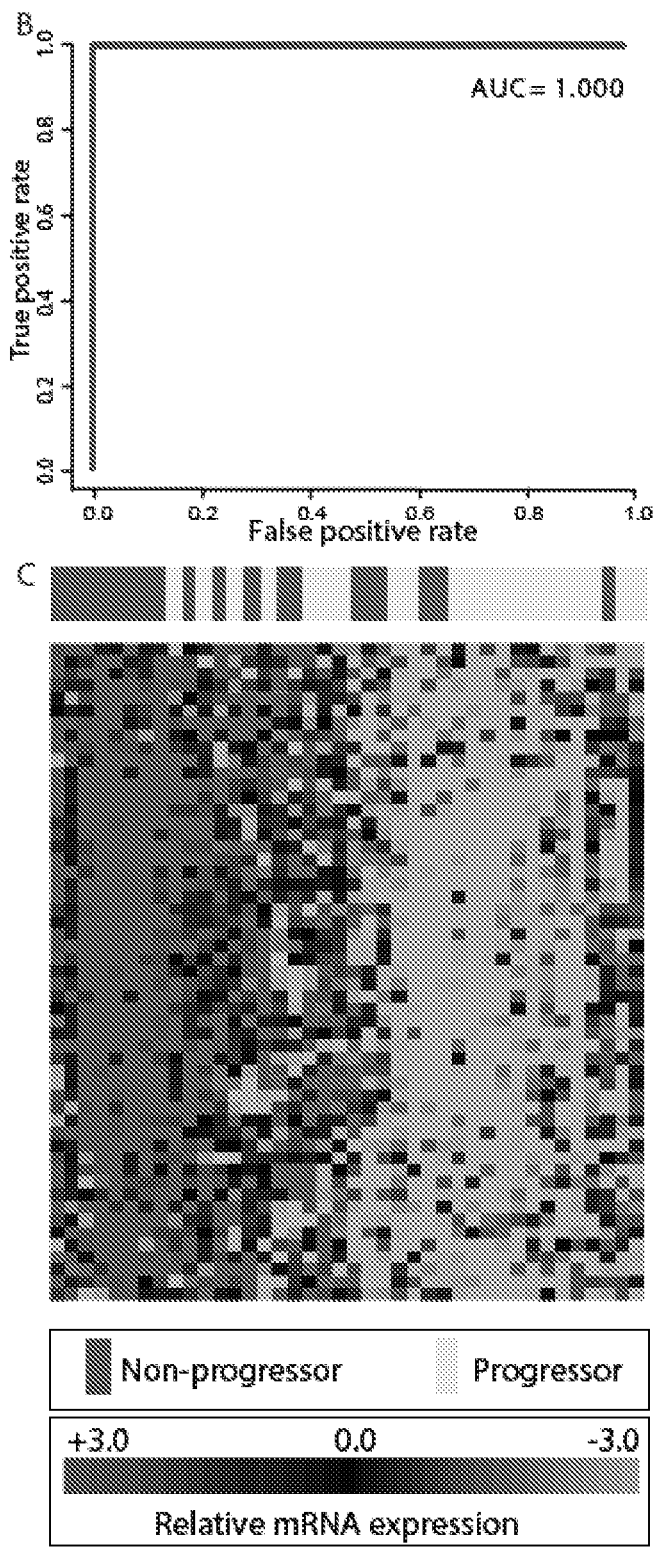

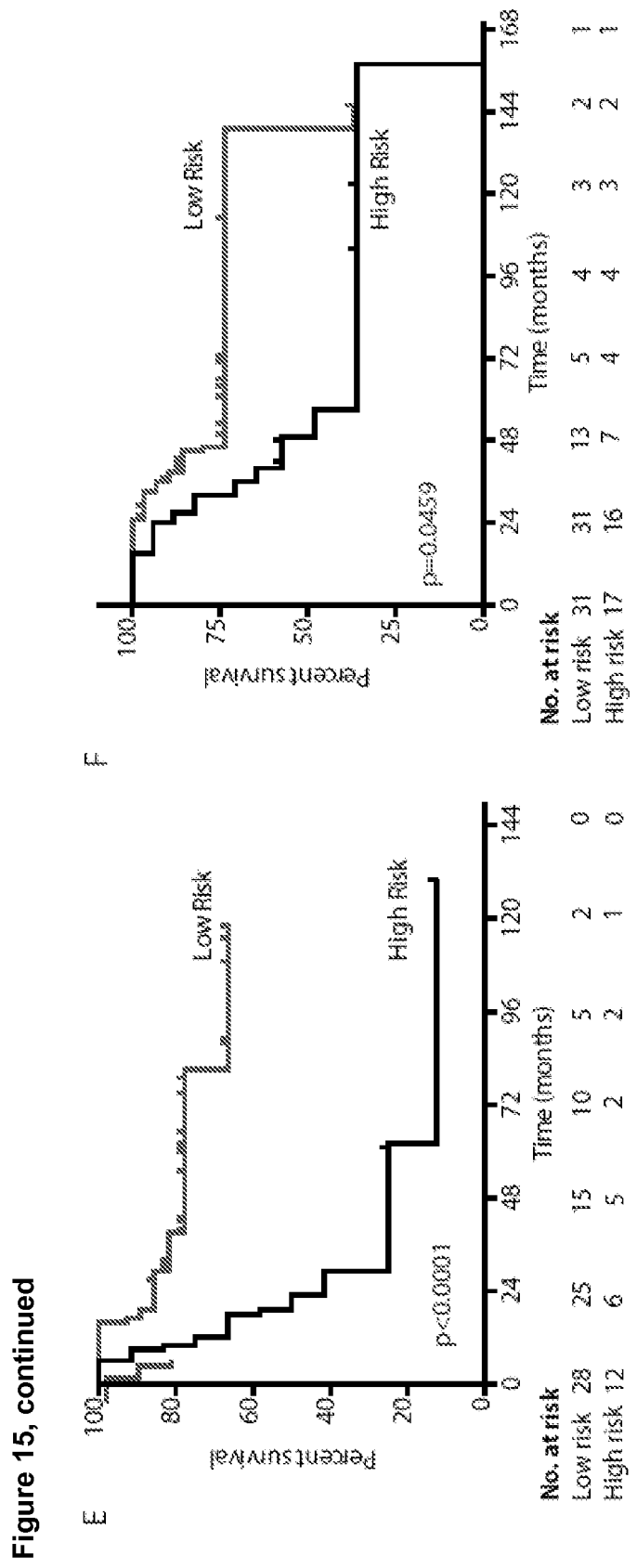
Figure 15, continued

| | Genes (Nodes) | Interactions (Edges) | Density | Average Local CC | Local CC SE | Average Local CC P-value | Global CC | Global CC P-value |
|---|---|---|---|---|---|---|---|---|
| 53-gene panel network | 406 | 1927 | 0.023 | 0.286 | 0.014 | 0 | 0.192 | 0 |
| 446-gene panel network | 2474 | 14866 | 0.005 | 0.206 | 0.005 | 0.511 | 0.092 | 0 |
| Fold Change | | | 4.815 | 1.39 | | | 2.08 | |

A.  Non-recurrent          Recurrent

Figure 19, continued
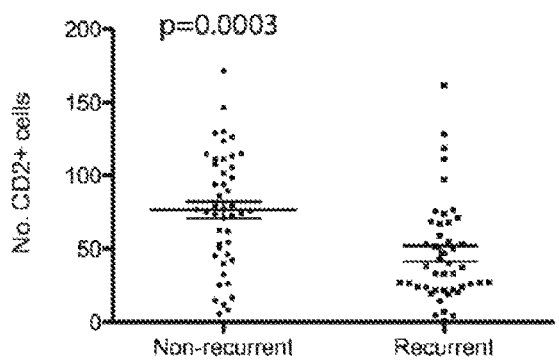
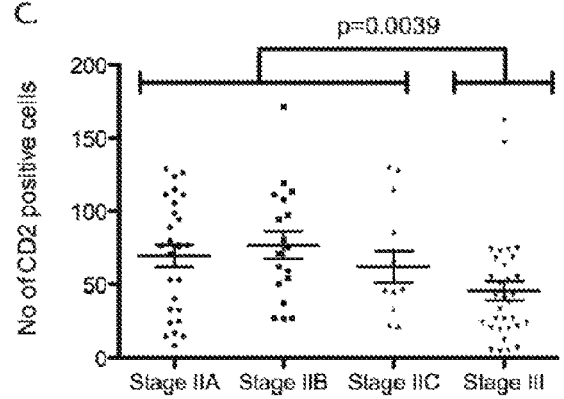
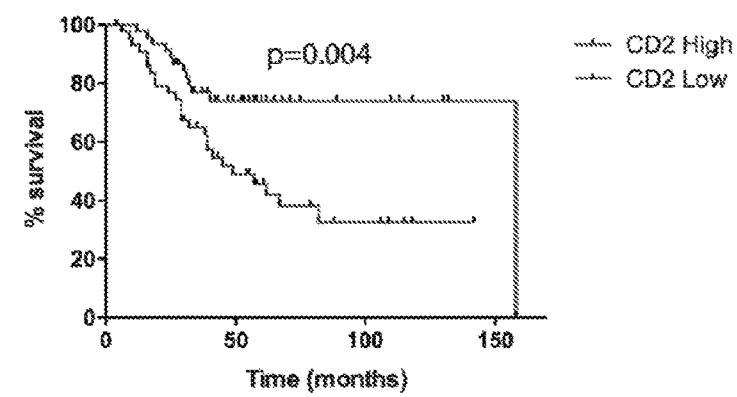
Figure 20
A.      Anti-CD3                    Anti-CD2
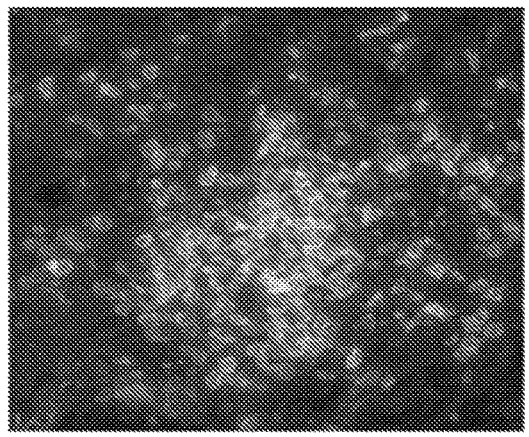
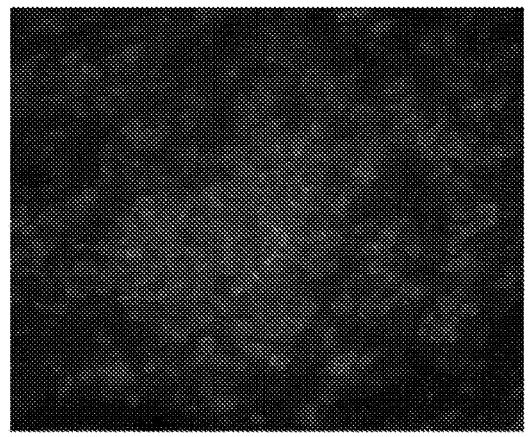

Figure 20, continued
B.
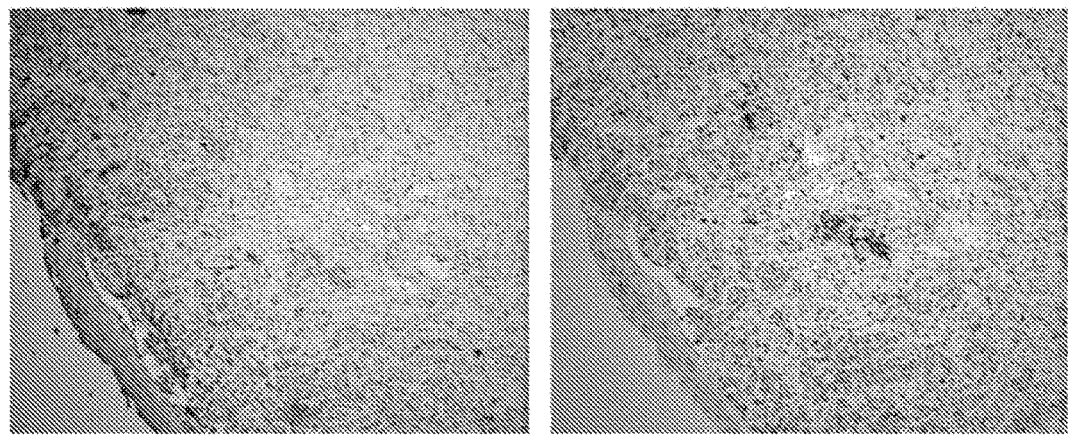
Figure 21
A.
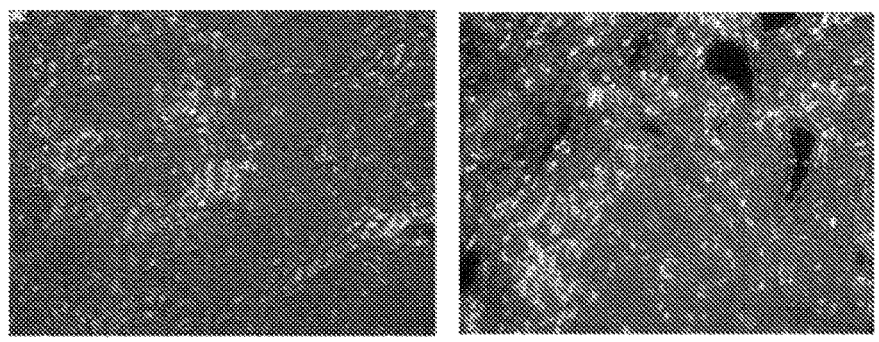

A.

Figure 22 (continued)
B.
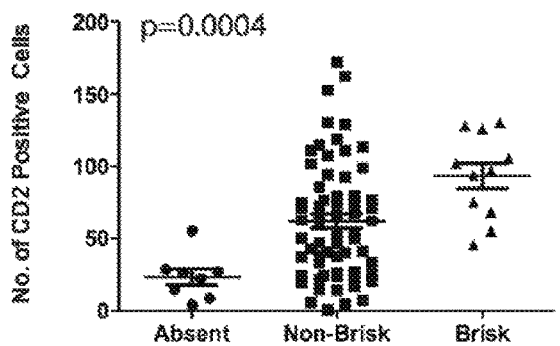
C.
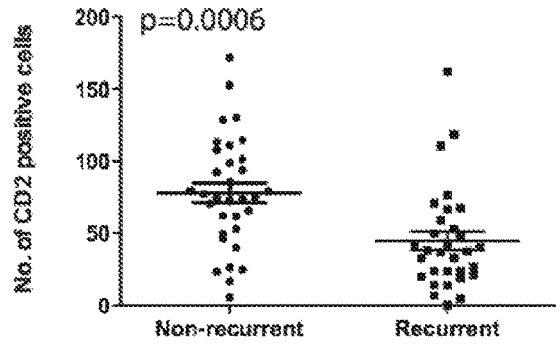
D.
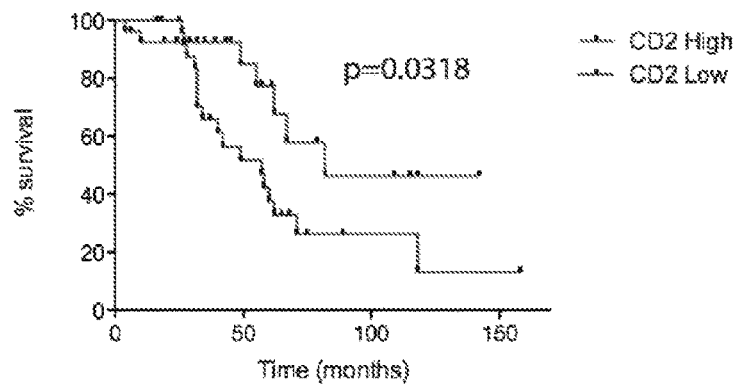
Figure 23
A.
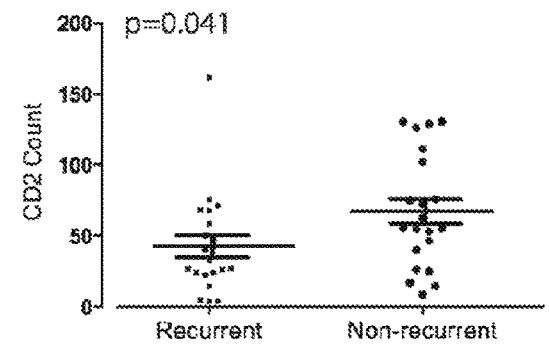
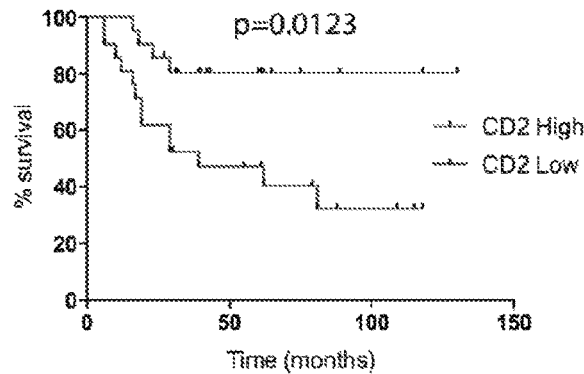

Figure 23 (continued)
B.
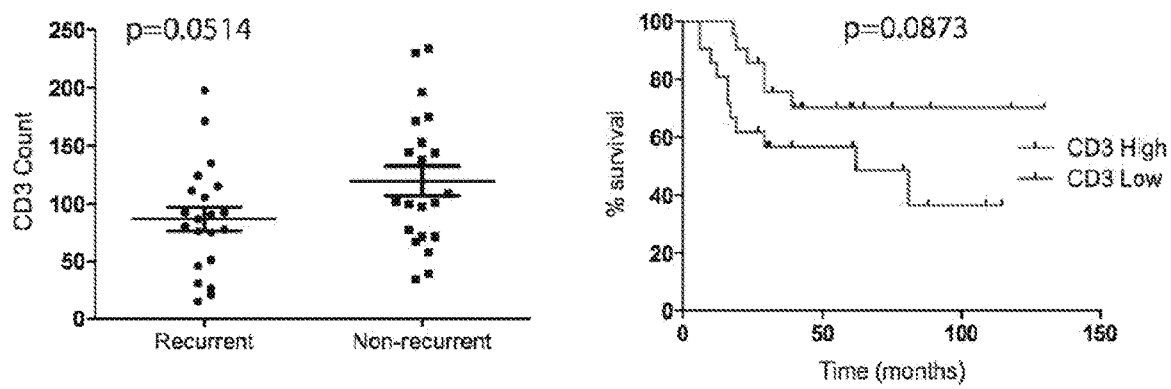
Figure 24
A.
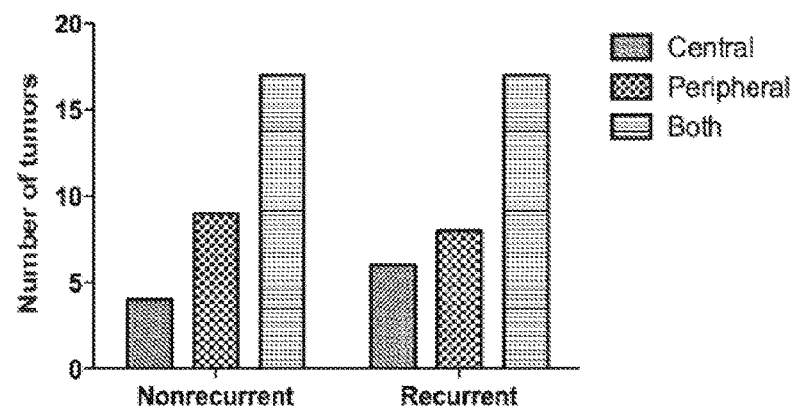
B.
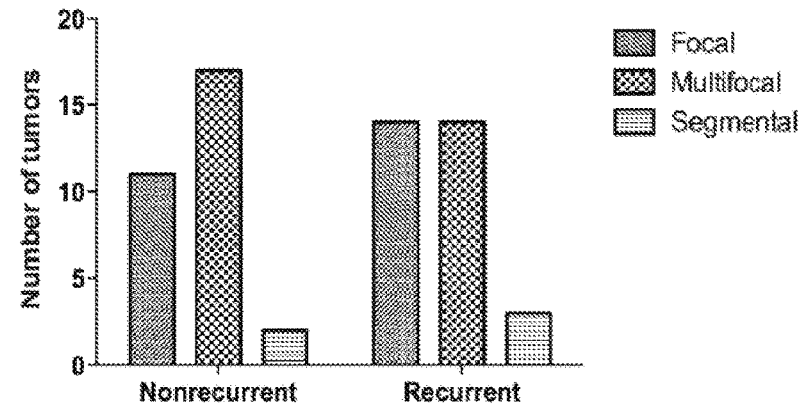

| A2M | CCR8 | CSF1 | HLAA | IKBKG | IRF1 | MRC1 | TIA1 |
|---|---|---|---|---|---|---|---|
| ABCF1 | CCR9 | CSF1R | HLAB | IKZF1 | IRF2 | MSR1 | TICAM1 |
| ACTB | CCRL1 | CSF2 | HLAC | IKZF5 | IRF3 | MST1R | TICAM2 |
| ALAS1 | CCRL2 | CSF2RA | HLA-DMA | IL10 | IRF4 | MX1 | TIMP3 |
| ALCAM | CD101 | CSF2RB | HLA-DOB | IL10RA | IRF5 | MYADM | TIRAP |
| ALOX5 | CD14 | CSF3 | HLA-DPA1 | IL11 | IRF6 | MYD88 | TLR1 |
| AMICA1 | CD163 | CSF3R | HLA-DPB1 | IL12A | IRF7 | NFAM1 | TLR10 |
| ANGPTL4 | CD164 | CTLA4 | HLA-DQA1 | IL12B | IRF8 | NFATC3 | TLR2 |
| ANXA1 | CD180 | CTSS | HLA-DQA2 | IL12RB1 | IRF9 | NFKB1 | TLR3 |
| ANXA11 | CD19 | CX3CL1 | HLA-DQB1 | IL12RB2 | ISG15 | NFKB2 | TLR4 |
| B2M | CD1A | CX3CR1 | HLA-DRB1 | IL13 | ISG20 | NFKBIA | TLR5 |
| BCL10 | CD1B | CXCL1 | HLA-DRB3 | IL13RA1 | ITGA1 | NFKBIZ | TLR6 |
| BCL2A1 | CD1C | CXCL10 | HLA-DRB4 | IL13RA2 | ITGA2 | NLRC3 | TLR7 |
| BCL3 | CD1D | CXCL11 | HLAE | IL15 | ITGA4 | NLRC5 | TLR8 |
| BCL6 | CD2 | CXCL12 | HLAF | IL15RA | ITGA5 | NOS2A | TLR9 |
| BDCA3 | CD20 | CXCL13 | HLAG | IL17D | ITGA6 | OAS1 | TNF |
| BIK | CD200 | CXCL14 | HMGB1 | IL17F | ITGA9 | OPTN | TNFAIP3 |
| BIRC5 | CD207 | CXCL16 | HPRT1 | IL17RA | ITGAL | OSM | TNFAIP6 |
| CXCR5 | CD209 | CXCL2 | ICAM1 | IL17RB | ITGAM | PDCD1 | TNFRSF10B |
| BTK | CD24 | CXCL3 | ICOS | IL18 | ITGB1 | PDL1 | TNFRSF11A |
| C1QA | CD27 | CXCL5 | ICOSLG | IL18RAP | ITGB2 | PGK1 | TNFRSF11B |
| C3 | CD36 | CXCL6 | IFI27 | IL19 | ITGB3 | PILRA | TNFRSF12A |
| C3AR1 | CD37 | CXCL7 | IFI35 | IL1A | ITGB4 | PILRB | TNFRSF13B |
| CASP1 | CD38 | CXCL9 | IFI44 | IL1B | ITK | PLCG2 | TNFRSF13C |
| CCBP2 | CD3E | CXCR3 | IFI6 | IL1F10 | JAK1 | POLR1B | TNFRSF14 |
| CCL1 | CD4 | CXCR4 | IFIH1 | IL1R1 | KCNIP2 | POLR2A | TNFRSF17 |
| CCL11 | CD40 | CXCR6 | IFIT1 | IL1R2 | KLF6 | PPARG | TNFRSF18 |

FIG. 25A

| CCL13 | CD40LG | CYBB | IFIT2 | IL1RAP | KLRD1 | PRG1 | TNFRSF19L |
|---|---|---|---|---|---|---|---|
| CCL14 | CD47 | CYFIP2 | IFITM1 | IL1RAPL2 | KLRK1 | PTGS2 | TNFRSF1A |
| CCL15 | CD48 | DUSP1 | IFITM2 | IL1RL1 | LAMP1 | PTPRC | TNFRSF21 |
| CCL16 | CD5 | DUSP5 | IFNA1 | IL1RL2 | LAMP2 | REL | TNFRSF25 |
| CCL17 | CD53 | EHD1 | IFNA14 | IL1RN | LAMP3 | RELA | TNFRSF4 |
| CCL18 | CD55 | ENG | IFNA2 | IL2 | LAT2 | RELB | TNFRSF8 |
| CCL19 | CD58 | F13A1 | IFNA21 | IL21 | LAX1 | RIPK2 | TNFRSF9 |
| CCL2 | CD63 | FAS | IFNA4 | IL22RA1 | LCK | RPL19 | TNFSF10 |
| CCL20 | CD68 | FCAMR | IFNA5 | IL23A | LDHA | RPLP0 | TNFSF11 |
| CCL21 | CD70 | FCER1A | IFNA6 | IL23R | LEPR | Runx1 | TNFSF12 |
| CCL22 | CD74 | FCER2 | IFNA8 | IL24 | LGMN | S100A12 | TNFSF13 |
| CCL23 | CD79A | FCGR1A | IFNAR1 | IL25 | LRP1 | SAA1 | TNFSF13B |
| CCL24 | CD79B | FCGR2A | IFNAR2 | IL27 | LSP1 | SDHA | TNFSF14 |
| CCL25 | CD80 | FCGR3A | IFNE1 | IL28A | LTA | SERPINB2 | TNFSF18 |
| CCL26 | CD83 | FCGR3B | IFNG | IL28RA | LTB | SIGIRR | TNFSF4 |
| CCL27 | CD86 | FCGRT | IFNGR1 | IL2R | LTBR | SIGLEC1 | TNFSF9 |
| CCL28 | CD8A | FLT3 | IFNGR2 | IL33 | LY9 | SKAP1 | TRAF1 |
| CCL3 | CDC42 | FN1 | IFNK | IL34 | LY96 | SOCS1 | TRAF2 |
| CCL3L1 | CEACAM1 | Foxp3 | IFRG28 | IL37 | LYVE1 | SP110 | TRAF3 |
| CCL4 | CEBPA | FPR1 | IGCL2 | IL3RA | MAL2 | SPP1 | TRAF6 |
| CCL5 | CHST4 | FYN | IGF1R | IL4 | MALT1 | STAT1 | TRAT1 |
| CCL7 | CISH3 | G6PD | IGHA1 | IL4R | MAP3K7 | STAT2 | TSLP |
| CCL8 | CKLF | GAPDH | IGHG1 | IL5 | MAPK1 | STAT3 | TUBB |
| CCR1 | CLEC2A | GATA3 | IGHG2 | IL6 | MCAM | SYK | TXK |
| CCR10 | CLEC4C | GBP1 | IGHG3 | IL6R | MDK | TAP1 | VCAM1 |
| CCR2 | CLECL1 | GBP2 | IGHG4 | IL7 | MERTK | TAP2 | VEGFC |
| CCR3 | CLTC | GHR | IGHM | IL8 | MFGE8 | TARP | XCL1 |
| CCR4 | CMKLR1 | GPR44 | IGKC | CXCR2 | MGLL | TBP | XCL2 |
| CCR5 | COLEC12 | GUSB | IGLL1 | INHBA | MIF | TBX21 | XCR1 |
| CCR6 | CREB1 | GZMK | IGSF4 | IRAK1 | MITF | TCL1A | ZAP70 |
| CCR7 | CRP | HIF1A | IGSF9 | IRAK2 | MMP9 | THBS1 | |

FIG. 25B

| Characteristic | Training Set | | Validation Set | |
| --- | --- | --- | --- | --- |
| | Characteristic Alone | + Gene signature | Characteristic Alone | + Gene signature |
| | coefficient of determination $R^2$ | | | |
| Stage | 0.061 | 0.710 | 0.040 | 0.678 |
| Depth | 0.118 | 0.719 | 0.049 | 0.679 |
| Lymph node status | 0.073 | 0.710 | 0.073 | 0.677 |
| Inflammatory infiltrate | 0.001 | 0.710 | 0.059 | 0.684 |
| Location of tumor | 0.057 | 0.723 | 0.001 | 0.688 |
| Ulceration | 0.052 | 0.707 | 0.014 | 0.678 |
| Age | 0.097 | 0.713 | 0.001 | 0.853 |
| Gender | 0.000 | 0.719 | 0.054 | 0.700 |
| All clinical factors | 0.318 | 0.794 | 0.224 | 0.947 |
| Gene signature | 0.706 | - | 0.676 | - |

FIG. 26

| Total Input Genes | Training AUC | Validation AUC | Total AUC | Total misclassification in training |
|---|---|---|---|---|
| 29 | 0.983437 | 0.794117647 | 1.7775545 | 4 |
| 30 | 0.983437 | 0.794117647 | 1.7775545 | 4 |
| 31 | 0.983437 | 0.794117647 | 1.7775545 | 4 |
| 32 | 0.983437 | 0.794117647 | 1.7775545 | 4 |
| 33 | 0.983437 | 0.794117647 | 1.7775545 | 4 |
| 34 | 0.983437 | 0.794117647 | 1.7775545 | 4 |
| 35 | 0.983437 | 0.794117647 | 1.7775545 | 4 |
| 36 | 0.983437 | 0.794117647 | 1.7775545 | 4 |
| 37 | 0.983437 | 0.794117647 | 1.7775545 | 4 |
| 38 | 0.983437 | 0.794117647 | 1.7775545 | 4 |
| 39 | 0.983437 | 0.794117647 | 1.7775545 | 4 |
| 40 | 0.983437 | 0.794117647 | 1.7775545 | 4 |
| 41 | 0.983437 | 0.794117647 | 1.7775545 | 4 |
| 42 | 0.983437 | 0.794117647 | 1.7775545 | 4 |
| 43 | 0.983437 | 0.794117647 | 1.7775545 | 4 |
| 44 | 0.983437 | 0.794117647 | 1.7775545 | 4 |
| 45 | 0.983437 | 0.794117647 | 1.7775545 | 4 |
| 46 | 0.983437 | 0.794117647 | 1.7775545 | 4 |
| 47 | 0.983437 | 0.794117647 | 1.7775545 | 4 |
| 48 | 0.983437 | 0.794117647 | 1.7775545 | 4 |
| 49 | 0.983437 | 0.794117647 | 1.7775545 | 4 |
| 50 | 0.983437 | 0.794117647 | 1.7775545 | 4 |
| 51 | 0.983437 | 0.794117647 | 1.7775545 | 4 |
| 52 | 0.983437 | 0.794117647 | 1.7775545 | 4 |
| 53 | 0.983437 | 0.794117647 | 1.7775545 | 4 |

| Total misclassification in validation | Total misclassification | Final gene number | | | | |
|---|---|---|---|---|---|---|
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |
| 8 | 12 | 21 | CD2 | KLRK1 | ITK | HLAE |

FIG. 27B

| LCK | IFNAR1 | CD48 | CD4 | CTSS | CCR4 | HLA-DQB1 | TAP2 |
|-----|--------|------|-----|------|------|----------|------|
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |

FIG. 27C

| LGMN | CSF2RA | CCL27 | IFNGR1 | SYK | CD68 | IL18 | IFI27 | IL1F7 |
|------|--------|-------|--------|-----|------|------|-------|-------|
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |
| LGMN | CSF2RA | CCL27 | IFNGR1 | SYK | CD68 | IL18 | IFI27 | IL1F7 |

FROM FIG. 27C

FROM FIG. 27A

| | | | | | |
|---|---|---|---|---|---|
| 27 | 0.979296 | 0.791176471 | 1.77047254 | 4 | |
| 28 | 0.979296 | 0.791176471 | 1.77047254 | 4 | |
| 26 | 0.966874 | 0.794117647 | 1.76099135 | 5 | TO FIG. 27F |
| 20 | 0.971014 | 0.782352941 | 1.75336743 | 5 | |
| 21 | 0.971014 | 0.776470588 | 1.74748508 | 6 | |
| 22 | 0.971014 | 0.776470588 | 1.74748508 | 6 | |
| 23 | 0.971014 | 0.776470588 | 1.74748508 | 6 | |
| 24 | 0.971014 | 0.776470588 | 1.74748508 | 6 | |
| 25 | 0.971014 | 0.776470588 | 1.74748508 | 6 | |
| 16 | 0.960663 | 0.785294118 | 1.74595664 | 5 | |
| 19 | 0.973085 | 0.770588235 | 1.74367312 | 5 | |
| 17 | 0.94617 | 0.782352941 | 1.72852271 | 7 | |
| 18 | 0.94617 | 0.782352941 | 1.72852271 | 7 | |
| 14 | 0.954451 | 0.720588235 | 1.67503958 | 7 | |
| 15 | 0.954451 | 0.720588235 | 1.67503958 | 7 | |
| 13 | 0.929607 | 0.720588235 | 1.65019486 | 9 | |
| 12 | 0.929607 | 0.714705882 | 1.64431251 | 9 | |
| 2 | 0.84058 | 0.794117647 | 1.63459736 | 14 | |
| 3 | 0.836439 | 0.782352941 | 1.61879486 | 13 | |
| 4 | 0.834369 | 0.782352941 | 1.61672147 | 13 | |
| 11 | 0.904762 | 0.694117647 | 1.59887955 | 10 | |
| 10 | 0.904762 | 0.691176471 | 1.59593838 | 10 | |
| 8 | 0.886128 | 0.708823529 | 1.59495189 | 9 | |
| 9 | 0.89234 | 0.691176471 | 1.58351602 | 8 | |
| 7 | 0.869565 | 0.694117647 | 1.56368286 | 9 | |
| 5 | 0.861284 | 0.688235294 | 1.54951894 | 9 | |
| 6 | 0.859213 | 0.688235294 | 1.54744854 | 9 | |

FIG. 27E

FROM FIG. 27B

| | | | | | | |
|---|---|---|---|---|---|---|
| 8 | 12 | 20 | CD2 | KLRK1 | ITK | HLAE |
| 8 | 12 | 20 | CD2 | KLRK1 | ITK | HLAE |
| 9 | 14 | 19 | CD2 | KLRK1 | ITK | HLAE |
| 10 | 15 | 17 | CD2 | KLRK1 | ITK | HLAE |
| 10 | 16 | 18 | CD2 | KLRK1 | ITK | HLAE |
| 10 | 16 | 18 | CD2 | KLRK1 | ITK | HLAE |
| 10 | 16 | 18 | CD2 | KLRK1 | ITK | HLAE |
| 10 | 16 | 18 | CD2 | KLRK1 | ITK | HLAE |
| 10 | 16 | 18 | CD2 | KLRK1 | ITK | HLAE |
| 10 | 15 | 15 | CD2 | KLRK1 | ITK | HLAE |
| 10 | 15 | 16 | CD2 | KLRK1 | ITK | HLAE |
| 10 | 17 | 15 | CD2 | KLRK1 | ITK | HLAE |
| 10 | 17 | 15 | CD2 | KLRK1 | ITK | HLAE |
| 12 | 19 | 14 | CD2 | KLRK1 | ITK | HLAE |
| 12 | 19 | 14 | CD2 | KLRK1 | ITK | HLAE |
| 12 | 21 | 13 | CD2 | KLRK1 | ITK | HLAE |
| 12 | 21 | 12 | CD2 | KLRK1 | ITK | HLAE |
| 10 | 24 | 2 | CD2 | HLAE | | |
| 9 | 22 | 3 | CD2 | KLRK1 | HLAE | |
| 9 | 22 | 4 | CD2 | KLRK1 | ITK | HLAE |
| 12 | 22 | 11 | CD2 | KLRK1 | ITK | HLAE |
| 12 | 22 | 10 | CD2 | KLRK1 | ITK | HLAE |
| 12 | 21 | 8 | CD2 | KLRK1 | ITK | HLAE |
| 14 | 22 | 9 | CD2 | KLRK1 | ITK | HLAE |
| 13 | 22 | 7 | CD2 | KLRK1 | ITK | HLAE |
| 13 | 22 | 5 | CD2 | KLRK1 | ITK | HLAE |
| 13 | 22 | 6 | CD2 | KLRK1 | ITK | HLAE |

TO FIG. 27G

FROM FIG. 27E

FIG. 27F

FROM FIG. 27C

| LCK | IFNAR1 | CD48 | CD4 | CTSS | CCR4 | HLA-DQB1 | TAP2 |
|---|---|---|---|---|---|---|---|
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD4 | CTSS | CCR4 | HLA-DQB1 | TAP2 | LGMN |
| LCK | IFNAR1 | CD4 | CTSS | CCR4 | HLA-DQB1 | TAP2 | LGMN |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |
| LCK | IFNAR1 | CD48 | CD4 | CTSS | CCR4 | HLA-DQB1 | TAP2 |

TO FIG. 27H

FROM FIG. 27F

| LCK | IFNAR1 | CD4 | CTSS | CCR4 | HLA-DQB1 | TAP2 |
|---|---|---|---|---|---|---|
| LCK | IFNAR1 | CD4 | CTSS | CCR4 | TAP2 | |
| LCK | IFNAR1 | CD4 | CCR4 | | | |
| LCK | IFNAR1 | CD4 | CTSS | CCR4 | | |
| LCK | IFNAR1 | CD4 | | | | |
| IFNAR1 | | | | | | |
| LCK | IFNAR1 | | | | | |

FIG. 27G

FROM FIG. 27D

| | | | | | | | |
|---|---|---|---|---|---|---|---|
| LGMN | CSF2RA | CCL27 | IFNGR1 | SYK | CD68 | IFI27 | IL1F7 |
| LGMN | CSF2RA | CCL27 | IFNGR1 | SYK | CD68 | IFI27 | IL1F7 |
| LGMN | CSF2RA | CCL27 | IFNGR1 | | CD68 | IFI27 | IL1F7 |
| LGMN | CSF2RA | CCL27 | IFNGR1 | | CD68 | | |
| LGMN | CSF2RA | CCL27 | IFNGR1 | | CD68 | IL1F7 | |
| LGMN | CSF2RA | CCL27 | IFNGR1 | | CD68 | IL1F7 | |
| LGMN | CSF2RA | CCL27 | IFNGR1 | | CD68 | IL1F7 | |
| LGMN | CSF2RA | CCL27 | IFNGR1 | | CD68 | IL1F7 | |
| LGMN | CSF2RA | CCL27 | IFNGR1 | | CD68 | IL1F7 | |
| LGMN | CSF2RA | IFNGR1 | | | | | |
| LGMN | CSF2RA | IGNGR1 | CD68 | | | | |
| CSF2RA | IRFS | IGNGR1 | | | | | |
| CSF2RA | IRFS | IFNGR1 | | | | | |
| LGMN | CSF2RA | | | | | | |
| LGMN | CSF2RA | | | | | | |
| CSF2RA | | | | | | | |

FROM FIG. 27G

FIG. 27H

| A2M | CCR8 | CSF1 | HLAA | IKBKG | IRF1 | MRC1 | TIA1 |
|---|---|---|---|---|---|---|---|
| ABCF1 | CCR9 | CSF1R | HLAB | IKZF1 | IRF2 | MSR1 | TICAM1 |
| ACTB | CCRL1 | CSF2 | HLAC | IKZF5 | IRF3 | MST1R | TICAM2 |
| ALAS1 | CCRL2 | CSF2RA | HLA-DMA | IL10 | IRF4 | MX1 | TIMP3 |
| ALCAM | CD101 | CSR2RB | HLA-DOB | IL10RA | IRF5 | MYADM | TIRAP |
| ALOX5 | CD14 | CSF3 | HLA-DPA1 | IL11 | IRF6 | MYD88 | TLR1 |
| AMICA1 | CD163 | CSF3R | HLA-DPB1 | IL12A | IRF7 | NFAM1 | TLR10 |
| ANGPTL4 | CD164 | CTLA4 | HLA-DQA1 | IL12B | IRF8 | NFATC3 | TLR2 |
| ANXA1 | CD180 | CTSS | HLA-DQA2 | IL12RB1 | IRF9 | NFKB1 | TLR3 |
| ANXA11 | CD19 | CX3CL1 | HLA-DQB1 | IL12RB2 | ISG15 | NFKB2 | TLR4 |
| B2M | CD1A | CX3CR1 | HLA-DRB1 | IL13 | ISG20 | NFKBIA | TLR5 |
| BCL10 | CD1B | CXCL1 | HLA-DRB3 | IL13RA1 | ITGA1 | NFKBIZ | TLR6 |
| BCL2A1 | CD1C | CXCL10 | HLA-DRB4 | IL13RA2 | ITGA2 | NLRC3 | TLR7 |
| BCL3 | CD1D | CXCL11 | HLAE | IL15 | ITGA4 | NLRC5 | TLR8 |
| BCL6 | CD2 | CXCL12 | HLAF | IL15RA | ITGA5 | NOS2A | TLR9 |
| BDCA3 | CD20 | CXCL13 | HLAG | IL17D | ITGA6 | OAS1 | TNF |
| BIK | CD200 | CXCL14 | HMGB1 | IL17F | ITGA9 | OPTN | TNFAIP3 |
| BIRC5 | CD207 | CXCL16 | HPRT1 | IL17RA | ITGAL | OSM | TNFAIP6 |
| CXCR5 | CD209 | CXCL2 | ICAM1 | IL17RB | ITGAM | PDCD1 | TNFRSF10B |

FIG. 28A

| BTK | CD24 | CXCL3 | ICOS | IL18 | ITGB1 | PDL1 | TNFRSF11A |
|---|---|---|---|---|---|---|---|
| C1QA | CD27 | CXCL5 | ICOSLG | IL18RAP | ITGB2 | PGK1 | TNFRSF11B |
| C3 | CD36 | CXCL6 | IFI27 | IL19 | ITGB3 | PILRA | TNFRSF12A |
| C3AR1 | CD37 | CXCL7 | IFI35 | IL1A | ITGB4 | PILRB | TNFRSF13B |
| CASP1 | CD38 | CXCL9 | IFI44 | IL1B | ITK | PLCG2 | TNFRSF13C |
| CCBP2 | CD3E | CXCR3 | IFI6 | IL1F10 | JAK1 | POLR1B | TNFRSF14 |
| CCL1 | CD4 | CXCR4 | IFIH1 | IL1R1 | KCNIP2 | POLR2A | TNFRSF17 |
| CCL11 | CD40 | CXCR6 | IFIT1 | IL1R2 | KLF6 | PPARG | TNFRSF18 |
| CCL13 | CD40LG | CYBB | IFIT2 | IL1RAP | KLRD1 | PRG1 | TNFRSF19L |
| CCL14 | CD47 | CYFIP2 | IFITM1 | IL1RAPL2 | KLRK1 | PTGS2 | TNFRSF1A |
| CCL15 | CD48 | DUSP1 | IFITM2 | IL1RL1 | LAMP1 | PTPRC | TNFRSF21 |
| CCL16 | CD5 | DUSP5 | IFNA1 | IL1RL2 | LAMP2 | REL | TNFRSF25 |
| CCL17 | CD53 | EHD1 | IFNA14 | IL1RN | LAMP3 | RELA | TNFRSF4 |
| CCL18 | CD55 | ENG | IFNA2 | IL2 | LAT2 | RELB | TNFRSF8 |
| CCL19 | CD58 | F13A1 | IFNA21 | IL21 | LAX1 | RIPK2 | TNFRSF9 |
| CCL2 | CD63 | FAS | IFNA4 | IL22RA1 | LCK | RPL19 | TNFSF10 |
| CCL20 | CD68 | FCAMR | IFNA5 | IL23A | LDHA | RPLP0 | TNFSF11 |
| CCL21 | CD70 | FCER1A | IFNA6 | IL23R | LEPR | Runx1 | TNFSF12 |
| CCL22 | CD74 | FCER2 | IFNA8 | IL24 | LGMN | S100A12 | TNFSF13 |
| CCL23 | CD79A | FCGR1A | IFNAR1 | IL25 | LRP1 | SAA1 | TNFSF13B |
| CCL24 | CD79B | FCGR2A | IFNAR2 | IL27 | LSP1 | SDHA | TNFSF14 |
| CCL25 | CD80 | FCGR3A | IFNE1 | IL28A | LTA | SERPINB2 | TNFSF18 |
| CCL26 | CD83 | FCGR3B | IFNG | IL28RA | LTB | SIGIRR | TNFSF4 |
| CCL27 | CD86 | FCGRT | IFNGR1 | IL2R | LTBR | SIGLEC1 | TNFSF9 |
| CCL28 | CD8A | FLT3 | IFNGR2 | IL33 | LY9 | SKAP1 | TRAF1 |
| CCL3 | CDC42 | FN1 | IFNK | IL34 | LY96 | SOCS1 | TRAF2 |
| CCL3L1 | CEACAM1 | Foxp3 | IFRG28 | IL37 | LYVE1 | SP110 | TRAF3 |
| CCL4 | CEBPA | FPR1 | IGCL2 | IL3RA | MAL2 | SPP1 | TRAF6 |
| CCL5 | CHST4 | FYN | IGF1R | IL4v | MALT1 | STAT1 | TRAT1 |

FIG. 28B

| CCL7 | CISH3 | G6PD | IGHA1 | IL4R | MAP3K7 | STAT2 | TSLP |
|------|-------|------|-------|------|--------|-------|------|
| CCL8 | CKLF | GAPDH | IGHG1 | IL5 | MAPK1 | STAT3 | TUBB |
| CCR1 | CLEC2A | GATA3 | IGHG2 | IL6 | MCAM | SYK | TXK |
| CCR10 | CLEC4C | GBP1 | IGHG3 | IL6R | MDK | TAP1 | VCAM1 |
| CCR2 | CLECL1 | GBP2 | IGHG4 | IL7 | MERTK | TAP2 | VEGFC |
| CCR3 | CLTC | GHR | IGHM | IL8 | MFGE8 | TARP | XCL1 |
| CCR4 | CMKLR1 | GPR44 | IGKC | CXCR2 | MGLL | TBP | XCL2 |
| CCR5 | COLEC12 | GUSB | IGLL1 | INHBA | MIF | TBX21 | XCR1 |
| CCR6 | CREB1 | GZMK | IGSF4 | IRAK1 | MITF | TCL1A | ZAP70 |
| CCR7 | CRP | HIF1A | IGSF9 | IRAK2 | MMP9 | THBS1 | |

FIG. 28C

SEQUENCE LISTING

<160> NUMBER OF SEQ ID NOS: 80

<210> SEQ ID NO 1
<211> LENGTH: 656
<212> TYPE: DNA
<213> ORGANISM: Homo sapiens

<400> SEQUENCE: 1

```
gggaacacat ccaagcttaa gacggtgagg tcagcttcac attctcagga actctccttc     60
tttgggtctg gctgaagttg aggatctctt actctctagg ccacggaatt aacccgagca    120
ggcatggagg cctctgctct cacctcatca gcagtgacca gtgtggccaa agtggtcagg    180
gtggcctctg gctctgccgt agttttgccc ctggccagga ttgctacagt tgtgattgga    240
ggagttgtgg ctgtgcccat ggtgctcagt gccatgggct tcactgcggc gggaatcgcc    300
tcgtcctcca tagcagccaa gatgatgtcc gcggcggcca ttgccaatgg gggtggagtt    360
gcctcgggca gccttgtggc tactctgcag tcactgggag caactggact ctccggattg    420
accaagttca tcctgggctc cattgggtct gccattgcgg ctgtcattgc gaggttctac    480
tagctccctg cccctcgccc tgcagagaag agaaccatgc caggggagaa ggcacccagc    540
catcctgacc cagcgaggag ccaactatcc caaatatacc tggggtgaaa tataccaaat    600
tctgcatctc cagaggaaaa taagaaataa agatgaattg ttgcaactct tcaaaa        656
```

<210> SEQ ID NO 2
<211> LENGTH: 1501
<212> TYPE: DNA
<213> ORGANISM: Homo sapiens

<400> SEQUENCE: 2

```
agcgagtcct tcttttcctg actgcagctc ttttcatttt gccatccttt tccagctcca     60
tgatggttct gcaggtttct gcggcccccc ggacagtggc tctgacggcg ttactgatgg    120
tgctgctcac atctgtggtc cagggcaggg ccactccaga gaattacctt ttccagggac    180
ggcaggaatg ctacgcgttt aatgggacac agcgcttcct ggagagatac atctacaacc    240
gggaggagtt cgcgcgcttc gacagcgacg tgggggagtt ccgggcggtg acggagctgg    300 gcggcctgc tgcggagtac tggaacagcc agaaggacat cctggaggag aagcgggcag    360
tgccggacag gatgtgcaga cacaactacg agctgggcgg gccatgacc ctgcagcgcc    420 gagtccagcc tagggtgaat gtttcccct ccaagaaggg gcccttgcag caccacaacc    480
tgcttgtctg ccacgtgacg gatttctacc caggcagcat tcaagtccga tggttcctga    540
atggacagga ggaaacagct ggggtcgtgt ccaccaacct gatccgtaat ggagactgga    600
ccttccagat cctggtgatg ctggaaatga cccccagca gggagatgtc tacacctgcc    660
aagtggagca caccagcctg gatagtcctg tcaccgtgga gtggaaggca cagtctgatt    720
ctgcccggag taagacattg acgggagctg ggggcttcgt gctgggctc atcatctgtg    780
```

```
gagtgggcat cttcatgcac aggaggagca agaaagttca acgaggatct gcataaacag    840
ggttcctgag ctcactgaaa agactattgt gccttaggaa aagcatttgc tgtgtttcgt    900
tagcatctgg ctccaggaca gaccttcaac ttccaaattg gatactgctg ccaagaagtt    960
gctctgaagt cagtttctat cattctgctc tttgattcaa agcactgttt ctctcactgg   1020
gcctccaacc atgttccctt cttcttagca ccacaaataa tcaaaaccca acatgactgt   1080
ttgttttcct ttaaaaatat gcaccaaatc atctctcatc acttttctct gagggtttta   1140
gtagacagta ggagttaata aagaagttca ttttggttta acataggaa agaagagaac    1200
```
```
catgaaaatg gggatatgtt aactattgta taatggggcc tgttacacat gacactcttc   1260
tgaattgact gtatttcagt gagctgcccc caaatcaagt ttagtgccct catccattta   1320
tgtctcagac cactattctt aactattcaa tggtgagcag actgcaaatc tgcctgatag   1380
gacccatatt cccacagcac taattcaaca tataccttac tgagagcatg ttttatcatt   1440
accattaaga agttaaatga acatcagaat ttaaaatcat aaatataatc taatacactt   1500
t                                                                   1501

<210> SEQ ID NO 3
<211> LENGTH: 4157
<212> TYPE: DNA
<213> ORGANISM: Homo sapiens

<400> SEQUENCE: 3
agcggggcgg ggcgccagcg ctgccttttc tcctgccggg tagtttcgct ttcctgcgca     60
gagtctgcgg aggggctcgg ctgcaccggg gggatcgcgc ctggcagacc ccagaccgag    120
cagaggcgac ccagcgcgct cgggagaggc tgcaccgccg cgccccgcc tagcccttcc    180 ggatcctgcg cgcagaaaag tttcatttgc tgtatgccat cctcgagagc tgtctaggtt    240
aacgttcgca ctctgtgtat ataacctcga cagtcttggc acctaacgtg ctgtgcgtag    300
ctgctccttt ggttgaatcc ccaggccctt gttggggcac aaggtggcag gatgtctcag    360
tggtacgaac ttcagcagct tgactcaaaa ttcctggagc aggttcacca gctttatgat    420
gacagttttc ccatggaaat cagacagtac ctggcacagt ggttagaaaa gcaagactgg    480
gagcacgctg ccaatgatgt ttcatttgcc accatccgtt ttcatgacct cctgtcacag    540
ctggatgatc aatatagtcg cttttctttg gagaataact tcttgctaca gcataacata    600
aggaaaagca agcgtaatct tcaggataat tttcaggaag acccaatcca gatgtctatg    660
atcatttaca gctgtctgaa ggaagaaagg aaaattctgg aaaacgccca gagatttaat    720
caggctcagt cggggaatat tcagagcaca gtgatgttag acaaacagaa agagcttgac    780
agtaaagtca gaaatgtgaa ggacaaggtt atgtgtatag gcatgaaat caagagcctg    840
```
```
gaagatttac aagatgaata tgacttcaaa tgcaaaacct gcagaacag agaacacgag     900 accaatggtg tggcaaagag tgatcagaaa caagaacagc tgttactcaa gagatgtgtat    960 ttaatgcttg acaataagag aaaggaagta gttcacaaaa taatagagtt gctgaatgtc   1020
actgaactta cccagaatgc cctgattaat gatgaactag tggagtggaa gcggagacag   1080
cagagcgcct gtattggggg gccgcccaat gcttgcttgg atcagctgca gaactggttc   1140
actatagttg cggagagtct gcagcaagtt cggcagcagc ttaaaaagtt ggaggaattg   1200
gaacagaaat acacctacga acatgaccct atcacaaaaa acaaacaagt gttatgggac   1260
cgcaccttca gtcttttcca gcagctcatt cagagctcgt tgtggtgga aagacagccc   1320
```

```
tgcatgccaa cgcaccctca gaggccgctg gtcttgaaga caggggtcca gttcactgtg    1380
aagttgagac tgttggtgaa attgcaagag ctgaattata atttgaaagt caaagtctta    1440
tttgataaag atgtgaatga gagaaataca gtaaaaggat ttaggaagtt caacattttg    1500
ggcacgcaca caaaagtgat gaacatggag gagtccacca atggcagtct ggcggctgaa    1560
tttcggcacc tgcaattgaa agaacagaaa aatgctggca ccagaacgaa tgagggtcct    1620
ctcatcgtta ctgaagagct tcactcccct agttttgaaa cccaattgtg ccagcctggt    1680
ttggtaattg acctcgagac gacctctctg cccgttgtgg tgatctccaa cgtcagccag    1740
ctcccgagcg gttgggcctc catcctttgg tacaacatgc tggtggcgga acccaggaat    1800
ctgtccttct tcctgactcc accatgtgca cgatgggctc agctttcaga agtgctgagt    1860
tggcagtttt cttctgtcac caaaagaggt ctcaatgtgg accagctgaa catgttggga    1920
gagaagcttc ttggtcctaa cgccagcccc gatggtctca ttccgtggac gaggttttgt    1980
aaggaaaata taaatgataa aaattttccc ttctggcttt ggattgaaag catcctagaa    2040
ctcattaaaa aacacctgct ccctctctgg aatgatgggt gcatcatggg cttcatcagc    2100
aaggagcgag agcgtgccct gttgaaggac cagcagccgg ggaccttcct gctgcggttc    2160
agtgagagct cccgggaagg ggccatcaca ttcacatggg tggagcggtc ccagaacgga    2220
ggcgaacctg acttccatgc ggttgaaccc tacacgaaga agaactttc tgctgttact    2280 ttccctgaca tcattcgcaa ttacaaagtc atggctgctg agaatattcc tgagaatccc    2340
ctgaagtatc tgtatccaaa tattgacaaa gaccatgcct ttggaaagta ttactccagg    2400
ccaaaggaag caccagagcc aatggaactt gatggcccta aggaactggg atatatcaag    2460
actgagttga tttctgtgtc tgaagttcac ccttctagac ttcagaccac agacaacctg    2520
ctccccatgt ctcctgagga gtttgacgag gtgtctcgga gagtgggctc tgtagaattc    2580
gacagtatga tgaacacagt atagagcatg aatttttttc atcttctctg gcgacagttt    2640
tccttctcat ctgtgattcc ctcctgctac tctgttcctt cacatcctgt gtttctaggg    2700
aaatgaaaga aaggccagca aattcgctgc aacctgttga tagcaagtga attttttctct    2760 aactcagaaa catcagttac tctgaagggc atcatgcatc ttactgaagg taaaattgaa    2820
aggcattctc tgaagagtgg gtttcacaag tgaaaaacat ccagatacac ccaaagtatc    2880
aggacgagaa tgagggtcct ttgggaaagg agaagttaag caacatctag caaatgttat    2940
gcataaagtc agtgcccaac tgttataggt tgttggataa atcagtggtt atttagggaa    3000
ctgcttgacg taggaacggt aaatttctgt gggagaattc ttacatgttt tctttgcttt    3060
aagtgtaact ggcagttttc cattggttta cctgtgaaat agttcaaagc caagtttata    3120
tacaattata tcagtcctct ttcaaaggta gccatcatgg atctggtagg gggaaaatgt    3180
gtattttatt acatctttca cattggctat ttaaagacaa agacaaattc tgtttcttga    3240
gaagagaata ttagctttac tgtttgttat ggcttaatga cactagctaa tatcaataga    3300
aggatgtaca tttccaaatt cacaagttgt gtttgatatc caaagctgaa tacattctgc    3360
tttcatcttg gtcacataca attattttta cagttctccc aagggagtta ggctattcac    3420
aaccactcat tcaaaagttg aaattaacca tagatgtaga taaactcaga aatttaattc    3480
atgtttctta aatgggctac tttgtccttt ttgttattag ggtggtattt agtctattag    3540
ccacaaaatt gggaaaggag tagaaaaagc agtaactgac aacttgaata atacaccaga    3600
gataatatga gaatcagatc atttcaaaac tcatttccta tgtaactgca ttgagaactg    3660
catatgtttc gctgatatat gtgttttttca catttgcgaa tggttccatt ctctctcctg    3720
```

```
tacttttttcc agacactttt ttgagtggat gatgtttcgt gaagtatact gtattttttac    3780 cttttccctt ccttatcact gacacaaaaa gtagattaag agatgggttt gacaaggttc    3840
ttccctttta catactgctg tctatgtggc tgtatcttgt ttttccacta ctgctaccac    3900
aactatatta tcatgcaaat gctgtattct tctttggtgg agataaagat ttcttgagtt    3960
ttgttttaaa attaaagcta aagtatctgt attgcattaa atataatatg cacacagtgc    4020
tttccgtggc actgcataca atctgaggcc tcctctctca gttttatat agatggcgag     4080 aacctaagtt tcagttgatt ttacaattga aatgactaaa aaacaaagaa gacaacatta    4140
aaacaatatt gtttcta                                                    4157

<210> SEQ ID NO 4
<211> LENGTH: 5205
<212> TYPE: DNA
<213> ORGANISM: Homo sapiens

<400> SEQUENCE: 4
cttttcagct gggcagctct gggaacttgg attaggtgga gaggcagttg ggggcctcg       60 ttgttttgcg tcttagttcc gccctcctgt ccatcaggag aaggaaagga taaaccctgg     120
gccatgaggc taccctgct cctggttttt gcctctgtca ttccgggtgc tgttctccta     180
ctggacacca ggcaatttt aatctataat gaagatcaca agcgctgcgt ggatgcagtg     240
agtcccagtg ccgtccaaac cgcagcttgc aaccaggatg ccgaatcaca gaaattccga    300
tgggtgtccg aatctcagat tatgagtgtt gcatttaaat tatgcctggg agtgccatca    360
aaaacggact gggttgctat cactctctat gcctgtgact caaaaagtga atttcagaaa    420
tgggagtgca aaatgacac acttttgggg atcaaaggag aagatttatt ttttaactac     480
ggcaacagac aagaaaagaa tattatgctc tacaagggat cgggtttatg gagcaggtgg    540
aagatctatg gaaccacaga caatctgtgc tccagaggtt atgaagccat gtatacgcta    600
ctaggcaatg ccaatggagc aacctgtgca ttccgttca gtttgaaaaa caagtggtac    660
gcagattgca cgagtgctgg gcggtcggat ggatggctct ggtgcggaac cactactgac    720
tatgacacag acaagctatt tggatattgt ccattgaaat ttgagggcag tgaaagctta    780
tggaataaag acccgctgac cagcgtttcc taccagataa actccaaatc cgctttaacg    840
tggcaccagg cgaggaaaag ctgccaacaa cagaacgctg agctcctgag catcacagag    900
attcatgagc aaacatacct gacaggatta accagttcct tgacctcagg actctggatt    960
ggacttaaca gtctgagctt caacagcggt tggcagtgga gtgaccgcag tccttttccga   1020 tatttgaact ggttaccagg aagtccatca gctgaacctg gaaaaagctg tgtgtcacta   1080
aatcctggaa aaaatgctaa atgggaaaat ctggaatgtg ttcagaaact gggctatatt   1140
tgcaaaaagg gcaacaccac tttaaattct tttgttattc cctcagaaag tgatgtgcct   1200
actcactgtc ctagtcagtg gtggccgtat gccggtcact gttacaagat tcacagagat   1260
gagaaaaaaa tccagaggga tgctctgacc acctgcagga aggaaggcgg tgacctcaca   1320
agtatccaca ccatcgagga attggacttt attatctccc agctaggata tgagccaaat   1380
gacgaattgt ggatcggctt aaatgacatt aagattcaaa tgtactttga gtggagtgat   1440
gggacccctg taacgtttac caaatggctt cgtggagaac caagccatga aacaacaga   1500 caggaggatt gtgtggtgat gaaaggcaag gatgggtact gggcagatcg gggctgtgag   1560
tggcctcttg gctacatctg caagatgaaa tcacgaagcc aaggtccaga aatagtggaa   1620
```

-continued

```
gtcgaaaaag gctgcaggaa aggctggaaa aaacatcact tttactgcta tatgattgga   1680
catacgcttt caacatttgc agaagcaaac caaacctgta ataatgagaa tgcttattta   1740
acaactattg aagacagata tgaacaagcc ttcctgacta gtttcgttgg cttaaggcct   1800
gaaaaatatt tctggacagg actttcagat atacaaacca aagggacttt tcagtggacc   1860
atcgaggaag aggttcggtt cacccactgg aattcagata tgccagggcg aaagccaggg   1920
tgtgttgcca tgagaaccgg gattgcaggg ggcttatggg atgttttgaa atgtgatgaa   1980
aaggcaaaat ttgtgtgcaa gcactgggca gaaggagtaa cccacccacc gaagcccacg   2040
acgactcccg aacccaaatg tccggaggat tggggcgcca gcagtagaac aagcttgtgt   2100
ttcaagctgt atgcaaaagg aaaacatgag aagaaaacgt ggtttgaatc tcgagatttt   2160
tgtcgagctc tgggtggaga cttagctagc atcaataaca aagaggaaca gcaaacaata   2220
tggcgattaa taacagctag tggaagctac cacaaactgt tttggttggg attgacatat   2280
ggaagccctt cagaaggttt tacttggagt gatggttctc ctgtttcata tgaaaactgg   2340
gcttatggag aacctaataa ttatcaaaat gttgaatact gtggtgagct gaaaggtgac   2400
cctactatgt cttggaatga tattaattgt gaacacctta acaactggat ttgccagata   2460
caaaaaggac aaacaccaaa acctgagcca acaccagctc ctcaagacaa tccaccagtt   2520
actgaagatg ggtgggttat ttacaaagac taccagtatt atttcagcaa agagaaggaa   2580
accatggaca atgcgcgagc gttttgcaag aggaattttg gtgatcttgt ttctattcaa   2640
agtgaaagtg aaaagaagtt tctatggaaa tatgtaaaca gaaatgatgc acagtctgca   2700
tattttattg gtttattgat cagcttggat aaaaagtttg cttggatgga tggaagcaaa   2760
gtggattacg tgtcttgggc cacaggtgaa cccaattttg caaatgaaga tgaaaactgt   2820
gtgaccatgt attcaaattc agggttttgg aatgacatta actgtggcta tccaaacgcc   2880
ttcatttgcc agcgacataa cagtagtatc aatgctacca cagttatgcc taccatgccc   2940
tcggtcccat cagggtgcaa ggaaggttgg aatttctaca gcaacaagtg tttcaaaatc   3000
tttggattta tggaagaaga aagaaaaaat tggcaagagg cacgaaaagc ttgtataggc   3060
tttggaggga atctggtctc catacaaaat gaaaaagagc aagcatttct tacctatcac   3120
atgaaggact ccactttcag tgcctggact gggctgaatg atgtcaattc agaacacacg   3180
ttcctttgga cggatggacg aggagtccat tacacaaact gggggaaagg ttaccctggt   3240
ggaagaagaa gcagtctttc ttatgaagat gctgactgtg ttgttattat tggaggtgca   3300
tcaaatgaag caggaaaatg gatggatgat acctgcgaca gtaaacgagg ctacatatgc   3360
cagacacgat ccgacccttc cttgactaat cctccagcaa cgattcaaac agatggcttt   3420
gttaaatatg gcaaaagcag ctattcactc atgagacaaa aatttcaatg gcatgaagcg   3480
gagacatact gcaagcttca caattccctt atagccagca ttctggatcc ctacagtaat   3540
gcatttgcgt ggctgcagat ggaaacatct aatgaacgtg tgtggatcgc cctgaacagt   3600
aacttgactg ataatcaata cacttggact gataagtgga gggtgaggta cactaactgg   3660
gctgctgatg agcccaaatt gaaatcagca tgtgtttatc tggatcttga tggctactgg   3720
aagacagcac attgcaatga aagtttttac tttctctgta aaagatcaga tgaaatccct   3780
gctactgaac ccccacaact gcctggcaga tgcccggagt cagatcacac agcatggatt   3840
cctttccatg gtcactgtta ctatattgag tcctcatata caagaaactg gggccaagct   3900
tctctggaat gtcttcgaat gggttcctct ctggtttcca ttgaaagtgc tgcagaatcc   3960
agttttctgt catatcgggt tgagccactt aaaagtaaaa ccaatttttg gataggattg   4020
```

```
ttcagaaatg ttgaagggac gtggctgtgg ataaataaca gtccggtctc ctttgtcaac    4080
tggaacacag gagatccctc tggtgaacgg aatgattgtg tagctttaca tgcgtcttct    4140
gggttttgga gtaatattca ctgttcatcc tacaaaggat atatttgtaa aagaccaaaa    4200
attattgatg ctaaacctac tcatgaatta cttacaacaa aagctgacac aaggaagatg    4260
gaccctccta aaccgtcttc caacgtggcc ggagtagtca tcattgtgat cctcctgatt    4320
ttaacgggtg ctggccttgc cgcctatttc ttttataaga aaagacgtgt gcacctacct    4380
caagagggcg cctttgaaaa cactctgtat tttaacagtc agtcaagccc aggaactagt    4440
gatatgaaag atctcgtggg caatattgaa cagaatgaac actcggtcat ctagtacctc    4500
aatgcgattc tgagatattt gaatttcata aaattgtaac tgaaatttaa aattttagt     4560 tcaatgtgat tgttttcttt aaaatgagta ctgaattgta ctggtctgtc ctttttcct    4620 ttgcctaatt gaagaaataa ttgcttgttt tctagcctgg caagatattt tcataaaaga    4680
gggataacaa tgctgattac tacctttaa aatattttag ataaatgcac agcaccacag    4740
caccacatct aagcattagt gatgggtagc tgatgtcagc ttcatgtgga ttttaagcac    4800
tctagaaaca atgaagcttc ttggcatatt ttaaggagct cccaaaatgt gttacctatt    4860
aaattgtaac tcagcaagta aagaccatt tgaaaagtca ggtacaaatt tcctcaagtg    4920
gcataaaaat gtagtcagtt ttctctttta ccagttttta tttccactcc aattatttag    4980
aactttattt gtacatgtgc agaagaataa ggcagctgag aatcttgttt cccccaagag    5040
agttttacag gctgagtgtt gcaaatgtgt tctttgtcct gttatatgta tatcaggaat    5100
acaaggatgt gaaataaaac tgtaaatttg cataactgga tgtacttaga taatgtgaaa    5160
taaacattaa agacaaggtc tatttttaat aaaaaaaaaa aaaaa                    5205
```

<210> SEQ ID NO 5
<211> LENGTH: 987
<212> TYPE: DNA
<213> ORGANISM: Homo sapiens

<400> SEQUENCE: 5

```
aatataagtg gaggcgtcgc gctggcgggc attcctgaag ctgacagcat tcgggccgag     60
atgtctcgct ccgtggcctt agctgtgctc gcgctactct ctctttctgg cctggaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaagtggag cattcagact tgtctttcag caaggactgg    300
tctttctatc tcttgtacta cactgaattc accccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
```

```
gataaagtaa ggcatggttg tggttaatct ggtttatttt tgttccacaa gttaaataaa      960
tcataaaact tgatgtgtta tctctta                                          987

<210> SEQ ID NO 6
<211> LENGTH: 1145
<212> TYPE: DNA
<213> ORGANISM: Homo sapiens

<400> SEQUENCE: 6
attctctccc cagcttgctg agcccttttgc tcccctggcg actgcctgga cagtcagcaa      60
ggaattgtct cccagtgcat tttgccctcc tggctgccaa ctctggctgc taaagcggct     120
gccacctgct gcagtctaca cagcttcggg aagaggaaag gaacctcaga ccttccagat     180
cgcttcctct cgcaacaaac tatttgtcgc aggaataaag atggctgctg aaccagtaga     240
agacaattgc atcaactttg tggcaatgaa atttattgac aatacgcttt actttatagc     300
tgaagatgat gaaaacctgg aatcagatta ctttggcaag cttgaatcta aattatcagt     360
cataagaaat ttgaatgacc aagttctctt cattgaccaa ggaaatcggc tctatttga     420 agatatgact gattctgact gtagagataa tgcaccccgg accatattta ttataagtat     480
gtataaagat agccagccta aggtatggc tgtaactatc tctgtgaagt gtgagaaaat     540
ttcaactctc tcctgtgaga acaaaattat ttcctttaag gaatgaatc ctcctgataa     600 catcaaggat acaaaaagtg acatcatatt ctttcagaga agtgtcccag acatgataa     660 taagatgcaa tttgaatctt catcatacga aggatacttt ctagcttgtg aaaaagagag     720 agacctttt aaactcattt tgaaaaaga ggatgaattg ggggatagat ctataatgtt     780
cactgttcaa aacgaagact agctattaaa atttcatgcc gggcgcagtg gctcacgcct     840
gtaatcccag ccctttggga ggctgaggcg ggcagatcac cagaggtcag gtgttcaaga     900
ccagcctgac caacatggtg aaacctcatc tctactaaaa atacaaaaaa ttagctgagt     960
gtagtgacgc atgccctcaa tcccagctac tcaagaggct gaggcaggag aatcacttgc    1020
actccggagg tagaggttgt ggtgagccga gattgcacca ttgcgctcta gcctgggcaa    1080
caacagcaaa actccatctc aaaaaataaa ataaataaat aaacaaataa aaaattcata    1140
atgtg                                                                1145

<210> SEQ ID NO 7
<211> LENGTH: 2059
<212> TYPE: DNA
<213> ORGANISM: Homo sapiens

<400> SEQUENCE: 7
ccgcaggcgc tcggggttgg agccagcgac cgtcggtagc agcatggctc tcctctttct      60 cctaccccttt gtcatgcagg gtgtgagcag ggctgagatg ggcaccgcgg atctggggcc     120
gtcctcagtg cctacaccaa ctaatgttac aattgaatcc tataacatga acctatcgt      180 atattgggag taccagatca tgccacaggt ccctgttttt accgtagagg taaagaacta     240
tggtgttaag aattcagaat ggattgatgc ctgcatcaat atttctcatc attattgtaa     300
tatttctgat catgttggtg atccatcaaa ttctctttgg gtcagagtta agccagggt     360 tggacaaaaa gaatctgcct atgcaaagtc agaagaattt gctgtatgcc gagatggaaa     420
aattggacca cctaaactgg atatcagaaa ggaggagaag caaatcatga ttgacatatt     480
tcacccttca gttttttgtaa atggagacga gcaggaagtc gattatgatc ccgaaactac     540
ctgttacatt agggtgtaca atgtgtatgt gagaatgaac ggaagtgaga tccagtataa     600
```

| | |
|---|---|
| aatactcacg cagaaggaag atgattgtga cgagattcag tgccagttag cgattccagt | 660 |
| atcctcactg aattctcagt actgtgtttc agcagaagga gtcttacatg tgtggggtgt | 720 |
| tacaactgaa aagtcaaaag aagtttgtat taccattttc aatagcagta taaaaggttc | 780 |
| tctttggatt ccagttgttg ctgctttact actctttcta gtgcttagcc tggtattcat | 840 |
| ctgtttttat attaagaaaa ttaatccatt gaaggaaaaa agcataatat tacccaagtc | 900 |
| cttgatctct gtggtaagaa gtgctacttt agagacaaaa cctgaatcaa aatatgtatc | 960 |
| actcatcacg tcataccagc cattttcctt agaaaggag gtggtctgtg aagagccgtt | 1020 |
| gtctccagca acagttccag gcatgcatac cgaagacaat ccaggaaaag tggaacatac | 1080 |
| agaagaactt tctagtataa cagaagtggt gactactgaa gaaaatattc ctgacgtggt | 1140 |
| cccgggcagc catctgactc caatagagag agagagttct tcacctttaa gtagtaacca | 1200 |
| gtctgaacct ggcagcatcg ctttaaactc gtatcactcc agaaattgtt ctgagagtga | 1260 |
| tcactccaga aatggttttg atactgattc cagctgtctg gaatcacata gctccttatc | 1320 |
| tgactcagaa tttcccccaa ataataaagg tgaaataaaa acagaaggac aagagctcat | 1380 |
| aaccgtaata aaagccccca cctcctttgg ttatgataaa ccacatgtgc tagtggatct | 1440 |
| acttgtggat gatagcggta aagagtcctt gattggttat agaccaacag aagattccaa | 1500 |
| agaattttca tgagatcagc taagttgcac caactttgaa gtctgatttt cctggacagt | 1560 |
| tttctgcttt aatttcatga aaagattatg atctcagaaa ttgtatctta gttggtatca | 1620 |
| accaaatgga gtgacttagt gtacatgaaa gcgtaaagag gatgtgtggc attttcactt | 1680 |
| ttggcttgta aagtacagac ttttttttttt ttttaaacaa aaaaagcatt gtaacttatg | 1740 |
| aaccttaca tccagatagg ttaccagtaa cggaacatat ccagtactcc tggttcctag | 1800 |
| gtgagcaggt gatgccccag ggacctttgt agccacttca ctttttttct tttctctgcc | 1860 |
| ttggtatagc atatgtgttt tgtaagttta tgcatacagt aatttaagt aatttcagaa | 1920 |
| gaaattctcg aagcttttca aaattggact taaaatctaa ttcaaactaa tagaattaat | 1980 |
| ggaatatgta aatagaaacg tgtatatttt ttatgaaaca ttacagttag agatttttaa | 2040 |
| ataaagaatt ttaaaactc | 2059 |

<210> SEQ ID NO 8
<211> LENGTH: 1493
<212> TYPE: DNA
<213> ORGANISM: Homo sapiens

<400> SEQUENCE: 8

| | |
|---|---|
| ttcctttcat gttcagcatt tctactcctt ccaagaagag cagcaaagct gaagtagcag | 60 |
| caacagcacc agcagcaaca gcaaaaaaca aacatgagtg tgaagggcat ggctatagcc | 120 |
| ttggctgtga tattgtgtgc tacagttgtt caaggcttcc ccatgttcaa aagaggacgc | 180 |
| tgtctttgca taggccctgg ggtaaaagca gtgaaagtgg cagatattga aaagcctcc | 240 |
| ataatgtacc caagtaacaa ctgtgacaaa atagaagtga ttattaccct gaaagaaaat | 300 |
| aaaggacaac gatgcctaaa tcccaaatcg aagcaagcaa ggcttataat caaaaaagtt | 360 |
| gaaagaaaga atttttaaaa atatcaaaac atatgaagtc ctggaaaagg gcatctgaaa | 420 |
| aacctagaac aagtttaact gtgactactg aaatgacaag aattctacag taggaaactg | 480 |
| agactttct atggttttgt gactttcaac ttttgtacag ttatgtgaag gatgaaaggt | 540 |
| gggtgaaagg accaaaaaca gaaatacagt cttcctgaat gaatgacaat cagaattcca | 600 |

| | |
|---|---|
| ctgcccaaag gagtccagca attaaatgga tttctaggaa aagctacctt aagaaaggct | 660 |
| ggttaccatc ggagtttaca aagtgctttc acgttcttac ttgttgtatt atacattcat | 720 |
| gcatttctag gctagagaac cttctagatt tgatgcttac aactattctg ttgtgactat | 780 |
| gagaacattt ctgtctctag aagttatctg tctgtattga tctttatgct atattactat | 840 |
| ctgtggttac agtggagaca ttgacattat tactggagtc aagcccttat aagtcaaaag | 900 |
| catctatgtg tcgtaaagca ttcctcaaac atttttcat gcaaatacac acttctttcc | 960 |
| ccaaatatca tgtagcacat caatatgtag ggaaacattc ttatgcatca tttggtttgt | 1020 |
| tttataacca attcattaaa tgtaattcat aaaatgtact atgaaaaaaa ttatacgcta | 1080 |
| tgggatactg caacagtgc acatatttca taaccaaatt agcagcaccg gtcttaattt | 1140 |
| gatgttttc aacttttatt cattgagatg ttttgaagca attaggatat gtgtgtttac | 1200 |
| tgtactttt gttttgatcc gtttgtataa atgatagcaa tatcttggac acatttgaaa | 1260 |
| tacaaaatgt ttttgtctac caaagaaaaa tgttgaaaaa taagcaaatg tatacctagc | 1320 |
| aatcactttt acttttgta attctgtctc ttagaaaaat acataatcta atcaatttct | 1380 |
| ttgttcatgc ctatatactg taaaatttag gtatactcaa gactagttta aagaatcaaa | 1440 |
| gtcatttttt tctctaataa actaccacaa cctttctttt taaaaaaaa aaa | 1493 |

<210> SEQ ID NO 9
<211> LENGTH: 5679
<212> TYPE: DNA
<213> ORGANISM: Homo sapiens

<400> SEQUENCE: 9

| | |
|---|---|
| gcccgccctg gccgagcgta gctggcggac cagagccggt agcgaggttg ggagagacgg | 60 |
| agcggacctc agcgctgaag cagaagtccc cggagctgcg gtctcccgc cgcggctgag | 120 |
| ccatgcggct ccctgacctg agaccctgga cctccctgct gctggtggac gcggctttac | 180 |
| tgtggctgct tcagggccct ctggggactt tgcttcctca agggctgcca ggactatggc | 240 |
| tggaggggac cctgcggctg ggagggctgt gggggctgct aaagctaaga gggctgctgg | 300 |
| gatttgtggg gacactgctg ctcccgctct gtctggccac cccctgact gtctccctga | 360 |
| gagccctggt cgcgggggcc tcacgtgctc ccccagccag agtcgcttca gccccttgga | 420 |
| gctggctgct ggtggggtac ggggctgcgg ggctcagctg gtcactgtgg gctgttctga | 480 |
| gccctcctgg agcccaggag aaggagcagg accaggtgaa caacaaagtc ttgatgtgga | 540 |
| ggctgctgaa gctctccagg ccggacctgc ctctcctcgt tgccgccttc ttcttccttg | 600 |
| tccttgctgt ttgggtgag acattaatcc ctcactattc tggtcgtgtg attgacatcc | 660 |
| tgggaggtga ttttgacccc catgcctttg ccagtgccat cttcttcatg tgcctcttct | 720 |
| cctttggcag ctcactgtct gcaggctgcc gaggaggctg cttcacctac accatgtctc | 780 |
| gaatcaactt gcggatccgg gagcagcttt tctcctccct gctgcgccag gacctcggtt | 840 |
| tcttccagga gactaagaca ggggagctga actcacggct gagctcggat accaccctga | 900 |
| tgagtaactg gcttcctta aatgccaatg tgctcttgcg aagcctggtg aaagtggtgg | 960 |
| ggctgtatgg cttcatgctc agcatatcgc ctcgactcac cctcctttct ctgctgcaca | 1020 |
| tgcccttcac aatagcagcg gagaaggtgt acaacacccg ccatcaggaa gtgcttcggg | 1080 |
| agatccagga tgcagtggcc agggcggggc aggtggtgcg ggaagccgtt ggagggctgc | 1140 |
| agaccgttcg cagttttggg gccgagagc atgaagtctg tcgctataaa gaggcccttg | 1200 |
| aacaatgtcg gcagctgtat tggcggagag acctggaacg cgccttgtac ctgctcgtaa | 1260 |

```
ggagggtgct gcacttgggg gtgcagatgc tgatgctgag ctgtgggctg cagcagatgc    1320
aggatgggga gctcacccag ggcagcctgc tttcctttat gatctaccag agagcgtgg     1380 ggagctatgt gcagaccctg gtatacatat atggggatat gctcagcaac gtgggagctg    1440
cagagaaggt tttctcctac atggaccgac agccaaatct gccttcacct ggcacgcttg    1500
cccccaccac tctgcagggg gttgtgaaat tccaagacgt ctcctttgca tatcccaatc    1560
gccctgacag gcctgtgctc aaggggctga cgtttaccct acgtcctggt gaggtgacgg    1620
cgctggtggg acccaatggg tctgggaaga gcacagtggc tgccctgctg cagaatctgt    1680
accagcccac aggggacag gtgctgctgg atgaaaagcc catctcacag tatgaacact     1740
gctacctgca cagccaggtg gtttcagttg ggcaggagcc tgtgctgttc tccggttctg    1800
tgaggaacaa cattgcttat gggctgcaga gctgcgaaga tgataaggtg atggcggctg    1860
cccaggctgc ccacgcagat gacttcatcc aggaaatgga gcatggaata tacacagatg    1920
taggggagaa gggaagccag ctggctgcgg gacagaaaca acgtctggcc attgcccggg    1980
cccttgtacg agacccgcgg gtcctcatcc tggatgaggc tactagtgcc ctagatgtgc    2040
agtgcgagca ggccctgcag gactggaatt cccgtgggga tcgcacagtg ctggtgattg    2100
ctcacaggct gcaggcagtt cagcgcgccc accagatcct ggtgctccag gagggcaagc    2160
tgcagaagct tgcccagctc caggagggac aggacctcta ttcccgcctg gttcagcagc    2220
ggctgatgga ctgaggcccc aggatactg ggccctcttc tcaggggcgt ctccaggacc     2280
cagagctgtt cctgctttga gtttccctag agctgtgcgg ccagatagct gttcctgagt    2340
tgcaggcacg atggagattt ggacactgtg tgcttttggt ggggtagaga ggtggggtgg    2400
ggtggggtgg gggctgtctg tgtccaggaa acttaattcc ctggtgacta gagctttgcc    2460
tggtgatgag gagtatttg tggcataata catatatttt aaaatatttt ccttcttaca     2520
tgaactgtat acattcatat agaaaattta gacaatataa aaagtacaa agaagaaaag     2580 taaaagtacc cattgtttca cttcctggag ataaccatag ttgctatttt gctgcctgtc    2640
ccatcagtcg tttatctgtt gtttgagata gaaattaacc aaaaatgaca taaatattca    2700
tgagattgcc ttcctatatc cttccttgtt cctaccagtg tctgctattt tgaagaagct    2760
agggtctgga gggacagaga acagttccct gattaacagt attaatagcg acattggtaa    2820
cagctaccat ttatagagtt ttaatgggag taggagctat gctaagtgtt tttcatgtat    2880
tatcgttttt aatcattatc cccaaccta tgaggttggt tattatcccc attttacaga     2940
tgaggaaact gaagctcaaa gaggctcaat gactttccca aggtggtcgt agtggtggag    3000
ttggagtttg aacacaggcc tgaccctaga gtccacaccc tgacccaatc aattatattg    3060
catcttgggt ccataaaccc taatcctaaa tccatcaag aaaagctctg ctgctcttag     3120
ctctaaataa ttcagaatct attctcttct ctccagtccc gttgttatag tcttcactca    3180
tagacttaag atgatcccat caccagagag gtttctctac cattagcttc cctcttccgg    3240
ccattcttca caaagtcatt tttctaaatt ctgtgtcaca tacgatgatg gcatttctgg    3300 aaattcctc aggtgctctc aagccctgct gcagagatcc ttttcagagc acacactgtt     3360
ccagcccatc tgtctcaccc tctcctgttg tatccagctc cacgacaaac ttctgccttc    3420
cccaacacct ttgtgccttt gcatatggtg ttttcttgcc catttctgc tcgactcgcc     3480 cctgattttc aagttcaaga cttaactcag ggttcaggtc ttccaggagg ccttacttat    3540
gtcgtcagtc tggggaactc tccatgtgct tctatcactg tgcggttacc tctttcacag    3600
```

```
ccctttaaa gttctatctt ccctttccca ccttttttga ccttccacta gaccatgagc    3660
acctgggcgg aaagccatat atcttattaa gctttatatc tgctacctgg ccgagggcct    3720
aattcatagt ggagaataaa tagtcaattg aataaatgaa taaatatctc caccatcgta    3780
ctaatcttaa tcctccctgc ccactcccac cactgaaaat gcaacattgt acacatcact    3840
ggttgttggg agggacttac cttggaaagt tgctattcta ggaaagagaa accttcatat    3900
tcctggaaac agcaggtagt ttccagtgct ggcaatgaat tccccagaac tgctgttttg    3960
gattttttct tgcctggcag ctgttgggag cagggtgcag tgaggatggg gtgagagtgg    4020
gcagtttctt gtgcagattt gcctttcttt catcctgggg ctgacttgca gctccacacc    4080
catccatctc tcaaatttca cagagggtaa aataggcatt tggagagaaa gaactctggc    4140
ctgattcctt tctctcccac aaatgtcctt tattcataaa acaggaataa taattcctgt    4200
atctcccaac tacatggaag ctgcagccct cacagaagaa gatgatctga gaaattcttt    4260
gatttcctca gtacagttat acccatgcat cataatactt taagcctgga aggcatctta    4320
aaaataatgc aacagtcaaa cctaatttta cagagaaact gacatgaaat cacgcagcta    4380
atcatgataa agctgggtgg aaaacttatc ttgatgggca gtacaggaag atgcagtaga    4440
ccttaagatg tcctgaaagt ttcttatctc aggggaaact cccaggtagg ctttatgtca    4500
gggacacaga aaaatgctcc ctgaaagtca aaatattcgg gctagacaga caaattcctg    4560
taagtgtggt ttgtctggga accacagatg tcactaatcc tggtttgctc cagagttctt    4620
tttgttcact cctaccccc atcaccattt gattgatctc cttaccctgt aatttcccct    4680
tcttgtcgct tacctgcagt atcttttccca cccaggcatg ccttattctt tctaaaggaa    4740
agtatgaatg gagaggggaa agcttgggaa actgatagat ttccttggat gccaaaacac    4800
ctccatagcc tgtctgcccg gccctatgtg gaaacagcat tgagtttcaa gtcctttatg    4860
cctccaccca gggatagcca cttgtaatcc acatggcaat tgtgaaacaa gcaggaaatg    4920
cgtaattgtc agaattttgt ggggaaagga ctagggaata aggaaaacaa agatcttcct    4980
tgtgttttag agctgtcagc tagaggagca cctgcttgag tctgatgcca tctaatggtc    5040
ccagaagaaa ctgggttttg aacctagagt tccatggact cttaggaatt agactactac    5100
tactactaag cattcactgg tgcttactat gtgctattgc tgtgccaagt atctgaaacc    5160
tgtcttctta cctattttt caagataatt ctatgtggca ggtattacta tctcaattct    5220
aagagtgaga aaatggagtt ttagaaacat ttactaactt gcctgggtca catagctaag    5280
gaagaggtgg acttgcccag cttttgcataa aactcctcaa aagagttgcc tatactccct    5340
gactccactt atcttcctac tatcctcttt ttaaaatata ttatttattt atttaaataa    5400
gcaatatatg aatgtggttt gaaattcaaa agacacaaag aagtatacag aggaaagcct    5460
cactctcaat ccttctcaag gtttgctaat tcctcttgca taggcaatcc gttcttccag    5520
ctttgtgttt atctttccag agaagtttac tgtgtattaa gcaaatatgt atatctttat    5580
tcttgctcag tattttcgca aacagcagct gtctaagttc actgttctga actttatttt    5640
ttaaattaaa aatatatggc tatgtagtat tctatttta                          5679
```

```
<210> SEQ ID NO 10
<211> LENGTH: 2545
<212> TYPE: DNA
<213> ORGANISM: Homo sapiens

<400> SEQUENCE: 10
atccaataca ggagtgactt ggaactccat tctatcacta tgaagaaaag tggtgttctt      60
```

-continued

```
ttcctcttgg gcatcatctt gctggttctg attggagtgc aaggaacccc agtagtgaga      120
aagggtcgct gttcctgcat cagcaccaac caagggacta tccacctaca atccttgaaa      180
gaccttaaac aatttgcccc aagcccttcc tgcgagaaaa ttgaaatcat tgctacactg      240
aagaatggag ttcaaacatg tctaaaccca gattcagcag atgtgaagga actgattaaa      300
aagtgggaga acaggtcag ccaaaagaaa aagcaaaaga tgggaaaaa acatcaaaaa        360
aagaaagttc tgaaagttcg aaaatctcaa cgttctcgtc aaaagaagac tacataagag      420
accacttcac caataagtat tctgtgttaa aaatgttcta ttttaattat accgctatca      480
ttccaaagga ggatggcata taatacaaag gcttattaat ttgactagaa aatttaaaac      540
attactctga aattgtaact aaagttagaa agttgatttt aagaatccaa acgttaagaa      600
ttgttaaagg ctatgattgt ctttgttctt ctaccaccca ccagttgaat ttcatcatgc      660
ttaaggccat gattttagca atacccatgt ctacacagat gttcacccaa ccacatccca      720
ctcacaacag ctgcctggaa gagcagccct aggcttccac gtactgcagc tccagagag       780
tatctgaggc acatgtcagc aagtcctaag cctgttagca tgctggtgag ccaagcagtt      840
tgaaattgag ctggacctca ccaagctgct gtggccatca acctctgtat ttgaatcagc      900
ctacaggcct cacacacaat gtgtctgaga gattcatgct gattgttatt gggtatcacc      960
actggagatc accagtgtgt ggctttcaga gcctcctttc tggctttgga agccatgtga     1020
ttccatcttg cccgctcagg ctgaccactt tatttctttt tgttcccctt tgcttcattc     1080
aagtcagctc ttctccatcc taccacaatg cagtgccttt cttctctcca gtgcacctgt     1140
catatgctct gatttatctg agtcaactcc tttctcatct tgtccccaac accccacaga     1200
agtgctttct tctcccaatt catcctcact cagtccagct tagttcaagt cctgcctctt     1260
aaataaacct ttttggacac acaaattatc ttaaaactcc tgtttcactt ggttcagtac     1320
cacatgggtg aacactcaat ggttaactaa ttcttgggtg tttatcctat ctctccaacc     1380
agattgtcag ctccttgagg gcaagagcca cagtatattt ccctgtttct tccacagtgc     1440
ctaataatac tgtggaacta ggttttaata attttttaat tgatgttgtt atgggcagga     1500
tggcaaccag accattgtct cagagcaggt gctggctctt tcctggctac tccatgttgg     1560
ctagcctctg gtaacctctt acttattatc ttcaggacac tcactacagg gaccagggat     1620
gatgcaacat ccttgtcttt ttatgacagg atgtttgctc agcttctcca acaataagaa     1680
gcacgtggta aaacacttgc ggatattctg gactgttttt aaaaaatata cagtttaccg     1740
aaaatcatat aatcttacaa tgaaaaggac tttatagatc agccagtgac caaccttttc     1800
ccaaccatac aaaaattcct tttcccgaag gaaagggct ttctcaataa gcctcagctt      1860
tctaagatct aacaagatag ccaccgagat cctatcgaa actcatttta ggcaaatatg       1920
agttttattg tccgtttact tgtttcagag tttgtattgt gattatcaat taccacacca     1980
tctcccatga agaagggaa cggtgaagta ctaagcgcta gaggaagcag ccaagtcggt       2040
tagtggaagc atgattggtg cccagttagc ctctgcagga tgtggaaacc tccttccagg     2100
ggaggttcag tgaattgtgt aggagaggtt gtctgtggcc agaatttaaa cctatactca     2160
cttt cccaaa ttgaatcact gctcacactg ctgatgattt agagtgctgt ccggtggaga    2220
tcccacccga acgtcttatc taatcatgaa actccctagt tccttcatgt aacttccctg     2280
aaaaatctaa gtgtttcata aatttgagag tctgtgaccc acttaccttg catctcacag     2340
gtagacagta tataactaac aaccaaagac tacatattgt cactgacaca cacgttataa     2400
```

| | |
|---|---:|
| tcatttatca tatatataca tacatgcata cactctcaaa gcaaataatt tttcacttca | 2460 |
| aaacagtatt gacttgtata ccttgtaatt tgaaatattt tctttgttaa aatagaatgg | 2520 |
| tatcaataaa tagaccatta atcag | 2545 |

<210> SEQ ID NO 11
<211> LENGTH: 732
<212> TYPE: DNA
<213> ORGANISM: Homo sapiens

<400> SEQUENCE: 11

| | |
|---|---:|
| atcggttagc gccttgccat gattaatcca gagctgcggg atggcagagc tgatggcttc | 60 |
| atacatcgga tagttcccaa gttgatacaa aactggaaga ttggccttat gtgcttcctg | 120 |
| agtattatta ttactacagt ttgcattatt atgatagcca catggtccaa gcatgctaaa | 180 |
| cctgtggcat gttcagggga ctggcttgga gtgagagata agtgtttcta tttttctgat | 240 |
| gataccagaa attggacagc cagtaaaata ttttgtagtt tgcagaaagc agaacttgct | 300 |
| cagattgata cacaagaaga catggaattt ttgaagaggt acgcaggaac tgatatgcac | 360 |
| tggattggac taagcaggaa acaaggagat tcttggaaat ggacaaatgg caccacattc | 420 |
| aatggttggc catcaaactc caaatggtct tgcaactgga gcctccgaca atggcttctt | 480 |
| ctgctgggac cccttagata ggcctctgag ggagctctga ctgccgtttc cccaaaacaa | 540 |
| tgtcccctgt cagcaggaag cagttaaatc agtcttcatc cttatcctta atataacggc | 600 |
| agttagatgt acttctttag agggagtaaa tttatcaatt cagagcaatt catcctcctc | 660 |
| tttccatctt tgattcacag ttaataggct ataaattttg ataatgtaga ataaactaca | 720 |
| gaaaacttct tg | 732 |

<210> SEQ ID NO 12
<211> LENGTH: 1157
<212> TYPE: DNA
<213> ORGANISM: Homo sapiens

<400> SEQUENCE: 12

| | |
|---|---:|
| gctcacagtc atcaattata gaccccacaa catgcgccct gaagacagaa tgttccatat | 60 |
| cagagctgtg atcttgagag ccctctcctt ggctttcctg ctgagtctcc gaggagctgg | 120 |
| ggccatcaag gcggaccatg tgtcaactta tgccgcgttt gtacagacgc atagaccaac | 180 |
| aggggagttt atgtttgaat tgatgaaga tgagatgttc tatgtggatc tggacaagaa | 240 |
| ggagaccgtc tggcatctgg aggagttttgg ccaagccttt tcctttgagg ctcagggcgg | 300 |
| gctggctaac attgctatat tgaacaacaa cttgaatacc ttgatccagc gttccaacca | 360 |
| cactcaggcc accaacgatc ccctgaggt gaccgtgttt cccaaggagc tgtggagct | 420 |
| gggccagccc aacacccctca tctgccacat tgacaagttc ttcccaccag tgctcaacgt | 480 |
| cacgtggctg tgcaacgggg agctggtcac tgagggtgtc gctgagagcc tcttcctgcc | 540 |
| cagaacagat tacagcttcc acaagttcca ttacctgacc tttgtgccct cagcaggaga | 600 |
| cttctatgac tgcagggtgg agcactgggg cttggaccag ccgctcctca gcactggga | 660 |
| ggcccaagag ccaatccaga tgcctgagac aacggagact gtgctctgtg ccctgggcct | 720 |
| ggtgctgggc ctagtcggca tcatcgtggg caccgtcctc atcataaagt ctctgcgttc | 780 |
| tggccatgac ccccgggccc agggaccct gtgaaatact gtaaaggtga caaaatatct | 840 |
| gaacagaaga ggacttagga gagatctgaa ctccagctgc cctacaaact ccatctcagc | 900 |
| tttttcttctc acttcatgtg aaaactactc cagtggctga ctgaattgct gacccttcaa | 960 |

```
gctctgtcct tatccattac ctcaaagcag tcattcctta gtaaagtttc caacaaatag    1020
aaattaatga cactttggta gcactaatat ggagattatc ctttcattga gccttttatc    1080
ctctgttctc ctttgaagaa cccctcactg tcaccttccc gagaataccc taagaccaat    1140
aaatacttca gtatttc                                                   1157

<210> SEQ ID NO 13
<211> LENGTH: 566
<212> TYPE: DNA
<213> ORGANISM: Homo sapiens

<400> SEQUENCE: 13
actctccctg cacagctcag cgggacctca gccatgagac ttctcatcct ggccctcctt      60
ggcatctgct ctctcactgc atacattgtg aaggtgtag ggagtgaagt ctcacatagg     120
aggacctgtg tgagcctcac tacccagcga ctgccagtta gcagaatcaa gacctacacc    180
atcacggaag ctccttgag agcagtaatt tttattacca aacgtggcct aaaagtctgt     240
gctgatccac aagccacgtg ggtgagagac gtggtcagga gcatggacag gaaatccaac    300
accagaaata acatgatcca gaccaagcca acaggaaccc agcaatcgac caatacagct    360
gtgaccctga ctggctagta gtctctggca ccctgtccgt ctccagccag ccagctcatt    420
tcactttaca ccctcatgga ctgagattat actcacctttt atgaaagca ctgcatgaat    480 aaaattattc ctttgtattt ttacttttaa atgtcttctg tattcactta tatgttctaa    540
ttaataaatt atttattatt aagaaa                                         566

<210> SEQ ID NO 14
<211> LENGTH: 4100
<212> TYPE: DNA
<213> ORGANISM: Homo sapiens

<400> SEQUENCE: 14
gtacctcatg tgacaagttc caatttcttt tcaagtcaat tgaactgaaa tctccttgtt      60
gctttgaaat cttagaagag agcccactaa ttcaaggact cttactgtgg gagcaactgc     120
tggttctatc acaatgaaac ggctggtttg tgtgctcttg gtgtgctcct ctgcagtggc     180
acagttgcat aaagatccta ccctggatca ccactggcat ctctggaaga aaacctatgg    240
caaacaatac aaggaaaaga tgaagaagc agtacgacgt ctcatctggg aaaagaatct    300
aaagtttgtg atgcttcaca acctggagca ttcaatggga atgcactcat acgatctggg    360
catgaaccac ctgggagaca tgaccagtga agaagtgatg tctttgatga gttccctgag    420
agttcccagc cagtggcaga gaaatatcac atataagtca accctaatc ggatattgcc     480 tgattctgtg gactggagag agaaagggtg tgttactgaa gtgaaatatc aaggttcttg    540
tggtgcttgc tgggctttca gtgctgtggg ggccctggaa gcacagctga agctgaaaac    600
aggaaagctg gtgtctctca gtgcccagaa cctggtggat tgctcaactg aaaaatatgg    660
aaacaaaggc tgcaatggtg gcttcatgac aacggctttc cagtacatca ttgataacaa    720
gggcatcgac tcagacgctt cctatcccta caaagccatg gatcagaaat gtcaatatga    780
ctcaaaatat cgtgctgcca catgttcaaa gtacactgaa cttcccttatg cagagaaga    840 tgtcctgaaa gaagctgtgg ccaataaagg cccagtgtct gttggtgtag atgcgcgtca    900
tccttctttc ttcctctaca gaagtggtgt ctactatga ccatcctgta ctcagaatgt     960
gaatcatggt gtacttgtgg ttggctatgg tgatcttaat gggaaagaat actggctgt    1020
```

```
gaaaaacagc tggggccaca actttggtga agaaggatat attcggatgg caagaaataa    1080
aggaaatcat tgtgggattg ctagctttcc ctcttaccca gaaatctaga ggatctctcc    1140 ttttttataac aaatcaagaa atatgaagca ctttctctta acttaattttt tcctgctgta   1200 tccagaagaa ataattgtgt catgattaat gtgtatttac tgtactaatt agaaaatata    1260
gtttgaggcc gggcacggtg gctcacgcct gtaatcccag tacttgggag gccaaggcag    1320
gcatatcaac ttgaggccag gagttaaaga gcagcctggc taacatggtg aaacccatc     1380 tctactaaaa atacaaaaaa ttagccgagc acggtggtgc atgcctgtaa tcccagctac    1440
ttgggaggct gaggcacgag attccttgaa cccaagaggt tgaggctatg ttgagctgag    1500
atcacaccac tgtactccag cctggatgac agagtggaga ctctgtttca aaaaacaga     1560 aaagaaaata tagtttgatt cttcattttt ttaaatttgc aaatctcagg ataaagtttg    1620
ctaagtaaat tagtaatgta ctatagatat aactgtacaa aaattgttca acctaaaaca    1680
atctgtaatt gcttattgtt ttattgtata ctctttgtct ttttaagacc cctaatagcc    1740
ttttgtaact tgatggctta aaaatactta ataaatctgc catttcaaat ttctatcatt    1800
gccacatacc attcttattc ctaggcaact attaataatc tatcctgaga atattaattg    1860
tggtattctg gtgatggggt ttagcaactt tgatggaaga aaatattagg ctataaatgt    1920
cctaaggact cagattgtat ctttgtacag aagaggattc aaaacgccac gtgtagtggc    1980
tcatgcctgt aatcccaaca ctttgggagg ctgaagtagg aggatcgtct tgagcccagg    2040
agttcaagac cagcctggac aacatagtga gaccttgtct ccacaaaaat aaaaaagaaa    2100
ctatccagga gtggtggtgt gtgcctgtgg tccctgctat gcagatgtct aagacaggag    2160
gatcacaaga gcccaggagg ttgagaatgc agtgagcttg taattgcacc actgcactcc    2220
agcctgggtg acagagcaag accctgtctt aaaaaaagag gattcaacac atatttttat    2280
attatgttaa agtaaagaaa tgcataaaag acaagcactt tggaagaatt attttaatga    2340
tcaacaattt aatgtattag tccaaattat ttttacgtag tcatcaacaa tttgaccagg    2400
gcctttattt ggcaaataac tgagccaacc agaataaaat aaccaatact ccactgctca    2460 tattttttatc taattcagat ggatcttcct tacaactgct ctagattagt agatgcatct   2520
aagcaggcag caggaacttt aaatttttta agttcatgtc tatgacatga acaatgtgtg    2580
ggataatgtc attaatatat cctaaattaa cctaaacgta tttcactaac tctggctcct    2640
tctccataaa gcacatttta aggaacaaga attgctaaat ataaaacat aaataatacc     2700 ataatacatg gctatcatca aaagtgtata gaatattata gttaaaagt atttagttga     2760 ttacttttca gttttgtttt gttttttgag acggagtctc actctgttgc ccaggctgga    2820
gtgcagtggc accatctcag ttcactgcaa cttctgcctc ccgagttcaa gcgattctcc    2880
tgcctcagcc tcccgagtag ctggaattat aggcgtgcac caccacgccc agctaatttt    2940 tgtatttta gtaaagacag gttttgcca cattagccag gctggtctca aactcctgac      3000
ctcaggtgat ccacccaccc cagcctccca agtgctaag attacaggcg tgagccactg     3060
agcccagcct acttttcagt ttttaacata atttttgttt tatccacaac ttttcaagta    3120
ttgaaagtag aataaaaaca tgggttctta gtctttagct atctgttaaa gcctatgaat    3180
gccttcttaa aatcatgttt ttaaatgcat aaaatatata ggattacaaa ggaatctaat    3240
tatatcgaaa tacagttatt aaaatgttaa aagataagtt tgttatatat taatatgcat    3300
gcttctttat aaatgcatta aataagagtt aatagctatc ctaaatttga aatagtgata    3360
agcataatga aaatagatgc aaaaaactaa tgtgatatga aaatatctgg gttttctttt    3420
```

```
tgatgatgaa gtattgctaa tattaccgtg gtttatgaac tatgttcaga attgaagaaa    3480
atcctaactt tcagttagag gttagtgacg gggttcagga caccctacac aaaatacagc    3540
actttgacat attgaatatt ttaagctgaa ggcatttgag gaaattgcag aagcaggaag    3600
gtgactctga ccttctgcct gctgttctcc ccagaagcag ccataaaacc tgggaaggat    3660
tttctgacct tccccctgaag tagatcataa gactgtcatg taagaggtgc tctcctggca    3720
cccagagaaa aggagcatcc ttacctccaa aagcacaggg acacaaagag gaatctaaac    3780
aaacaggcct ctcagtttcc cccagtttat tacatttagc ttgttcacac tttgccctat    3840
gacatttcta catcactggc tgctcttcat caaacctact ataaaaaaca ttcaagttca    3900
actgtttctt tgggccttta tttccttatg gagcccctcg tgtcgtgtaa aacttatatt    3960
aaataaatgt gcatgctttt ctcttgctaa tctctctttt gttatagaga tctcagccct    4020
aaacctagga tggatagaag gaaacatatg ttctccccta cattagtaaa aataaaaatg    4080
gaatttttta cccatacaaa                                                4100

<210> SEQ ID NO 15
<211> LENGTH: 469
<212> TYPE: DNA
<213> ORGANISM: Homo sapiens

<400> SEQUENCE: 15
cccagataaa aggtaggggga ggaggagaga gagagaagga agagtctagg ctgagcaaca      60
tgaaggggcc cccaaccttc tgcagcctcc tgctgctgtc attgctcctg agcccagacc     120
ctacagcagc attcctactg ccacccagca ctgcctgctg tactcagctc taccgaaagc     180
cactctcaga caagctactg aggaaggtca tccaggtgga actgcaggag gctgacgggg     240
actgtcacct ccaggctttc gtgcttcacc tggctcaacg cagcatctgc atccacccc     300 agaaccccag cctgtcacag tggtttgagc accaagagag aaagctccat gggactctgc     360
ccaagctgaa ttttgggatg ctaaggaaaa tgggctgaag ccccaatag ccaaataata     420 aagcagcatt ggataataat ttctgaaaaa aaaaaaaaa aaaaaaaa                   469

<210> SEQ ID NO 16
<211> LENGTH: 2620
<212> TYPE: DNA
<213> ORGANISM: Homo sapiens

<400> SEQUENCE: 16
ctgaacgcga ggactgttaa ctgtttctgg caaacatgaa gtcaggcctc tggtatttct      60
ttctcttctg cttgcgcatt aaagttttaa caggagaaat caatggttct gccaattatg     120
agatgtttat atttcacaac ggaggtgtac aaattttatg caaatatcct gacattgtcc     180
agcaatttaa aatgcagttg ctgaaagggg ggcaaatact ctgcgatctc actaagacaa     240
aaggaagtgg aaacacagtg tccattaaga gtctgaaatt ctgccattct cagttatcca     300
acaacagtgt ctctttttttt ctatacaact tggaccattc tcatgccaac tattacttct     360
gcaacctatc aattttttgat cctcctcctt ttaaagtaac tcttacagga ggatatttgc     420
atatttatga atcacaactt tgttgccagc tgaagttctg gttacccata ggatgtgcag     480
cctttgttgt agtctgcatt ttgggatgca tacttatttg ttggcttaca aaaaagaagt     540
attcatccag tgtgcacgac cctaacggtg aatacatgtt catgagagca gtgaacacag     600
ccaaaaaatc tagactcaca gatgtgaccc tataatatgg aactctggca cccaggcatg     660
```

| | |
|---|---:|
| aagcacgttg gccagttttc ctcaacttga agtgcaagat tctcttattt ccgggaccac | 720 |
| ggagagtctg acttaactac atacatcttc tgctggtgtt ttgttcaatc tggaagaatg | 780 |
| actgtatcag tcaatgggga ttttaacaga ctgccttggt actgccgagt cctctcaaaa | 840 |
| caaacaccct cttgcaacca gctttggaga aagcccagct cctgtgtgct cactgggagt | 900 |
| ggaatccctg tctccacatc tgctcctagc agtgcatcag ccagtaaaac aaacacattt | 960 |
| acaagaaaaa tgttttaaag atgccagggg tactgaatct gcaaagcaaa tgagcagcca | 1020 |
| aggaccagca tctgtccgca tttcactatc atactacctc ttctttctgt agggatgaga | 1080 |
| attcctcttt taatcagtca agggagatgc ttcaaagctg gagctatttt atttctgaga | 1140 |
| tgttgatgtg aactgtacat tagtacatac tcagtactct ccttcaattg ctgaacccca | 1200 |
| gttgaccatt ttaccaagac tttagatgct tccttgtgcc ctcaattttc tttttaaaaa | 1260 |
| tacttctaca tgactgcttg acagcccaac agccactctc aatagagagc tatgtcttac | 1320 |
| attctttcct ctgctgctca atagttttat atatctatgc atacatatat acacacatat | 1380 |
| gtatataaaa ttcataatga atatatttgc ctatattctc cctacaagaa tattttttgct | 1440 |
| ccagaaagac atgttctttt ctcaaattca gttaaaatgg tttactttgt tcaagttagt | 1500 |
| ggtaggaaac attgcccgga attgaaagca aatttatttt attatcctat tttctaccat | 1560 |
| tatctatgtt ttcatggtgc tattaattac aagtttagtt cttttttgtag atcatattaa | 1620 |
| aattgcaaac aaaatcatct ttaatgggcc agcattctca tggggtagag cagaatattc | 1680 |
| atttagcctg aaagctgcag ttactatagg ttgctgtcag actatacccca tggtgcctct | 1740 |
| gggcttgaca ggtcaaaatg gtccccatca gcctggagca gccctccaga cctgggtgga | 1800 |
| attccagggt tgagagactc ccctgagcca gaggccacta ggtattcttg ctcccagagg | 1860 |
| ctgaagtcac cctgggaatc acagtggtct acctgcattc ataattccag gatctgtgaa | 1920 |
| gagcacatat gtgtcagggc acaattccct ctcataaaaa ccacacagcc tggaaattgg | 1980 |
| ccctggcccct tcaagatagc cttctttaga atatgatttg gctagaaaga ttcttaaata | 2040 |
| tgtggaatat gattattctt agctggaata ttttctctac ttcctgtctg catgcccaag | 2100 |
| gcttctgaag cagccaatgt cgatgcaaca acatttgtaa ctttaggtaa actgggatta | 2160 |
| tgttgtagtt taacattttg taactgtgtg cttatagttt acaagtgaga cccgatatgt | 2220 |
| cattatgcat acttatatta tcttaagcat gtgtaatgct ggatgtgtac agtacagtac | 2280 |
| tgaacttgta atttgaatct agtatggtgt tctgttttca gctgacttgg acaacctgac | 2340 |
| tggcttttgca caggtgttcc ctgagttgtt tgcaggtttc tgtgtgtggg gtggggtatg | 2400 |
| gggaggagaa ccttcatggt ggcccacctg gcctggttgt ccaagctgtg cctcgacaca | 2460 |
| tcctcatccc cagcatggga cacctcaaga tgaataataa ttcacaaaat ttctgtgaaa | 2520 |
| tcaaatccag ttttaagagg agccacttat caaagagatt ttaacagtag taagaaggca | 2580 |
| aagaataaac atttgatatt cagcaactga aaaaaaaaa | 2620 |

<210> SEQ ID NO 17
<211> LENGTH: 2678
<212> TYPE: DNA
<213> ORGANISM: Homo sapiens

<400> SEQUENCE: 17

| | |
|---|---:|
| agcgcggcag caagcgtggg aacgcgggcg gcgagacggc ggcaggacgg cggcaggatg | 60 |
| tgtgaccgga atggtggtcg gcggcttcga cagtggctga tcgagcagat tgacagtagc | 120 |
| atgtatccag gactgatttg ggagaatgag gagaagagca tgttccggat cccttggaaa | 180 |

```
cacgctggca agcaagatta taatcaggaa gtggatgcct ccattttaa ggcctgggca      240 gttttaaag ggaagtttaa agaaggggac aaagctgaac cagccacttg gaagacgagg      300
ttacgctgtg ctttgaataa gagcccagat tttgaggaag tgacggaccg gtcccaactg    360
gacatttccg agccatacaa agtttaccga attgttcctg aggaagagca aaaatgcaaa    420
ctaggcgtgg caactgctgg ctgcgtgaat gaagttacag agatggagtg cggtcgctct    480
gaaatcgacg agctgatcaa ggagccttct gtggacgatt acatgggat gatcaaaagg     540 agcccttccc cgccggaggc ctgtcggagt cagctccttc cagactggtg ggcgcagcag   600
cccagcacag gcgtgccgct ggtgacgggg tacaccacct acgacgcgca ccattcagca   660
ttctcccaga tggtgatcag cttctactat gggggcaagc tggtgggcca ggccaccacc   720
acctgccccg agggctgccg cctgtccctg agccagcctg gctgcccgg caccaagctg    780 tatgggcccg agggcctgga gctggtgcgc ttcccgccgg ccgacgccat ccccagcgag   840
cgacagaggc aggtgacgcg gaagctgttc gggcacctgg agcgcgggt gctgctgcac    900 agcagccggc agggcgtgtt cgtcaagcgg ctgtgccagg ccgcgtgtt ctgcagcggc     960 aacgccgtgg tgtgcaaagg caggcccaac aagctggagc gtgatgaggt ggtccaggtc   1020
ttcgacacca gccagttctt ccgagagctg cagcagttct ataacagcca gggccggctt   1080
cctgacggca gggtggtgct gtgctttggg gaagagtttc cggatatggc ccccttgcgc   1140
tccaaactca ttctcgtgca gattgagcag ctgtatgtcc ggcaactggc agaagaggct   1200
gggaagagct gtggagccgg ctctgtgatg caggcccccg aggagccgcc gccagaccag   1260
gtcttccgga tgtttccaga tatttgtgcc tcacaccaga gatcatttt cagagaaaac    1320 caacagatca ccgtctaagt gcgtcgcttg ggcgccccac cccgtctgcg tcctgcatcc    1380
atctccctgt tacagtggcc cgcatcatga ttaaagaatg tggatccctc tgtctggggt   1440
gggatgcctt actttgcact taatttaata agggcattct cggaggagta gacgtttaat   1500
acgaagtggc ggcatagccc tgccgagatg tcggtgatgg cctggatgct gtaaccacaa   1560
cctgtggcta aaaattttat tttctatcct ttacccgtca ttatcattag ttgctatgat   1620
tctttctgca ttttcggtta actatcattt ccaaagactt gtcattcagt aatattagca   1680
gatagctgct tcgataaagg aatttggagt ttaaaaatca acttgtgaaa caaggttgt    1740 ttttgtcttt atcgtttgtt agagttatag atttatgatt tcataggctt gattctatgt   1800
gaaatatctt tttacttta tgcatttaa taagatttaa aaatatttag attaaagccc     1860
cctttaatga gtacaagaaa aactcttggc ttgttagaag aaagtatatt ctttctagaa   1920
tttggtgcag gaatatgtgt tcatatccag gcaaacgggt gtgttttat cttcagacaa    1980 tgaaaccttc tcctctgggg ctttgttgcc aggaagatta gaactaaatt tatttttttc   2040
atttctgtca tgaaatcatt ccagatacct cttttcttct ttccaaatgg ttttcacatg   2100
tgtttgaaat atttgtactt cgaattgtcg gattttccat gtcctccttt ctcctttgtg   2160
cccagcctga gtcagcacca atcccgcatt cagaacctcc cagtgaaagg gcagccttca   2220
ttttgagaag gtggaaggtg ttagggtttg ggagacagct catccaatct cccaagtctc   2280
atggtggatt tgtgactgtg agagtttccg gtttaaaatc tgaaaagcca gatatgcctg   2340
tttccttttc ccagcaccat gcctgtggag gggacagtca gacccagagg tcctttacgt   2400
gtggatggag ttcacaggcg aatagaggag aggaccaggg gacgtggctt gtccctttg    2460 tccaacaaag cattatattt ttaagaatgg cagacctgtt tgctgaagtg ttcataagat   2520
```

```
aacaataggc ttgaatctcc aattcaaatg aatgtcaaag cacatatctt taatatgctg    2580
aatgaatatt tattttttgta tccattaaaa cagtatattg atctctttta ttctttatta    2640
aaataaaatg ctctttttta aaaaaaaaa aaaaaaa                              2678

<210> SEQ ID NO 18
<211> LENGTH: 733
<212> TYPE: DNA
<213> ORGANISM: Homo sapiens

<400> SEQUENCE: 18
aaacagcagg aaatagaaac ttaagagaaa tacacacttc tgagaaactg aaacgacagg      60
ggaaaggagg tctcactgag caccgtccca gcatccggac accacagcgg cccttcgctc    120
cacgcagaaa accacacttc tcaaaccttc actcaacact tccttcccca agccagaag      180 atgcacaagg aggaacatga ggtggctgtg ctggggcac cccccagcac catccttcca    240
aggtccaccg tgatcaacat ccacagcgag acctccgtgc cgaccatgt cgtctggtcc     300 ctgttcaaca ccctcttctt gaactggtgc tgtctgggct tcatagcatt cgcctactcc    360
gtgaagtcta gggacaggaa gatggttggc gacgtgaccg gggcccaggc ctatgcctcc    420
accgccaagt gcctgaacat ctgggccctg attctgggca tcctcatgac cattggattc    480
atcctgttac tggtattcgg ctctgtgaca gtctaccata ttatgttaca gataatacag    540
gaaaaacggg gttactagta gccgcccata gcctgcaacc tttgcactcc actgtgcaat    600
gctggccctg cacgctgggg ctgttgcccc tgccccttg gtcctgcccc tagatacagc     660
agtttatacc cacacacctg tctacagtgt cattcaataa agtgcacgtg cttgtgaaaa    720
aaaaaaaaaa aaa                                                        733

<210> SEQ ID NO 19
<211> LENGTH: 1701
<212> TYPE: DNA
<213> ORGANISM: Homo sapiens

<400> SEQUENCE: 19
cggactcaag aagttctcag gactcagagg ctgggatcat ggtagatgga accctccttt      60
tactcctctc ggaggccctg gcccttaccc agacctgggc gggctccac tccttgaagt     120 atttccacac ttccgtgtcc cggcccggcc gcggggagcc ccgcttcatc tctgtgggct    180
acgtggacga caccccagttc gtgcgcttcg acaacgacgc cgcgagtccg aggatggtgc    240
cgcgggcgcc gtggatggag caggaggggt cagagtattg ggaccgggag acacggagcg    300
ccagggacac cgcacagatt ttccgagtga acctgcggac gctgcgcggc tactacaatc    360
agagcgaggc cgggtctcac accctgcagt ggatgcatgg ctgcgagctg gggcccgacg    420
ggcgcttcct ccgcgggtat gaacagttcg cctacgacgg caaggattat ctcacccctga    480 atgaggacct gcgctcctgg accgcggtgg acacggcggc tcagatctcc gagcaaaagt    540
caaatgatgc ctctgaggcg gagcaccaga gagcctacct ggaagacaca tgcgtggagt    600
ggctccacaa atacctggag aaggggaagg agacgctgct tcacctggag ccccaaaga    660 cacacgtgac tcaccacccc atctctgacc atgaggccac cctgaggtgc tgggccctgg    720
gcttctaccc tgcggagatc acactgacct ggcagcagga tggggagggc catacccagg    780
acacggagct cgtggagacc aggcctgcag gggatggaac cttccagaag tgggcagctg    840
tggtggtgcc ttctgagag gagcagagat acacgtgcca tgtgcagcat gaggggctac    900
ccgagcccgt caccctgaga tggaagccgg cttcccagcc caccatcccc atcgtgggca    960
```

-continued

| | |
|---|---|
| tcattgctgg cctggttctc cttggatctg tggtctctgg agctgtggtt gctgctgtga | 1020 |
| tatggaggaa gaagagctca ggtggaaaag gagggagcta ctctaaggct gagtggagcg | 1080 |
| acagtgccca ggggtctgag tctcacagct tgtaaagcct gagacagctg ccttgtgtgc | 1140 |
| gactgagatg cacagctgcc ttgtgtgcga ctgagatgca ggatttcctc acgcctcccc | 1200 |
| tatgtgtctt aggggactct ggcttctctt tttgcaaggg cctctgaatc tgtctgtgtc | 1260 |
| cctgttagca caatgtgagg aggtagagaa acagtccacc tctgtgtcta ccatgacccc | 1320 |
| cttcctcaca ctgacctgtg ttccttccct gttctctttt ctattaaaaa taagaacctg | 1380 |
| ggcagagtgc ggcagctcat gcctgtaatc ccagcactta gggaggccga ggagggcaga | 1440 |
| tcacgaggtc aggagatcga accatcctg gctaacacgg tgaaaccccg tctctactaa | 1500 |
| aaaatacaaa aaattagctg gcgcagagg cacgggcctg tagtcccagc tactcaggag | 1560 |
| gcggaggcag gagaatggcg tcaacccggg aggcggaggt tgcagtgagc caggattgtg | 1620 |
| cgactgcact ccagcctggg tgacagggtg aaacgccatc tcaaaaaata aaaattgaaa | 1680 |
| aataaaaaaa aaaaaaaaa a | 1701 |

<210> SEQ ID NO 20
<211> LENGTH: 3070
<212> TYPE: DNA
<213> ORGANISM: Homo sapiens

<400> SEQUENCE: 20

| | |
|---|---|
| ggcgccgtct tgatactttc agaaagaatg cattccctgt aaaaaaaaaa aaaaaatact | 60 |
| gagagaggga gagagagaga gaagaagaga gagagacgga gggagagcga gacagagcga | 120 |
| gcaacgcaat ctgaccgagc aggtcgtacg ccgccgcctc ctcctcctct ctgctcttcg | 180 |
| ctacccaggt gaccccgagga gggactccgc ctccgagcgg ctgaggaccc cggtgcagag | 240 |
| gagcctggct cgcagaattg cagagtcgtc gccccttttt acaacctggt cccgttttat | 300 |
| tctgccgtac ccagttttg gattttgtc ttcccttct tctctttgct aaacgacccc | 360 |
| tccaagataa tttttaaaaa accttctcct ttgctcacct ttgcttccca gccttcccat | 420 |
| cccccaccg aaagcaaatc attcaacgac ccccgaccct ccgacggcag gagcccccg | 480 |
| acctcccagg cggaccgccc tccctcccg cgcgcgggtt ccgggcccgg cgagagggcg | 540 |
| cgagcacagc cgaggccatg gaggtgacgg cggaccagcc gcgctgggtg agccaccacc | 600 |
| accccgccgt gctcaacggg cagcacccgg acacgcacca cccgggcctc agccactcct | 660 |
| acatggacgc ggcgcagtac ccgctgccgg aggaggtgga tgtgctttt aacatcgacg | 720 |
| gtcaaggcaa ccacgtcccg ccctactacg gaaactcggt cagggccacg gtgcagaggt | 780 |
| accctccgac ccaccacggg agccaggtgt gccgccgcc tctgcttcat ggatccctac | 840 |
| cctggctgga cggcggcaaa gccctgggca gccaccacac cgcctccccc tggaatctca | 900 |
| gccccttctc caagacgtcc atccaccacg gctccccggg gccctctcc gtctaccccc | 960 |
| cggcctcgtc ctcctccttg tcgggggcc acgccagccc gcacctcttc accttcccgc | 1020 |
| ccacccccgcc gaaggacgtc tccccggacc catcgctgtc cacccaggc tcggccggct | 1080 |
| cggcccggca ggacgagaaa gagtgcctca gtaccaggt gcccctgccc gacagcatga | 1140 |
| agctggagtc gtcccactcc cgtggcagca tgaccgccct gggtggagcc tcctcgtcga | 1200 |
| cccaccaccc catcaccacc tacccgcccct acgtgcccga gtacagctcc ggactcttcc | 1260 |
| cccccagcag cctgctgggc ggctccccca ccggcttcgg atgcaagtcc aggcccaagg | 1320 |

| | |
|---|---|
| cccggtccag cacagaaggc agggagtgtg tgaactgtgg ggcaacctcg accccactgt | 1380 |
| ggcggcgaga tggcacggga cactacctgt gcaacgcctg cgggctctat cacaaaatga | 1440 |
| acggacagaa ccggcccctc attaagccca agcgaaggct gtctgcagcc aggagagcag | 1500 |
| ggacgtcctg tgcgaactgt cagaccacca caaccacact ctggaggagg aatgccaatg | 1560 |
| gggaccctgt ctgcaatgcc tgtgggctct actacaagct tcacaatatt aacagacccc | 1620 |
| tgactatgaa gaaggaaggc atccagacca gaaaccgaaa aatgtctagc aaatccaaaa | 1680 |
| agtgcaaaaa agtgcatgac tcactggagg acttccccaa gaacagctcg tttaacccgg | 1740 |
| ccgccctctc cagacacatg tcctccctga gccacatctc gcccttcagc cactccagcc | 1800 |
| acatgctgac cacgcccacg ccgatgcacc cgccatccag cctgtccttt ggaccacacc | 1860 |
| accccctccag catggtcacc gccatggtt agagccctgc tcgatgctca cagggccccc | 1920 |
| agcgagagtc cctgcagtcc ctttcgactt gcatttttgc aggagcagta tcatgaagcc | 1980 |
| taaacgcgat ggatatatgt ttttgaaggc agaaagcaaa attatgtttg ccactttgca | 2040 |
| aaggagctca ctgtggtgtc tgtgttccaa ccactgaatc tggaccccat ctgtgaataa | 2100 |
| gccattctga ctcatatccc ctatttaaca gggtctctag tgctgtgaaa aaaaaaatgc | 2160 |
| tgaacattgc atataactta tattgtaaga aatactgtac aatgacttta ttgcatctgg | 2220 |
| gtagctgtaa ggcatgaagg atgccaagaa gtttaaggaa tatgggagaa atagtgtgga | 2280 |
| aattaagaag aaactaggtc tgatattcaa atggacaaac tgccagtttt gtttcctttc | 2340 |
| actggccaca gttgtttgat gcattaaaag aaaataaaaa aagaaaaaa gagaaaagaa | 2400 |
| aaaaaagaa aaaagttgta ggcgaatcat ttgttcaaag ctgttggcct ctgcaaagga | 2460 |
| ataccagtt ctgggcaatc agtgttaccg ttcaccagtt gccgttgagg gtttcagaga | 2520 |
| gcctttttct aggcctacat gctttgtgaa caagtccctg taattgttgt ttgtatgtat | 2580 |
| aattcaaagc accaaaataa gaaaagatgt agatttattt catcatatta tacagaccga | 2640 |
| actgttgtat aaatttattt actgctagtc ttaagaactg ctttctttcg tttgtttgtt | 2700 |
| tcaatatttt ccttctctct caattttttgg ttgaataaac tagattacat tcagttggcc | 2760 |
| taaggtggtg gtgctcggag ggtttcttgt ttcttttcca ttttgttttt ggatgatatt | 2820 |
| tattaaatag cttctaagag tccggcggca tctgtcttgt ccctattcct gcagcctgtg | 2880 |
| ctgagggtag cagtgtatga gctaccagcg tgcatgtcag cgaccctggc ccgacaggcc | 2940 |
| acgtcctgca atcggcccgg ctgcctcttc gccctgtcgt gttctgtgtt agtgatcact | 3000 |
| gcctttaata cagtctgttg gaataatatt ataagcataa taataaagtg aaaatatttt | 3060 |
| aaaactacaa | 3070 |

<210> SEQ ID NO 21
<211> LENGTH: 2974
<212> TYPE: DNA
<213> ORGANISM: Homo sapiens

<400> SEQUENCE: 21

| | |
|---|---|
| gtgtgcgtga tggagaaaat tgggcaccag ggctgctccc gagattctca gatctgattt | 60 |
| ccacgcttgc taccaaaata gtctgggcag gccacttttg gaagtaggcg ttatctagtg | 120 |
| agcaggcggc cgctttcgat ttcgctttcc cctaaatggc tgagcttctc gccagcgcag | 180 |
| gatcagcctg ttcctgggac tttccgagag cccgccctc gttccctccc ccagccgcca | 240 |
| gtaggggagg actcggcggt acccggagct tcaggcccca ccggggcgcg gagagtccca | 300 |
| ggcccggccg ggaccgggac ggcgtccgag tgccaatggc tagctctagg tgtcccgctc | 360 |

```
cccgcgggtg ccgctgcctc cccggagctt ctctcgcatg gctggggaca gtactgctac    420
ttctcgccga ctgggtgctg ctccggaccg cgctgccccg catattctcc ctgctggtgc    480
ccaccgcgct gccactgctc cgggtctggg cggtgggcct gagccgctgg gccgtgctct    540
ggctgggggc ctgcgggtc ctcagggcaa cggttggctc caagagcgaa aacgcaggtg    600
cccagggctg gctggctgct ttgaagccat tagctgcggc actgggcttg ccctgccgg    660 gacttgcctt gttccgagag ctgatctcat ggggagcccc cgggtccgcg gatagcacca    720
ggctactgca ctggggaagt caccctaccg ccttcgttgt cagttatgca gcggcactgc    780
ccgcagcagc cctgtggcac aaactcggga gcctctgggt gcccggcggt cagggcggct    840
ctggaaaccc tgtgcgtcgg cttctaggct gcctgggctc ggagacgcgc cgcctctcgc    900
tgttcctggt cctggtggtc ctctcctctc ttggggagat ggccattcca ttctttacgg    960
gccgcctcac tgactggatt ctacaagatg gctcagccga taccttcact cgaaacttaa   1020
ctctcatgtc cattctcacc atagccagtg cagtgctgga gttcgtgggt gacgggatct   1080
ataacaacac catgggccac gtgcacagcc acttgcaggg agaggtgttt ggggctgtcc   1140
tgcgccagga gacggagttt ttccaacaga accagacagg taacatcatg tctcgggtaa   1200
cagaggacac gtccaccctg agtgattctc tgagtgagaa tctgagctta tttctgtggt   1260
acctggtgcg aggcctatgt ctcttgggga tcatgctctg gggatcagtg tccctcacca   1320
tggtcaccct gatcaccctg cctctgcttt tccttctgcc caagaaggtg ggaaaatggt   1380
accagttgct ggaagtgcag gtgcgggaat ctctggcaaa gtccagccag gtggccattg   1440
aggctctgtc ggccatgcct acagttcgaa gctttgccaa cgaggagggc gaagcccaga   1500
agtttaggga aaagctgcaa gaaataaaga cactcaacca aaggaggct gtggcctatg   1560 cagtcaactc ctggaccact agtatttcag gtatgctgct gaaagtggga atcctctaca   1620
ttggtgggca gctggtgacc agtggggctg taagcagtgg gaaccttgtc acatttgttc   1680
tctaccagat gcagttcacc caggctgtgg aggtactgct ctccatctac cccagagtac   1740
agaaggctgt gggctcctca gagaaaatat ttgagtacct ggaccgcacc cctcgctgcc   1800
cacccagtgg tctgttgact cccttacact tggagggcct tgtccagttc caagatgtct   1860
cctttgccta cccaaaccgc ccagatgtct tagtgctaca ggggctgaca ttcaccctac   1920
gccctggcga ggtgacggcg ctggtgggac ccaatgggtc tgggaagagc acagtggctg   1980
ccctgctgca gaatctgtac cagcccaccg ggggacagct gctgttggat gggaagcccc   2040
ttccccaata tgagcaccgc tacctgcaca ggcaggtggc tgcagtggga caagagccac   2100
aggtatttgg aagaagtctt caagaaaata ttgcctatgg cctgacccag aagccaacta   2160
tggaggaaat cacagctgct gcagtaaagt ctggggccca tagtttcatc tctggactcc   2220
ctcagggcta tgacacagag gtagacgagg ctgggagcca gctgtcaggg ggtcagcgac   2280
aggcagtggc gttggcccga gcattgatcc ggaaaccgtg tgtacttatc ctggatgatg   2340
ccaccagtgc cctggatgca aacagccagt acaggtgga gcagctcctg tacgaaagcc   2400
ctgagcggta ctcccgctca gtgcttctca tcacccagca cctcagcctg gtggagcagg   2460
ctgaccacat cctctttctg gaaggaggcg ctatccggga gggggaacc caccagcagc   2520 tcatggagaa aaggggtgc tactgggcca tggtgcaggc tcctgcagat gctccagaat   2580
gaaagccttc tcagacctgc gcactccatc tccctcccct ttcttctctc tgtggtggag   2640
aaccacagct gcagagtagg cagctgcctc caggatgagt tacttgaaat ttgccttgag   2700
```

| | |
|---|---:|
| tgtgttacct cctttccaag ctcctcgtga taatgcagac ttcctggagt acaaacacag | 2760 |
| gatttgtaat tccttactgt aacggagttt agagccaggg ctgatgcttt ggtgtggcca | 2820 |
| gcactctgaa actgagaaat gttcagaatg tacggaaaga tgatcagcta ttttcaacat | 2880 |
| aactgaaggc atatgctggc ccataaacac cctgtaggtt cttgatattt ataataaaat | 2940 |
| tggtgttttg taaaaaaaaa aaaaaaaaa aaaa | 2974 |

```
<210> SEQ ID NO 22
<211> LENGTH: 1579
<212> TYPE: DNA
<213> ORGANISM: Homo sapiens

<400> SEQUENCE: 22
```

| | |
|---|---:|
| accaacccct aagatgagct ttccatgtaa atttgtagcc agcttccttc tgattttcaa | 60 |
| tgtttcttcc aaaggtgcag tctccaaaga gattacgaat gccttggaaa cctggggtgc | 120 |
| cttgggtcag gacatcaact tggacattcc tagttttcaa atgagtgatg atattgacga | 180 |
| tataaaatgg gaaaaaactt cagacaagaa aaagattgca caattcagaa aagagaaaga | 240 |
| gactttcaag gaaaaagata catataagct atttaaaaat ggaactctga aaattaagca | 300 |
| tctgaagacc gatgatcagg atatctacaa ggtatcaata tatgatacaa aaggaaaaaa | 360 |
| tgtgttggaa aaaatatttg atttgaagat tcaagagagg gtctcaaaac caaagatctc | 420 |
| ctggacttgt atcaacacaa ccctgacctg tgaggtaatg aatggaactg accccgaatt | 480 |
| aaacctgtat caagatggga acatctaaa actttctcag agggtcatca cacacaagtg | 540 |
| gaccaccagc ctgagtgcaa aattcaagtg cacagcaggg aacaaagtca gcaaggaatc | 600 |
| cagtgtcgag cctgtcagct gtccagagaa aggtctggac atctatctca tcattggcat | 660 |
| atgtggagga ggcagcctct tgatggtctt tgtggcactg ctcgttttct atatcaccaa | 720 |
| aaggaaaaaa cagaggagtc ggagaaatga tgaggagctg agacaagag cccacagagt | 780 |
| agctactgaa gaaaggggcc ggaagcccca acaaattcca gcttcaaccc ctcagaatcc | 840 |
| agcaacttcc caacatcctc ctccaccacc tggtcatcgt tcccaggcac ctagtcatcg | 900 |
| tcccccgcct cctggacacc gtgttcagca ccagcctcag aagaggcctc ctgctccgtc | 960 |
| gggcacacaa gttcaccagc agaaaggccc gcccctcccc agacctcgag ttcagccaaa | 1020 |
| acctccccat ggggcagcag aaaactcatt gtccccttcc tctaattaaa aaagatagaa | 1080 |
| actgtctttt tcaataaaaa gcactgtgga tttctgccct cctgatgtgc atatccgtac | 1140 |
| ttccatgagg tgttttctgt gtgcagaaca ttgtcacctc ctgaggctgt gggccacagc | 1200 |
| cacctctgca tcttcgaact cagccatgtg gtcaacatct ggagtttttg gtctcctcag | 1260 |
| agagctccat cacaccagta aggagaagca atataagtgt gattgcaaga atggtagagg | 1320 |
| accgagcaca gaaatcttag agatttcttg tcccctctca ggtcatgtgt agatgcgata | 1380 |
| aatcaagtga ttggtgtgcc tgggtctcac tacaagcagc ctatctgctt aagagactct | 1440 |
| ggagtttctt atgtgccctg gtggacactt gcccaccatc ctgtgagtaa aagtgaaata | 1500 |
| aaagctttga ctagaaaaaa aaaaaaaaa aaaaaaaaa aaaaaaaaa aaaaaaaaa | 1560 |
| aaaaaaaaaa aaaaaaaaa | 1579 |

```
<210> SEQ ID NO 23
<211> LENGTH: 1263
<212> TYPE: DNA
<213> ORGANISM: Homo sapiens

<400> SEQUENCE: 23
```

```
ttcctttctc tctcagctct ccgtctctct ttctctctca gcctctttct ttctccctgt    60
ctcccccact gtcagcacct cttctgtgtg gtgagtggac cgcttacccc actaggtgaa   120
gatgtcagcc caggagagct gcctcagcct catcaagtac ttcctcttcg ttttcaacct   180
cttcttcttc gtcctcggca gcctgatctt ctgcttcggc atctggatcc tcattgacaa   240
gaccagcttc gtgtcctttg tgggcttggc cttcgtgcct ctgcagatct ggtccaaagt   300
cctggccatc tcaggaatct tcaccatggg catcgccctc tgggttgtg tggggccct    360
caaggagctc cgctgcctcc tgggcctgta ttttgggatg ctgctgctcc tgtttgccac   420
acagatcacc ctgggaatcc tcatctccac tcagcgggcc cagctggagc gaagcttgcg   480
ggacgtcgta gagaaaacca tccaaaagta cggcaccaac cccgaggaga ccgcggccga   540
ggagagctgg gactatgtgc agttccagct gcgctgctgc ggctggcact acccgcagga   600
ctggttccaa gtcctcatcc tgagaggtaa cgggtcggag gcgcaccgcg tgccctgctc   660
ctgctacaac ttgtcggcga ccaacgactc cacaatccta gataaggtga tcttgcccca   720
gctcagcagg cttggacacc tggcgcggtc cagacacagt gcagacatct gcgctgtccc   780
tgcagagagc cacatctacc gcgagggctg cgcgcagggc ctccagaagt ggctgcacaa   840
caaccttatt tccatagtgg gcatttgcct gggcgtcggc ctactcgagc tcgggttcat   900
gacgctctcg atattcctgt gcagaaacct ggaccacgtc tacaaccggc tgctcgata   960
ccgttaggcc ccgccctccc caaagtcccg ccccgccccc gtcacgtgcg ctgggcactt  1020
ccctgctgcc tgtaaatatt tgtttaatcc ccagttcgcc tggagccctc cgccttcaca  1080
ttcccctggg gacccacgtg gctgcgtgcc cctgctgctg tcacctctcc cacgggacct  1140
ggggctttcg tccacagctt cctgtcccca tctgtcggcc taccaccacc cacaagatta  1200
tttttcaccc aaacctcaaa taaatcccct gcgttttggg taaaaaaaaa aaaaaaaaa   1260
aaa                                                                1263
```

<210> SEQ ID NO 24
<211> LENGTH: 1606
<212> TYPE: DNA
<213> ORGANISM: Homo sapiens

<400> SEQUENCE: 24

```
actaagtatc tccactttca attctagatc aggaactgag gacatatcta aattttctag    60
ttttatagaa ggcttttatc cacaagaatc aagatcttcc ctctctgagc aggaatcctt   120
tgtgcattga agactttaga ttcctctctg cggtagacgt gcacttataa gtatttgatg   180
gggtggattc gtggtcggag gtctcgacac agctgggaga tgagtgaatt tcataattat   240
aacttggatc tgaagaagag tgattttca acacgatggc aaaagcaaag atgtccagta   300
gtcaaaagca aatgtagaga aaatgcatct ccatttttt tctgctgctt catcgctgta   360
gccatgggaa tccgtttcat tattatggta acaatatgga gtgctgtatt cctaaactca   420
ttattcaacc aagaagttca aattcccttg accgaaagtt actgtggccc atgtcctaaa   480
aactggatat gttacaaaaa taactgctac caattttttg atgagagtaa aaactggtat   540
gagagccagg cttcttgtat gtctcaaaat gccagccttc tgaaagtata cagcaaagag   600
gaccaggatt tacttaaact ggtgaagtca tatcattgga tgggactagt acacattcca   660
acaaatggat cttggcagtg ggaagatggc tccattctct cacccaacct actaacaata   720
attgaaatgc agaagggaga ctgtgcactc tatgcctcga gctttaaagg ctatatagaa   780
```

| | |
|---|---|
| aactgttcaa ctccaaatac gtacatctgc atgcaaagga ctgtgtaaag atgatcaacc | 840 |
| atctcaataa aagccaggaa cagagaagag attacaccag cggtaacact gccaactgag | 900 |
| actaaaggaa acaaacaaaa acaggacaaa atgaccaaag actgtcagat ttcttagact | 960 |
| ccacaggacc aaaccataga acaatttcac tgcaaacatg catgattctc aagacaaaa | 1020 |
| gaagagagat cctaaaggca attcagatat ccccaaggct gcctctccca ccacaagccc | 1080 |
| agagtggatg ggctggggga ggggtgctgt tttaatttct aaaggtagga ccaacaccca | 1140 |
| ggggatcagt gaaggaagag aaggccagca gatcactgag agtgcaaccc caccctccac | 1200 |
| aggaaattgc ctcatgggca gggccacagc agagagacac agcatgggca gtgccttccc | 1260 |
| tgcctgtggg ggtcatgctg ccacttttaa tgggtcctcc acccaacggg gtcagggagg | 1320 |
| tggtgctgcc ccagtgggcc atgattatct taaaggcatt attctccagc cttaagtaag | 1380 |
| atcttaggac gtttcctttg ctatgatttg tacttgcttg agtcccatga ctgtttctct | 1440 |
| tcctctcttt cttccttttg gaatagtaat atccatccta tgtttgtccc actattgtat | 1500 |
| tttggaagca cataacttgt ttggtttcac aggttcacag ttaagaagga attttgcctc | 1560 |
| tgaataaata gaatcttgag tctcatgcaa aaaaaaaaa aaaaaa | 1606 |

<210> SEQ ID NO 25
<211> LENGTH: 3151
<212> TYPE: DNA
<213> ORGANISM: Homo sapiens

<400> SEQUENCE: 25

| | |
|---|---|
| cccggccaga caccctcacc tgcggtgccc agctgcccag gctgaggcaa gagaaggcca | 60 |
| gaaaccatgc ccatggggtc tctgcaaccg ctggccacct tgtacctgct ggggatgctg | 120 |
| gtcgcttcct gcctcggacg gctcagctgg tatgacccag atttccaggc aaggctcacc | 180 |
| cgttccaact cgaagtgcca gggccagctg gaggtctacc tcaaggacgg atggcacatg | 240 |
| gtttgcagcc agagctgggg ccggagctcc aagcagtggg aggacccag tcaagcgtca | 300 |
| aaagtctgcc agcggctgaa ctgtggggtg cccttaagcc ttggccccctt ccttgtcacc | 360 |
| tacacacctc agagctcaat catctgctac ggacaactgg gctccttctc caactgcagc | 420 |
| cacagcagaa atgacatgtg tcactctctg ggcctgacct gcttagaacc ccagaagaca | 480 |
| acacctccaa cgacaaggcc cccgcccacc acaactccag agcccacagc tcctcccagg | 540 |
| ctgcagctgg tggcacagtc tggcggccag cactgtgccg gcgtggtgga gttctacagc | 600 |
| ggcagcctgg ggggtaccat cagctatgag gcccaggaca agacccagga cctggagaac | 660 |
| ttcctctgca caacctcca gtgtggctcc ttcttgaagc atctgccaga gactgaggca | 720 |
| ggcagagccc aagacccagg ggagccacgg gaacaccagc ccttgccaat ccaatggaag | 780 |
| atccagaact caagctgtac ctccctggag cattgcttca ggaaaatcaa gccccagaaa | 840 |
| agtggccgag ttcttgccct cctttgctca ggttccagc ccaaggtgca gagccgtctg | 900 |
| gtgggggca gcagcatctg tgaaggcacc gtggaggtgc gccagggggc tcagtgggca | 960 |
| gccctgtgtg acagctcttc agccaggagc tcgctgcggt gggaggaggt gtgccgggag | 1020 |
| cagcagtgtg gcagcgtcaa ctcctatcga gtgctggacg ctggtgaccc aacatcccgg | 1080 |
| gggctcttct gtccccatca gaagctgtcc cagtgccacg aactttggga gagaaattcc | 1140 |
| tactgcaaga aggtgttgt cacatgccag gatccaaacc ccgcaggcct ggccgcaggc | 1200 |
| acggtggcaa gcatcatcct ggccctggtg ctcctggtgg tgctgctggt cgtgtgcggc | 1260 |
| ccccttgcct acaagaagct agtgaagaaa ttccgccaga agaagcagcg ccagtggatt | 1320 |

-continued

```
ggcccaacgg gaatgaacca aaacatgtct ttccatcgca accacacggc aacgtccga    1380 tcccatgctg agaaccccac agcctcccac gtggataacg aatacagcca acctcccagg    1440
aactcccgcc tgtcagctta tccagctctg aagggggttc tgcatcgctc ctccatgcag    1500
cctgacaact cctccgacag tgactatgat ctgcatgggg ctcagaggct gtaaagaact    1560
gggatccatg agcaaaaagc cgagagccag acctgtttgt cctgagaaaa ctgtccgctc    1620
ttcacttgaa atcatgtccc tatttctacc ccggccagaa catggacaga ggccagaagc    1680
cttccggaca ggcgctgctg ccccgagtgg caggccagct cacactctgc tgcacaacag    1740
ctcggccgcc cctccacttg tggaagctgt ggtgggcaga gccccaaaac aagcagcctt    1800
ccaactagag actcggggt gtctgaaggg ggccccttt ccctgcccgc tggggagcgg    1860
cgtctcagtg aaatcggctt tctcctcaga ctctgtccct ggtaaggagt gacaaggaag    1920
ctcacagctg ggcgagtgca ttttgaatag tttttttgtaa gtagtgcttt tcctccttcc    1980
tgacaaatcg agcgctttgg cctcttctgt gcagcatcca cccctgcgga tccctctggg    2040
gaggacagga aggggactcc cggagacctc tgcagccgtg gtggtcagag gctgctcatc    2100
tgagcacaaa gacagctctg cacattcacc gcagctgcca gccaggggtc tgggtgggca    2160
ccaccctgac ccacagcgtc accccactcc ctctgtctta tgactcccct ccccaacccc    2220
ctcatctaaa gacaccttcc tttccactgg ctgtcaagcc cacagggcac cagtgccacc    2280
cagggccctg cacaaagggg cgcctagtaa accttaacca acttggtttt ttgcttcacc    2340
cagcaattaa aagtcccaag ctgaggtagt ttcagtccat cacagttcat cttctaaccc    2400
aagagtcaga gatgggctg gtcatgttcc tttggtttga ataactccct tgacgaaaac    2460
agactcctct agtacttgga gatcttggac gtacacctaa tcccatgggg cctcggcttc    2520
cttaactgca agtgagaaga ggaggtctac ccaggagcct cgggtctgat caaggagag    2580 gccaggcgca gctcactgcg gcctctaaga aggtgaagca acatgggaac acatcctaag    2640
acacatccta agacaggtcc tttctccacg ccatttgatg ctgtatctcc tgggagcaca    2700
ggcatcaatg gtccaagccg cataataagt ctggaagagc aaaagggagt tactaggata    2760
tggggtgggc tgctcccaga atctgctcag ctttctgccc ccaccaacac cctccaacca    2820
ggccttgcct tctgagagcc cccgtggcca agcccaggtc acagatcttc ccccgaccat    2880
gctgggaatc cagaaacagg accccattt gtcttcccat atctggtgga ggtgagggg    2940 ctcctcaaaa gggaactgag aggctgctct tagggagggc aaaggttcgg gggcagccag    3000
tgtctcccat cagtgccttt tttaataaaa gctctttcat ctatagtttg gccaccatac    3060
agtggcctca agcaaccat ggcctactta aaaaccaaac caaaaataaa gagtttagtt    3120
gaggagaaaa aaaaaaaaa aaaaaaaaaa a                                    3151
```

<210> SEQ ID NO 26
<211> LENGTH: 1424
<212> TYPE: DNA
<213> ORGANISM: Homo sapiens
<400> SEQUENCE: 26

```
gctgtggtaa gtgcatcctc cttcagtctc agttctgaaa atagatcatc atggtggcac     60
caaagagtca cacagatgac tgggctcctg ggcctttctc cagtaagcca cagaggagtc    120
agctgcaaat attctcttct gttctacaga ccctctctcct cttcctgctc atgggactaa    180
gagcctctgg aaaggactca gccccaacag tggtgtcagg atcctaggg ggttccgtga    240
```

-continued

```
ctctccccct aaacatctca gtagacacag agattgagaa cgtcatctgg attggtccca      300
aaaatgctct tgctttcgca cgtcccaaag aaaatgtaac cattatggtc aaaagctacc      360
tgggccgact agacatcacc aagtggagtt actccctgtg catcagcaat ctgactctga      420
atgatgcagg atcctacaaa gcccagataa accaaaggaa ttttgaagtc accactgagg      480
aggaattcac cctgttcgtc tatgcaccat ttattgaaaa gttgtccgtc cacgtcatcg      540
agggtgacca ccgcacactc ctggagggca gcggcctgga gtccatcatc agcaccctgg      600
ctgagccacg tgtgagcgtg cgggagggct aggccctcgc ccccacctgc cactggagac      660
cgctccgcca tccccacctc accgccgcgc agcagagctg aagggtcctg ccgatgggac      720
ccctgccagg cccagtgcca ctgcccccccg aggctgctag acgtgggcgt taggcgtgtc      780
ccacccaccc gccgcctccc atggcacgtc gggaacaccg gagccgccaa cttggagact      840
cctggtctgt gaagagccgc tgacgcccgc aggaaccggg ctgggccttg tgtgccagtg      900
gggtttgtgc ttggtctttc tccgcttgga tttgcttatt tattgcattg ctggtagaga      960
ctcccaagcc tgtccaccct gcaaagactc ctcgggcagc atgcgggtcc cgcacactgc     1020
acccatttcc tggatgtccc ctgcaggcgc gggaggccat ccgggcctgc tggctgcggc     1080
ccctctcag ccaggcctgg ctcagcccac tgcgtgggag gtcaccggcc actccccgag     1140
gagctgggat ccccgggatg caggcccaca gtgcggggct gcacccatga tgcggagctg     1200
gcctccaacc ctgcgggccg cgccaggcac caactcagtg tttgtcagtg tttgtttttc     1260
caagaaatgg ttcaaattgc tgctcagatt tttaaattta ctgtagctgc cagtgtacac     1320
gtgtggaccc catttttattt ttacaccaat ttggtgaaaa tgctgctttc ctcagcctcc     1380
ccacaattaa actgcacatg gtctctaaaa aaaaaaaaa aaaa                       1424
```

<210> SEQ ID NO 27
<211> LENGTH: 1670
<212> TYPE: DNA
<213> ORGANISM: Homo sapiens

<400> SEQUENCE: 27

```
ccaaccacaa gcaccaaagc agaggggcag gcagcacacc acccagcagc cagagcacca       60
gcccagccat ggtccttgag gtgagtgacc accaagtgct aaatgacgcc gaggttgccg      120
ccctcctgga gaacttcagc tcttcctatg actatggaga aaacgagagt gactcgtgct      180
gtacctcccc gccctgccca caggacttca gcctgaactt cgaccgggcc ttcctgccag      240
ccctctacag cctcctcttt ctgctggggc tgctgggcaa cggcgcggtg gcagccgtgc      300
tgctgagccg gcggacagcc ctgagcagca ccgacacctt cctgctccac ctagctgtag      360
cagacacgct gctggtgctg acactgccgc tctgggcagt ggacgctgcc gtccagtggg      420
tctttggctc tggcctctgc aaagtggcag gtgccctctt caacatcaac ttctacgcag      480
gagcctcct gctggcctgc atcagctttg accgctacct gaacatagtt catgccaccc      540
agctctaccg ccgggggccc ccgggcccgcg tgaccctcac ctgcctggct gtctggggc      600
tctgcctgct tttcgccctc ccagacttca tcttcctgtc ggcccaccac gacgagcgcc      660
tcaacgccac ccactgccaa tacaacttcc cacaggtggg ccgcacggct ctgcgggtgc      720
tgcagctggt ggctggcttt ctgctgcccc tgctggtcat ggcctactgc tatgcccaca      780
tcctggccgt gctgctggtt tccagggggcc agcggcgcct gcgggccatg cggctggtgg      840
tggtggtcgt ggtggccttt gccctctgct ggacccccta tcacctggtg gtgctggtgg      900
acatcctcat ggacctgggc gctttggccc gcaactgtgg ccgagaaagc agggtagacg      960
```

```
tggccaagtc ggtcacctca ggcctgggct acatgcactg ctgcctcaac ccgctgctct    1020
atgcctttgt aggggtcaag ttccgggagc ggatgtggat gctgctcttg cgcctgggct    1080
gccccaacca gagagggctc cagaggcagc catcgtcttc ccgccgggat tcatcctggt    1140
ctgagacctc agaggcctcc tactcggact tgtgaggccg gaatccgggc tcccctttcg    1200
cccacagtct gacttccccg cattccaggc tcctccctcc ctctgccggc tctggctctc    1260
cccaatatcc tcgctcccgg gactcactgg cagcccagc accaccaggt ctcccgggaa     1320
gccaccctcc cagctctgag gactgcacca ttgctgctcc ttagctgcca gccccatcc     1380 tgccgcccga ggtggctgcc tggagcccca ctgcccttct catttggaaa ctaaaacttc    1440
atcttcccca agtgcgggga gtacaaggca tggcgtagag ggtgctgccc catgaagcca    1500
cagcccaggc ctccagctca gcagtgactg tggccatggt ccccaagacc tctatatttg    1560 ctctttatt tttatgtcta aaatcctgct taaaacttt caataaacaa gatcgtcagg       1620
accaaaaaaa aaaaaaaaaa aaaaaaaaaa aaaaaaaaaa                           1670

<210> SEQ ID NO 28
<211> LENGTH: 1377
<212> TYPE: DNA
<213> ORGANISM: Homo sapiens

<400> SEQUENCE: 28
ctcctcccct cccagcctca ggtgcctgct tcagaaaatg aagtagtaag tctgctggcc    60
tccgccatct tagtaaagta acagtcccat gaaacaaaga tgcagtcggg cactcactgg    120
agagttctgg gcctctgcct cttatcagtt ggcgtttggg ggcaagatgg taatgaagaa    180
atgggtggta ttacacagac accatataaa gtctccatct ctggaaccac agtaatattg    240
acatgccctc agtatcctgg atctgaaata ctatggcaac acaatgataa aaacataggc    300
ggtgatgagg atgataaaaa cataggcagt gatgaggatc acctgtcact gaaggaattt    360
tcagaattgg agcaaagtgg ttattatgtc tgctacccca gaggaagcaa accagaagat    420
gcgaactttt atctctacct gagggcaaga gtgtgtgaga actgcatgga gatggatgtg    480
atgtcggtgg ccacaattgt catagtggac atctgcatca ctgggggctt gctgctgctg    540
gtttactact ggagcaagaa tagaaaggcc aaggccaagc ctgtgacacg aggagcgggt    600
gctggcggca ggcaaagggg acaaaacaag gagaggccac cacctgttcc caacccagac    660
tatgagccca tccggaaagg ccagcgggac ctgtattctg gcctgaatca gagacgcatc    720
tgaccctctg gagaacactg cctcccgctg gcccaggtct cctctccagt cccctgcga    780 ctccctgttt cctgggctag tcttggaccc cacgagagag aatcgttcct cagcctcatg    840
gtgaactcgc gccctccagc ctgatccccc gctccctcct ccctgccttc tctgctggta    900
cccagtccta aaatattgct gcttcctctt cctttgaagc atcatcagta gtcacaccct    960
cacagctggc ctgccctctt gccaggatat ttatttgtgc tattcactcc cttccctttg    1020
gatgtaactt ctccgttcag ttccctcctt ttcttgcatg taagttgtcc cccatcccaa    1080
agtattccat ctacttttct atcgccgtcc ccttttgcag ccctctctgg ggatggactg    1140
ggtaaatgtt gacagaggcc ctgccccgtt cacagatcct ggccctgagc cagccctgtg    1200
ctcctcccct ccccaacact ccctaccaac cccctaatcc cctactccct ccacccccc     1260 tccactgtag gccactggat ggtcatttgc atctccgtaa atgtgctctg ctcctcagct    1320
gagagagaaa aaaataaact gtatttggct gcaagaaaaa aaaaaaaaaa aaaaaaa       1377
```

<210> SEQ ID NO 29
<211> LENGTH: 1204
<212> TYPE: DNA
<213> ORGANISM: Homo sapiens

<400> SEQUENCE: 29

| | | | | | |
|---|---|---|---|---|---|
| gaaattctta | caaaaactga | aagtgaaatg | aggaagacag | attgagcaat | ccaatcggag | 60 |
| ggtaaatgcc | agcaaaccta | ctgtacagta | ggggtagaga | tgcagaaagg | cagaaaggag | 120 |
| aaaattcagg | ataactctcc | tgaggggtga | gccaagccct | gccatgtagt | gcacgcagga | 180 |
| catcaacaaa | cacagataac | aggaaatgat | ccattccctg | tggtcactta | ttctaaaggc | 240 |
| cccaacctte | aaagttcaag | tagtgatatg | gatgactcca | cagaaaggga | gcagtcacgc | 300 |
| cttacttctt | gccttaagaa | aagagaagaa | atgaaactga | aggagtgtgt | ttccatcctc | 360 |
| ccacggaagg | aaagcccctc | tgtccgatcc | tccaaagacg | gaaagctgct | ggctgcaacc | 420 |
| ttgctgctgg | cactgctgtc | ttgctgcctc | acggtggtgt | ctttctacca | ggtggccgcc | 480 |
| ctgcaagggg | acctggccag | cctccgggca | gagctgcagg | ccaccacgc | ggagaagctg | 540 |
| ccagcaggag | caggagcccc | caaggccggc | ctggaggaag | ctccagctgt | caccgcggga | 600 |
| ctgaaaatct | ttgaaccacc | agctccagga | gaaggcaact | ccagtcagaa | cagcagaaat | 660 |
| aagcgtgccg | ttcagggtcc | agaagaaaca | gtcactcaag | actgcttgca | actgattgca | 720 |
| gacagtgaaa | caccaactat | acaaaaagga | tcttacacat | ttgttccatg | cttctcagc | 780 |
| tttaaaggg | gaagtgccct | agaagaaaaa | gagaataaaa | tattggtcaa | agaaactggt | 840 |
| tactttttta | tatatggtca | ggttttatat | actgataaga | cctacgccat | gggacatcta | 900 |
| attcagagga | agaaggtcca | tgtctttggg | gatgaattga | gtctggtgac | tttgtttcga | 960 |
| tgtattcaaa | atatgcctga | aacactaccc | aataattcct | gctattcagc | tggcattgca | 1020 |
| aaactggaag | aaggagatga | actccaactt | gcaataccaa | gagaaaatgc | acaaatatca | 1080 |
| ctggatggag | atgtcacatt | ttttggtgca | ttgaaactgc | tgtgacctac | ttacaccatg | 1140 |
| tctgtagcta | ttttcctccc | tttctctgta | cctctaagaa | gaaagaatct | aactgaaaat | 1200 |
| acca | | | | | | 1204 |

<210> SEQ ID NO 30
<211> LENGTH: 2032
<212> TYPE: DNA
<213> ORGANISM: Homo sapiens

<400> SEQUENCE: 30

| | | | | | |
|---|---|---|---|---|---|
| cgcctggacc | atgtgaatgg | ggccagaggg | ctcccgggct | gggcagggac | catgggctgt | 60 |
| ggctgcagct | cacacccgga | agatgactgg | atggaaaaca | tcgatgtgtg | tgagaactgc | 120 |
| cattatccca | tagtcccact | ggatggcaag | ggcacgctgc | tcatccgaaa | tggctctgag | 180 |
| gtgcgggacc | cactggttac | ctacgaaggc | tccaatccgc | cggcttcccc | actgcaagac | 240 |
| aacctggtta | tcgctctgca | cagctatgag | ccctctcacg | acggagatct | gggctttgag | 300 |
| aagggggaac | cactccgcat | cctggagcag | agcggcgagt | ggtggaaggc | gcagtccctg | 360 |
| accacgggcc | aggaaggctt | catcccctte | aattttgtgg | ccaaagcgaa | cagcctggag | 420 |
| cccgaaccct | ggttcttcaa | gaacctgagc | cgcaaggacg | cggagcggca | gctcctggcg | 480 |
| cccgggaaca | ctcacggctc | cttcctcatc | cgggagagcg | agagcaccgc | cgggtcctt | 540 |
| tcactgtcgg | tccgggactt | cgaccaaaac | caggagagg | tggtgaaaca | ttacaagatc | 600 |
| cgtaatctgg | acaacggtgg | cttctacatc | tcccctcgaa | tcacttttcc | cggcctgcat | 660 |

```
gaactggtcc gccattacac caatgcttca gatgggctgt gcacacggtt gagccgcccc    720
tgccagaccc agaagcccca gaagccgtgg tgggaggacg agtgggaggt tcccagggag    780
acgctgaagc tggtggagcg gctgggggct ggacagttcg gggaggtgtg gatggggtac    840
tacaacgggc acacgaaggt ggcggtgaag agcctgaagc agggcagcat gtccccggac    900
gccttcctgg ccgaggccaa cctcatgaag cagctgcaac accagcggct ggttcggctc    960
tacgctgtgt caccccagga gcccatctac atcatcactg aatacatgga gaatgggagt   1020
ctagtggatt ttctcaagac cccttcaggc atcaagttga ccatcaacaa actcctggac   1080
atggcagccc aaattgcaga aggcatggca ttcattgaag agcggaatta tattcatcgt   1140
gaccttcggg ctgccaacat tctggtgtct gacaccctga gctgcaagat tgcagacttt   1200
ggcctagcac gcctcattga ggacaacgag tacacagcca gggaggggc caagtttccc   1260 attaagtgga cagcgccaga agccattaac tacgggacat tcaccatcaa gtcagatgtg   1320
tggtcttttg ggatcctgct gacggaaatt gtcacccacg gccgcatccc ttacccaggg   1380
atgaccaacc cggaggtgat tcagaacctg gagcgaggct accgcatggt gcgccctgac   1440
aactgtccag aggagctgta ccaactcatg aggctgtgct ggaaggagcg cccagaggac   1500
cggcccacct ttgactacct gcgcagtgtg ctggaggact tcttcacggc cacagagggc   1560
cagtaccagc tcagccttg agaggaggcc ttgagaggcc ctggggttct ccccctttct   1620
ctccagcctg acttggggag atggagttct tgtgccatag tcacatggcc tatgcacata   1680
tggactctgc acatgaatcc cacccacatg tgacacatat gcaccttgtg tctgtacacg   1740
tgtcctgtag ttgcgtggac tctgcacatg tcttgtgcat gtgtagcctg tgcatgtatg   1800
tcttggacac tgtacaaggt accccttct ggctctccca tttcctgaga ccaccagaga   1860
gaggggagaa gcctgggatt gacagaagct tctgcccacc tactttctt tcctcagatc   1920 atccagaagt tcctcaaggg ccaggacttt atctaatacc tctgtgtgct cctccttggt   1980
gcctggcctg gcacacatca ggagttcaat aaatgtctgt tgatgactgc cg           2032

<210> SEQ ID NO 31
<211> LENGTH: 787
<212> TYPE: DNA
<213> ORGANISM: Homo sapiens

<400> SEQUENCE: 31
cttcattcca ttttctgttg agtaataaac tcaacgttga aaatgtcctt tgtgggggag     60
aactcaggag tgaaaatggg ctctgaggac tgggaaaaag atgaacccca gtgctgctta    120
gaagacccgg ctggaagccc cctggaacca ggcccaagcc tccccaccat gaattttgtt    180
cacacaagtc caaggtgaa gaacttaaac ccgaagaaat tcagcattca tgaccaggat    240
cacaaagtac tggtcctgga ctctgggaat ctcatagcag ttccagataa aaactacata    300
cgcccagaga tcttctttgc attagcctca tccttgagct cagcctctgc ggagaaagga    360
agtccgattc tcctgggggt ctctaaaggg gagttttgtc tctactgtga caaggataaa    420
ggacaaagtc atccatccct tcagctgaag aaggagaaac tgatgaagct ggctgcccaa    480
aaggaatcag cacgccggcc cttcatcttt tatagggctc aggtgggctc ctggaacatg    540
ctggagtcgg cggctcaccc cggatggttc atctgcacct cctgcaattg taatgagcct    600
gttggggtga cagataaatt tgagaacagg aaacacattg aatttcatt tcaaccagtt    660 tgcaaagctg aaatgagccc cagtgaggtc agcgattagg aaactgcccc attgaacgcc    720
```

```
ttcctcgcta atttgaacta attgtataaa acaccaaac ctgctcacta aaaaaaaaaa    780
aaaaaaa                                                              787

<210> SEQ ID NO 32
<211> LENGTH: 1373
<212> TYPE: DNA
<213> ORGANISM: Homo sapiens

<400> SEQUENCE: 32
ctttaagtga aatatgaaac agagaagcac catttctgcc tcaagacgca tgtaaagagg     60
tgtagattca ggttggagtg cagtggcatg atcacagctc tctgcagtct cgccctcctg    120
ggctcaagca atcttttcccc accccccggt ttcctgagta gctgggacta taggcatgcg    180
ccaccacacc cggatgctct aaacgtccct gccatctggt ccagatggag tcctcaggca    240
acccagagag caccacccttt ttttactatg accttcagag ccagccgtgt gagaaccagg    300
cctgggtctt tgctaccctc gccaccactg tcctatactg cctggtgttt ctcctcagcc    360
tagtgggcaa cagcctggtc ctgtgggtcc tggtgaagta tgagagcctg gagtccctca    420
ccaacatctt catcctcaac ctgtgcctct cagacctggt gttcgcctgc ttgttgcctg    480
tgtggatctc cccataccac tggggctggg tgctgggaga cttcctctgc aaactcctca    540
atatgatctt ctccatcagc ctctacagca gcatcttctt cctgaccatc atgaccatcc    600
accgctacct gtcggtagtg agccccctct ccacccgcg cgtccccacc ctccgctgcc    660
gggtgctggt gaccatggct gtgtgggtag ccagcatcct gtcctccatc ctcgacacca    720
tcttccacaa ggtgctttct tcgggctgtg attattccga actcacgtgg tacctcacct    780
ccgtctacca gcacaacctc ttcttcctgc tgtccctggg gattatcctg ttctgctacg    840
tggagatcct caggaccctg ttccgctcac gctccaagcg cgccaccgc acggtcaagc    900 tcatcttcgc catcgtggtg gcctacttcc tcagctgggg tccctacaac ttcaccctgt    960
ttctgcagac gctgtttcgg acccagatca tccggagctg cgaggccaaa cagcagctag   1020
aatacgccct gctcatctgc cgcaacctcg ccttctccca ctgctgctttt aacccggtgc   1080 tctatgtctt cgtgggggtc aagttccgca cacacctgaa acatgttctc cggcagttct   1140
ggttctgccg gctgcaggca cccagcccag cctcgatccc ccactcccct ggtgccttcg   1200
cctatgaggg cgcctccttc tactgagggg cctgtggcgg tgcaggcgca ggtgcaggtg   1260
gacagggact ggaatggggg tcatggagaa gcgggcctgg aaggagcatt gcagaacaca   1320
gcagggtgga gacgtctcct ccgctgcagg cgtgcagtga aggtcattca tta           1373

<210> SEQ ID NO 33
<211> LENGTH: 5101
<212> TYPE: DNA
<213> ORGANISM: Homo sapiens

<400> SEQUENCE: 33
cactcctccc catcctctcc ctctgtccct ctgtccctct gaccctgcac tgtcccagca     60
ccatgggacc cacctcaggt cccagcctgc tgctcctgct actaacccac ctcccctgg    120 ctctggggag tccatgtac tctatcatca ccccaacat cttgcggctg gagagcgagg    180
agaccatggt gctggaggcc cacgacgcgc aaggggatgt tccagtcact gttactgtcc    240
acgacttccc aggcaaaaaa ctagtgctgt ccagtgagaa gactgtgctg acccctgcca    300
ccaaccacat gggcaacgtc accttcacga tcccagccaa cagggagttc aagtcagaaa    360 agggcgcaa caagttcgtg accgtgcagg ccaccttcgg gacccaagtg gtggagaagg    420
```

```
tggtgctggt cagcctgcag agcgggtacc tcttcatcca gacagacaag accatctaca    480
cccctggctc cacagttctc tatcggatct tcaccgtcaa ccacaagctg ctacccgtgg    540
gccggacggt catggtcaac attgagaacc cggaaggcat cccggtcaag caggactcct    600
tgtcttctca gaaccagctt ggcgtcttgc ccttgtcttg ggacattccg gaactcgtca    660
acatgggcca gtggaagatc cgagcctact atgaaaactc accacagcag gtcttctcca    720
ctgagtttga ggtgaaggag tacgtgctgc ccagtttcga ggtcatagtg gagcctacag    780
agaaattcta ctacatctat aacgagaagg gcctggaggt caccatcacc gccaggttcc    840
tctacgggaa gaaagtggag ggaactgcct ttgtcatctt cgggatccag gatggcgaac    900
agaggatttc cctgcctgaa tccctcaagc gcattccgat tgaggatggc tcggggagg    960
ttgtgctgag ccggaaggta ctgctggacg gggtgcagaa cccccgagca gaagacctgg   1020
tggggaagtc tttgtacgtg tctgccaccg tcatcttgca ctcaggcagt gacatggtgc   1080
aggcagagcg cagcgggatc ccatcgtga cctctcccta ccagatccac ttcaccaaga   1140
cacccaagta cttcaaacca ggaatgccct ttgacctcat ggtgttcgtg acgaaccctg   1200
atggctctcc agcctaccga gtccccgtgg cagtccaggg cgaggacact gtgcagtctc   1260
taacccaggg agatggcgtg gccaaactca gcatcaacac acaccccagc cagaagccct   1320
tgagcatcac ggtgcgcacg aagaagcagg agctctcgga ggcagagcag gctaccagga   1380
ccatgcaggc tctgccctac agcaccgtgg gcaactccaa caattacctg catctctcag   1440
tgctacgtac agagctcaga cccggggaga ccctcaacgt caacttcctc ctgcgaatgg   1500
accgcgccca cgaggccaag atccgctact acacctacct gatcatgaac aagggcaggc   1560
tgttgaaggc gggacgccag gtgcgagagc ccggccagga cctggtggtg ctgcccctgt   1620
ccatcaccac cgacttcatc ccttccttcc gcctggtggc gtactacacg ctgatcggtg   1680
ccagcggcca gagggaggtg gtggccgact ccgtgtgggt ggacgtcaag gactcctgcg   1740
tgggctcgct ggtggtaaaa agcggccagt cagaagaccg gcagcctgta cctgggcagc   1800
agatgaccct gaagatagag ggtgaccacg gggcccgggt ggtactggtg gccgtggaca   1860
agggcgtgtt cgtgctgaat aagaagaaca aactgacgca gagtaagatc tgggacgtgg   1920
tggagaaggc agacatcggc tgcacccccg gcagtgggaa ggattacgcc ggtgtcttct   1980
ccgacgcagg gctgaccttc acgagcagca gtggccagca gaccgcccag agggcagaac   2040
ttcagtgccc gcagccagcc gcccgccgac gccgttccgt gcagctcacg gagaagcgaa   2100
tggacaaagt cggcaagtac cccaaggagc tgcgcaagtg ctgcgaggac ggcatgcggg   2160
agaaccccat gaggttctcg tgccagcgcc ggacccgttt catctccctg ggcgaggcgt   2220
gcaagaaggt cttcctggac tgctgcaact acatcacaga gctgcggcgg cagcacgcgc   2280
gggccagcca cctgggcctg gccaggagta acctggatga ggacatcatt gcagaagaga   2340
acatcgtttc ccgaagtgag ttcccagaga gctggctgtg gaacgttgag gacttgaaag   2400
agccaccgaa aaatggaatc tctacgaagc tcatgaatat attttttgaaa gactccatca   2460
ccacgtggga gattctggct gtgagcatgt cggacaagaa agggatctgt gtggcagacc   2520
ccttcgaggt cacagtaatg caggacttct tcatcgacct cgcggctaccc tactctgttg   2580
ttcgaaacga gcaggtggaa atccgagccg ttctctacaa ttaccggcag aaccaagagc   2640
tcaaggtgag ggtggaacta ctccacaatc cagccttctg cagcctggcc accaccaaga   2700
ggcgtcacca gcagaccgta accatccccc ccaagtcctc gttgtccgtt ccatatgtca   2760
```

```
tcgtgccgct aaagaccggc ctgcaggaag tggaagtcaa ggctgctgtc taccatcatt    2820
tcatcagtga cggtgtcagg aagtccctga aggtcgtgcc ggaaggaatc agaatgaaca    2880
aaactgtggc tgttcgcacc ctggatccag aacgcctggg ccgtgaagga gtgcagaaag    2940
aggacatccc acctgcagac ctcagtgacc aagtcccgga caccgagtct gagaccagaa    3000
ttctcctgca agggacccca gtggcccaga tgacagagga tgccgtcgac gcggaacggc    3060
tgaagcacct cattgtgacc ccctcgggct gcggggaaca gaacatgatc ggcatgacgc    3120
ccacggtcat cgctgtgcat tacctggatg aaacggagca gtgggagaag ttcggcctag    3180
agaagcggca gggggccttg gagctcatca agaaggggta cacccagcag ctggccttca    3240
gacaacccag ctctgccttt gcggccttcg tgaaacgggc acccagcacc tggctgaccg    3300
cctacgtggt caaggtcttc tctctggctg tcaacctcat cgccatcgac tcccaagtcc    3360
tctgcgggc tgttaaatgg ctgatcctgg agaagcagaa gcccgacggg gtcttccagg    3420
aggatgcgcc cgtgatacac caagaaatga ttggtggatt acggaacaac aacgagaaag    3480
acatggccct cacggccttt gttctcatct cgctgcagga ggctaaagat atttgcgagg    3540
agcaggtcaa cagcctgcca ggcagcatca ctaaagcagg agacttcctt gaagccaact    3600
acatgaacct acagagatcc tacactgtgg ccattgctgg ctatgctctg cccagatgg    3660
gcaggctgaa ggggcctctt cttaacaaat ttctgaccac agccaaagat aagaaccgct    3720
gggaggaccc tggtaagcag ctctacaacg tggaggccac atcctatgcc ctcttggccc    3780
tactgcagct aaaagacttt gactttgtgc ctcccgtcgt gcgttggctc aatgaacaga    3840
gatactacgg tggtggctat ggctctaccc aggccacctt catggtgttc caagccttgg    3900
ctcaatacca aaaggacgcc cctgaccacc aggaactgaa ccttgatgtg tccctccaac    3960
tgcccagccg cagctccaag atcacccacc gtatccactg gaatctgcc agcctcctgc    4020
gatcagaaga gaccaaggaa aatgagggtt tcacagtcac agctgaagga aaaggccaag    4080
gcaccttgtc ggtggtgaca atgtaccatg ctaaggccaa agatcaactc acctgtaata    4140
aattcgacct caaggtcacc ataaaaccag caccggaaac agaaaagagg cctcaggatg    4200
ccaagaacac tatgatcctt gagatctgta ccaggtaccg gggagaccag gatgccacta    4260
tgtctatatt ggacatatcc atgatgactg gctttgctcc agacacagat gacctgaagc    4320
agctggccaa tggtgttgac agatacatct ccaagtatga gctggacaaa gccttctccg    4380
ataggaacac cctcatcatc tacctggaca aggtctcaca ctctgaggat gactgtctag    4440
ctttcaaagt tcaccaatac tttaatgtag agcttatcca gcctggagca gtcaaggtct    4500
acgcctatta caacctggag gaaagctgta cccggttcta ccatccggaa aaggaggatg    4560
gaaagctgaa caagctctgc cgtgatgaac tgtgccgctg tgctgaggag aattgcttca    4620
tacaaaagtc ggatgacaag gtcaccctgg aagaacggct ggacaaggcc tgtgagccag    4680
gagtggacta tgtgtacaag acccgactgg tcaaggttca gctgtccaat gactttgacg    4740
agtacatcat ggccattgag cagaccatca agtcaggctc ggatgaggtg caggttggac    4800
agcagcgcac gttcatcagc cccatcaagt gcagagaagc cctgaagctg gaggagaaga    4860
aacactacct catgtggggt ctctcctccg atttctgggg agagaagccc aacctcagct    4920
acatcatcgg gaaggacact tgggtggagc actggcccga ggaggacgaa tgccaagacg    4980
aagagaacca gaaacaatgc caggacctcg gcgccttcac cgagagcatg gttgtctttg    5040
ggtgccccaa ctgaccacac ccccattccc ccactccaga taaagcttca gttatatctc    5100
a                                                                   5101
```

<210> SEQ ID NO 34
<211> LENGTH: 3103
<212> TYPE: DNA
<213> ORGANISM: Homo sapiens

<400> SEQUENCE: 34

| | | | | | |
|---|---|---|---|---|---|
| ccaggcctag | ggtgtggagg | agccttgcca | tcgggcttcc | tgtctctctt | catttaagca | 60 |
| cgactctgca | gaaggaacaa | agcaccctcc | ccactgggct | cctggttgca | gagctccaag | 120 |
| tcctcacaca | gatacgcctg | tttgagaagc | agcgggcaag | aaagacgcaa | gcccagaggc | 180 |
| cctgccattt | ctgtgggctc | aggtccctac | tggctcaggc | ccctgcctcc | ctcggcaagg | 240 |
| ccacaatgaa | ccggggagtc | cctttaggc | acttgcttct | ggtgctgcaa | ctggcgctcc | 300 |
| tcccagcagc | cactcaggga | aagaaagtgg | tgctgggcaa | aaaaggggat | acagtggaac | 360 |
| tgacctgtac | agcttcccag | aagaagagca | tacaattcca | ctggaaaaac | tccaaccaga | 420 |
| taaagattct | gggaaatcag | ggctccttct | taactaaagg | tccatccaag | ctgaatgatc | 480 |
| gcgctgactc | aagaagaagc | ctttgggacc | aaggaaactt | tcccctgatc | atcaagaatc | 540 |
| ttaagataga | agactcagat | acttacatct | gtgaagtgga | ggaccagaag | gaggaggtgc | 600 |
| aattgctagt | gttcggattg | actgccaact | ctgacaccca | cctgcttcag | gggcagagcc | 660 |
| tgaccctgac | cttggagagc | ccccctggta | gtagccccctc | agtgcaatgt | aggagtccaa | 720 |
| ggggtaaaaa | catacagggg | gggaagaccc | tctccgtgtc | tcagctggag | ctccaggata | 780 |
| gtggcacctg | gacatgcact | gtcttgcaga | accagaagaa | ggtggagttc | aaaatagaca | 840 |
| tcgtggtgct | agcttccag | aaggcctcca | gcatagtcta | taagaaagag | ggggaacagg | 900 |
| tggagttctc | cttcccactc | gcctttacag | ttgaaaagct | gacgggcagt | ggcgagctgt | 960 |
| ggtggcaggc | ggagagggct | tcctcctcca | agtcttggat | cacctttgac | ctgaagaaca | 1020 |
| aggaagtgtc | tgtaaaacgg | gttacccagg | accctaagct | ccagatgggc | aagaagctcc | 1080 |
| cgctccacct | caccctgccc | caggccttgc | ctcagtatgc | tggctctgga | aacctcaccc | 1140 |
| tggcccttga | agcgaaaaca | ggaaagttgc | atcaggaagt | gaacctggtg | gtgatgagag | 1200 |
| ccactcagct | ccagaaaaat | ttgacctgtg | aggtgtgggg | acccacctcc | cctaagctga | 1260 |
| tgctgagttt | gaaactggag | aacaaggagg | caaaggtctc | gaagcgggag | aaggcggtgt | 1320 |
| gggtgctgaa | ccctgaggcg | gggatgtggc | agtgtctgct | gagtgactcg | ggacaggtcc | 1380 |
| tgctggaatc | caacatcaag | gttctgccca | catggtccac | cccggtgcag | ccaatggccc | 1440 |
| tgattgtgct | gggggggcgtc | gccggcctcc | tgcttttcat | tgggctaggc | atcttcttct | 1500 |
| gtgtcaggtg | ccggcaccga | aggcgccaag | cagagcggat | gtctcagatc | aagagactcc | 1560 |
| tcagtgagaa | gaagacctgc | cagtgtcctc | accggtttca | gaagacatgt | agccccattt | 1620 |
| gaggcacgag | gccaggcaga | tcccacttgc | agcctcccca | ggtgtctgcc | ccgcgttttcc | 1680 |
| tgcctgcgga | ccagatgaat | gtagcagatc | cccagcctct | ggcctcctgt | tcgcctcctc | 1740 |
| tacaatttgc | cattgtttct | cctgggttag | gccccggctt | cactggttga | gtgttgctct | 1800 |
| ctagtttcca | gaggcttaat | cacaccgtcc | tccacgccat | ttccttttcc | ttcaagccta | 1860 |
| gcccttctct | cattatttct | ctctgaccct | tccccactg | ctcatttgga | tcccagggga | 1920 |
| gtgttcaggg | ccagccctgg | ctggcatgga | gggtgaggct | gggtgtctgg | aagcatggag | 1980 |
| catgggactg | ttcttttaca | agacaggacc | ctggaccac | agagggcagg | aacttgcaca | 2040 |
| aaatcacaca | gccaagccag | tcaaggatgg | atgcagatcc | agaggtttct | ggcagccagt | 2100 |

```
acctcctgcc ccatgctgcc cgcttctcac cctatgtggg tgggaccaca gactcacatc    2160
ctgaccttgc acaaacagcc cctctggaca cagccccatg tacacggcct caagggatgt    2220
ctcacatcct ctgtctattt gagacttaga aaaatcctac aaggctggca gtgacagaac    2280
taagatgatc atctccagtt tatagaccag aaccagagct cagagaggct agatgattga    2340
ttaccaagtg ccggactagc aagtgctgga gtcgggacta acccaggtcc cttgtcccaa    2400
gttccactgc tgcctcttga atgcaggac aaatgccaca cggctctcac cagtggctag     2460
tggtgggtac tcaatgtgta cttttgggtt cacagaagca cagcacccat gggaagggtc    2520
catctcagag aatttacgag cagggatgaa ggcctccctg tctaaaatcc ctccttcatc    2580
ccccgctggt ggcagaatct gttaccagag acaaagcct ttggctcttc taatcagagc     2640
gcaagctggg agcacaggca ctgcaggaga aatgcccag tgaccagtca ctgaccctgt     2700
gcagaacctc ctggaagcga gctttgctgg gagaggggt agctagcctg agagggaacc     2760
ctctaaggga cctcaaaggt gattgtgcca ggctctgcgc ctgccccaca ccctccctta    2820
ccctcctcca gaccattcag gacacaggga aatcaggggt acaaatcttc ttgatccact    2880
tctctcagga tcccctctct tcctacccttcctcaccact tccctcagtc ccaactcctt     2940
ttccctattt ccttctcctc ctgtctttaa agcctgcctc ttccaggaag accccctat     3000 tgctgctggg ctccccatt tgcttacttt gcatttgtgc ccactctcca cccctgctcc     3060
cctgagctga aataaaaata caataaactt actataaaga tgc                      3103

<210> SEQ ID NO 35
<211> LENGTH: 1099
<212> TYPE: DNA
<213> ORGANISM: Homo sapiens

<400> SEQUENCE: 35
tcctgcgttg ctgggaagtt ctggaaggaa gcatgtgctc cagaggttgg gattcgtgtc      60
tggctctgga attgctactg ctgcctctgt cactcctggt gaccagcatt caaggtcact     120
tggtacatat gaccgtggtc tccggcagca acgtgactct gaacatctct gagagcctgc     180
ctgagaacta caaacaacta acctggtttt atactttcga ccagaagatt gtagaatggg     240
attccagaaa atctaagtac tttgaatcca aatttaaagg cagggtcaga cttgatcctc     300
agagtggcgc actgtacatc tctaaggtcc agaaagagga caacagcacc tacatcatga    360
gggtgttgaa aaagactggg aatgagcaag aatggaagat caagctgcaa gtgcttgacc    420
ctgtacccaa gcctgtcatc aaaattgaga agatagaaga catggatgac aactgttatt     480
tgaaactgtc atgtgtgata cctggcgagt ctgtaaacta cacctggtat ggggacaaaa    540
ggcccttccc aaaggagctc cagaacagtg tgcttgaaac cacccttatg ccacataatt     600
actccaggtg ttatacttgc caagtcagca attctgtgag cagcaagaat ggcacggtct    660
gcctcagtcc accctgtacc ctggcccggt cctttggagt agaatggatt gcaagttggc    720
tagtggtcac ggtgcccacc attcttggcc tgttacttac ctgagatgag ctcttttaac    780
tcaagcgaaa cttcaaggcc agaagatctt gcctgttggt gatcatgctc ctcaccagga    840
cagagactgt ataggctgac cagaagcatg ctgctgaatt atcaacgagg attttcaagt    900
taacttttaa atactggtta ttatttaatt ttatatccct ttgttgtttt ctagtacaca    960
gagatataga gatacacatg cttttttccc acccaaaatt gtgacaacat tatgtgaatg   1020
ttttattatt ttttaaaata aacatttgat ataattatca attaactgaa aaaaaaaaa    1080 aaaaaaaaaa aaaaaaaa                                                 1099
```

<210> SEQ ID NO 36
<211> LENGTH: 2166
<212> TYPE: DNA
<213> ORGANISM: Homo sapiens

<400> SEQUENCE: 36

| | | | | | |
|---|---|---|---|---|---|
| gcacagtggc | ccttaagcga | ggagcggcgg | cgcccgcagc | aatcacagca | gtgccgacgt | 60 |
| cgtgggtgtt | tggtgtgagg | ctgcgagccg | ccgcgagttc | tcacggtccc | gccggcgcca | 120 |
| ccaccgcggt | cactcaccgc | cgccgccgcc | accactgcca | ccacggtcgc | ctgccacagg | 180 |
| gtcttactct | gttgcccagg | ctggagtgca | gtggcacaat | cttggctcac | tgcaacctct | 240 |
| gcctcccggg | ttcaagcaat | tctcctgcct | cagcctcccg | agtagctggg | attacaggtg | 300 |
| tctgcaattg | aactccaagg | tgcagaatgg | tttggaaagt | agctgtattc | tcagtgtgg | 360 |
| ccctgggcat | tggtgccgtt | cctatagatg | atcctgaaga | tggaggcaag | cactgggtgg | 420 |
| tgatcgtggc | aggttcaaat | ggctggtata | attataggca | ccaggcagac | gcgtgccatg | 480 |
| cctaccagat | cattcaccgc | aatgggattc | ctgacgaaca | gatcgttgtg | atgatgtacg | 540 |
| atgacattgc | ttactctgaa | gacaatccca | ctccaggaat | tgtgatcaac | aggcccaatg | 600 |
| gcacagatgt | ctatcaggga | gtcccgaagg | actacactgg | agaggatgtt | accccacaaa | 660 |
| atttccttgc | tgtgttgaga | ggcgatgcag | aagcagtgaa | gggcatagga | tccggcaaag | 720 |
| tcctgaagag | tggcccccag | gatcacgtgt | tcatttactt | cactgaccat | ggatctactg | 780 |
| gaatactggt | ttttcccaat | gaagatcttc | atgtaaagga | cctgaatgag | accatccatt | 840 |
| acatgtacaa | acacaaaatg | taccgaaaga | tggtgttcta | cattgaagcc | tgtgagtctg | 900 |
| ggtccatgat | gaaccacctg | ccggataaca | tcaatgttta | tgcaactact | gctgccaacc | 960 |
| ccagagagtc | gtcctacgcc | tgttactatg | atgagaagag | gtccacgtac | ctgggggact | 1020 |
| ggtacagcgt | caactggatg | gaagattcgg | acgtggaaga | tctgactaaa | gagaccctgc | 1080 |
| acaagcagta | ccacctggta | aaatcgcaca | ccaacaccag | ccacgtcatg | cagtatggaa | 1140 |
| acaaaacaat | ctccaccatg | aaagtgatgc | agtttcaggg | tatgaaacgc | aaagccagtt | 1200 |
| ctcccgtccc | cctacctcca | gtcacacacc | ttgacctcac | cccagccct | gatgtgcctc | 1260 |
| tcaccatcat | gaaaaggaaa | ctgatgaaca | ccaatgatct | ggaggagtcc | aggcagctca | 1320 |
| cggaggagat | ccagcggcat | ctggatgcca | ggcacctcat | tgagaagtca | gtgcgtaaga | 1380 |
| tcgtctcctt | gctggcagcg | tccgaggctg | aggtggagca | gctcctgtcc | gagagagccc | 1440 |
| cgctcacggg | gcacagctgc | tacccagagg | ccctgctgca | cttccggacc | cactgcttca | 1500 |
| actggcactc | ccccacgtac | gagtatgcgt | tgagacattt | gtacgtgctg | gtcaaccttt | 1560 |
| gtgagaagcc | gtatccgctt | cacaggataa | aattgtccat | ggaccacgtg | tgccttggtc | 1620 |
| actactgaag | agctgcctcc | tggaagcttt | tccaagtgtg | agcgccccac | cgactgtgtg | 1680 |
| ctgatcagag | actggagagg | tggagtgaga | agtctccgct | gtcgggccc | tcctggggag | 1740 |
| cccccgctcc | agggctcgct | ccaggacctt | cttcacaaga | tgacttgctc | gctgttacct | 1800 |
| gcttccccag | tctttctga | aaaactacaa | attagggtgg | aaaagctct | gtattgagaa | 1860 |
| gggtcatatt | tgctttctag | gaggtttgtt | gttttgcctg | ttagttttga | ggagcaggaa | 1920 |
| gctcatgggg | gcttctgtag | cccctctcaa | aaggagtctt | tattctgaga | atttgaagct | 1980 |
| gaaacctctt | taaatcttca | gaatgatttt | attgaagagg | gccgcaagcc | ccaaatggaa | 2040 |
| aactgttttt | agaaaatatg | atgatttttg | attgcttttg | tatttaattc | tgcaggtgtt | 2100 |

| caagtcttaa aaaataaaga tttataacag aacccaaaaa aaaaaaaaaa aaaaaaaaaa | 2160 |
| aaaaaa | 2166 |

<210> SEQ ID NO 37
<211> LENGTH: 1214
<212> TYPE: DNA
<213> ORGANISM: Homo sapiens

<400> SEQUENCE: 37

| gtctacaccc cctcctcaca cgcacttcac ctgggtcggg attctcaggt catgaacggt | 60 |
| cccagccacc tccgggcagg gcgggtgagg acggggacgg ggcgtgtcca actggctgtg | 120 |
| ggctcttgaa acccgagcat ggcacagcac ggggcgatgg gcgcgtttcg ggccctgtgc | 180 |
| ggcctggcgc tgctgtgcgc gctcagcctg ggtcagcgcc ccaccggggg tcccgggtgc | 240 |
| ggccctgggc gcctcctgct tgggacggga acggacgcgc gctgctgccg ggttcacacg | 300 |
| acgcgctgct gccgcgatta cccgggcgag gagtgctgtt ccgagtggga ctgcatgtgt | 360 |
| gtccagcctg aattccactg cggagaccct tgctgcacga cctgccggca ccaccttgt | 420 |
| cccccaggcc aggggtaca gtcccagggg aaattcagtt ttggcttcca gtgtatcgac | 480 |
| tgtgcctcgg ggaccttctc cggggccac gaaggccact gcaaacccttg acagactgc | 540 |
| acccagttcg ggtttctcac tgtgttccct gggaacaaga cccacaacgc tgtgtgcgtc | 600 |
| ccagggtccc cgccggcaga gccgcttggg tggctgaccg tcgtcctcct ggccgtggcc | 660 |
| gcctgcgtcc tcctcctgac ctcggcccag cttggactgc acatctggca gctgaggagt | 720 |
| cagtgcatgt ggccccgaga gacccagctg ctgctggagg tgccgccgtc gaccgaagac | 780 |
| gccagaagct gccagttccc cgaggaagag cggggcgagc gatcggcaga ggagaagggg | 840 |
| cggctgggag acctgtgggt gtgagcctgg ccgtcctccg gggccaccga ccgcagccag | 900 |
| cccctcccca ggagctcccc aggccgcagg ggctctgcgt tctgctctgg gccgggccct | 960 |
| gctcccctgg cagcagaagt gggtgcagga aggtggcagt gaccagcgcc ctggaccatg | 1020 |
| cagttcggcg gccgcggctg ggccctgcag gagggagaga gagacacagt catggccccc | 1080 |
| ttcctcccctt gctggccctg atggggtggg gtcttaggac gggaggctgt gtccgtgggt | 1140 |
| gtgcagtgcc cagcacggga cccggctgca ggggaccttc aataaacact tgtccagtga | 1200 |
| aaaaaaaaaa aaaa | 1214 |

<210> SEQ ID NO 38
<211> LENGTH: 1699
<212> TYPE: DNA
<213> ORGANISM: Homo sapiens

<400> SEQUENCE: 38

| ggccctcccct ggaggagaac tgaaacttag ggtggggact gtagaaaggg gcggagagat | 60 |
| cagccgccca gccaggagtt aagctgaggt cgtctgagcc ctgcgacagc ctggacagca | 120 |
| actcaggatg gcatcaggca gggcacgctg caccccgaaaa ctccggaact gggtggtgga | 180 |
| gcaagtggag agtgggcagt ttcccggagt gtgctgggat gatacagcta agaccatgtt | 240 |
| ccggattccc tggaaacatg caggcaagca ggacttccgg gaggaccagg atgctgcctt | 300 |
| cttcaaggcc tgggcaatat ttaagggaaa gtataaggag ggggacacag gaggtccagc | 360 |
| tgtctggaag actcgcctgc gctgtgcact caacaagagt tctgaattta aggaggttcc | 420 |
| tgagaggggc gcatggatg ttgctgagcc ctacaaggtg tatcagttgc tgccaccagg | 480 |
| aatcgtctct ggccagccag ggactcagaa agtaccatca aagcgacagc acagttctgt | 540 |

```
gtcctctgag aggaaggagg aagaggatgc catgcagaac tgcacactca gtccctctgt    600
gctccaggac tccctcaata atgaggagga gggggccagt gggggagcag tccattcaga    660
cattgggagc agcagcagca gcagcagccc tgagccacag gaagttacag acacaactga    720 ggccccctttt caaggggatc agaggtccct ggagtttctg cttcctccag agccagacta    780
ctcactgctg ctcaccttca tctacaacgg gcgcgtggtg ggcgaggccc aggtgcaaag    840
cctggattgc cgccttgtgg ctgagccctc aggctctgag agcagcatgg agcaggtgct    900
gttccccaag cctggcccac tggagcccac gcagcgcctg ctgagccagc ttgagagggg    960
catcctagtg gccagcaacc cccgaggcct cttcgtgcag cgcctttgcc ccatccccat   1020
ctcctggaat gcaccccagg ctccacctgg gccaggcccg catctgctgc ccagcaacga   1080
gtgcgtggag ctcttcagaa ccgcctactt ctgcagagac ttggtcaggt actttcaggg   1140
cctgggcccc ccaccgaagt tccaggtaac actgaatttc tgggaagaga gccatggctc   1200
cagccatact ccacagaatc ttatcacagt gaagatggag caggcctttg cccgatactt   1260
gctggagcag actccagagc agcaggcagc cattctgtcc ctggtgtaga gcctggggga   1320
cccatcttcc acctcacctc tttgttcttc ctgtctcctt tgaagtagac tcattcttca   1380
cacgattgac ctgtcctctt tgtgataatt ctcagtagtt gtccgtgata atcgtgtcct   1440
gaaaatcctc gcacacactg gctggtggag aactcaaggc taattttta tcctttttt   1500 ttttttaattt tgagatatac gccctctttc atctgtaagg gactaggaaa ttccaaatgg   1560
tgtgaaccca gggggccttt ccctcttccc tgacctccca actctaaagc caagcacttt   1620
atattttcct cttagatatt cactaaggac ttaaaataaa attttattga aagaggaaaa   1680
aaaaaaaaaa aaaaaaaa                                                 1699
```

<210> SEQ ID NO 39
<211> LENGTH: 1601
<212> TYPE: DNA
<213> ORGANISM: Homo sapiens

<400> SEQUENCE: 39

```
ggcgaccgcg gctgaggtac aggtgcctcg cggtgcagcc gggtcgcctt ccagcccgtc     60
cgcctcccga ccagggcccg cgccccgtcc cgcctctctc ccgcccagcc aaatgcaggc    120
cgccgccctc cctgaggaga tccgttggct cctggaagat gctgaagagt ttctggcaga    180
aggtttgcgg aatgagaacc tcagcgctgt tgcaagggat cacagagacc atattctacg    240
gggctttcag caaatcaaag ccaggtacta ttgggatttt cagccccaag ggggagacat    300
tggacaggac agctctgatg ataatcacag cgggactctt ggcctgtccc tcacatccga    360 tgcaccctttt ttgtcagatt atcaggatga gggaatggaa gacatcgtaa aaggagctca    420
agaacttgat aacgtaatca agcaaggata cttggagaag aaaagcaaag atcatagttt    480
ctttggatcg gagtggcaga agcgatggtg tgttgtcagc agaggtctct tctactacta    540
tgctaatgag aagagcaagc agcccaaagg gaccttcctc attaagggct acggtgtacg    600
gatggccccc cacctgcgaa gagattccaa gaaagaatcc tgctttgaac tgacctccca    660
ggataggcgc agctatgagt ttacagctac tagtccagca gaagccagag actgggtgga    720
tcaaataagt ttcttgttaa aggatctgag ctccttaacc attccatatg aagaggatga    780
ggaggaagaa gaaaaagaag agacatatga tgatattgat ggttttgact ccccaagttg    840
tggttcccag tgcagaccca ctatcttgcc tgggagtgtg gggataaaag agcctacaga    900
```

| ggagaaagaa gaagaagata tttatgaagt cttgccagat gaagagcatg atctagaaga | 960 |
| ggatgagagt ggcactcgac gaaaaggagt agactatgcc agttactacc agggcctatg | 1020 |
| ggattgccat ggtgaccagc cagatgaact gtccttccaa cggggtgacc tcatccgtat | 1080 |
| tctgagcaag gagtataaca tgtatggctg gtgggtggga gaactgaaca gcctcgttgg | 1140 |
| gattgttcca aaggagtatc tcaccactgc ctttgaagtg gaagaaagat gaaacccagg | 1200 |
| aaatatattc ttccctctct cctgccttta tgaggaaact gatcatcaaa gttcccact | 1260 |
| ccctacttct gccaccccac caacgccttg gactcctctc tttgctgaag agacccaagt | 1320 |
| ctcttgacac ctcagagtga ctgtaagcta ccagtaagac aagtgggaag aggcacgttc | 1380 |
| atcaaacctg ttactaaacc agcctagtca tagctcatcc ccatctctaa atgtgtccac | 1440 |
| acaaccacat ctgccttttc cacaagcttt tcacaaagaa ggtgagagag aaggaaacct | 1500 |
| tgggaggagg acattactgg ttgttctggc tggtttgaaa agcacaaata aacttgggat | 1560 |
| gtggttcctt gccatgaaaa aaaaaaaaaa aaaaaaaaa a | 1601 |

<210> SEQ ID NO 40
<211> LENGTH: 1027
<212> TYPE: DNA
<213> ORGANISM: Homo sapiens

<400> SEQUENCE: 40

| gggcaagagt tgggcaaaaa aatcaaggta tttggtcccg gaacaaagct tatcattaca | 60 |
| gataaacaac ttgatgcaga tgtttccccc aagcccacta tttttcttcc ttcaattgct | 120 |
| gaaacaaagc tccagaaggc tggaacatac ctttgtcttc ttgagaaatt tttccctgat | 180 |
| gttattaaga tacattggca agaaaagaag agcaacacga ttctgggatc ccaggagggg | 240 |
| aacaccatga agactaacga cacatacatg aaatttagct ggttaacggt gccagaaaag | 300 |
| tcactggaca agaacacag atgtatcgtc agacatgaga ataataaaaa cggagttgat | 360 |
| caagaaatta tctttcctcc aataaagaca gatgtcatca caatggatcc caagacaat | 420 |
| tgttcaaaag atgcaaatga tacactactg ctgcagctca caaacacctc tgcatattac | 480 |
| atgtacctcc tcctgctcct caagagtgtg gtctattttg ccatcatcac ctgctgtctg | 540 |
| cttagaagaa cggctttctg ctgcaatgga gagaaatcat aacagacggt ggcacaagga | 600 |
| ggccatcttt tcctcatcgg ttattgtccc tagaagcgtc ttctgaggat ctagttgggc | 660 |
| tttctttctg ggtttgggcc atttcagttc tcatgtgtgt actattctat cattattgta | 720 |
| taacggtttt caaaccagtg ggcacacaga gaacctcact ctgtaataac aatgaggaat | 780 |
| agccacggcg atctccagca ccaatctctc catgttttcc acagctcctc cagccaaccc | 840 |
| aaatagcgcc tgctatagtg tagacatcct gcggcttcta gccttgtccc tctcttagtg | 900 |
| ttctttaatc agataactgc ctggaagcct ttcattttac acgccctgaa gcagtcttct | 960 |
| ttgctagttg aattatgtgg tgtgtttttc cgtaataagc aaaataaatt taaaaaaatg | 1020 |
| aaaagtt | 1027 |

<210> SEQ ID NO 41
<211> LENGTH: 1074
<212> TYPE: DNA
<213> ORGANISM: Homo sapiens

<400> SEQUENCE: 41

| gatcaacaca tttcatctgg gcttcttaaa tctaaatctt taaaatgact aagttttctt | 60 |
| ccttttctct gttttttccta atagttgggg cttatatgac tcatgtgtgt ttcaatatgg | 120 |

```
aaattattgg agggaaagaa gtgtcacctc attccaggcc atttatggcc tccatccagt    180
atggcggaca tcacgtttgt ggaggtgttc tgattgatcc acagtgggtg ctgacagcag    240
cccactgcca atatcggttt accaaaggcc agtctcccac tgtggtttta ggcgcacact    300
ctctctcaaa gaatgaggcc tccaaacaaa cactggagat caaaaaattt ataccattct    360
caagagttac atcagatcct caatcaaatg atatcatgct ggttaagctt caaacagccg    420
caaaactcaa taaacatgtc aagatgctcc acataagatc aaaaacctct cttagatctg    480
gaaccaaatg caaggttact ggctggggag ccaccgatcc agattcatta agaccttctg    540
acaccctgcg agaagtcact gttactgtcc taagtcgaaa actttgcaac agccaaagtt    600
actacaacgg cgaccctttt atcaccaaag acatggtctg tgcaggagat gccaaaggcc    660
agaaggattc ctgtaagggt gactcagggg gccccttgat ctgtaaaggt gtcttccacg    720
ctatagtctc tggaggtcat gaatgtggtg ttgccacaaa gcctggaatc tacaccctgt    780
taaccaagaa ataccagact tggatcaaaa gcaaccttgt cccgcctcat acaaattaag    840
ttacaaataa ttttattgga tgcacttgct tctttttttcc taatatgctc gcaggttaga    900
gttgggtgta agtaaagcag agcacatatg gggtccattt ttgcacttgt aagtcattt     960 attaaggaat caagttcttt ttcacttgta tcactgatgt atttctacca tgctggtttt   1020
attctaaata aaatttagaa gactcaaaaa aaaaaaaaaa aaaaaaaaaa aaaa          1074
```

<210> SEQ ID NO 42
<211> LENGTH: 4366
<212> TYPE: DNA
<213> ORGANISM: Homo sapiens

<400> SEQUENCE: 42

```
tgcattcttt gccccaaaac tctttccttt ggttgtgcta agaggtgatg cccaaggtgc     60
accacctttc aagaactgga tcatgaacaa ctttatcctc ctggaagaac agctcatcaa    120
gaaatcccaa caaagagaa gaacttctcc ctcgaacttt aaagtccgct tctttgtgtt    180
aaccaaagcc agcctggcat actttgaaga tcgtcatggg aagaagcgca cgctgaaggg    240
gtccattgag ctctcccgaa tcaaatgtgt tgagattgtg aaaagtgaca tcagcatccc    300
atgccactat aaatacccgt tcaggtggt gcatgacaac tacctcctat atgtgtttgc    360
tccagatcgt gagagccggc agcgctgggt gctggccctt aaagaagaaa cgaggaataa    420
taacagtttg gtgcctaaat atcatcctaa tttctggatg gatgggaagt ggaggtgctg    480
ttctcagctg gagaagcttg caacaggctg tgcccaatat gatccaacca gaatgcttc     540 aaagaagcct cttcctccta ctcctgaaga caacaggcga ccactttggg aacctgaaga    600
aactgtggtc attgccttat atgactacca aaccaatgat cctcaggaac tcgcactgcg    660
gcgcaacgaa gagtactgcc tgctggacag ttctgagatt cactggtgga gagtccagga    720
caggaatggg catgaaggat atgtaccaag cagttatctg gtggaaaaat ctccaaataa    780
tctggaaacc tatgagtggt acaataagag tatcagccga gacaaagctg aaaaacttct    840
tttggacaca ggcaaagaag gagccttcat ggtaagggat tccaggactg caggaacata    900
caccgtgtct gttttcacca aggctgttgt aagtgagaac aatccctgta taaagcatta    960
tcacatcaag gaaacaaatg acaatcctaa gcgatactat gtggctgaaa agtatgtgtt   1020
cgattccatc cctcttctca tcaactatca ccaacataat ggaggaggcc tggtgactcg   1080
actccggtat ccagtttgtt ttgggaggca gaaagccccca gttacagcag ggctgagata   1140
```

```
cgggaaatgg gtgatcgacc cctcagagct cacttttgtg caagagattg gcagtgggca    1200 atttggttg gtgcatctgg gctactggct caacaaggac aaggtggcta tcaaaaccat     1260
tcgggaaggg gctatgtcag aagaggactt catagaggag gctgaagtaa tgatgaaact    1320
ctctcatccc aaactggtgc agctgtatgg ggtgtgcctg gagcaggccc ccatctgcct    1380
ggtgtttgag ttcatggagc acggctgcct gtcagattat ctacgcaccc agcgggggact  1440 ttttgctgca gagaccctgc tgggcatgtg tctggatgtg tgtgagggca tggcctacct    1500
ggaagaggca tgtgtcatcc acagagactt ggctgccaga aattgtttgg tgggagaaaa    1560
ccaagtcatc aaggtgtctg actttgggat gacaaggttc gttctggatg atcagtacac    1620
cagttccaca ggcaccaaat tcccggtgaa gtgggcatcc ccagaggttt tctctttcag    1680
tcgctatagc agcaagtccg atgtgtggtc atttggtgtg ctgatgtggg aagttttcag    1740
tgaaggcaaa atcccgtatg aaaaccgaag caactcagag gtggtggaag acatcagtac    1800
cggatttcgg ttgtacaagc cccggctggc ctccacacac gtctaccaga ttatgaatca    1860
ctgctggaaa gagagaccag aagatcggcc agccttctcc agactgctgc gtcaactggc    1920
tgaaattgca gaatcaggac tttagtagag actgagtacc aggccacggg ctgcagatcc    1980
tgaatggagg aaggatatgt cctcattcca tagagcatta gaagctgcca ccagcccagg    2040
accctccaga ggcagcctgg cctgtggcat cagtccctga gtcaccatgg aagcagcatc    2100
ctgaccacag ctggcagtca agccacagct ggagggtcag ccaccaagct gggagctgag    2160
ccagaacagg agtgatgtct ctgcccttcc tctagcctct tgtcacatgt ggtgcacaaa    2220
cctcaacctg acagctttca gacagcattc ttgcacttct tagcaacaga gagagacatg    2280
agtaagaccc agattgctat ttttattgtt attttttaaca tgaatctaaa gtttatggtt    2340
ccagggactt tttatttgac ccaacaacac agtatcccag gatatggagg caaggggaac    2400
aaagagcatg agtcttttc caagaaaact ggtgagttaa gtaagattag agtgagtgtg    2460
ctctgttgct gtgatgctgt cagccacagc ttcctgccgt agagaatgat agagcagctg    2520
ctcacacagg aggccggata ttctgagaag cagctttatg aggttttaca gagtatgctg    2580
ctacctctct ccttgaaggg agcatggcga gacccattgg atggattggg gtgaacagtt    2640
caggtcccat gcttggagca ttgggtatct gatgtctgca ccagaacaag agaacctctg    2700
acggtggaga accatgtggt gcaagaagag atcttaggtc tcttcttta taccaagctc     2760 atctttata ccaagctgtg caggtgacta tgcctcctct tctgcacaga atgcttccac     2820
cagcatcctg agaagaaatg attacttctg aaaaacatcc tttttccag cctctgggaa    2880 tcagcccccc ctctctgcac tatccgatcc tcatcaacag agggcagcat tgtgttggtc    2940
aatgttccct tggcgagcaa ttgaaacttg tttaggccct agggttgagc aattttaagg   3000
ttgagactcc aagtctccta aaattctagg agagaaataa agagtctgtt tttgctcaaa    3060
ccatcaggat ggaaacagtc aggcactgac tggggtgctt ccaagaggca tgagagtgcc    3120
tactctggct tgagcacttc tatatgcaag gtgaatatgt actgagctag agacttccc    3180 tgcaaaatct ctgttcaccc tgggttcaca tccccatgag gtaatattat tattcccatt    3240
ttacaaataa tgtaactgag gctttaaaaa gccaagacat ctgcccaaag tgatggaact    3300
agaaagtcta gagctggtat tctagcccaa atctgtctga ccgcaataca cagattcttt    3360
attcctattc gacactggct tctactgaaa atgaaacgga ttgcagaggg aataaataca    3420
aagatggaaa gccagtaaag aagtcagtat agaaccacta gcgaatagtg ttgctctggc    3480
acagaccact gtggttgatg gcatggccct ccaacttgga ataggatttt ccttttccta    3540
```

| | |
|---|---|
| ttctgtatcc ttaccttggt catgttaatg actttggagt tattcagtta atgacccttt | 3600 |
| aattctcaca accaaccagt catgttgctt gaagccattt atagacgagc ttcaaagcaa | 3660 |
| ctttaaaaga ttcttctgta gaagtatgag ttcttccttt aattatcatt ccaactttca | 3720 |
| gctgtagtct tcttgaacac ttcatgagga gggacattcc ctgatataag agaggatggt | 3780 |
| gttgcaattg gctctttcta aatcatgtga cgttttgact ggcttgagat tcagatgcat | 3840 |
| aatttttaat tataattatt gtgaagtgga gagcctcaag ataaaactct gtcattcaga | 3900 |
| agatgatttt actcagctta tccaaaatta tctctgttta ctttttagaa ttttgtacat | 3960 |
| tatcttttgg gatccttaat tagagatgat ttctggaaca ttcagtctag aaagaaaaca | 4020 |
| ttggaattga ctgatctctg tggtttggtt tagaaaattc ccctgtgcat ggtattacct | 4080 |
| ttttcaagct cagattcatc taatcctcaa ctgtacatgt gtacattctt cacctcctgg | 4140 |
| tgccctatcc cgcaaaatgg gcttcctgcc tggttttttct cttctcacat ttttaaatg | 4200 |
| gtcccctgtg tttgtagaga actcccttat acagagtttt ggttctagtt ttatttcgta | 4260 |
| gattttgcat tttgtacctt ttgagactat gtatttatat ttggatcaga tgcatattta | 4320 |
| ttaatgtaca gtcactgcta gtgttcaaaa taaaaatgtt acaaat | 4366 |

<210> SEQ ID NO 43
<211> LENGTH: 1844
<212> TYPE: DNA
<213> ORGANISM: Homo sapiens

<400> SEQUENCE: 43

| | |
|---|---|
| ggagctactc agaagcggga gtctccgaga aagaaaagc aggtggaagg agaggaagcg | 60 |
| gatgccgtgg ggtttacagc aggaaaatcc gtggagacag cagatccgag aagcggcgat | 120 |
| gtttgcgtag aaccctgtac gtgcttcctt cggcctgtcg ctcttccctt ctctctgacc | 180 |
| agcaccatgc ttctcctggt gacaagcctt ctgctctgtg agttaccaca cccagcattc | 240 |
| ctcctgatcc cagagaaatc ggatctgcga acagtggcac cagcctctag tctcaatgtg | 300 |
| aggtttgact ccaggacgat gaatttaagc tgggactgcc aagaaaacac aaccttcagc | 360 |
| aagtgttttct taactgacaa gaagaacaga gtcgtggaac ccaggctcag taacaacgaa | 420 |
| tgttcgtgca catttcgtga aatttgtctg catgaaggag tcacatttga ggttcacgtg | 480 |
| aatactagtc aaagaggatt tcaacagaaa ctgctttatc caaattcagg aagggagggt | 540 |
| accgctgctc agaatttctc ctgtttcatc tacaatgcgg atttaatgaa ctgtacctgg | 600 |
| gcgaggggtc cgacggcccc ccgtgacgtc cagtattttt tgtacatacg aaactcaaag | 660 |
| agaaggaggg agatccggtg tccttattac atacaagact caggaaccca tgtgggatgt | 720 |
| cacctggata acctgtcagg attaacgtct cgcaattact ttctggttaa cggaaccagc | 780 |
| cgagaaattg gcatccaatt cttttgattca cttttggaca caaagaaaat gaacgattc | 840 |
| aaccctccca gcaatgtcac cgtacgttgc aacacgacgc actgcctcgt acggtggaaa | 900 |
| cagcccagga cctatcagaa gctgtcgtac ctggactttc agtaccagct ggacgtccac | 960 |
| agaaagaata cccagcctgg cacggaaaac ctactgatta atgtttctgg tgatttggaa | 1020 |
| aatagataca acttttccaag ctctgagccc agagcaaaac acagtgtgaa gatcagagct | 1080 |
| gcagacgtcc gcatcttgaa ttggagctcc tggagtgaag ccattgaatt tggttctgac | 1140 |
| gacgggaacc tcggctctgt gtacatttat gtgctcctaa tcgtgggaac ccttgtctgt | 1200 |
| ggcatcgtcc tcggcttcct ctttaaaagg ttccttagga tacagcggct gttcccgcca | 1260 |

| | |
|---|---|
| gttccacaga tcaaagacaa actgaatgat aaccatgagg tggaagacga gatcatctgg | 1320 |
| gaggaattca ccccagagga agggaaaggc taccgcgaag aggtcttgac cgtgaaggaa | 1380 |
| attacctgag acccagaggg tgtaggaatg gcatggacat ctccgcctcc gcgacacggg | 1440 |
| ggaactgttt tcttgatgat gctgtgaacc tttatatcat tttctatgtt tttatttaaa | 1500 |
| aacatgacat ttggggccag gcgcggtggc tcacgcctgt aatcccagca ctttgggagg | 1560 |
| ccaaggcagg cggatcacct gaggtcagga gttcaagacc agcctgccca acatggtgaa | 1620 |
| accccatctg gactaaaaat gcagaaattt acccaggcac ggcggcggac gcccatcatc | 1680 |
| ccagctactt gggaggctga ggcaggaaa ttgcttgaac ccgtgaggcg gaggttgtag | 1740 |
| tgagccaaga tcgcaccatt gcacaccaac ctgggtgaca gagcaagatt gcatctcaaa | 1800 |
| acaaacaata ataataaata ataaaaacct gatatttggc tggg | 1844 |

<210> SEQ ID NO 44
<211> LENGTH: 2338
<212> TYPE: DNA
<213> ORGANISM: Homo sapiens

<400> SEQUENCE: 44

| | |
|---|---|
| agcgcacgtc ggcagtcggc tccctcgttg accgaatcac cgacctctct ccccagctgt | 60 |
| atttccaaaa tgtcgctttc taacaagctg acgctggaca agctggacgt taagggaag | 120 |
| cgggtcgtta tgagagtcga cttcaatgtt cctatgaaga caaccagat aacaaacaac | 180 |
| cagaggatta aggctgctgt cccaagcatc aaattctgct tggacaatgg agccaagtcg | 240 |
| gtagtcctta tgagccacct aggccggcct gatggtgtgc ccatgcctga caagtactcc | 300 |
| ttagagccag ttgctgtaga actcaaatct ctgctgggca aggatgttct gttcttgaag | 360 |
| gactgtgtag gccagaagt ggagaaagcc tgtgccaacc cagctgctgg gtctgtcatc | 420 |
| ctgctggaga acctccgctt tcatgtggag gaagaaggga agggaaaaga tgcttctggg | 480 |
| aacaaggtta agccgagcc agccaaaata gaagctttcc gagcttcact ttccaagcta | 540 |
| ggggatgtct atgtcaatga tgcttttggc actgctcaca gagcccacag ctccatggta | 600 |
| ggagtcaatc tgccacagaa ggctggtggg tttttgatga agaaggagct gaactacttt | 660 |
| gcaaaggcct tggagagccc agagcgaccc ttcctggcca tcctgggcgg agctaaagtt | 720 |
| gcagacaaga tccagctcat caataatatg ctggacaaag tcaatgagat gattattggt | 780 |
| ggtggaatgg ctttttacctt ccttaaggtg ctcaacaaca tggagattgg cacttctctg | 840 |
| tttgatgaag agggagccaa gattgtcaaa gacctaatgt ccaaagctga agaatggt | 900 |
| gtgaagatta ccttgcctgt tgactttgtc actgctgaca gtttgatga aatgccaag | 960 |
| actggccaag ccactgtggc ttctggcata cctgctggct ggatgggctt ggactgtggt | 1020 |
| cctgaaagca gcaagaagta tgctgaggct gtcactcggg ctaagcagat tgtgtggaat | 1080 |
| ggtcctgtgg gggtatttga atgggaagct tttgcccggg aaccaaagc tctcatggat | 1140 |
| gaggtggtga aagccacttc taggggctgc atcaccatca taggtggtgg agacactgcc | 1200 |
| acttgctgtg ccaaatggaa cacggaggat aaagtcagcc atgtgagcac tggggtggt | 1260 |
| gccagtttgg agctcctgga aggtaaagtc cttcctgggg tggatgctct cagcaatatt | 1320 |
| tagtactttc ctgccttta gttcctgtgc acagcccta agtcaactta gcattttctg | 1380 |
| catctccact tggcattagc taaaaccttc catgtcaaga ttcagctagt ggccaagaga | 1440 |
| tgcagtgcca ggaacccta aacagttgca cagcatctca gctcatcttc actgcaccct | 1500 |
| ggatttgcat acattcttca agatcccatt tgaattttt agtgactaaa ccattgtgca | 1560 |

```
ttctagagtg catatattta tattttgcct gttaaaaaga aagtgagcag tgttagctta    1620
gttctctttt gatgtaggtt attatgatta gctttgtcac tgtttcacta ctcagcatgg    1680
aaacaagatg aaattccatt tgtaggtagt gagacaaaat tgatgatcca ttaagtaaac    1740
aataaaagtg tccattgaaa ccgtgatttt tttttttttc ctgtcatact ttgttaggaa    1800
gggtgagaat agaatcttga ggaacggatc agatgtctat attgctgaat gcaagaagtg    1860
gggcagcagc agtggagaga tgggacaatt agataaatgt ccattcttta tcaagggcct    1920
actttatggc agacattgtg ctagtgcttt tattctaact tttatttta tcagttacac     1980 atgatcataa tttaaaaagt caaggcttat aacaaaaaag ccccagccca ttcctcccat    2040
tcaagattcc cactccccag aggtgaccac tttcaactct tgagttttc aggtatatac     2100 ctccatgttt ctaagtaata tgcttatatt gttcacttcc tttttttta tttttaaag     2160 aaatctattt cataccatgg aggaaggctc tgttccacat atatttccac ttcttcattc    2220
tctcggtata gttttgtcac aattatagat tagatcaaaa gtctacataa ctaatacagc    2280
tgagctatgt agtatgctat gattaaattt acttatgtaa aaaaaaaaaa aaaaaaa      2338
```

<210> SEQ ID NO 45
<211> LENGTH: 1190
<212> TYPE: DNA
<213> ORGANISM: Homo sapiens

<400> SEQUENCE: 45

```
cagatccatc aggtccgagc tgtgttgact accactttc ccttcgtctc aattatgtct      60
tggaaaaagg ctttgcggat ccccggaggc cttcgggcag caactgtgac cttgatgctg    120
tcgatgctga gcaccccagt ggctgagggc agagactctc ccgaggattt cgtgtaccag    180
tttaagggca tgtgctactt caccaacggg acagagcgcg tgcgtcttgt gagcagaagc    240
atctataacc gagaagagat cgtgcgcttc gacagcgacg tgggggagtt ccgggcggtg    300
acgctgctgg ggctgcctgc cgccgagtac tggaacagcc agaaggacat cctggagagg    360
aaacgggcgg cggtggacag ggtgtgcaga cacaactacc agttggagct ccgcacgacc    420
ttgcagcggc gagtggagcc cacagtgacc atctccccat ccaggacaga ggccctcaac    480
caccacaacc tgctggtctg ctcggtgaca gatttctatc cagcccagat caaagtccgg    540
tggtttcgga tgaccaggga ggagacagct ggcgttgtgt ccaccccct tattaggaat    600 ggtgactgga ccttccagat cctggtgatg ctggaaatga ctccccagcg tggagacgtc    660
tacacctgcc acgtggagca ccccagcctc cagagcccca tcaccgtgga gtggcgggct    720
caatctgaat ctgcccagag caagatgctg agtggcattg gaggcttcgt gctggggctg    780
atcttcctcg ggctgggcct tatcatccat cacaggagtc agaaagggct cctgcactga    840
ctcctgagac tatttaact gggattggtt atcactttc tgtaacgcct gcttgtccct      900
gcccagaatt cccagctgtc tgtgtcagcc tgtcccctg agatcagagt cctacagtgg    960
ctgtcacgca gccaccaggt catctccttt catccccacc ttgaggcgga tggctgtgac    1020
cctacttcct gcactgaccc acagcctctg cctgtgcacg gccagctgca tctactcagg    1080
ccccaagggg tttctgtttc tattctctcc tcagactgct caagagaagc acatgaaaac    1140
cattacctga ctttagagct tttttacata attaaacatg atcctgagtt                1190
```

<210> SEQ ID NO 46
<211> LENGTH: 1616
<212> TYPE: DNA

<213> ORGANISM: Homo sapiens

<400> SEQUENCE: 46

```
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaacagtac ctaataaaca      180
gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc cagcagaagg     360
gcacctcaga aacagacacc atctgcacct gtgaagaagg ctggcactgt acgagtgagg     420
cctgtgagag ctgtgtcctg caccgctcat gctcgcccgg cttgggggtc aagcagattg     480
ctacaggggt ttctgatacc atctgcgagc cctgcccagt cggcttcttc tccaatgtgt     540
catctgcttt cgaaaaatgt cacccttgga caagctgtga gaccaaagac ctggttgtgc     600
aacaggcagg cacaaacaag actgatgttg tctgtggtcc ccaggatcgg ctgagagccc     660
tggtggtgat cccatcatc ttcgggatcc tgtttgccat cctcttggtg ctggtctttta     720
tcaaaaggt ggccaagaag ccaaccaata aggcccccca cccaagcag gaaccccagg      780
agatcaattt tccgacgat cttcctggct ccaacactgc tgctccagtg caggagactt      840
tacatggatg ccaaccggtc acccaggagg atggcaaaga gagtcgcatc tcagtgcagg     900
agagacagtg aggctgcacc cacccaggag tgtggccacg tgggcaaaca ggcagttggc     960
cagagagcct ggtgctgctg ctgctgtggc gtgagggtga ggggctggca ctgactgggc    1020
atagctcccc gcttctgcct gcaccctgc agtttgagac aggagacctg gcactggatg     1080
cagaaacagt tcaccttgaa gaacctctca cttcaccctg gagcccatcc agtctcccaa    1140
cttgtattaa agacagaggc agaagtttgg tggtggtggt gttggggtat ggtttagtaa    1200
tatccaccag accttccgat ccagcagttt ggtgcccaga gaggcatcat ggtggcttcc    1260
ctgcgcccag gaagccatat acacagatgc ccattgcagc attgtttgtg atagtgaaca    1320
actggaagct gcttaactgt ccatcagcag gagactggct aaataaaatt agaatatatt    1380
tatacaacag aatctcaaaa acactgttga gtaaggaaaa aaaggcatgc tgctgaatga    1440
tgggtatgga acttttttaaa aaagtacatg cttttatgta tgtatattgc ctatggatat    1500
atgtataaat acaatatgca tcatatattg atataacaag ggttctggaa gggtacacag    1560
aaaacccaca gctcgaagag tggtgacgtc tgggggtgggg aagaagggtc tggggg       1616
```

<210> SEQ ID NO 47
<211> LENGTH: 4353
<212> TYPE: DNA
<213> ORGANISM: Homo sapiens

<400> SEQUENCE: 47

```
attggaagaa gaagcatagt atagaagaaa ggcaaacaca acacattcaa cctctgccac      60
catggggaac tgggctgtga atgaggggct ctccattttt gtcattctgg tttggctggg     120
gttgaacgtc ttcctctttg tctggtatta ccgggtttat gatattccac ctaagttctt     180
ttacacaaga aaacttcttg ggtcagcact ggcactggcc agggcccctg cagcctgcct     240
gaatttcaac tgcatgctga ttctcttgcc agtctgtcga atctgctgt ccttcctcag     300
gggttccagt gcgtgctgct caacaagagt tcgaagacaa ctggacagga atctcacctt    360
tcataaaatg gtggcatgga tgattgcact tcactctgcg attcacacca ttgcacatct     420
```

```
atttaatgtg gaatggtgtg tgaatgcccg agtcaataat tctgatcctt attcagtagc    480
actctctgaa cttggagaca ggcaaaatga aagttatctc aattttgctc gaaagagaat    540
aaagaaccct gaaggaggcc tgtacctggc tgtgaccctg ttggcaggca tcactggagt    600
tgtcatcacg ctgtgcctca tattaattat cacttcctcc accaaaacca tccggaggtc    660
ttactttgaa gtcttttggt acacacatca tctctttgtg atcttcttca ttggccttgc    720
catccatgga gctgaacgaa ttgtacgtgg gcagaccgca gagagtttgg ctgtgcataa    780
tataacagtt tgtgaacaaa aaatctcaga atggggaaaa ataaaggaat gcccaatccc    840
tcagtttgct ggaaaccctc ctatgacttg gaaatggata gtgggtccca tgtttctgta    900
tctctgtgag aggttggtgc ggttttggcg atctcaacag aaggtggtca tcaccaaggt    960
ggtcactcac cctttcaaaa ccatcgagct acagatgaag aagaaggggt caaaatggaa    1020
agtgggacaa tacatttttg tcaagtgccc aaaggtgtcc aagctggagt ggcacccttt    1080
tacactgaca tccgcccctg aggaagactt ctttagtatc catatccgca tcgttgggga    1140
ctggacagag gggctgttca atgcttgtgg ctgtgataag caggagtttc aagatgcgtg    1200
gaaactacct aagatagcgg ttgatgggcc ctttggcact gccagtgaag atgtgttcag    1260
ctatgaggtg gtgatgttag tgggagcagg gattggggtc acaccttcg catccattct    1320 caagtcagtc tggtacaaat attgcaataa cgccaccaat ctgaagctca aaagatcta    1380 cttctactgg ctgtgccggg acacacatgc ctttgagtgg tttgcagatc tgctgcaact    1440
gctggagagc cagatgcagg aaaggaacaa tgccggcttc ctcagctaca acatctacct    1500
cactggctgg gatgagtctc aggccaatca ctttgctgtg caccatgatg aggagaaaga    1560
tgtgatcaca ggcctgaaac aaaagacttt gtatggacgg cccaactggg ataatgaatt    1620
caagacaatt gcaagtcaac ccctaatac cagaataggha gttttcctct gtggacctga    1680
agccttggct gaaaccctga gtaaacaaag catctccaac tctgagtctg ccctcggggg    1740
agtgcatttc attttcaaca ggaaaaactt ctaacttgtc tcttccatga ggaaataaat    1800
gtgggttgtg ctgccaaatg ctcaaataat gctaattgat aatataaata cccctgctt    1860 aaaaatggac aaaaagaaac tataatgtaa tggttttccc ttaaaggaat gtcaaagatt    1920
gtttgatagt gataagttac atttatgtgg agctctatgg ttttgagagc acttttacaa    1980
acattatttc atttttttcc tctcagtaat gtcagtggaa gttagggaaa agattcttgg    2040 actcaattt agaatcaaaa gggaaaggat caaaaggttc agtaacttcc ctaagattat    2100
gaaactgtga ccagatctag cccatcttac tccaggtttg atactctttc cacaatactg    2160
agctgcctca gaatcctcaa aatcagtttt tatattcccc aaaagaagaa ggaaaccaag    2220
gagtagctat atatttctac tttgtgtcat ttttgccatc attattatca tactgaagga    2280
aattttccag atcattagga cataatacat gttgagagtg tctcaacact tattagtgac    2340
agtattgaca tctgagcata ctccagttta ctaatacagc agggtaactg gccagatgt     2400 tctttctaca gaagaatatt ggattgattg gagttaatgt aatactcatc atttaccact    2460
gtgcttggca gagagcggat actcaagtaa gttttgttaa atgaatgaat gaatttagaa    2520
ccacacaatg ccaagataga attaatttaa agccttaaac aaaatttatc taagaaata     2580 acttctatta ctgtcataga ccaaaggaat ctgattctcc ctagggtcaa gaacaggcta    2640
aggatactaa ccaataggat tgcctgaagg gttctgcaca ttcttatttg aagcatgaaa    2700
aaagagggtt ggaggtggag aattaacctc ctgccatgac tctggctcat ctagtcctgc    2760
```

```
tccttgtgct ataaaataaa tgcagactaa tttcctgccc aaagtggtct tctccagcta   2820
gcccttatga atattgaact taggaattgt gacaaatatg tatctgatat ggtcatttgt   2880
tttaaataac acccacccct tattttccgt aaatacacac acaaaatgga tcgcatctgt   2940
gtgactaatg gtttatttgt attatatcat catcatcatc ctaaaattaa caacccagaa   3000
acaaaaatct ctatacagag atcaaattca cactcaatag tatgttctga atatatgttc   3060
aagagagagt ctctaaatca ctgttagtgt ggccaagagc agggttttct ttttgttctt   3120
agaactgctc ccatttctgg gaactaaaac cagttttatt tgccccaccc cttggagcca   3180
caaatgttta gaactcttca acttcggtaa tgaggaagaa ggagaaagag ctgggggaag   3240
ggcagaagac tggtttagga ggaaaaggaa ataaggagaa aagagaatgg gagagtgaga   3300
gaaaataaaa aaggcaaaag ggagagagag gggaagggggg tctcatattg gtcattccct   3360
gccccagatt tcttaaagtt tgatatgtat agaatataat tgaaggaggt atacacatat   3420
tgatgttgtt ttgattatct atggtattga atcttttaaa atctggtcac aaattttgat   3480
gctgagggggg attattcaag ggactaggat gaactaaata agaactcagt tgttctttgt   3540
catactacta ttcctttcgt ctcccagaat cctcagggca ctgagggtag gtctgacaaa   3600
taaggcctgc tgtgcgaata tagcctttct gaaatgtacc aggatggttt ctgcttagag   3660
acacttaggt ccagcctgtt cacactgcac ctcaggtatc aattcatcta ttcaacagat   3720
atttattgtt ttattactat gagtcaggct ctgtttattg tttcaattct ttacaccaaa   3780
gtatgaactg gagagggtac ctcagttata aggagtctga gaatattggc cctttctaac   3840
ctatgtgcat aattaaaacc agcttcattt gttgctccga gagtgtttct ccaaggtttt   3900
ctatcttcaa aaccaactaa gttatgaaag tagagagatc tgccctgtgt tatccagtta   3960
tgagataaaa aatgaatata agagtgcttg tcattataaa agtttccttt tttattctct   4020
caagccacca gctgccagcc accagcagcc agctgccagc ctagcttttt ttttttttt   4080
ttttttttag cacttagtat ttagcattta ttaacaggta ctctaagaat gatgaagcat   4140
tgttttttaat cttaagacta tgaaggtttt tcttagttct tctgcttttg caattgtgtt   4200
tgtgaaattt gaatacttgc aggctttgta tgtgaataat tctagcgggg gacctgggag   4260
ataattccta cggggaattc ttaaaactgt gctcaactat taaaatgaat gagctttcaa   4320
aaaaaaaaaa aaaaaaaaaa aaaaaaaaaa aaa                                4353
```

<210> SEQ ID NO 48
<211> LENGTH: 1237
<212> TYPE: DNA
<213> ORGANISM: Homo sapiens

<400> SEQUENCE: 48

```
gctgcagagg attcctgcag aggatcaaga cagcacgtgg acctcgcaca gcctctccca     60
caggtaccat gaaggtctcc gcggcagccc tcgctgtcat cctcattgct actgccctct    120
gcgctcctgc atctgcctcc ccatattcct cggacaccac ccctgctgc tttgcctaca    180
ttgcccgccc actgccccgt gcccacatca aggagtattt ctacaccagt ggcaagtgct    240
ccaacccagc agtcgtcttt gtcacccgaa agaaccgcca agtgtgtgcc aacccagaga    300
agaaatgggt tcgggagtac atcaactctt tggagatgag ctaggatgga gagtccttga    360
acctgaactt acacaaattt gcctgttttct gcttgctctt gtcctagctt gggaggcttc    420
ccctcactat cctaccccac ccgctccttg aaggggcccag attctaccac acagcagcag    480
ttacaaaaac cttccccagg ctggacgtgg tggctcacgc ctgtaatccc agcacttttgg    540
```

```
gaggccaagg tgggtggatc acttgaggtc aggagttcga gaccagcctg gccaacatga      600
tgaaacccca tctctactaa aaatacaaaa aattagccgg gcgtggtagc gggcgcctgt      660
agtcccagct actcgggagg ctgaggcagg agaatggcgt gaacccggga ggcggagctt      720
gcagtgagcc gagatcgcgc cactgcactc cagcctgggc gacagagcga gactccgtct      780
caaaaaaaaa aaaaaaaaa aaaatacaaa aattagccgg gcgtggtggc ccacgcctgt      840
aatcccagct actcgggagg ctaaggcagg aaaattgttt gaacccagga ggtgaggct      900 gcagtgagct gagattgtgc cacttcactc cagcctgggt gacaaagtga gactccgtca      960
caacaacaac aacaaaaagc ttccccaact aaagcctaga agagcttctg aggcgctgct      1020
ttgtcaaaag gaagtctcta ggttctgagc tctggctttg ccttggcttt gccagggctc      1080
tgtgaccagg aaggaagtca gcatgcctct agaggcaagg aggggaggaa cactgcactc      1140
ttaagcttcc gccgtctcaa cccctcacag gagcttactg gcaaacatga aaaatcggct      1200
taccattaaa gttctcaatg caaccataaa aaaaaaa                              1237

<210> SEQ ID NO 49
<211> LENGTH: 5026
<212> TYPE: DNA
<213> ORGANISM: Homo sapiens

<400> SEQUENCE: 49
agaggaggaa attgttcctc gtctgataag acaacagtgg agaaaggacg catgctgttt       60
cttagggaca cggctgactt ccagatatga ccatgtattt gtggcttaaa ctcttggcat      120
ttggctttgc ctttctggac acagaagtat tgtgacagg gcaaagccca acaccttccc      180
ccactggatt gactacagca agatgcccca gtgttccact ttcaagtgac cccttaccta      240
ctcacaccac tgcattctca cccgcaagca cctttgaaag agaaatgac ttctcagaga      300 ccacaacttc tcttagtcca gacaatactt ccacccaagt atccccggac tctttggata      360
atgctagtgc tttaatacc acaggtgttt catcagtaca gacgcctcac cttcccacgc      420
acgcagactc gcagacgccc tctgctggaa ctgacacgca gacattcagc ggctccgccg      480
ccaatgcaaa actcaaccct accccaggca gcaatgctat ctcagatgtc ccaggagaga      540
ggagtacagc cagcaccttt cctacagacc cagtttcccc attgacaacc accctcagcc      600
ttgcacacca cagctctgct gccttacctg cacgcacctc caacaccacc atcacagcga      660
acacctcaga tgcctacctt aatgcctctg aaacaaccac tctgagccct tctggaagcg      720
ctgtcatttc aaccacaaca atagctacta ctccatctaa gccaacatgt gatgaaaaat      780
atgcaaacat cactgtggat tacttatata caaggaaac taaattattt acagcaaagc      840
taaatgttaa tgagaatgtg gaatgtgaa acaatacttg cacaaacaat gaggtgcata      900
accttacaga atgtaaaaat gcgtctgttt ccatatctca taattcatgt actgctcctg      960
ataagacatt aatattagat gtgccaccag gggttgaaaa gtttcagtta catgattgta     1020
cacaagttga aaaagcagat actactattt gtttaaaatg gaaaaatatt gaaacctta     1080 cttgtgatac acagaatatt acctacagat tcagtgtgg taatatgata tttgataata     1140
aagaaattaa attagaaaac cttgaacccg aacatgagta aagtgtgac tcagaaatac     1200 tctataataa ccacaagttt actaacgcaa gtaaaattat taaacagat tttgggagtc     1260 caggagagcc tcagattatt ttttgtagaa gtgaagctgc acatcaagga gtaattacct     1320
ggaatccccc tcaaagatca tttcataatt ttaccctctg ttatataaaa gagacagaaa     1380
```

```
aagattgcct caatctggat aaaaacctga tcaaatatga tttgcaaaat ttaaaacctt      1440
atacgaaata tgttttatca ttacatgcct acatcattgc aaaagtgcaa cgtaatggaa      1500
gtgctgcaat gtgtcatttc acaactaaaa gtgctcctcc aagccaggtc tggaacatga      1560
ctgtctccat gacatcagat aatagtatgc atgtcaagtg taggcctccc agggaccgta      1620
atggccccca tgaacgttac catttggaag ttgaagctgg aaatactctg gttagaaatg      1680
agtcgcataa gaattgcgat ttccgtgtaa aagatcttca atattcaaca gactacactt      1740
ttaaggccta ttttcacaat ggagactatc ctggagaacc ctttatttta catcattcaa      1800
catcttataa ttctaaggca ctgatagcat ttctggcatt tctgattatt gtgacatcaa      1860
tagccctgct tgttgttctc tacaaaatct atgatctaca taagaaaaga tcctgcaatt      1920
tagatgaaca gcaggagctt gttgaaaggg atgatgaaaa acaactgatg aatgtggagc      1980
caatccatgc agatattttg ttggaaactt ataagaggaa gattgctgat gaaggaagac      2040
tttttctggc tgaatttcag agcatcccgc gggtgttcag caagtttcct ataaaggaag      2100
ctcgaaagcc ctttaaccag aataaaaacc gttatgttga cattcttcct tatgattata      2160
accgtgttga actctctgag ataaacggag atgcagggtc aaactacata aatgccagct      2220
atattgatgg tttcaaagaa cccaggaaat acattgctgc acaaggtccc agggatgaaa      2280
ctgttgatga tttctggagg atgatttggg aacagaaagc cacagttatt gtcatggtca      2340
ctcgatgtga agaggaaac aggaacaagt gtgcagaata ctggccgtca atggaagagg      2400
gcactcgggc ttttggagat gttgttgtaa agatcaacca gcacaaaaga tgtccagatt      2460
acatcattca gaaattgaac attgtaaata aaaagaaaa agcaactgga agagaggtga      2520
ctcacattca gttcaccagc tggccagacc acggggtgcc tgaggatcct cacttgctcc      2580
tcaaactgag aaggagagtg aatgccttca gcaatttctt cagtggtccc attgtggtgc      2640
actgcagtgc tggtgttggg cgcacaggaa cctatatcgg aattgatgcc atgctagaag      2700
gcctggaagc cgagaacaaa gtggatgttt atggttatgt tgtcaagcta aggcgacaga      2760
gatgcctgat ggttcaagta gaggcccagt acatcttgat ccatcaggct ttggtggaat      2820
acaatcagtt tggagaaaca gaagtgaatt tgtctgaatt acatccatat ctacataaca      2880
tgaagaaaag ggatccaccc agtgagccgt ctccactaga ggctgaattc cagagacttc      2940
cttcatatag gagctggagg acacagcaca ttggaaatca agaagaaat aaaagtaaaa      3000 acaggaattc taatgtcatc ccatatgact ataacagagt gccacttaaa catgagctgg      3060
aaatgagtaa agagagtgag catgattcag atgaatcctc tgatgatgac agtgattcag      3120
aggaaccaag caaatacatc aatgcatctt ttataatgag ctactggaaa cctgaagtga      3180
tgattgctgc tcagggacca ctgaaggaga ccattggtga ctttttggcag atgatcttcc      3240 aaagaaaagt caaagttatt gttatgctga cagaactgaa acatggagac caggaaatct      3300
gtgctcagta ctggggagaa ggaaagcaaa catatggaga tattgaagtt gacctgaaag      3360
acacagacaa atcttcaact tatacccttc gtgtctttga actgagacat tccaagagga      3420
aagactctcg aactgtgtac cagtaccaat atacaaactg gagtgtggag cagcttcctg      3480
cagaacccaa ggaattaatc tctatgatcc aggtcgtcaa acaaaaactt ccccagaaga      3540
attcctctga agggaacaag catcacaaga gtacacctct actcattcac tgcagggatg      3600
gatctcagca acgggaata ttttgtgctt tgttaaatct cttagaaagt gcggaaacag      3660
aagaggtagt ggatatttt caagtggtaa aagctctacg caaagctagg ccaggcatgg      3720
tttccacatt cgagcaatat caattcctat atgacgtcat tgccagcacc taccctgctc      3780
```

```
agaatggaca agtaaagaaa aacaaccatc aagaagataa aattgaattt gataatgaag    3840
tggacaaagt aaagcaggat gctaattgtg ttaatccact tggtgcccca gaaaagctcc    3900
ctgaagcaaa ggaacaggct gaaggttctg aacccacgag tggcactgag gggccagaac    3960
attctgtcaa tggtcctgca agtccagctt taaatcaagg ttcataggaa aagacataaa    4020
tgaggaaact ccaaacctcc tgttagctgt tatttctatt tttgtagaag taggaagtga    4080
aaataggtat acagtggatt aattaaatgc agcgaaccaa tatttgtaga agggttatat    4140
tttactactg tggaaaaata tttaagatag ttttgccaga acagtttgta cagacgtatg    4200
cttattttaa aattttatct cttattcagt aaaaaacaac ttctttgtaa tcgttatgtg    4260
tgtatatgta tgtgtgtatg ggtgtgtgtt tgtgtgagag acagagaaag agagagaatt    4320
ctttcaagtg aatctaaaag cttttgcttt tcctttgttt ttatgaagaa aaaatacatt    4380
ttatattaga agtgttaact tagcttgaag gatctgtttt taaaaatcat aaactgtgtg    4440
cagactcaat aaaatcatgt acatttctga aatgacctca agatgtcctc cttgttctac    4500
tcatatatat ctatcttata tacttactat tttacttcta gagatagtac ataaaggtgg    4560
tatgtgtgtg tatgctacta caaaaaagtt gttaactaaa ttaacattgg gaaatcttat    4620
attccatata ttagcattta gtccaatgtc tttttaagct tatttaatta aaaaatttcc    4680
agtgagctta tcatgctgtc tttacatggg gttttcaatt ttgcatgctc gattattccc    4740
tgtacaatat ttaaaattta ttgcttgata cttttgacaa caaattaggt tttgtacaat    4800
tgaacttaaa taaatgtcat taaaataaat aaatgcaata tgtattaata ttcattgtat    4860
aaaaatagaa gaatacaaac atatttgtta aatatttaca tatgaaattt aatatagcta    4920
tttttatgga atttttcatt gatatgaaaa atatgatatt gcatatgcat agttcccatg    4980
ttaaatccca ttcataactt tcattaaagc atttactttg aatttc                   5026
```

<210> SEQ ID NO 50
<211> LENGTH: 5226
<212> TYPE: DNA
<213> ORGANISM: Homo sapiens

<400> SEQUENCE: 50

```
acacctccct ccccgcctgc cagtgtcacc agcctgttgc ctctgtgaga aagtaccact     60
gtaagaggcc aaagggcatg atcatttttcc tctttcaccc tgtctaggtt gccagcaaat    120
cccacgggcc tcctgacgct gcccctgggg ccacaggtcc ctcgagtgct ggaaggatga    180
aggattcctg catcactgtg atggccatgg cgctgctgtc tgggttcttt tcttcgcgc     240
cggcctcgag ctacaacctg gacgtgcggg gcgcgcggag cttctcccca ccgcgcgccg    300
ggaggcactt tggataccgc gtcctgcagg tcggaaacgg ggtcatcgtg ggagctccag    360
gggagggggaa cagcacagga agcctctatc agtgccagtc gggcacagga cactgcctgc    420
cagtcaccct gagaggttcc aactatacct ccaagtactt gggaatgacc ttggcaacag    480
accccacaga tggaagcatt ttggcctgtg accctgggct gtctcgaacg tgtgaccaga    540
acacctatct gagtggcctg tgttacctct tccgccagaa tctgcagggt cccatgctgc    600
agggggcgccc tggttttcag gaatgtatca agggcaacgt agacctggta tttctgtttg    660
atggttcgat gagcttgcag ccagatgaat tcagaaaaat tctggacttc atgaaggatg    720
tgatgaagaa actcagcaac acttcgtacc agtttgctgc tgttcagttt tccacaagct    780
acaaaacaga atttgatttc tcagattatg ttaaacggaa ggaccctgat gctctgctga    840
```

```
agcatgtaaa gcacatgttg ctgttgacca ataccttggg tgccatcaat tatgtcgcga    900
cagaggtgtt ccgggaggag ctgggggccc ggccagatgc caccaaagtg cttatcatca    960
tcacggatgg ggaggccact gacagtggca acatcgatgc ggccaaagac atcatccgct   1020
acatcatcgg gattggaaag catttcaga ccaaggagag tcaggagacc ctccacaaat    1080
ttgcatcaaa acccgcgagc gagtttgtga aaattctgga cacatttgag aagctgaaag   1140
atctattcac tgagctgcag aagaagatct atgtcattga gggcacaagc aaacaggacc   1200
tgacttcctt caacatggag ctgtcctcca gcggcatcag tgctgacctc agcaggggcc   1260
atgcagtcgt gggggcagta ggagccaagg actgggctgg gggctttctt gacctgaagg   1320
cagacctgca ggatgacaca tttattggga atgaaccatt gacaccagaa gtgagagcag   1380
gctatttggg ttacaccgtg acctggctgc cctcccggca aaagacttcg ttgctggcct   1440
cgggagcccc tcgataccag cacatgggcc gagtgctgct gttccaagag ccacagggcg   1500
gaggacactg gagccaggtc cagacaatcc atgggaccca gattggctct tatttcggtg   1560
gggagctgtg tggcgtcgac gtggaccaag atggggagac agagctgctg ctgattggtg   1620
ccccactgtt ctatggggag cagagaggag gccgggtgtt tatctaccag agaagacagt   1680
tggggtttga agaagtctca gagctgcagg ggaccccgg ctacccactc gggcggtttg    1740
gagaagccat cactgctctg acagacatca acggcgatgg gctggtagac gtggctgtgg   1800
gggcccctct ggaggagcag ggggctgtgt acatcttcaa tgggaggcac ggggggctta   1860
gtccccagcc aagtcagcgg atagaaggga cccaagtgct ctcaggaatt cagtggtttg   1920
gacgctccat ccatggggtg aaggaccttg aaggggatgg cttggcagat gtggctgtgg   1980
gggctgagag ccagatgatc gtgctgagct cccggcccgt ggtggatatg gtcaccctga   2040
tgtccttctc tccagctgag atcccagtgc atgaagtgga gtgctcctat caaccagta    2100
acaagatgaa agaaggagtt aatatcacaa tctgtttcca gatcaagtct ctcatccccc   2160
agttccaagg ccgcctggtt gccaatctca cttacactct gcagctggat ggccaccgga   2220
ccagaagacg ggggttgttc ccaggaggga gacatgaact cagaaggaat atagctgtca   2280
ccaccagcat gtcatgcact gacttctcat tcatttcccc ggtatgtgtt caagacctca   2340
tctcccccat caatgtttcc ctgaatttct ctctttggga ggaggaaggg acaccgaggg   2400
accaaagggc gcagggcaag gacataccgc ccatcctgag accctccctg cactcggaaa   2460
cctgggagat ccctttgag aagaactgtg gggaggacaa gaagtgtgag gcaaacttga    2520
gagtgtcctt ctctcctgca agatccgag ccctgcgtct aactgctttt gccagcctct    2580
ctgtggagct gagcctgagt aacttggaag aagatgctta ctgggtccag ctggacctgc   2640
acttccccc gggactctcc ttccgcaagg tggagatgct gaagcccat agccagatac     2700
ctgtgagctg cgaggagctt cctgaagagt ccaggcttct gtccagggca ttatcttgca   2760
atgtgagctc tccatcttc aaagcaggcc actcggttgc tctgcagatg atgtttaata    2820
cactggtaaa cagctcctgg ggggactcgg ttgaattgca cgccaatgtg acctgtaaca   2880
atgaggactc agacctcctg gaggacaact cagccactac catcatcccc atcctgtacc   2940
ccatcaacat cctcatccag gaccaagaag actccacact ctatgtcagt ttcacccca    3000
aaggccccaa gatccaccaa gtcaagcaca tgtaccaggt gaggatccag ccttccatcc   3060
acgaccacaa cataccccacc ctggaggctg tggttggggt gccacagcct cccagcgagg   3120
ggcccatcac acaccagtgg agcgtgcaga tggagcctcc cgtgccctgc cactatgagg   3180
atctggagag gctcccggat gcagctgagc cttgtctccc cggagccctg ttccgctgcc   3240
```

```
ctgttgtctt caggcaggag atcctcgtcc aagtgatcgg gactctggag ctggtgggag      3300
agatcgaggc ctcttccatg ttcagcctct gcagctccct ctccatctcc ttcaacagca      3360
gcaagcattt ccacctctat ggcagcaacg cctccctggc ccaggttgtc atgaaggttg      3420
acgtggtgta tgagaagcag atgctctacc tctacgtgct gagcggcatc gggggggctgc    3480
tgctgctgct gctcattttc atagtgctgt acaaggttgg tttcttcaaa cggaacctga      3540
aggagaagat ggaggctggc agaggtgtcc cgaatggaat ccctgcagaa gactctgagc      3600
agctggcatc tgggcaagag gctggggatc ccggctgcct gaagcccctc catgagaagg      3660
actctgagag tggtggtggc aaggactgag tccaggcctg tgaggtgcag agtgcccaga      3720
actggactca ggatgcccag ggccactctg cctctgcctg cattctgccg tgtgccctcg      3780
ggcgagtcac tgcctctccc tggccctcag tttccctatc tcgaacatgg aactcattcc      3840
tgcctgtctc ctttgcaggc tcatagggaa gacctgctga gggaccagcc aagagggctg      3900
caaaagtgag ggcttgtcat taccagacgg ttcaccagcc tctcttggtt tccttccttg      3960
gaagagaatg tctgatctaa atgtggagaa actgtagtct caggacctag ggatgttctg      4020
gccctcaccc ctgccctggg atgtccacag atgcctccac cccccagaac ctgtccttgc      4080
acactcccct gcactggagt ccagtctctt ctgctggcag aaagcaaatg tgacctgtgt      4140
cactacgtga ctgtggcaca cgccttgttc ttggccaaag accaaattcc ttggcatgcc      4200
ttccagcacc ctgcaaaatg agaccctcgt ggccttcccc agcctcttct agagccgtga      4260
tgcctccctg ttgaagctct ggtgacacca gcctttctcc caggccaggc tccttcctgt      4320
cttcctgcat tcacccagac agctccctct gcctgaacct tccatctcgc caccCctcct      4380
tccttgacca gcagatccca gctcacgtca cacttggttg ggtcctcaca tctttcacac      4440
ttccaccagc ctgcactact ccctcaaagc acacgtcatg tttcttcatc cggcagcctg      4500
gatgttttt ccctgtttaa tgattgacgt acttagcagc tatctctcag tgaactgtga      4560
gggtaaaggc tatacttgtc ttgttcacct tgggatgatg cctcatgata tgtcagggcg      4620
tgggacatct agtaggtgct tgacataatt tcactgaatt aatgacagag ccagtgggaa      4680
gatacagaaa aagaggggct gggctgggcg cggtggttca cgcctgtaat cccagcactt      4740
tgggaggcca aggagggtgg atcacctgag gtcaggagtt agaggccagc ctggcgaaac      4800
cccatctcta ctaaaaatac aaaatccagg cgtggtggca cacacctgta gtcccagcta      4860
ctcaggaggt tgaggtagga gaattgcttg aacctgggag gtggaggttg cagtgagcca      4920
agattgcgcc attgcactcc agcctgggca acacagcgag actccgtctc aaggaaaaaa      4980
taaaaataaa aagcgggcac gggcccgtga catccccacc cttggaggct gtcttctcag      5040
gctctgccct gccctagctc cacaccctct cccaggaccc atcacgcctg tgcagtggcc      5100
cccacagaaa gactgagctc aaggtgggaa ccacgtctgc taacttggag ccccagtgcc      5160
aagcacagtg cctgcatgta tttatccaat aaatgtgaaa ttctgtccaa aaaaaaaaa      5220
aaaaaa                                                                5226
```

<210> SEQ ID NO 51
<211> LENGTH: 2223
<212> TYPE: DNA
<213> ORGANISM: Homo sapiens

<400> SEQUENCE: 51

```
tctccttgtt ttgctttcga tctggactgt tctcaggcaa gccggggagt aacttttagt       60
```

```
tttgctcctg cgattattca actgacgggc tttcatttcc atttcacaca ccctagcaac    120
acttatacct tgcggaattg tattggtagc gtgaaaaaag cacactgaga gggcaccatg    180
ccggtggaaa ggatgcgcat gcgcccgtgg ctggaggagc agataaactc caacacgatc    240
ccggggctca agtggcttaa caaggaaaag aagattttc agatcccctg gatgcatgcg    300
gctagacatg ggtgggatgt ggaaaaagat gcaccactct ttagaaaccg gcaatccat    360 acaggaaagc atcaaccagg agtagataaa cctgatccca aaacatggaa ggcgaatttc    420
agatgcgcca tgaattcctt gcctgatatt gaagaagtca aggataaaag cataaagaaa    480
ggaaataatg ccttcaggt ctaccgaatg ctgcccctat cagaacggcc ttctaagaaa    540
ggaaagaaac caagacaga aaagaagac aagttaagc acatcaagca agaaccagtt    600
gagtcatctc tggggcttag taatggagta agtgatcttt ctcctgagta tgcggtcctg    660
acttcaacta aaaaaatga agtggatagt acggtgaaca tcatagttgt aggacagtcc    720
catctggaca gcaacattga gaatcaagag attgtcacca atccgccaga catttgccaa    780
gttgtagagg tgaccactga gagcgacgag cagccggtca gcatgagcga gctctaccct    840
ctgcagatct cccccgtgtc ttcctatgca gaaagcgaaa cgactgatag tgtgcccagc    900
gatgaagaga gtgccgaggg gcggccacac tggcggaaga ggaatattga aggcaaacag    960
tacctcagca acatggggac tcgaggctcc tacctgctgc ccggcatggc gtccttcgtc    1020
acttccaaca aaccggacct ccaggtcacc atcaaagagg agagcaatcc ggtgccttac    1080
aacagctcct ggccccctt tcaagacctc cccctttctt cctccatgac cccagcatcc    1140
agcagcagtc ggccagaccg ggagacccgg gccagcgtca tcaagaaaac atcggatatc    1200
acccaggccc gcgtcaagag ctgttaagcc tctgactctc cgcggtggtt gttggggctt    1260
cttggctttg ttttgttgtt tgtttgtatt ttatttttt ctctctgaca cctatttag    1320 acaaatctaa gggaaaaagc cttgacaata gaacattgat tgctgtgtcc aactccagta    1380
cctggagctt ctctttaact caggactcca gcccattggt agacgtgtgt ttctagagcc    1440
tgctggatct cccagggcta ctcactcaag ttcaaggacc aacaagggca gtggaggtgc    1500
tgcattgcct gcggtcaagg ccagcaaggt ggagtggatg cctcagaacg gacgagataa    1560
tgtgaactag ctggaatttt ttattcttgt gaatatgtac ataggcagca ctagcgacat    1620
tgcagtctgc ttctgcacct tatcttaaag cacttacaga taggccttct tgtgatcttg    1680
ctctatctca cagcacactc agcaccccct tctctgccca ttccccagcc tctcttccta    1740
tcccatccca tcccatccca tcccatccca tcccatcccg ctcttttcct acttttcctt    1800
ccctcaaagc ttccattcca catccggagg agaagaagga aatgaatttc tctacagatg    1860 tcccatttc agactgcttt aaaaaaaatc cttctaatct gctatgcttg aatgccacgc    1920
ggtacaaagg aaaaagtatc atggaaatat tatgcaaatt cccagatttg aagacaaaaa    1980
tactctaatt ctaaccagag caagctttt tatttttat acaggggaat attttattca    2040
aggtaaaatt ctaaataaaa tataattgtt ttttatcttt tctacagcaa atttataatt    2100
ttaagattcc ttttcttgtt tatcagcagt tgttattaca tccttgtggc acattttttt    2160
ttaattttgt aaaggtgaaa aaagcttta tgagctcatc tagcaatcag attttcctgt    2220
gga                                                                  2223

<210> SEQ ID NO 52
<211> LENGTH: 1872
<212> TYPE: DNA
<213> ORGANISM: Homo sapiens
```

<400> SEQUENCE: 52

```
ttaattacaa aaactaatga ctaagagaga ggtggctaga gctgaggccc ctgagtcagg      60
ctgtgggtgg gatcatctcc agtacaggaa gtgagacttt catttcctcc tttccaagag     120
agggctgagg gagcagggtt gagcaactgg tgcagacagc ctagctggac tttgggtgag     180
gcggttcagc catgaggctg gctgtgcttt tctcggggc cctgctgggg ctactggcag      240
cccaggggac agggaatgac tgtcctcaca aaaatcagc tactttgctg ccatccttca      300
cggtgacacc cacggttaca gagagcactg gaacaaccag ccacaggact accaagagcc     360
acaaaaccac cactcacagg acaaccacca caggcaccac cagccacgga cccacgactg     420
ccactcacaa ccccaccacc accagccatg gaaacgtcac agttcatcca acaagcaata     480
gcactgccac cagccaggga ccctcaactg ccactcacag tcctgccacc actagtcatg     540
gaaatgccac ggttcatcca acaagcaaca gcactgccac cagcccagga ttcaccagtt     600
ctgcccaccc agaaccacct ccaccctctc cgagtcctag cccaacctcc aaggagacca     660
ttggagacta cacgtggacc aatggttccc agccctgtgt ccacctccaa gcccagattc     720
agattcgagt catgtacaca acccaggtg aggagaggc ctggggcatc tctgtactga       780
accccaacaa aaccaaggtc cagggaagct gtgagggtgc ccatccccac ctgcttctct     840
cattccccta tggacacctc agctttggat tcatgcagga cctccagcag aaggttgtct     900
acctgagcta catggcggtg gagtacaatg tgtccttccc ccacgcagca cagtggacat     960
tctcggctca gaatgcatcc cttcgagatc tccaagcacc cctggggcag agcttcagtt    1020
gcagcaactc gagcatcatt cttttcaccag ctgtccacct cgacctgctc tccctgaggc   1080
tccaggctgc tcagctgccc cacacagggg tctttgggca aagtttctcc tgccccagtg    1140
accggtccat cttgctgcct ctcatcatcg gcctgatcct tcttggcctc ctcgccctgg    1200
tgcttattgc tttctgcatc atccggagac gcccatccgc ctaccaggcc ctctgagcat    1260
ttgcttcaaa ccccagggca ctgaggggt tggggtgtgg tgggggggta cccttatttc     1320
ctcgacacgc aactggctca aagacaatgt tattttcctt cccttcttg aagaacaaaa     1380
agaaagccgg gcatgacggc tcatgcctgt aatcccagca ctttgggagg ctgaggcagg    1440
tggatcactg gaggtcagga gtttgagacc agcctggcca acatggtgaa accctgtctc    1500
tactaaaat acaattagcc aggtgtggcg gcgtaatccc agctggcctg taatcccagc     1560
tacttgggag gctgaggcag aactgcttga acccaggagg tggaggttgc agtgagccgt    1620
catcgcgcca ctaagccaag atcgcgccac tgcactccag cctgggcgac agagccagac    1680
tgtctcaaat aaataaatat gagataatgc agtcgggaga agggagggag agaattttat    1740
taaatgtgac gaactgcccc cccccccccc ccagcaggag agcagcaaaa tttatgcaaa    1800
tcttgacgg ggttttcctt gtcctgccag gattaaaagc catgagtttc ttgtcaaaaa     1860
aaaaaaaaaa aa                                                        1872
```

<210> SEQ ID NO 53
<211> LENGTH: 4992
<212> TYPE: DNA
<213> ORGANISM: Homo sapiens

<400> SEQUENCE: 53

```
gaagactcca gatataggat cactccatgc catcaagaaa gttgatgcta ttgggcccat      60
ctcaagctga tcttggcacc tctcatgctc tgctctcttc aaccagacct ctacattcca     120
```

-continued

```
ttttggaaga agactaaaaa tggtgtttcc aatgtggaca ctgaagagac aaattcttat    180
ccttttttaac ataatcctaa tttccaaact ccttggggct agatggtttc ctaaaactct   240
```



```
ttttggaaga agactaaaaa tggtgtttcc aatgtggaca ctgaagagac aaattcttat    180
ccttttaac  ataatcctaa tttccaaact ccttggggct agatggtttc ctaaaactct    240
gccctgtgat gtcactctgg atgttccaaa gaaccatgtg atcgtggact gcacagacaa    300
gcatttgaca gaaattcctg gaggtattcc cacgaacacc acgaacctca ccctcaccat    360
taaccacata ccagacatct ccccagcgtc ctttcacaga ctggaccatc tggtagagat    420
cgatttcaga tgcaactgtg tacctattcc actggggtca aaaacaaca  tgtgcatcaa    480
gaggctgcag attaaaccca gaagctttag tggactcact tatttaaaat ccctttacct    540
ggatggaaac cagctactag atataccgca gggcctcccg cctagcttac agcttctcag    600
ccttgaggcc aacaacatct tttccatcag aaaagagaat ctaacagaac tggccaacat    660
agaaatactc tacctgggcc aaaactgtta ttatcgaaat ccttgttatg tttcatattc    720
aatagagaaa gatgccttcc taaacttgac aaagttaaaa gtgctctccc tgaaagataa    780
caatgtcaca gccgtcccta ctgttttgcc atctacttta acagaactat atctctacaa    840
caacatgatt gcaaaaatcc aagaagatga ttttaataac ctcaaccaat tacaaattct    900
tgacctaagt ggaaattgcc ctcgttgtta taatgcccca tttccttgtg cgccgtgtaa    960
aaataattct cccctacaga tccctgtaaa tgcttttgat gcgctgacag aattaaaagt   1020
tttacgtcta cacagtaact ctcttcagca tgtgccccca agatggttta agaacatcaa   1080
caaactccag gaactggatc tgtcccaaaa cttcttggcc aaagaaattg gggatgctaa   1140
atttctgcat tttctcccca gcctcatcca attggatctg tctttcaatt ttgaacttca   1200
ggtctatcgt gcatctatga atctatcaca agcattttct tcactgaaaa gcctgaaaat   1260
tctgcggatc agaggatatg tctttaaaga gttgaaaagc tttaacctct cgccattaca   1320
taatcttcaa aatcttgaag ttcttgatct tggcactaac tttataaaaa ttgctaacct   1380
cagcatgttt aaacaattta aaagactgaa agtcatagat ctttcagtga ataaaatatc   1440
accttcagga gattcaagtg aagttggctt ctgctcaaat gccagaactt ctgtagaaag   1500
ttatgaaccc caggtcctgg aacaattaca ttatttcaga tatgataagt atgcaaggag   1560
ttgcagattc aaaaacaaag aggcttcttt catgtctgtt aatgaaagct gctacaagta   1620
tgggcagacc ttggatctaa gtaaaaatag tatatttttt gtcaagtcct ctgattttca   1680
gcatctttct ttcctcaaat gcctgaatct gtcaggaaat ctcattagcc aaactcttaa   1740
tggcagtgaa ttccaacctt tagcagagct gagatatttg gacttctcca caaccggct   1800
tgatttactc cattcaacag catttgaaga gcttcacaaa ctggaagttc tggatataag   1860
cagtaatagc cattattttc aatcagaagg aattactcat atgctaaact ttaccaagaa   1920
cctaaaggtt ctgcagaaac tgatgatgaa cgacaatgac atctcttcct ccaccagcag   1980
gaccatggag agtgagtctc ttagaactct ggaattcaga ggaaatcact tagatgtttt   2040
atggagagaa ggtgataaca gatacttaca attattcaag aatctgctaa aattagagga   2100
attagacatc tctaaaaatt ccctaagttt cttgccttct ggagttttg  atggtatgcc   2160
tccaaatcta aagaatctct ctttggccaa aaatgggctc aaatctttca gttggaagaa   2220
actccagtgt ctaaagaacc tggaaacttt ggacctcagc acaaccaac  tgaccactgt   2280
ccctgagaga ttatccaact gttccagaag cctcaagaat ctgattctta agaataatca   2340
aatcaggagt ctgacgaagt attttctaca agatgccttc agttgcgat  atctggatct   2400
cagctcaaat aaaatccaga tgatccaaaa gaccagcttc ccagaaaatg tcctcaacaa   2460
tctgaagatg ttgcttttgc atcataatcg gtttctgtgc acctgtgatg ctgtgtggtt   2520
```

```
tgtctggtgg gttaaccata cggaggtgac tattccttac ctggccacag atgtgacttg    2580
tgtggggcca ggagcacaca agggccaaag tgtgatctcc ctggatctgt acacctgtga    2640
gttagatctg actaacctga ttctgttctc actttccata tctgtatctc tctttctcat    2700
ggtgatgatg acagcaagtc acctctattt ctgggatgtg tggtatattt accatttctg    2760
taaggccaag ataaaggggt atcagcgtct aatatcacca gactgttgct atgatgcttt    2820
tattgtgtat gacactaaag acccagctgt gaccgagtgg gttttggctg agctggtggc    2880
caaactggaa gacccaagag agaaacattt taatttatgt ctcgaggaaa gggactggtt    2940
accagggcag ccagttctgg aaaacctttc ccagagcata cagcttagca aaagacagt     3000
gtttgtgatg acagacaagt atgcaaagac tgaaaatttt aagatagcat tttacttgtc    3060
ccatcagagg ctcatggatg aaaaagttga tgtgattatc ttgatatttc ttgagaagcc    3120
cttcagaag tccaagttcc tccagctccg gaaaaggctc tgtgggagtt ctgtccttga     3180
gtggccaaca aacccgcaag ctcacccata cttctggcag tgtctaaaga acgccctggc    3240
cacagacaat catgtggcct atagtcaggt gttcaaggaa acggtctagc ccttctttgc    3300
aaaacacaac tgcctagttt accaaggaga ggcctggctg tttaaattgt tttcatatat    3360
atcacaccaa aagcgtgttt tgaaattctt caagaaatga gattgcccat atttcagggg    3420
agccaccaac gtctgtcaca ggagttggaa agatgggtt tatataatgc atcaagtctt     3480
cttcttatc tctctgtgtc tctatttgca cttgagtctc tcacctcagc tcctgtaaaa     3540
gagtggcaag taaaaaacat ggggctctga ttctcctgta attgtgataa ttaaatatac    3600
acacaatcat gacattgaga agaactgcat ttctacccct aaaaagtact ggtatataca    3660
gaaatagggt taaaaaaaac tcaagctctc tctatatgag accaaaatgt actagagtta    3720
gtttagtgaa ataaaaaacc agtcagctgg ccgggcatgg tggctcatgc ttgtaatccc    3780
agcactttgg gaggccgagg caggtggatc acgaggtcag gagtttgaga ccagtctggc    3840
caacatggtg aaaccccgtc tgtactaaaa atacaaaaat tagctgggcg tggtggtggg    3900
tgcctgtaat cccagctact tgggaggctg aggcaggaga atcgcttgaa cccgggaggt    3960
ggaggtggca gtgagccgag atcacgccac tgcaatgcag cccgggcaac agagctagac    4020
tgtctcaaaa gaacaaaaaa aaaaaaacac aaaaaaactc agtcagcttc ttaaccaatt    4080
gcttccgtgt catccagggc cccattctgt gcagattgag tgtgggcacc acacaggtgg    4140
ttgctgcttc agtgcttcct gctctttttc cttgggcctg cttctgggtt ccatagggaa    4200
acagtaagaa agaaagacac atccttacca taaatgcata tggtccacct acaaatagaa    4260
aaatatttaa atgatctgcc tttatacaaa gtgatattct ctacctttga taatttacct    4320
gcttaaatgt tttatctgc actgcaaagt actgtatcca agtaaaatt tcctcatcca      4380
atatctttca aactgttttg ttaactaatg ccatatattt gtaagtatct gcacacttga    4440
tacagcaacg ttagatggtt ttgatggtaa accctaaagg aggactccaa gagtgtgtat    4500
ttatttatag ttttatcaga gatgacaatt atttgaatgc caattatatg gattcctttc    4560
attttttgct ggaggatggg agaagaaacc aaagtttata gaccttcaca ttgagaaagc    4620
ttcagttttg aacttcagct atcagattca aaaacaacag aaagaaccaa gacattctta    4680
agatgcctgt actttcagct gggtataaat tcatgagttc aaagattgaa acctgaccaa    4740
tttgctttat ttcatggaag aagtgatcta caaaggtgtt tgtgccattt ggaaaacagc    4800
gtgcatgtgt tcaagcctta gattggcgat gtcgtatttt cctcacgtgt ggcaatgcca    4860
```

| | |
|---|---|
| aaggctttac tttacctgtg agtacacact atatgaatta tttccaacgt acatttaatc | 4920 |
| aataagggtc acaaattccc aaatcaatct ctggaataaa tagagaggta attaaattgc | 4980 |
| tggagccaac ta | 4992 |

<210> SEQ ID NO 54
<211> LENGTH: 1567
<212> TYPE: DNA
<213> ORGANISM: Homo sapiens

<400> SEQUENCE: 54

| | |
|---|---|
| gtcgtcacag catgatcata ttttttcacc cttcacttct ccttttacac aaatagcccc | 60 |
| ggatatctgt gttaccagcc ttgtctcggc cacctcaagg ataatcacta aattctgccg | 120 |
| aaaggactga ggaacggtgc ctggaaaagg gcaagaatat cacggcatgg gcatgagtag | 180 |
| cttgaaactg ctgaagtatg tcctgttttt cttcaacttg ctcttttgga tctgtggctg | 240 |
| ctgcattttg ggctttggga tctacctgct gatccacaac aacttcggag tgctcttcca | 300 |
| taacctcccc tccctcacgc tgggcaatgt gttttgtcatc gtgggctcta ttatcatggt | 360 |
| agttgccttc ctgggctgca tgggctctat caaggaaaac aagtgtctgc ttatgtcgtt | 420 |
| cttcatcctg ctgctgatta tcctccttgc tgaggtgacc ttggccatcc tgctctttgt | 480 |
| atatgaacag aagctgaatg agtatgtggc taagggtctg accgacagca tccaccgtta | 540 |
| ccactcagac aatagcacca aggcagcgtg ggactccatc cagtcatttc tgcagtgttg | 600 |
| tggtataaat ggcacgagtg attggaccag tgcccacca gcatcttgcc cctcagatcg | 660 |
| aaaagtggag ggttgctatg cgaaagcaag actgtggttt cattccaatt tcctgtatat | 720 |
| cggaatcatc accatctgtg tatgtgtgat tgaggtgttg gggatgtcct ttgcactgac | 780 |
| cctgaactgc cagattgaca aaaccagcca gaccataggg ctatgatctg cagtagtcct | 840 |
| gtggtgaaga gacttgtttc atctccggaa atgcaaaacc atttatagca tgaagcccta | 900 |
| catgatcact gcaggatgat cctcctccca tcctttccct ttttaggtcc ctgtcttata | 960 |
| caaccagaga agtgggtgtt ggccaggcac atcccatctc aggcagcaag acaatctttc | 1020 |
| actcactgac ggcagcagcc atgtctctca aagtggtgaa actaatatct gagcatcttt | 1080 |
| tagacaagag aggcaaagac aaactggatt taatggccca acatcaaagg gtgaacccag | 1140 |
| gatatgaatt tttgcatctt cccattgtcg aattagtctc cagcctctaa ataatgccca | 1200 |
| gtcttctccc caaagtcaag caagagacta gttgaaggga gttctggggc caggctcact | 1260 |
| ggaccattgt cacaaccctc tgtttctctt tgactaagtg ccctggctac aggaattaca | 1320 |
| cagttctctt tctccaaagg gcaagatctc atttcaattt ctttattaga gggccttatt | 1380 |
| gatgtgttct aagtctttcc agaaaaaaac tatccagtga tttatatcct gatttcaacc | 1440 |
| agtcacttag ctgataatca cagtaagaag acttctggta ttatctctct atcagataag | 1500 |
| attttgttaa tgtactattt tactcttcaa taaataaaag tttattatct caatcacaac | 1560 |
| attgcta | 1567 |

<210> SEQ ID NO 55
<211> LENGTH: 2277
<212> TYPE: DNA
<213> ORGANISM: Homo sapiens

<400> SEQUENCE: 55

| | |
|---|---|
| gactgcgcgg cggcaacagc agacatgtcg ggggtccggg gcctgtcgcg gctgctgagc | 60 |
| gctcggcgcc tggcgctggc caaggcgtgg ccaacagtgt tgcaaacagg aacccgaggt | 120 |

```
tttcacttca ctgttgatgg gaacaagagg gcatctgcta aagtttcaga ttccatttct    180
gctcagtatc cagtagtgga tcatgaattt gatgcagtgg tggtaggcgc tggagggggca   240
ggcttgcgag ctgcatttgg cctttctgag gcagggttta atacagcatg tgttaccaag    300
ctgtttccta ccaggtcaca cactgttgca gcgcagggag gaatcaatgc tgctctgggg    360
aacatggagg aggacaactg gaggtggcat ttctacgaca ccgtgaaggg ctccgactgg    420
ctgggggacc aggatgccat ccactacatg acggagcagg cccccgccgc cgtggtcgag    480
ctagaaaatt atggcatgcc gtttagcaga actgaagatg gaagatttta tcagcgtgca    540
tttggtggac agagcctcaa gtttggaaag ggcgggcagg cccatcggtg ctgctgtgtg    600
gctgatcgga ctggccactc gctattgcac accttatatg gacggtctct gcgatatgat    660
accagctatt ttgtggagta ttttgccttg gatctcctga tggagaacgg ggagtgccgt    720
ggtgtcatcg cactgtgcat agaggacggg tccatccatc gcataagagc aaagaacact    780
gttgttgcca caggaggcta cgggcgcacc tacttcagct gcacgtctgc ccacaccagc    840
actggcgacg gcacggccat gatcaccagg gcaggccttc cttgccagga cctagagttt    900
gttcagttcc accccacagg catatatggt gctggttgtc tcattacgga aggatgtcgt    960
ggagagggag gcattctcat taacagtcaa ggcgaaaggt ttatggagcg atacgcccct   1020
gtcgcgaagg acctggcgtc tagagatgtg gtgtctcggt cgatgactct ggagatccga   1080
gaaggaagag gctgtggccc tgagaaagat cacgtctacc tgcagctgca ccacctacct   1140
ccagagcagc tggccacgcg cctgcctggc atttcagaga cagccatgat cttcgctggc   1200
gtggacgtca cgaaggagcc gatccctgtc ctccccaccg tgcattataa catgggcggc   1260
attcccacca actacaaggg gcaggtcctg aggcacgtga atggccagga tcagattgtg   1320
cccggcctgt acgcctgtgg ggaggccgcc tgtgcctcgg tacatggtgc caaccgcctc   1380
ggggcaaact cgctcttgga cctggttgtc tttggtcggg catgtgccct gagcatcgaa   1440
gagtcatgca ggcctggaga taaagtccct ccaattaaac caaacgctgg ggaagaatct   1500
gtcatgaatc ttgacaaatt gagatttgct gatggaagca taagaacatc ggaactgcga   1560
ctcagcatgc agaagtcaat gcaaaatcat gctgccgtgt tccgtgtggg aagcgtgttg   1620
caagaaggtt gtgggaaaat cagcaagctc tatggagacc taaagcacct gaagacgttc   1680
gaccggggaa tggtctggaa cacagacctg gtggagaccc tggagctgca gaacctgatg   1740
ctgtgtgcgc tgcagaccat ctacggagca gaggcgcgga aggagtcacg gggcgcgcat   1800
gccagggaag actacaaggt gcggattgat gagtacgatt actccaagcc catccagggg   1860
caacagaaga gcccttttga ggagcactgg aggaagcaca ccctgtcctt tgtggacgtt   1920
ggcactggga aggtcactct ggaatataga cccgtaatcg acaaaacttt gaacgaggct   1980
gactgtgcca ccatcccgcc agccattcgc tcctactgat gagacaagat gtggtgatga   2040
cagaatcagc ttttgtaatt atgtataata gctcatgcat gtgtccatgt cataactgtc   2100
ttcatacgct tctgcactct ggggaagaag gagtacattg aagggagatt ggcacctagt   2160
ggctgggagc ttgccaggaa cccagtggcc agggagcgtg gcacttacct ttgtcccttg   2220
cttcattctt gtgagatgat aaaactgggc acagctctta aataaaatat aaatgag      2277
```

<210> SEQ ID NO 56
<211> LENGTH: 2325
<212> TYPE: DNA
<213> ORGANISM: Homo sapiens

<400> SEQUENCE: 56

```
cgaaaaggag ggtgactctc ctcggcgggg gcttcgggtg acatcacatc ctccaaatgc      60
gaaatcaggc tccgggccgg ccgaagggcg caactttccc ccctcggcgc cccaccggct     120
cccgcgcgcc tccctcgcg cccgagcttc gagccaagca gcgtcctggg gagcgcgtca     180
tggccttacc agtgaccgcc ttgctcctgc cgctggcctt gctgctccac gccgccaggc     240
cgagccagtt ccgggtgtcg ccgctggatc ggacctggaa cctgggcgag acagtggagc     300
tgaagtgcca ggtgctgctg tccaacccga cgtcgggctg ctcgtggctc ttccagccgc     360
gcggcgccgc cgccagtccc accttcctcc tatacctctc ccaaaacaag cccaaggcgg     420
ccgaggggct ggacacccag cggttctcgg gcaagaggtt ggggacacc ttcgtcctca     480
ccctgagcga cttccgccga gagaacgagg gctactattt ctgctcggcc ctgagcaact     540
ccatcatgta cttcagccac ttcgtgccgg tcttcctgcc agcgaagccc accacgacgc     600
cagcgccgcg accaccaaca ccggcgccca ccatcgcgtc gcagcccctg tccctgcgcc     660
cagaggcgtg ccgccagcg gcgggggcg cagtgcacac gaggggctg gacttcgcct     720
gtgatatcta catctgggcg cccttggccg ggacttgtgg ggtccttctc ctgtcactgg     780
ttatcaccct ttactgcaac cacaggaacc gaagacgtgt tgcaaatgt ccccggcctg     840
tggtcaaatc gggagacaag cccagccttt cggcgagata cgtctaaccc tgtgcaacag     900
ccactacatt acttcaaact gagatccttc cttttgaggg agcaagtcct tcccttcat     960
ttttccagt cttcctccct gtgtattcat tctcatgatt attattttag tgggggcggg    1020
gtgggaaaga ttactttttc tttatgtgtt tgacgggaaa caaaactagg taaaatctac    1080
agtacaccac aagggtcaca atactgttgt gcgcacatcg cggtagggcg tggaaagggg    1140
caggccagag ctaccgcag agttctcaga atcatgctga gagagctgga ggcacccatg    1200
ccatctcaac ctcttccccg cccgttttac aaaggggag gctaaagccc agagacagct    1260
tgatcaaagg cacacagcaa gtcagggttg gagcagtagc tggagggacc ttgtctccca    1320
gctcagggct ctttcctcca caccattcag gtctttcttt ccgaggcccc tgtctcaggg    1380
tgaggtgctt gagtctccaa cggcaaggga acaagtactt cttgatacct gggatactgt    1440
gcccagagcc tcgaggaggt aatgaattaa agaagagaac tgcctttggc agagttctat    1500
aatgtaaaca atatcagact ttttttttttt ataatcaagc ctaaaattgt atagacctaa    1560
aataaaatga agtggtgagc ttaaccctgg aaaatgaatc cctctatctc taaagaaaat    1620
ctctgtgaaa cccctatgtg gaggcggaat tgctctccca gcccttgcat tgcagagggg    1680
cccatgaaag aggacaggct accccttta c aaatagaatt tgagcatcag tgaggttaaa    1740
ctaaggccct cttgaatctc tgaatttgag atacaaacat gttcctggga tcactgatga    1800
cttttttatac tttgtaaaga caattgttgg agagccctc acacagccct ggcctctgct    1860
caactagcag atacagggat gaggcagacc tgactctctt aaggaggctg agagcccaaa    1920
ctgctgtccc aaacatgcac ttccttgctt aaggtatggt acaagcaatg cctgcccatt    1980
ggagagaaaa aacttaagta gataaggaaa taagaaccac tcataattct tcaccttagg    2040
aataatctcc tgttaatatg gtgtacattc ttcctgatta ttttctacac atacatgtaa    2100
aatatgtctt tctttttaa atagggttgt actatgctgt tatgagtggc tttaatgaat    2160
aaacatttgt agcatcctct ttaatgggta aacagcatcc gaaaaaaaaa aaaaaaaaa    2220
aaaaaaaaaa aaaaaaaaaa aaaaaaaaaa aaaaaaaaaa aaaaaaaaaa aaaaaaaaaa    2280
aaaaaaaaaa aaaaaaaaaa aaaaaaaaaa aaaaaaaaaa aaaaa                    2325
```

<210> SEQ ID NO 57
<211> LENGTH: 5968
<212> TYPE: DNA
<213> ORGANISM: Homo sapiens

<400> SEQUENCE: 57

| | | | | | |
|---|---|---|---|---|---|
| gactttggcc | ggatgactcc | ccagggtcgg | catcagcgtg | ggactgggaa | caggtgaagg | 60 |
| gaaacagaag | agagcctgag | aagaccgctc | tcctccgatc | ctaattgact | gagccaatga | 120 |
| gagccaaaga | ggtcacatgc | tcaactgggc | ggggagcggg | tttccacctg | cggcatcttt | 180 |
| cgcgagcggg | gagatgagtg | gggcggaata | tgggagaaag | ggagggcccg | ccacgctctg | 240 |
| gctggacacg | gccttaatcg | gcccgttcac | tcgacgtttt | tggttctacg | ttgaccccga | 300 |
| gaaaccgaaa | ccgcagggcc | tagggcgggt | ggaacgagag | ggaactacat | ttcccagcag | 360 |
| gctgcggaaa | cgggactgcg | gccactactt | ccggcgtgta | ccgagagact | ggcgtccggc | 420 |
| gtgtaccgag | agactggcgt | ccggtgtgca | ggtggccaca | tggatcctgg | cagccggtgg | 480 |
| cggaacctgc | ccagcgggcc | tagcctaaag | cacttgactg | accctctta | tggaatcccg | 540 |
| cgggaacagc | aaaaggcagc | gttgcaggag | ctgacgcggg | cgcacgtgga | gtccttcaac | 600 |
| tacgctgtgc | acgagggtct | cggcctcgcg | gtgcaggcta | tacctcccctt | tgaatttgct | 660 |
| ttcaaagatg | agcgtatctc | ttttactatt | ctggatgctg | ttatcagtcc | acctacagtt | 720 |
| ccaaaaggga | ccatctgcaa | agaggccaat | gtttatccag | cagaatgccg | gggccgaagg | 780 |
| agtacctacc | gtgggaagtt | gacagctgat | atcaactggg | cagtgaatgg | aatctcaaaa | 840 |
| ggaatcatta | agcagtttct | tggctatgtt | cccatcatgg | tgaaatccaa | gctttgcaac | 900 |
| ttacgtaacc | ttcccccaca | agccctcatt | gagcaccatg | aggaggcaga | ggaaatgggg | 960 |
| ggctatttta | taatcaatgg | cattgaaaaa | gtcatccgaa | tgttgattat | gcctcggaga | 1020 |
| aattttccca | ttgcaatgat | aagaccaaaa | tggaaaacca | gagggcctgg | ttatactcag | 1080 |
| tatggagttt | caatgcactg | tgtgagggaa | gaacattccg | ctgtcaatat | gaacctccac | 1140 |
| tacttggaaa | atggcacagt | tatgttgaac | tttatttacc | gaaaagaact | gttctttctt | 1200 |
| cctttgggat | ttgcacttaa | ggcacttgtc | agcttttctg | attatcagat | cttttcaggag | 1260 |
| ctcatcaaag | gaaaagagga | tgattctttc | cttaggaact | ctgtttctca | gatgttaagg | 1320 |
| attgtaatgg | aagagggttg | ttcgacacaa | aaacaggtcc | ttaactacct | aggtgaatgc | 1380 |
| ttcagagtaa | aactcaatgt | tcctgactgg | tacccaaatg | agcaagctgc | ggagttcctg | 1440 |
| tttaaccagt | gcatctgtat | ccacttgaaa | tccaatactg | aaaagttta | tatgctttgt | 1500 |
| ctcatgacgc | gaaagctctt | tgctttagcc | aaaggagagt | gcatggagga | caatcctgat | 1560 |
| agttggtga | accaggaagt | cctcacaccg | ggtcagctct | tccttatgtt | cctgaaggaa | 1620 |
| aaactggaag | gttggttagt | gtctattaaa | atagcttttg | ataagaaggc | tcagaagacc | 1680 |
| agtgtttcca | tgaacactga | caatttgatg | aggattttta | caatgggcat | agaccttaca | 1740 |
| aaaccatttg | aatacctttt | tgctactggg | aatctgcgtt | ctaaaacagg | tcttggcctc | 1800 |
| ctacaagatt | ctggactttg | tgttgtggct | gacaagctga | acttcatacg | ctacctctcc | 1860 |
| catttccgct | gcgtgcacag | aggggctgat | tttgccaaga | tgaggaccac | cacagtacgc | 1920 |
| aggctgctgc | cagagtcctg | gggcttcctt | tgtccgtgc | ataccccaga | cggggagccc | 1980 |
| tgtggcctga | tgaaccacct | aactgccgta | tgtgaggttg | tcacacagtt | tgtgtatacg | 2040 |
| gcatctattc | cagctttact | gtgcaacttg | ggggtcactc | ccattgatgg | agctccccac | 2100 |

```
cgatcataca gtgagtgcta ccctgtcctg ctggacggtg tcatggttgg ctgggtggat    2160
aaggatcttg ctccaggcat cgcagattct cttcgtcatt ttaaggtgtt gagagagaaa    2220
agaattcctc cctggatgga agtggtcctt atacccatga caggaaaacc aagtctgtac    2280
ccaggattgt tccttttac cactccttgt agactggtac ggcctgtgca gaacttagca     2340
ttgggcaaag aagagctaat tggaactatg aaacagatct tcatgaatgt cgctatcttt    2400
gaggatgaag tttttgctgg agttaccaca caccaggaac tctttccaca cagcctgctg    2460
agtgtgattg ccaacttcat ccctttctct gatcacaacc agagtccacg aacatgtac     2520 caatgccaga tgggtaagca aactatgggc tttccacttc tcacttatca agaccgatcg    2580
gataacaaac tgtatcgtct tcagactcct cagagtccct tggtgagacc ctccatgtat    2640
gattattatg acatggataa ctatccaatt gggaccaatg ccatcgttgc tgtgatttct    2700
tacactggct atgatatgga agatgccatg attgtgaata aggcctcttg gaacgaggc     2760 tttgcccatg gaagtgtcta caagtctgag ttcatagacc tctctgaaaa aattaaacaa    2820
ggagatagta gcctggtgtt tggcatcaaa cctggtgacc cacgcgttct gcagaagtta    2880
gatgacgatg gattgccgtt tataggagca aaactgcagt acggagatcc gtattacagc    2940
tacctcaacc tcaacaccgg ggaaagtttt gtgatgtact ataagagtaa agaaaattgt    3000
gttgtggata acatcaaagt gtgcagtaat gacactggga gtggaaaatt caagtgtgtt    3060
tgcatcacta tgagagtgcc tcggaaccca actatcggag ataaatttgc cagtcgccat    3120
gggcagaagg gcattttaag cagattgtgg ccggctgagg acatgccttt tactgagagt    3180
gggatggtcc cagacattct gttcaatccc catggttttc catcccgcat gaccattggg    3240
atgttaattg agagtatggc cgggaagtct gcagctttgc atggtctctg ccatgatgct    3300
acacccttca tcttctcaga ggagaactcg gccttagaat actttggtga gatgttaaag    3360
gctgctggct acaatttcta tggcaccgag aggttatata gtggcatcag tgggctagaa    3420
ctggaagcag acatcttcat aggagtggtt tattatcagc gcttacgcca tatggtctca    3480
gacaaatttc aagtaaggac aactggagcc cgagacagag tcaccaacca gcctattggg    3540
ggaagaaatg tccagggtgg aatccgtttt ggggagatgg aacgggatgc gcttttagct    3600
catggtacat cttttctcct tcatgaccgc ctcttcaact gctcagatcg gtcggtagcc    3660
catgtgtgtg tgaagtgtgg cagtttactc tctccactgt tggagaagcc accccttct    3720 tggtctgcca tgcgcaacag aaaatacaac tgtactctgt gtagtcgcag tgacactatc    3780
gatactgttt ctgtgcctta tgttttcgg tattttgtag ctgaactggc agctatgaac     3840
atcaaagtga aactggatgt tgtttaactt gatgttgacc ttttggatta agaggactat    3900
cagattaaag caaaatgtaa ttttaattca atgaagatat cattaccagg ttactcttga    3960
gatttttcaa cggtgttaga actctcaacc aagacctgaa aaccaagtat gcaaggtttc    4020
tgaatctctc tggtagatta actattgaca atgattttct gttatctttg ttcaaaaagt    4080
tcatgtcttc tcaaaatatg aaatattgat aaatggaaga gcatacggtg acaagtctcc    4140
tttccaaccc caggttccct acaccctgct ctcagcaggc agtgagtgtc acacacctgt    4200
taatccatct tgagcaggac agtactatac aaatagaatg caagctgtaa tgtaatttta    4260
tattttctta tagccacgtt gaagtaaaaa caaacaggta cagtgttttt taccagcttt    4320
atagaagtac agttgttaca tatttaatga atacaatttg atgggtctga ctatatgcac    4380
acacctttga taccatcacc acaatcaggg taataaacat acctgtcatc tccacaagtt    4440
tcctcctgcc cctttgtttt ttgctttttg gttgctgttg agttttgtt ttgtcttctg      4500
```

```
tggtaagaac acttaactca agacctaccc tcttaacaaa tctttaagtg cacgatatag    4560
tattgttaat tccaggcacc atgttgtaca acagatcttt agaccttact tgtcttgcat    4620
aactgaagct ttatacctgt tgaacaactc tccatttccc tggcccctag caaccaccct    4680
tctaccctgt ttctatgagt ttgactatta cagatatctc atatagtggg atcatgcaat    4740
atttgtcctg tgactggctt atttcactta gcatagtgaa ataagattca tccattttgg    4800
aagccaggca tggtgctgtg catctatagt ccctgctatt tgagaggctg aggtgggagg    4860
atcatttgag tgcaggagtt caaggacagc ctgggtaata taggaagacc ctgtcttgaa    4920
gaccctgacc tcaagtgatc cacccacctc ggcctccgaa agtgctagga ttacaggtgt    4980
gagccactgt gcctggcctc cggtgagtat tttatattta gtctacactt ccatacttgg    5040
cttttttctg cttttatatt gatctgcttt catagcagtg tgtagagtgc acttatgtt     5100 ttctttcttg tgtacagtat tttattgtat ggatttacca tccctgtgt atttaagttg     5160 ttccattctt tggccattat aacttttttc tgcaaatatt ctggtgactt atctttggcc    5220
attataaact gttgataata gatcatcttg tatatacttc tgcaattata agatgttttt    5280
tgatgatgaa agctttccta aggtaattct ttcctgagtt tggttcagat ggtctgtcac    5340
taattataag gcagatagga acagacagaa aaatctatca tttcaagata ggcttagcag    5400
gatgggcgca gtggctcacg ccactaatcc caacatttta ggaggcctag caggagcaa     5460 tcacttgtgc ctgggagttc tagactagcc tgggcgagac ttcatctcta caaaaaagc    5520 aacaacgaca aaaaattag ccaagcatag tggcacaccc ctgtagtccc agctacttgg     5580
gaggctgagg tgggaggatt gcttgaaccc aagaggtcga ggctgcagtg agccaagatt    5640
gtgccactgc actccagcct gggtgacaga gcaggaccct gtctctattt tataaattaa    5700
aaagggctgg gtgtggtggc tcacacccat aatcccaaca ctttggctca gcagattgct    5760
tgaacccagg aattcaagtc caatctgggc aacatgggga accccagct ctacaaaaaa     5820 aattagcctg gtgtggtggc acatgcctgt agttccagct actcaggagg ctgaggtggg    5880
agaatctcct gagcctggaa ggtccaggca gtgagccaag attgtgccac cacactccag    5940
cctgggcgac agaatgagac cctgtctc                                      5968

<210> SEQ ID NO 58
<211> LENGTH: 6202
<212> TYPE: DNA
<213> ORGANISM: Homo sapiens

<400> SEQUENCE: 58
gaattccggc gtcgcggacg catcccagtc tgggcgggac gctcggccgc ggcgaggcgg     60
gcaagcctgg cagggcagag ggagcccggg ctccgaggtt gctcttcgcc cccgaggatc    120
agtcttggcc ccaaagcgcg acgcacaaat ccacataacc tgaggaccat ggatgctgat    180
gagggtcaag acatgtccca gtttcaggg aaggaaagcc cccctgtaag cgatactcca    240
gatgagggcg atgagcccat gccgatcccc gaggacctct ccaccacctc gggaggacag    300
caaagctcca agagtgacag agtcgtggcc agtaatgtta agtagagac tcagagtgat    360 gaagagaatg ggcgtgcctg tgaaatgaat ggggaagaat gtgcggagga tttacgaatg    420
cttgatgcct cgggagagaa aatgaatggc tcccacaggg accaaggcag ctcggctttg    480
tcgggagttg gaggcattcg acttcctaac ggaaaactaa agtgtgatat ctgtgggatc    540
atttgcatcg ggcccaatgt gctcatggtt cacaaaagaa gccacactgg agaacggccc    600
```

-continued

```
ttccagtgca atcagtgcgg ggcctcattc acccagaagg gcaacctgct ccggcacatc    660
aagctgcatt ccggggagaa gcccttcaaa tgccacctct gcaactacgc ctgccgccgg    720
agggacgccc tcactggcca cctgaggacg cactccgttg gtaaacctca caaatgtgga    780
tattgtggcc gaagctataa acagcgaagc tctttagagg aacataaaga gcgctgccac    840
aactacttgg aaagcatggg ccttccgggc acactgtacc cagtcattaa agaagaaact    900
aatcacagtg aaatggcaga agacctgtgc aagataggat cagagagatc tctcgtgctg    960
gacagactag caagtaacgt cgccaaacgt aagagctcta tgcctcagaa atttcttggg   1020
gacaagggcc tgtccgacac gccctacgac agcagcgcca gctacgagaa ggagaacgaa   1080
atgatgaagt cccacgtgat ggaccaagcc atcaacaacg ccatcaacta cctggggggcc  1140 gagtccctgc gcccgctggt gcagacgccc ccgggcggtt ccgaggtggt cccggtcatc   1200
agcccgatgt accagctgca aagccgctc gcggagggca ccccgcgctc caaccactcg    1260
gcccaggaca cgccgtgga gaacctgctg ctgctctcca aggccaagtt ggtgccctcg    1320
gagcgcgagg cgtccccgag caacagctgc caagactcca cggacaccga gagcaacaac   1380
gaggagcagc gcagcggtct catctacctg accaaccaca tcgccccgca cgcgcgcaac   1440
gggctgtcgc tcaaggagga gcaccgcgcc tacgacctgc tgcgcgccgc ctccgagaac   1500
tcgcaggacg cgctccgcgt ggtcagcacc agcggggagc agatgaaggt gtacaagtgc   1560
gaacactgcc gggtgctctt cctggatcac gtcatgtaca ccatccacat gggctgccac   1620
ggcttccgtg atcctttga gtgcaacatg tgcggctacc acagccagga ccggtacgag   1680
ttctcgtcgc acataacgcg aggggagcac cgcttccaca tgagctaaag ccctcccgcg   1740
ccccaccccc agaccccgag ccaccccagg aaaagcacaa ggactgccgc cttctcgctc   1800
ccgccagcag catagactgg actggaccag acaatgttgt gtttggattt gtaactgttt   1860
tttgtttttt gtttgagttg gttgattggg gtttgatttg cttttgaaaa gattttattt   1920
tttagaggca gggctgcatt gggagcatcc agaactgcta ccttcctaga tgtttcccca   1980
gaccgctggc tgagattccc tcacctgtcg cttcctagaa tccccttctc caaacgatta   2040
gtctaaattt tcagagagaa atagataaaa cacgccacag cctgggaagg agcgtgctct   2100
accctgtgct aagcacgggg ttcgcgcacc aggtgtcttt ttccagtccc cagaagcaga   2160
gagcacagcc cctgctgtgt gggtctgcag gtgagcagac aggacaggtg tgccgccacc   2220
caagtgccaa gacacagcag ggccaacaac ctgtgcccag gccagcttcg agctacatgc   2280
atctagggcg gagaggctgc acttgtgaga gaaaatacta tttcaagtca tattctgcgt   2340
aggaaaatga attggttggg gaaagtcgtg tctgtcagac tgccctgggt ggagggagac   2400
gccgggctag agcctttggg atcgtcctgg attcactggc tttgcggagg ctgctcagat   2460
ggcctgagcc tcccgaggct tgctgccccg taggaggaga ctgtcttccc gtgggcatat   2520
ctggggagcc ctgttccccg cttttttcact cccatacctt taatggcccc caaaatctgt   2580
cactacaatt taaacaccag tcccgaaatt tggatcttct ttcttttga atctctcaaa    2640 cggcaacatt cctcagaaac caaagcttta tttcaaatct cttccttccc tggctggttc   2700
catctagtac cagaggcctc ttttcctgaa gaaatccaat cctagccctc atttttaatta  2760 tgtacatctg tttgtagcca caagcctgaa tttctcagtg ttggtaagtt tctttaccta   2820
ccctcactat atattattct cgttttaaaa cccataaagg agtgatttag aacagtcatt    2880
aattttcaac tcaatgaaat atgtgaagcc cagcatctct gttgctaaca cacagagctc   2940
acctgtttga aaccaagctt tcaaacatgt tgaagctctt tactgtaaag gcaagccagc   3000
```

```
atgtgtgtcc acacatacat aggatggctg gctctgcacc tgtaggatat tggaatgcac    3060
agggcaattg agggactgag ccagaccttc ggagagtaat gccaccagat cccctaggaa    3120
agaggaggca aatggcactg caggtgagaa ccccgcccat ccgtgctatg acatggaggc    3180
actgaagccc gaggaaggtg tgtggagatt ctaatcccaa caagcaaggg tctccttcaa    3240
gattaatgct atcaatcatt aaggtcatta ctctcaacca cctaggcaat gaagaatata    3300
ccatttcaaa tatttacagt acttgtcttc accaacactg tcccaaggtg aaatgaagca    3360
acagagagga aattgtacat aagtacctca gcatttaatc caaacagggg ttcttagtct    3420
cagcactatg acattttggg ctgactactt atttgttagg cgggagctct cctgtgcatt    3480
gtaggataat tagcagtatc cctggtggct acccaataga cgccagtagc accccgaatt    3540
gacaacccaa actctccaga catcaccaac tgtcccctgc gaggagaaat cactcctggg    3600
ggagaaccac tgacccaaat gaattctaaa ccaatcaaat gtctgggaag ccctccaaga    3660
aaaaaaatag aaaagcactt gaagaatatt cccaatattc ccggtcagca gtatcaaggc    3720
tgacttgtgt tcatgtggag tcattataaa ttctataaat caattattcc ccttcggtct    3780
taaaaatata tttcctcata aacatttgag ttttgttgaa aagatggagt ttacaaagat    3840
accattcttg agtcatggat ttctctgctc acagaagggt gtggcatttg gaaacgggaa    3900
taaacaaaat tgctgcacca atgcactgag tgaaggaaga gagacagagg atcaagggct    3960
ttagacagca ctccttcaat atgcaatcac agagaaagat gcgccttatc caagttaata    4020
tctctaaggt gagagccttc ttagagtcag tttgttgcaa atttcaccta ctctgttctt    4080
ttccatccat cccctgagt cagttggttg aagggagtta tttttcaag tggaattcaa    4140 acaaagctca aaccagaact gtaaatagtg attgcaggaa ttcttttcta aactgctttg    4200 cccttttcctc tcactgcctt ttatagccaa tataaatgtc tctttgcaca ccttttgttg    4260
tggttttata ttgtaacacc atttttcttt gaaactattg tatttaaagt aaggtttcat    4320
attatgtcag caagtaatta acttatgttt aaaaggtggc catatcatgt accaaaagtt    4380
gctgaagttt ctcttctagc tggtaaagta ggagtttgca tgacttcaca cttttttgc    4440 gtagtttctt ctgttgtatg atggcgtgag tgtgtgtctt gggtaccgct gtgtactact    4500
gtgtgcctag attccatgca ctctcgttgt gtttgaagta aatattggag accggagggt    4560
aacaggttgg cctgttgatt acagctagta atcgctgtgt cttgttccgc cccctccctg    4620
acaccccagc ttcccaggat gtggaaagcc tggatctcag ctccttgccc catatccctt    4680
ctgtaatttg tacctaaaga gtgtgattat cctaattcaa gagtcactaa aactcatcac    4740
attatcattg catatcagca aagggtaaag tcctagcacc aattgcttca cataccagca    4800
tgttccattt ccaatttaga attagccaca taataaaatc ttagaatctt ccttgagaaa    4860
gagctgcctg agatgtagtt ttgttatatg gttccccacc gaccattttt gtgctttttt    4920
cttgttttgt tttgttttga ctgcactgtg agttttgtag tgtcctcttc ttgccaaaac    4980
aaacgcgaga tgaactggac ttatgtagac aaatcgtgat gccagtgtat ccttcctttc    5040
ttcagttcca gcaataatga atggtcaact ttttttaaaat ctagatctct ctcattcatt    5100
tcaatgtatt tttactttaa gatgaaccaa aattattaga cttatttaag atgtacaggc    5160
atcagaaaaa agaagcacat aatgcttttg gtgcgatggc actcactgtg aacatgtgta    5220
accacatatt aatatgcaat attgtttcca atactttcta atacagtttt ttataatgtt    5280
gtgtgtggtg attgttcagg tcgaatctgt tgtatccagt acagctttag gtcttcagct    5340
```

| | |
|---|---|
| gcccttctgg cgagtacatg cacaggattg taaatgagaa atgcagtcat atttccagtc | 5400 |
| tgcctctatg atgatgttaa attattgctg tttagctgtg aacaaggat gtaccactgg | 5460 |
| aggaatagag tatccttttg tacacatttt gaaatgcttc ttctgtagtg atagaacaaa | 5520 |
| taaatgcaac gaatactctg tctgccctat cccgtgaagt ccacactggc gtaagagaag | 5580 |
| gcccagcaga gcaggaatct gcctagactt tctcccaatg agatcccaat atgagaggga | 5640 |
| gaagagatgg gcctcaggac agctgcaata ccacttggga acacatgtgg tgtcttgatg | 5700 |
| tggccagcgc agcagttcag cacaacgtac ctcccatcta aacagtgct ggacgtggga | 5760 |
| attctaagtc ccagtcttga gggtgggtgg agatggaggg caacaagaga tacatttcca | 5820 |
| gttctccact gcagcatgct tcagtcattc tgtgagtggc cgggcccagg ccctcacaa | 5880 |
| tttcactacc ttgtctttta catagtcata agaattatcc tcaacatagc cttttgacgc | 5940 |
| tgtaaatctt gagtattcat ttacccttt ctgatctcct ggaaacagct gcctgcctgc | 6000 |
| attgcacttc tcttcccgag gagtgggta aatttaaaag tcaagttata gtttggatgt | 6060 |
| tagtatagaa ttttgaaatt gggaattaaa aatcaggact ggggactggg agaccaaaaa | 6120 |
| tttctgatcc cattctgat ggatgtgtca cacctttct gtcaaaataa aatgtcttgg | 6180 |
| aggttatgac tccttggtga aa | 6202 |

<210> SEQ ID NO 59
<211> LENGTH: 2887
<212> TYPE: DNA
<213> ORGANISM: Homo sapiens

<400> SEQUENCE: 59

| | |
|---|---|
| ggagctgaga ggaacaggaa gtgtcaggac tttacgaccc gcgcctccag ctgaggtttc | 60 |
| tagacgtgac ccagggcaga ctggtagcaa agccccacg cccagccagg agcaccgccg | 120 |
| aggactccag cacaccgagg acatgctggg gcctgcgccc ccactgctc gccctggtgg | 180 |
| ggctgctctc cctcgggtgc gtcctctctc aggagtgcac gaagttcaag gtcagcagct | 240 |
| gccgggaatg catcgagtcg gggcccggct gcacctggtg ccagaagctg aacttcacag | 300 |
| ggccggggga tcctgactcc attcgctgcg acacccggcc acagctgctc atgaggggct | 360 |
| gtgcggctga cgacatcatg gaccccacaa gcctcgctga aacccaggaa gaccacaatg | 420 |
| ggggccagaa gcagctgtcc ccacaaaaag tgacgcttta cctgcgacca ggccaggcag | 480 |
| cagcgttcaa cgtgaccttc cggcgggcca agggctaccc catcgacctg tactatctga | 540 |
| tggaccctct ctactccatg cttgatgacc tcaggaatgt caagaagcta ggtggcgacc | 600 |
| tgctccgggc cctcaacgag atcaccgagt ccggccgcat tggcttcggg tccttcgtgg | 660 |
| acaagaccgt gctgccgttc gtgaacacgc accctgataa gctgcgaaac ccatgcccca | 720 |
| acaaggagaa agagtgccag ccccgttttg ccttcaggca cgtgctgaag ctgaccaaca | 780 |
| actccaacca gtttcagacc gaggtcggga agcagctgat ttccggaaac tggatgcac | 840 |
| ccgagggtgg gctggacgcc atgatgcagg tcgccgcctg cccggaggaa atcggctggc | 900 |
| gcaacgtcac gcggctgctg gtgtttgcca ctgatgacgg cttccatttc gcgggcgacg | 960 |
| ggaagctggg cgccatcctg accccaacg acggccgctg tcacctggag acaacttgt | 1020 |
| acaagaggag caacgaattc gactacccat cggtgggcca gctggcgcac aagctggctg | 1080 |
| aaaacaacat ccagcccatc ttcgcggtga ccagtaggat ggtgaagacc tacgagaaac | 1140 |
| tcaccgagat catccccaag tcagccgtgg gggagctgtc tgaggactcc agcaatgtgg | 1200 |
| tccaactcat taagaatgct tacaataaac tctcctccag ggtcttcctg gatcacaacg | 1260 |

```
ccctccccga cacccctgaaa gtcacctacg actccttctg cagcaatgga gtgacgcaca    1320
ggaaccagcc cagaggtgac tgtgatggcg tgcagatcaa tgtcccgatc accttccagg    1380
tgaaggtcac ggccacagag tgcatccagg agcagtcgtt tgtcatccgg gcgctgggct    1440
tcacggacat agtgaccgtg caggttcttc cccagtgtga gtgccggtgc cgggaccaga    1500
gcagagaccg cagcctctgc catggcaagg gcttcttgga gtgcggcatc tgcaggtgtg    1560
acactggcta cattgggaaa aactgtgagt gccagacaca gggccggagc agccaggagc    1620
tggaaggaag ctgccggaag gacaacaact ccatcatctg ctcagggctg ggggactgtg    1680
tctgcgggca gtgcctgtgc cacaccgcg acgtccccgg caagctgata tacgggcagt    1740
actgcgagtg tgacaccatc aactgtgagc gctacaacgg ccaggtctgc ggcggcccgg    1800
ggaggggct ctgcttctgc gggaagtgcc gctgccaccc gggctttgag ggctcagcgt    1860
gccagtgcga gaggaccact gagggctgcc tgaacccgcg gcgtgttgag tgtagtggtc    1920
gtggccggtg ccgctgcaac gtatgcgagt gccattcagg ctaccagctg cctctgtgcc    1980
aggagtgccc cggctgcccc tcaccctgtg gcaagtacat ctcctgcgcc gagtgcctga    2040
agttcgaaaa gggccccttt gggaagaact gcagcgcggc gtgtccgggc ctgcagctgt    2100
cgaacaaccc cgtgaagggc aggacctgca aggagaggga ctcagagggc tgctgggtgg    2160
cctacacgct ggagcagcag gacgggatgg accgctacct catctatgtg gatgagagcc    2220
gagagtgtgt ggcaggcccc aacatcgccg ccatcgtcgg gggcaccgtg gcaggcatcg    2280
tgctgatcgg cattctcctg ctggtcatct ggaaggctct gatccacctg agcgacctcc    2340
gggagtacag gcgctttgag aaggagaagc tcaagtccca gtggaacaat gataatcccc    2400
ttttcaagag cgccaccacg acggtcatga acccccaagtt tgctgagagt taggagcact    2460
tggtgaagac aaggccgtca ggacccacca tgtctgcccc atcacgcggc cgagacatgg    2520
cttgccacag ctcttgagga tgtcaccaat taaccagaaa tccagttatt ttccgccctc    2580
aaaatgacag ccatggccgg ccgggtgctt ctggggctc gtcgggggga cagctccact    2640
ctgactggca cagtctttgc atggagactt gaggagggag ggcttgaggt tggtgaggtt    2700
aggtgcgtgt ttcctgtgca agtcaggaca tcagtctgat taaaggtggt gccaatttat    2760
ttacatttaa acttgtcagg gtataaaatg acatcccatt aattatattg ttaatcaatc    2820
acgtgtatag aaaaaaaata aaacttcaat acaggctgtc catggaaaaa aaaaaaaaaa    2880
aaaaaaa                                                              2887
```

<210> SEQ ID NO 60
<211> LENGTH: 1793
<212> TYPE: DNA
<213> ORGANISM: Homo sapiens

<400> SEQUENCE: 60

```
cgcgtccgcc ccgcgagcac agagcctcgc ctttgccgat ccgccgcccg tccacacccg      60
ccgccagctc accatggatg atgatatcgc cgcgctcgtc gtcgacaacg gctccggcat     120
gtgcaaggcc ggcttcgcgg gcgacgatgc ccccgggcc gtcttcccct ccatcgtggg     180
gcgccccagg caccagggcg tgatggtggg catgggtcag aaggattcct atgtgggcga     240
cgaggcccag agcaagagag gcatcctcac cctgaagtac cccatcgagc acggcatcgt     300
caccaactgg gacgacatgg agaaaatctg gcaccacacc ttctacaatg agctgcgtgt     360
ggctcccgag gagcaccccg tgctgctgac cgaggccccc ctgaacccca aggccaaccg     420
```

```
cgagaagatg acccagatca tgtttgagac cttcaacacc ccagccatgt acgttgctat    480
ccaggctgtg ctatccctgt acgcctctgg ccgtaccact ggcatcgtga tggactccgg    540
tgacggggtc acccacactg tgcccatcta cgaggggtat gccctccccc atgccatcct    600
gcgtctggac ctggctggcc gggacctgac tgactacctc atgaagatcc tcaccgagcg    660
cggctacagc ttcaccacca cggccgagcg ggaaatcgtg cgtgacatta aggagaagct    720
gtgctacgtc gccctggact cgagcaaga gatggccacg gctgcttcca gctcctccct    780
ggagaagagc tacgagctgc ctgacggcca ggtcatcacc attggcaatg agcggttccg    840
ctgccctgag gcactcttcc agccttcctt cctgggcatg gagtcctgtg catccacga    900
aactaccttc aactccatca tgaagtgtga cgtggacatc cgcaaagacc tgtacgccaa    960
cacagtgctg tctggcggca ccaccatgta ccctggcatt gccgacagga tgcagaagga   1020
gatcactgcc ctggcaccca gcacaatgaa gatcaagatc attgctcctc ctgagcgcaa   1080
gtactccgtg tggatcggcg gctccatcct ggcctcgctg tccaccttcc agcagatgtg   1140
gatcagcaag caggagtatg acgagtccgg ccctccat cgtccaccgca aatgcttcta   1200
ggcggactat gacttagttg cgttacaccc tttcttgaca aaacctaact tgcgcagaaa   1260
acaagatgag attggcatgg ctttatttgt tttttttgtt ttgttttggt tttttttttt   1320
tttttggctt gactcaggat ttaaaaactg gaacggtgaa ggtgacagca gtcggttgga   1380
gcgagcatcc cccaaagttc acaatgtggc cgaggacttt gattgcacat tgttgttttt   1440
ttaatagtca ttccaaatat gagatgcatt gttacaggaa gtcccttgcc atcctaaaag   1500
ccaccccact tctctctaag gagaatggcc cagtcctctc ccaagtccac acaggggagg   1560
tgatagcatt gctttcgtgt aaattatgta atgcaaaatt tttttaatct tcgccttaat   1620
acttttttat tttgttttat tttgaatgat gagccttcgt gccccccctt cccccttttt   1680
gtccccccaac ttgagatgta tgaaggcttt tggtctccct gggagtgggt ggaggcagcc   1740
agggcttacc tgtacactga cttgagacca gttgaataaa agtgcacacc tta           1793
```

<210> SEQ ID NO 61
<211> LENGTH: 6541
<212> TYPE: DNA
<213> ORGANISM: Homo sapiens

<400> SEQUENCE: 61

```
agccgtttcc ggagtctgcg ctgcgcccgg ttccgccatt gcggctctcc tggcccctgg     60
agcctccgcc cccgacccga gctctttcgt ctgcctgcca gtttcctgcg tccccggaga    120
ggatcctgct gagcccagcc tccccctcc ccttctcctc ctctcccttg gagagccgg     180
gcagccactg ccccgcagcc ccagtgacag gaggagacca taaccccga cagcgccatg    240
gcccagattc tgccaattcg ttttcaggag catctccagc tccagaacct gggtatcaac    300
ccagcaaaca ttggcttcag taccctgact atggagtctg acaaattcat ctgcattaga    360
gaaaaagtag gagagcaggc ccaggtggta atcattgata tgaatgaccc aagtaatcca    420
attcgaagac caatttcagc agacagcgcc atcatgaatc cagctagcaa agtaattgca    480
ctgaaagctg ggaaaactct tcagattttt aacattgaaa tgaaaagtaa atgaaggct    540
cataccatga ctgatgatgt caccttttgg aaatggatct ctttgaatac ggttgctctt    600
gttacggata atgcagttta tcactggagt atgaaggag agtctcagcc agtgaaaatg    660
tttgatcgcc attctagcct tgcagggtgc cagattatca attaccgtac agatgcaaaa    720
caaaagtggt tacttctgac tggtatatct gcacagcaaa atcgtgtggt gggagctatg    780
```

```
cagctatatt ctgtagatag gaaagtgtct cagcccattg aaggacatgc agctagcttt    840
gcacagttta agatggaagg aaatgcagaa gaatcaacgt tattttgttt tgcagttcgg    900
ggccaagctg gagggaagtt acatattatt gaagttggca caccacctac agggaaccag    960 cccttttccaa agaaggcagt ggatgtcttc tttcctccag aagcacaaaa tgattttcct   1020
gttgcaatgc agatcagtga aaagcatgat gtggtgttct tgataaccaa gtatggttat   1080
atccacctct atgatcttga gactggtacc tgcatctaca tgaatagaat cagtggagaa   1140 acaattttg ttactgcacc tcatgaagcc acagctggaa taattggagt aaacagaaag    1200
ggacaagttc tgtcagtgtg tgtggaagaa gaaaacataa ttccttacat caccaatgtt   1260
ctacaaaatc ctgatttggc tctgagaatg gctgtacgta ataacttagc cggtgctgaa   1320
gaactctttg cccggaaatt taatgctctt tttgcccagg gaaattactc ggaggcagca   1380
aaggtggctg ctaatgcacc aaagggaatt cttcgtactc cagacactat ccgtcggttc   1440
cagagtgtcc cagcccagcc aggtcaaact tctcctctac ttcagtactt tggtatcctt   1500
ttggaccagg gacagctcaa caaatacgaa tccttagagc tttgtaggcc tgtacttcag   1560
caagggcgaa aacagctttt ggagaaatgg ttaaaagaag ataagctgga atgttctgaa   1620
gaactgggtg atcttgtgaa atctgtggac cctacattgg cacttagtgt gtacctaagg   1680
gctaacgtcc caaataaagt cattcagtgc tttgcagaaa caggtcaagt ccaaaagatt   1740
gttttatatg ctaaaaaagt tggatacact ccagattgga tatttctgct gagaaatgta   1800
atgcgaatca gtccagatca gggacagcag tttgcccaaa tgttagttca agatgaagag   1860
cctcttgctg acatcacaca gattgtagat gtctttatgg aatacaatct aattcagcag   1920
tgtactgcat tcttgcttga tgctctgaag aataatcgcc catctgaagg tcctttacag   1980
acgcggttac ttgagatgaa ccttatgcat gcgcctcaag ttgcagatgc tattctaggc   2040
aatcagatgt tcacacatta tgaccgggct catattgctc aactgtgtga aaaggctggc   2100
ctactgcagc gtgcattaga acatttcact gatttatatg atataaaacg tgcagtggtt   2160
cacacccatc ttcttaaccc tgagtggtta gtcaactact ttggttcctt atcagtagaa   2220
gactccctag aatgtctcag agccatgctg tctgccaaca tccgtcagaa tctgcagatt   2280
tgtgttcagg tggcttctaa atatcatgaa caactgtcaa ctcagtctct gattgaactt   2340
tttgaatctt tcaagagttt tgaaggtctc ttttattttc tgggatccat tgttaacttt   2400
agccaggacc cagatgtgca ctttaaatat attcaggcag cttgcaagac tgggcaaatc   2460
aaagaagtag aaagaatctg tagagaaagc aactgctacg atcctgagcg agtcaagaat   2520
tttcttaagg aagcaaaact aacagatcag ctaccactta tcattgtgtg tgatcgattt   2580
gactttgtcc atgatttggt gctctattta tatagaaata tcttcaaaa gtatatagag   2640 atatatgtac agaaggtgaa tccaagtcga cttcctgtag ttattggagg attacttgat   2700
gttgactgtt ctgaagatgt cataaaaaac ttgattcttg ttgtaagagg tcaattctct   2760
actgatgagc ttgttgctga ggttgaaaaa agaaacagat tgaaactgct tctgccttgg   2820
ctagaggcca gaattcatga gggctgtgag gagcctgcta ctcacaatgc cttagccaaa   2880
atctacatag acagtaataa caacccggag agatttcttc gtgaaaatcc ctactatgac   2940
agtcgcgttg ttggaaagta ttgtgagaag agagatccac atctggcctg tgttgcttat   3000
gaacgtggcc aatgtgatct ggaacttatt aatgtttgca atgagaattc cctcttcaaa   3060
agtctttctc gctacctggt acgtcgaaag gatccagaat tgtggggcag cgtgctgctg   3120
```

```
gaaagcaatc cttacaggag acccctaatt gaccaggttg tacaaacagc tttgtctgag    3180
actcaggacc ctgaagaagt gtcagtaact gtaaaggctt tcatgactgc agaccttcct    3240
aatgaactca ttgaactgct ggagaaaatt gtccttgata actctgtatt cagtgaacac    3300
aggaatctgc aaaacctcct tatcctcact gcaattaagg ctgaccgtac acgtgttatg    3360
gagtatatta accgcctgga taattatgat gccccagata ttgccaatat cgccatcagc    3420
aatgagctgt ttgaagaagc atttgccatt ttccggaaat ttgatgtcaa tacttcagca    3480
gttcaggtct taattgagca tattggaaac ttggatcggg catatgagtt tgctgaacgt    3540
tgcaatgaac ctgcggtctg gagtcaactt gcaaaagccc agttgcagaa aggaatggtg    3600
aaagaagcca ttgattctta tatcaaagca gatgatcctt cctcctacat ggaagttgtt    3660
caggctgcca atactagtgg aaactgggaa gaactggtga agtacttgca gatggcccgt    3720
aagaaggctc gagagtccta tgtggagaca gaactgatat tcgcactggc taaaacaaac    3780
cgccttgcag agttagaaga atttatcaat ggaccaaata atgctcatat ccaacaagtt    3840
ggtgaccgtt gttatgatga aaaaatgtat gatgctgcta agttgttgta caataatgtt    3900
tccaattttg gacgtttggc atctaccctg gttcacctgg gtgaatatca ggcagctgtt    3960
gatgggcta ggaaagctaa cagtactcga acatggaaag aggtctgctt cgcctgtgta    4020
gatgggaaag aattccgtct tgctcagatg tgtggacttc atattgttgt acatgcagat    4080
gaattagaag aacttatcaa ctactatcag gatcgtggct attttgaaga gctgatcacc    4140
atgttggaag cagcactggg acttgagcga gctcacatgg gaatgtttac tgaattagct    4200
attctatact ctaaatttaa gcctcagaaa atgagggagc acctggagct gttctggtct    4260
agagtgaata ttcccaaggt gctaagagct gcagaacaag ctcatctttg gcagaactg    4320
gtgttttgt atgacaagta tgaagaatat gataatgcca taattaccat gatgaatcat    4380
ccaactgatg cctggaaaga agggcaattc aaagatatca ttaccaaggt tgccaatgtg    4440
gaactatact acagagcaat acagttctac ttagaattca gcctctgtt gttaaatgat    4500
ttgctgatgg tgctgtctcc acggttggat cacactcgtg cagtcaatta tttcagcaag    4560
gttaaacagc taccactggt gaaaccgtat tgcgttcag ttcagaacca taacaacaaa    4620
tctgtgaatg aatcattgaa caatctttt attacagaag aagattatca ggctctgcga    4680
acatcaatag atgcttatga caactttgac aatatctcgc ttgctcagcg tttggaaaaa    4740
catgaactca ttgagttcag gagaattgct gcttatctct tcaaaggcaa caatcgctgg    4800
aaacagagtg tagagctgtg caagaaagac agcctttaca aggatgcaat gcagtatgct    4860
tctgaatcta agatactga attggctgaa gaactcctgc agtggttttt gcaggaagaa    4920
aaaagagagt gctttggagc ttgtctgttt acctgttacg atcttttaag gccagatgtc    4980
gtcctagaaa ctgcatggag gcacaatatc atggattttg ccatgcccta tttcatccag    5040
gtcatgaagg agtacttgac aaaggtggat aaattagatg cttcagaatc actgagaaaa    5100
gaagaagaac aagctacaga gacacaaccc attgtttatg gtcagcccca gttgatgctg    5160
acagcaggac ccagtgttgc cgtccctccc caggcacctt ttggttatgg ttataccgca    5220
ccaccgtatg acagccaca gcctggcttt gggtacagca tgtgagatga agcgctgatc    5280
ctgtagtcac ctattttcgt actgaaacat cgtctttacc cacttctcag tttataatgg    5340
gggaaaacag gcaacgtgtt cttgtaacct ttatttcatg aaggacttct ttttgtttct    5400
aactataaac ttggatcacc tatgttaaaa ccttatttca cattccacat cattttagaa    5460
tttattttcg aagggaata gtttcaatgt tttattcact tgggcttttt ttcttccccc    5520
```

| | |
|---|---|
| tctttcttta aagaactgct caatattcaa tctgttgtga agaacctgat ttgcactctg | 5580 |
| tagtgtttaa agaaacaaag aaactctaat attgaatctc ttaaatttag tgtatgtaaa | 5640 |
| cagcttacaa atacgtattg tctaaatgca tttaaatctg ttttattcaa agaaaagcta | 5700 |
| aagcaaaaac actggcatat gaccatgcaa gactgtcagt gccaacaaag acaacactaa | 5760 |
| tcagcacatc gtacactgga ttgcagtgct cccagatta ttgaaaaatg ttacagacaa | 5820 |
| cttgcctgat ttttaaatga gcgtaaaagg ccctctaacc tatgcaggtt tccccattat | 5880 |
| gcatatagaa aatgctagta tgttttgctc acttcatatg taacaggtgc ccttatgttg | 5940 |
| tgctgtatcc tgtgcttttt ctgtgggacc attccattca ggagcaaaga gcaccatgat | 6000 |
| tccaatcttg tgtgtgttta ctaacccttc cctgaggttt gtgtatgttg gatattgtgg | 6060 |
| tgttttagat cactgagtgt acagaagaga gaaattcaaa caaatattg ctgttcttca | 6120 |
| gttttgtttg tggaatttga aattactcaa atttaaaata aattactgga ctgtggaaat | 6180 |
| aacatagaat tgaagtttta attaaatacc actcaaacga aaagaacagt agttttgta | 6240 |
| gttttatatt ggatactgag gcattaggga ggcatgaaag gaagaggaat gaggattgag | 6300 |
| acatgtgaag acattgtgca ttatatcaat gtgcattcct gtagttcatt aacaaggtac | 6360 |
| atgcaatagt ctaaagaacc agagtcacta ctatagtggc ttaacattta atctgtctcc | 6420 |
| aatattttaa ccaagtgaca ccgaggtttt tatcgaagca tttcacttaa atgaacaaat | 6480 |
| catggctgtt atattaactt gaaataaaat atatttaaac atgtaaaaaa aaaaaaaaa | 6540 |
| a | 6541 |

<210> SEQ ID NO 62
<211> LENGTH: 1657
<212> TYPE: DNA
<213> ORGANISM: Homo sapiens

<400> SEQUENCE: 62

| | |
|---|---|
| gctcacagga agccacgcac ccttgaaagg caccgggtcc ttcttagcat cgtgcttcct | 60 |
| gagcaagcct ggcattgcct cacagacctt cctcagagcc gctttcagaa aagcaagctg | 120 |
| cttctggttg ggcccagacc tgccttgagg agcctgtaga gttaaaaaat gaaccccacg | 180 |
| gatatagcag acaccaccct cgatgaaagc atatacagca attactatct gtatgaaagt | 240 |
| atccccaagc cttgcaccaa agaaggcatc aaggcatttg gggagctctt cctgccccca | 300 |
| ctgtattcct tggttttgt atttggtctg cttggaaatt ctgtggtggt tctggtcctg | 360 |
| ttcaaataca agcggctcag gtccatgact gatgtgtacc tgctcaacct tgccatctcg | 420 |
| gatctgctct tcgtgttttc cctccctttt tggggctact atgcagcaga ccagtgggtt | 480 |
| tttgggctag gtcgtgcaa gatgatttcc tggatgtact tggtgggctt ttacagtggc | 540 |
| atattctttg tcatgctcat gagcattgat agatacctgg caattgtgca cgcggtgttt | 600 |
| tccttgaggg caaggacctt gacttatggg gtcatcacca gtttggctac atggtcagtg | 660 |
| gctgtgttcg cctcccttcc tggctttctg ttcagcactt gttatactga gcgcaaccat | 720 |
| acctactgca aaaccaagta ctctctcaac tccacgacgt ggaaggttct cagctccctg | 780 |
| gaaatcaaca ttctcggatt ggtgatcccc ttagggatca tgctgttttg ctactccatg | 840 |
| atcatcagga ccttgcagca ttgtaaaaat gagaagaaga acaaggcggt gaagatgatc | 900 |
| tttgccgtgg tggtcctctt ccttgggttc tggacacctt acaacatagt gctcttccta | 960 |
| gagaccctgg tggagctaga agtccttcag gactgcacct ttgaaagata cttggactat | 1020 |

```
gccatccagg ccacagaaac tctggctttt gttcactgct gccttaatcc catcatctac    1080 tttttctgg gggagaaatt tcgcaagtac atcctacagc tcttcaaaac ctgcaggggc    1140 cttttgtgc tctgccaata ctgtgggctc ctccaaattt actctgctga caccccagc    1200 tcatcttaca cgcagtccac catggatcat gatctccatg atgctctgta gaaaaatgaa    1260
atggtgaaat gcagagtcaa tgaactttcc acattcagag cttacttaaa attgtatttt    1320
agtaagagat tcctgagcca gtgtcaggag gaaggcttac acccacagtg gaaagacagc    1380
ttctcatcct gcaggcagct ttttctctcc cactagacaa gtccagcctg caagggttc     1440 acctgggctg aggcatcctt cctcacacca ggcttgcctg caggcatgag tcagtctgat    1500
gagaactctg agcagtgctt gaatgaagtt gtaggtaata ttgcaaggca aagactattc    1560
ccttctaacc tgaactgatg ggtttctcca gagggaattg cagagtactg gctgatggag    1620
taaatcgcta ccttttgctg tggcaaatgg gccctct                             1657

<210> SEQ ID NO 63
<211> LENGTH: 6099
<212> TYPE: DNA
<213> ORGANISM: Homo sapiens

<400> SEQUENCE: 63
aggcggcgcg tgcgtagagg ggcggtgaga gctaagaggg gcagcgcgtg tgcagagggg      60
cggtgtgact taggacgggg cgatggcggc tgagaggagc tgcgcgtgcg cgaacatgta     120
actggtggga tctgcggcgg ctcccagatg atggtcgtcc tcctgggcgc gacgaccta     180 gtgctcgtcg ccgtggcgcc atgggtgttg tccgcagccg caggtggaaa aaatctaaaa     240
tctcctcaaa aagtagaggt cgacatcata gatgacaact ttatcctgag gtggaacagg     300
agcgatgagt ctgtcgggaa tgtgactttt tcattcgatt atcaaaaaac tgggatggat     360
aattggataa aattgtctgg gtgtcagaat attactagta ccaaatgcaa cttttcttca     420
ctcaagctga atgtttatga agaaattaaa ttgcgtataa gagcagaaaa agaaaacact     480
tcttcatggt atgaggttga ctcatttaca ccatttcgca aagctcagat tggtcctcca     540
gaagtacatt tagaagctga agataaggca atagtgatac acatctctcc tggaacaaaa     600
gatagtgtta tgtgggcttt ggatggttta agctttacat atagcttagt tatctggaaa     660
aactcttcag gtgtagaaga aaggattgaa aatatttatt ccagacataa aatttataaa     720
ctctcaccag agactactta ttgtctaaaa gttaaagcag cactacttac gtcatggaaa     780
attggtgtct atagtccagt acattgtata aagaccacag ttgaaaatga actacctcca     840
ccagaaaata tagaagtcag tgtccaaaat cagaactatg ttcttaaatg ggattataca     900
tatgcaaaca tgaccttca agttcagtgg ctccacgcct tttaaaaag gaatcctgga     960 aaccatttgt ataaatggaa acaaatacct gactgtgaaa atgtcaaaac tacccagtgt    1020
gtctttcctc aaaacgtttt ccaaaaagga atttaccttc tccgcgtaca agcatctgat    1080
ggaaataaca catcttttg gtctgaagag ataaagtttg tactgaaat acaagctttc    1140 ctacttcctc cagtctttaa cattagatcc ttagtgatt cattccatat ctatatcggt    1200
gctccaaaac agtctggaaa cacgcctgtg atccaggatt atccactgat ttatgaaatt    1260
attttttggg aaaacacttc aaatgctgag agaaaaatta tcgagaaaaa aactgatgtt    1320
acagttccta atttgaaacc actgactgta tattgtgtga agccagagc acacaccatg    1380 gatgaaaagc tgaataaaag cagtgttttt agtgacgctg tatgtgagaa acaaaaacca    1440
ggaaatacct ctaaaatttg gcttatagtt ggaatttgta ttgcattatt tgctctcccg    1500
```

```
tttgtcattt atgctgcgaa agtcttcttg agatgcatca attatgtctt ctttccatca   1560
cttaaacctt cttccagtat agatgagtat ttctctgaac agccattgaa gaatcttctg   1620
ctttcaactt ctgaggaaca aatcgaaaaa tgtttcataa ttgaaaatat aagcacaatt   1680
gctacagtag aagaaactaa tcaaactgat gaagatcata aaaatacag ttcccaaact    1740
agccaagatt caggaaatta ttctaatgaa gatgaaagcg aaagtaaaac aagtgaagaa   1800
ctacagcagg actttgtatg accagaaatg aactgtgtca agtataaggt ttttcagcag   1860
gagttacact gggagcctga ggtcctcacc ttcctctcag taactacaga gaggacgttt   1920
ccctgtttag ggaagaaaaa aacatcttca gatcataggt cctaaaaata cgggcaagct   1980
cttaactatt taaaaatgaa attacaggcc cgggcacggt ggctcacacc tgtaatccca   2040
gcactttggg aggctgaggc aggcagatca tgaggtcaag agatcgagac cagcctggcc   2100
aacgtggtga aaccccatct ctactaaaaa tacaaaaatt agccgggtgt ggtggcgcgc   2160
gcctgttgtc ttagctactc aggaggctga ggcaggagaa tcgcttgaaa acaggaggtg   2220
gaggttgcag tgagccgaga tcacgccact gcactccagc ctggtgacag cgtgagactc   2280
tttaaaaaaa gaaattaaaa gagttgagac aaacgtttcc tacattcttt tccatgtgta   2340
aaatcatgaa aaagcctgtc accggacttg cattggatga gatgagtcag accaaaacag   2400
tggccacccg tcttcctcct gtgagcctaa gtgcagccgt gctagctgcg caccgtggct   2460
aaggatgacg tctgtgttcc tgtccatcac tgatgctgct ggctactgca tgtgccacac   2520
ctgtctgttc gccattccta acattctgtt tcattcttcc tcgggagata tttcaaacat   2580
ttggtctttt cttttaacac tgagggtagg cccttaggaa atttatttag gaaagtctga   2640
acacgttatc acttggtttt ctggaaagta gcttacccta gaaaacagct gcaaatgcca   2700
gaaagatgat ccctaaaaat gttgagggac ttctgttcat tcatcccgag aacattggct   2760
tccacatcac agtatctacc cttacatggt ttaggattaa agccaggcaa tcttttacta   2820
tgcattaaga cctctgattc aaaacttatt agaacagtag cttctgctgg aatttgcaat   2880
cactgaagtc atagaaaata ggtaactatc taattagaga aataattgtt gtattttaag   2940
atctgagagt gtgtacaagt tttagtatac atgccatgcc agaagatagt gtatgcaaga   3000
agtcttggga ccagaaaatg gcaatgatag gagactgaca tagaagaaga atgcttccct   3060
aggaaaaagg tcgctggctt tggtgcaaga ggaagaagaa tgttccactg gaagcctgag   3120
cacctaatca gctctcagtg atcaacccac tcttgttatg ggtggtctct gtcactttga   3180
atgccaggct ggcttctcgt ctagcagtat tcagataccc cttctgctca gcctgcttgg   3240
cgttaaaata caaatcattg aactgagggg gaaaaatgta actaggaaga aaaacccaat   3300
ttaagaaatt acataatgct ttccaaaggc acctacaact tagttttaaa ttacttgcta   3360
ctggggatta cccatggata tccttaatag gcaggaagtc tgggaattct ggtggcctct   3420
agggcagtgt tctcacagca ccgttccgac agggaccagt gaaagaaaag agacaaagtt   3480
agaacgtgct ggggagcggc catttctaag gccagtctgg tttaagtagt catttctgct   3540
gaaaaaacag atgatcctgg tggaagaaaa ggttgaaggc agctgccctc gggagggctg   3600
tgatgctcgg cacatcctgc ctggcacata acgtgtctg caggccacac cgtgcatgtc    3660
cccagacctg ccgcctggct tctggagtgc ttcaagcaga gcatggtggg tcattgagga   3720
gacccaggaa tctcatctga gaacccactc tctgccggag aacccatgg tgacacattt    3780
tcatctttct gaccagaggc tgttttttttt tttttttgag acagtctcat tctgttgccc   3840
```

```
aggctggagt gcagtggctt gatctcggct cactgcaacc tcgcctcccg ggttcaagca    3900
attctctgcc gcagcctcca gagtagctgg gataacaggt gcccaccacc acacccact    3960 aattttgta tttgtatttt tagtagagat ggggtttcac catgttggtc aggctggtct    4020
tggactcctg acctcatgct ccacccgctt cggcctccca aagttctggg attacaggtg    4080
tgagccaccg tgcacggccg gcctgacctt tggaaaagcc ttgtcacttt ggacgtttgc    4140
gtctttgaag aggcgatggg agcatatcat gactgcctgc caccattgct tttcagacta    4200
ccacaactca atcatgctgt ccaggacttc tggccctgtg ttcaccactg ggaaaacgta    4260
cttcagactg gatagcctaa aaaggagcaa tgcccttgta ggatgtggag aagggaaaat    4320
acggacatta acattaaaag acaccagtga aattgttagg tctctaggaa gttggagcac    4380
aaggcttcac gctttaagac catctgtggt tttcagtgaa caagcgctga gcaccagcag    4440
cagaaaacaa caacaaaaaa acacctcgtt tttaccttgt cttctagaca tgaaaaggca    4500
gttgcattcc actctgcatt atgttctaca tgttgcttta tcagtatatg cttagctgta    4560
agtgacaagt atttttctg aacagaagtt tacttagaaa taccatgcac ttgggggtac    4620
caattaaccg cctgaaaatt agcatattga tagttcttag agagaccaga tataatctaa    4680
gaatttatat gaaagatttg tatcattaga gccagaaata attttatatt aatatataat    4740
acagattaac attatatata atatgtacct gtgtcacttc tgacatgagc ctgtaaacat    4800
atattcatat atgtacctgc acatgtaccc acctgatgta ggtcttattc ctttagtatg    4860
gacttaaagt acttattcat ataccttgta actaaaaatt agaacagctc cctagaattg    4920
tgaactttta agagtctgac tagaaatttg caacttataa aaaagttact tttaaaaata    4980
taagttaggg ctaggcacag tggctcatgc ctataatctc agcactttg ggaggccaag    5040 acaggaggat cacttcaggc caggagttca agatcaacca acctgggtaa catgccaga    5100 ccccatctct atttatatat atatatataa aacttagagt ttttatcttc ccctaaaaga    5160
ggccgtgata tttgcagcag cctcaaattg ctcttaaggg gttaggtgt gcagaagctt    5220 tcctttccct acccagtaac catgtgacta ctaacgtggt atattgattt attttgtttg    5280
ctgtctgtct cccctgcccc actgctggaa cagaggctcc aagaaaacag ggaccttatt    5340
attcattact gcatccccag taatgaaagt acttagaaaa taattattga atgaatgaaa    5400
tctaaactgt gaacctgagg gtgtttgtgg cagtgtttgt tttactgaat tgtagaagga    5460
cataaccgtg ttttcagtgt ttctatggaa caaacttgta catttattt cacttgtgtt    5520 ttgtcttaaa ccctactgct ggaaacaatt ttatgtaata agcaatgggc ccaaaagtct    5580
aggagttttt ttgtacttag tgaatttgta tgcaacagag atgctgcagc tgatgccttt    5640
aaaaggtatt catcatggaa gagctgaggc ctgtgcttgg tgttccagag cccagggttg    5700
agcatcctga aggagccact gcagccgtca ctgtccccag agcctgtgga gatagagcct    5760
gtttgctgct ttttcttccc gctcttaaga catggctgga gctcagtctt cattgaatga    5820
agtttgctgt ggtattgcat agccttgctt tcttgaacta aactgtttgc ccttcacaag    5880
tagttcttct ttcaggatta gttcgttcca aggaggctct tcagtctcac agataagtag    5940
atctctcctg ctgtctggac acatttcact cggaaattga atacaatttg tattcaggct    6000
gggaacctga acacacactt gtgtttttaa gcttccettt tttacagtgg acaaggacac    6060
aaataataaa taaatcatcc ctaatgccca agaaaaaaa                           6099
```

<210> SEQ ID NO 64
<211> LENGTH: 2672

<212> TYPE: DNA
<213> ORGANISM: Homo sapiens

<400> SEQUENCE: 64

```
aggaagagcc gcgggcccgg cggctgaggc caccccggcg gcggctggag agcgaggagg      60
agcgggtggc ccgcgctgc gcccgccctc gcctcacctg gcgcaggtgg acacctgcgc     120
aggtgtgtgc cctccggccc ctgaagcatg gccagcagcg gcatggctga cagcgccaac     180
cacctgcccct tcttttttcgg caacatcacc cgggaggagg cagaagatta cctggtccag     240
ggggcatga gtgatgggct ttatttgctg cgccagagcc gcaactacct gggtggcttc     300
gccctgtccg tggcccacgg gaggaaggca caccactaca ccatcgagcg ggagctgaat     360
ggcacctacg ccatcgccgg tggcaggacc catgccagcc ccgccgacct ctgccactac     420
cactcccagt agtctgatgg cctggtctgc ctcctcaaga agcccttcaa ccggccccaa     480
ggggtgcagc ccaagactgg gccctttgag gatttgaagg aaaacctcat cagggaatat     540
gtgaagcaga catggaacct gcagggtcag gctctggagc aggccatcat cagtcagaag     600
cctcagctgg agaagctgat cgctaccaca gcccatgaaa aaatgccttg gttccatgga     660
aaaatctctc gggaagaatc tgagcaaatt gtcctgatag gatcaaagac aaatggaaag     720
ttcctgatcc gagccagaga caacaacggc tcctacgccc tgtgcctgct gcacgaaggg     780
aaggtgctgc actatcgcat cgacaaagac aagacaggga agctctccat ccccgaggga     840
aagaagttcg acacgctctg gcagctagtc gagcattatt cttataaagc agatggtttg     900
ttaagagttc ttactgtccc atgtcaaaaa atcggcacac agggaaatgt taattttgga     960
ggccgtccac aacttccagg ttcccatcct gcgacttggt cagcgggtgg aataatctca    1020
agaatcaaat catactcctt cccaaagcct ggccacagaa agtcctcccc tgcccaaggg    1080
aaccggcaag agagtactgt gtcattcaat ccgtatgagc agaacttgc accctgggct    1140
gcagacaaag ccccccagag agaagcccta cccatggaca cagaggtgta cgagagcccc    1200
tacgcggacc ctgaggagat caggcccaag gaggtttacc tggaccgaaa gctgctgacg    1260
ctggaagaca agaactggg ctctggtaat tttggaactg tgaaaaaggg ctactaccaa    1320
atgaaaaaag ttgtgaaaac cgtggctgtg aaaatactga aaaacgaggc caatgacccc    1380
gctcttaaag atgagttatt agcagaagca aatgtcatgc agcagctgga caacccgtac    1440
atcgtgcgca tgatcgggat atgcgaggcc gagtcctgga tgctagttat ggagatggca    1500
gaacttggtc ccctcaataa gtatttgcag cagaacagac atgtcaagga taagaacatc    1560
atagaactgg ttcatcaggt ttccatgggc atgaagtact tggaggagag caattttgtg    1620
cacagagatc tggctgcaag aaatgtgttg ctagttaccc aacattatgc caagatcagt    1680
gatttcggac tctccaaagc actgcgtgct gatgaaaact actacaaggc ccagacccat    1740
ggaaagtggc ctgtcaagtg gtacgctccg gaatgcatca actactacaa gttctccagc    1800
aaaagcgatg tctggagctt tggagtgttg atgtgggaag cattctccta tgggcagaag    1860
ccatatcgag ggatgaaagg aagtgaagtc accgctatgt tagagaaagg agagcggatg    1920
gggtgccctg cagggtgtcc aagagagatg tacgatctca tgaatctgtg ctggacatac    1980
gatgtggaaa acaggcccgg attcgcagca gtggaactgc ggctgcgcaa ttactactat    2040
gacgtggtga actaaccgct cccgcacctg tcggtggctg cctttgatca caggagcaat    2100
cacaggaaaa tgtatccaga ggaattgatt gtcagccacc tccctctgcc agtcgggaga    2160
gccaggcttg gatggaacat gcccacaact tgtcacccaa agcctgtccc aggactcacc    2220
```

-continued

| | | | |
|---|---|---|---|
| ctccacaaag | caaaggcagt | cccgggagaa | aagacggatg gcaggatcca aggggctagc | 2280 |
| tggatttgtt | tgttttcttg | tctgtgtgat | tttcatacag gttatttta cgatctgttt | 2340 |
| ccaaatccct | ttcatgtctt | tccacttctc | tgggtcccgg ggtgcatttg ttactcatcg | 2400 |
| ggcccaggga | cattgcagag | tggcctagag | cactctcacc ccaagcggcc ttttccaaat | 2460 |
| gcccaaggat | gccttagcat | gtgactcctg | aagggaaggc aaaggcagag gaatttggct | 2520 |
| gcttctacgg | ccatgagact | gatccctggc | cactgaaaag ctttcctgac aataaaaatg | 2580 |
| ttttgaggct | ttaaaagaa | aatcaagttt | gaccagtgca gtttctaagc atgtagccag | 2640 |
| ttaaggaaag | aaagaaaaaa | aaaaaaaaaa | aa | 2672 |

<210> SEQ ID NO 65
<211> LENGTH: 2650
<212> TYPE: DNA
<213> ORGANISM: Homo sapiens

<400> SEQUENCE: 65

| | | | | |
|---|---|---|---|---|
| agggacagcc | cagaggaggc | gtggccacgc | tgccggcgga agtggagccc tccgcgagcg | 60 |
| cgcgaggccg | ccggggcagg | cggggaaacc | ggacagtagg ggcggggccg ggccggcgat | 120 |
| ggggatgcgg | gagcactacg | cggagctgca | cccgtgcccg ccggaattgg ggatgcagag | 180 |
| cagcggcagc | gggtatggca | ggcagccggc | gggccggcct ccagcgcagg tgcccgagag | 240 |
| gcaggggctg | gcctgggatg | cgcgcgcacc | tgccctcgcc ccgccccgcc cgcacgaggg | 300 |
| gtggtggccg | aggccccgcc | ccgcacgcct | cgcctgaggc gggtccgctc agcccaggcg | 360 |
| cccgcccccg | ccccgccga | ttaaatgggc | cggcggggct cagcccccgg aaacggtcgt | 420 |
| aacttcgggg | ctgcgagcgc | ggagggcgac | gacgacgaag cgcagacagc gtcatggcag | 480 |
| agcaggtggc | cctgagccgg | acccaggtgt | gcgggatcct gcgggaagag ctttcccagg | 540 |
| gcgatgcctt | ccatcagtcg | gatacacaca | tattcatcat catgggtgca tcgggtgacc | 600 |
| tggccaagaa | gaagatctac | cccaccatct | ggtggctgtt ccgggatggc cttctgcccg | 660 |
| aaaacacctt | catcgtgggc | tatgcccgtt | cccgcctcac agtggctgac atccgcaaac | 720 |
| agagtgagcc | cttcttcaag | gccacccag | aggagaagct caagctggag gacttctttg | 780 |
| cccgcaactc | ctatgtggct | ggccagtacg | atgatgcagc ctcctaccag cgcctcaaca | 840 |
| gccacatgga | tgccctccac | ctggggtcac | aggccaaccg cctcttctac ctggccttgc | 900 |
| ccccgaccgt | ctacgaggcc | gtcaccaaga | acattcacga gtcctgcatg agccagatag | 960 |
| gctggaaccg | catcatcgtg | gagaagccct | cgggaggga cctgcagagc tctgaccggc | 1020 |
| tgtccaacca | catctcctcc | ctgttccgtg | aggaccagat ctaccgcatc gaccactacc | 1080 |
| tgggcaagga | gatggtgcag | aacctcatgg | tgctgagatt tgccaacagg atcttcggcc | 1140 |
| ccatctggaa | ccgggacaac | atcgcctgcg | ttatcctcac cttcaaggag ccctttggca | 1200 |
| ctgagggtcg | cggggctat | ttcgatgaat | ttgggatcat ccgggacgtg atgcagaacc | 1260 |
| acctactgca | gatgctgtgt | ctggtggcca | tggaagcc cgcctccacc aactcagatg | 1320 |
| acgtccgtga | tgagaaggtc | aaggtgttga | atgcatctc agaggtgcag gccaacaatg | 1380 |
| tggtcctggg | ccagtacgtg | gggaaccccg | atggagaggg cgaggccacc aaagggtacc | 1440 |
| tggacgaccc | cacggtgccc | cgcgggtcca | ccaccgccac ttttgcagcc gtcgtcctct | 1500 |
| atgtggagaa | tgagaggtgg | gatgggtgc | ccttcatcct gcgctgcggc aaggccctga | 1560 |
| acgagcgcaa | ggccgaggtg | aggctgcagt | tccatgatgt ggccggcgac atcttccacc | 1620 |
| agcagtgcaa | gcgcaacgag | ctggtgatcc | gcgtgcagcc caacgaggcc gtgtacacca | 1680 |

```
agatgatgac caagaagccg ggcatgttct tcaaccccga ggagtcggag ctggacctga   1740
cctacggcaa cagatacaag aacgtgaagc tccctgacgc ctacgagcgc ctcatcctgg   1800
acgtcttctg cgggagccag atgcacttcg tgcgcagcga cgagctccgt gaggcctggc   1860
gtattttcac cccactgctg caccagattg agctggagaa gcccaagccc atccccatta   1920
tttatggcag ccgaggcccc acggaggcag acgagctgat gaagagagtg ggtttccagt   1980
atgagggcac ctacaagtgg gtgaaccccc acaagctctg agccctgggc acccacctcc   2040
acccccgcca cggccaccct ccttcccgcc gcccgacccc gagtcgggag gactccggga   2100
ccattgacct cagctgcaca ttcctggccc ggggctctgg ccaccctggc ccgcccctcg   2160
ctgctgctac taccccgagcc cagctacatt cctcagctgc caagcactcg agaccatcct   2220 ggccccctcca gaccctgcct gagcccagga gctgagtcac ctcctccact cactccagcc   2280
caacagaagg aaggaggagg gcgcccattc gtctgtccca gagcttattg ccactgggt   2340 ctcactcctg agtggggcca gggtggggag gagggacaag ggggaggaaa ggggcgagca   2400
cccacgtgag agaatctgcc tgtggccttg cccgccagcc tcagtgccac ttgacattcc   2460
ttgtcaccag caacatctcg agccccctgg atgtcccctg tcccaccaac tctgcactcc   2520
atggccaccc cgtgccaccc gtaggcagcc tctctgctat aagaaaagca gacgcagcag   2580
ctgggacccc tcccaacctc aatgccctgc cattaaatcc gcaaacagcc aaaaaaaaaa   2640
aaaaaaaaa                                                           2650

<210> SEQ ID NO 66
<211> LENGTH: 2870
<212> TYPE: DNA
<213> ORGANISM: Homo sapiens

<400> SEQUENCE: 66
gcccggcagg ttggcggacc ggcgggaggc gcagcctggg cagagctcag cttggtcccg     60
ccgcccggcc ggtgctccct ggcgcagcca cgcaggcgca ccgcagacag acccctctgc    120
catgaaccag tccatcccag tggctcccac cccaccccgc cgcgtgcggc tgaagccctg    180
gctggtggcc caggtgaaca gctgccagta cccagggctt caatgggtca acggggaaaa    240
gaaattattc tgcatcccct ggaggcatgc cacaaggcat ggtcccagcc aggacggaga    300
taacaccatc ttcaaggcct gggccaagga gacagggaaa tacaccgaag gcgtggatga    360
agccgatccg gccaagtgga aggccaacct gcgctgtgcc cttaacaaga gccgggactt    420
ccgcctcatc tacgacgggc ccgggacat gccacctcag ccctacaaga tctacgaggt    480
ctgctccaat ggccctgctc ccacagactc ccagcccct gaggattact cttttggtgc     540
aggagaggag gaggaagaag aggaagagct gcagaggatg ttgccaagcc tgagcctcac    600
agatgcagtg cagtctggcc cccacatgac accctattct ttactcaaag aggatgtcaa    660
gtggccgcct actctgcagc cgccactct gcagccgccc gtggtgctgg gtccccctgc    720
tccagacccc agcccctgg ctcctccccc tggcaaccct gctggcttca gggagcttct    780
ctctgaggtc ctggagcctg ggcccctgcc tgccagcctg cccccctgcag gcgaacagct    840 cctgccagac ctgctgatca gccccccat gctgcctctg accgacctgg agatcaagtt    900
tcagtaccgg gggcggccac ccgggccct caccatcagc aaccccatg gctgccggct    960 cttctacagc cagctggagg ccaccccagga gcaggtggaa ctcttcggcc ccataagcct   1020
ggagcaagtg cgcttcccca gccctgagga catccccagt gacaagcagc gcttctacac   1080
```

| | |
|---|---|
| gaaccagctg ctggatgtcc tggaccgcgg gctcatcctc agctacagg gccaggacct | 1140 |
| ttatgccatc cgcctgtgtc agtgcaaggt gttctggagc gggccttgtg cctcagccca | 1200 |
| tgactcatgc cccaacccca tccagcggga ggtcaagacc aagcttttca gcctggagca | 1260 |
| ttttctcaat gagctcatcc tgttccaaaa gggccagacc aacacccac cacccttcga | 1320 |
| gatcttcttc tgctttgggg aagaatggcc tgaccgcaaa ccccgagaga agaagctcat | 1380 |
| tactgtacag gtggtgcctg tagcagctcg actgctgctg gagatgttct caggggagct | 1440 |
| atcttggtca gctgatagta ccggctaca gatctcaaac ccagacctca agaccgcat | 1500 |
| ggtggagcaa ttcaaggagc tccatcacat ctggcagtcc cagcagcggt tgcagcctgt | 1560 |
| ggcccaggcc cctcctggag caggccttgg tgttggccag gggccctggc ctatgcaccc | 1620 |
| agctggcatg caataacaag gctgcagacg gtgactggcc ctggcttcct gggtggcggt | 1680 |
| gcggactgat gtggagatgt gacagccccg atgagcacct ggctggctgc agggtcctac | 1740 |
| ctctgggttt cctggaagtg gatttgggcc aagaaggaga gggagaaagg cccgagcccc | 1800 |
| tgccttcccg ggccttttctc tcctgggctg tctctggtct ggtcagcctg gctctcggga | 1860 |
| aattcagcca tgagcaggga agaactctc ccaaccctgg ggcctagctg tataggagga | 1920 |
| attgcctaag ggtggcccac tcttgtgatt gccccatttc ctctggcaac aaaagccaga | 1980 |
| gtgttgtggg ccaagtcccc ccacagggcc tctgcagggc atggccctga tttccctggt | 2040 |
| ttgagactca cttcctcatc tccctgtcct ctgagataat atgagtgagc acttaggtat | 2100 |
| catatcagat gctcaaggct ggcagctacc cccttcttga gagtccaaga acctggagca | 2160 |
| gaaataattt ttatgtattt ttggattaat gaatgttaaa aacagactca gctgtttctt | 2220 |
| tccttttact actaccagtt gctcccatgc tgctccacca ggccctgttt cggatgccaa | 2280 |
| ctggcccact cccaagcac ttgccccag cttgcgacca ttggcactgg gagggcctgg | 2340 |
| cttctgggct gatgggtcag ttgggccttc ataaacactc acctggctgg ctttgccttc | 2400 |
| caggaggaag ctggctgaag caagggtgtg gaattttaaa tgtgtgcaca gtctggaaaa | 2460 |
| ctgtcagaat cagtttttccc ataaaagggt gggctagcat tgcagctgca tttgggacca | 2520 |
| ttcaaatctg tcactctctt gtgtatattc ctgtgctatt aaatatatca gggcagtgca | 2580 |
| tgtaaatcat cctgatatat ttaatatatt tattatattg tccccccgagg tggggacagt | 2640 |
| gagtgagttc tcttagtccc ccagagctg gttgttaaag agcctggcac ctacccgctc | 2700 |
| tcacttcatc tgtgtcatct ctgcacactc cagcccactt tctgccttca gccattgagt | 2760 |
| ggaagctgcc ccaggccctt accaggtgca gatgcccaat cttgatgccc agccatcaga | 2820 |
| actgtgagcc aaataaacct ttttctgtat aaaaaaaaaa aaaaaaaaa | 2870 |

<210> SEQ ID NO 67
<211> LENGTH: 1229
<212> TYPE: DNA
<213> ORGANISM: Homo sapiens

<400> SEQUENCE: 67

| | |
|---|---|
| gtctgacggg cgatggcgca gccaatagac aggagcgcta ccgcggtttt ctgattggct | 60 |
| actttgttcg cattataaaa ggcacgcgcg ggcgcgaggc ccttctctcg ccaggcgtcc | 120 |
| tcgtggaagt gacatcgtct ttaaaccctg cgtggcaatc cctgacgcac cgccgtgatg | 180 |
| cccagggaag acagggcgac ctggaagtcc aactacttcc ttaagatcat ccaactattg | 240 |
| gatgattatc cgaaatgttt cattgtggga gcagacaatg tgggctccaa gcagatgcag | 300 |
| cagatccgca tgtcccttcg cgggaaggct gtggtgctga tgggcaagaa caccatgatg | 360 |

| | |
|---|---|
| cgcaaggcca tccgagggca cctggaaaac aacccagctc tggagaaact gctgcctcat | 420 |
| atccggggga atgtgggctt tgtgttcacc aaggaggacc tcactgagat cagggacatg | 480 |
| ttgctggcca ataaggtgcc agctgctgcc cgtgctggtg ccattgcccc atgtgaagtc | 540 |
| actgtgccag cccagaacac tggtctcggg cccgagaaga cctccttttt ccaggcttta | 600 |
| ggtatcacca ctaaaatctc caggggcacc attgaaatcc tgagtgatgt gcagctgatc | 660 |
| aagactggag acaaagtggg agccagcgaa gccacgctgc tgaacatgct caacatctcc | 720 |
| cccttctcct ttgggctggt catccagcag gtgttcgaca atggcagcat ctacaaccct | 780 |
| gaagtgcttg atatcacaga ggaaactctg cattctcgct tcctggaggg tgtccgcaat | 840 |
| gttgccagtg tctgtctgca gattggctac ccaactgttg catcagtacc ccattctatc | 900 |
| atcaacgggt acaaacgagt cctggccttg tctgtggaga cggattacac cttcccactt | 960 |
| gctgaaaagg tcaaggcctt cttggctgat ccatctgcct tgtggctgc tgcccctgtg | 1020 |
| gctgctgcca ccacagctgc tcctgctgct gctgcagccc cagctaaggt tgaagccaag | 1080 |
| gaagagtcgg aggagtcgga cgaggatatg ggatttggtc tctttgacta atcaccaaaa | 1140 |
| agcaaccaac ttagccagtt ttatttgcaa aacaaggaaa taaaggctta cttctttaaa | 1200 |
| aagtaaaaaa aaaaaaaaaa aaaaaaaaa | 1229 |

<210> SEQ ID NO 68
<211> LENGTH: 1661
<212> TYPE: DNA
<213> ORGANISM: Homo sapiens

<400> SEQUENCE: 68

| | |
|---|---|
| tgctgcagcc gctgccgccg attccggatc tcattgccac gcgcccccga cgaccgcccg | 60 |
| acgtgcattc ccgattcctt ttggttccaa gtccaatatg gcaactctaa aggatcagct | 120 |
| gatttataat cttctaaagg aagaacagac cccccagaat aagattacag ttgttggggt | 180 |
| tggtgctgtt ggcatggcct gtgccatcag tatcttaatg aaggacttgg cagatgaact | 240 |
| tgctcttgtt gatgtcatcg aagacaaatt gaagggagag atgatggatc tccaacatgg | 300 |
| cagccttttc cttagaacac caaagattgt ctctggcaaa gactataatg taactgcaaa | 360 |
| ctccaagctg gtcattatca cggctggggc acgtcagcaa gagggagaaa gccgtcttaa | 420 |
| tttggtccag cgtaacgtga acatatttaa attcatcatt cctaatgttg taaaatacag | 480 |
| cccgaactgc aagttgctta ttgttttcaaa tccagtggat atcttgacct acgtggcttg | 540 |
| gaagataagt ggttttccca aaaccgtgt tattggaagt ggttgcaatc tggattcagc | 600 |
| ccgattccgt tacctgatgg gggaaaggct gggagttcac ccattaagct gtcatgggtg | 660 |
| ggtccttggg gaacatggag attccagtgt gcctgtatgg agtggaatga atgttgctgg | 720 |
| tgtctctctg aagactctgc acccagattt agggactgat aaagataagg aacagtggaa | 780 |
| agaggttcac aagcaggtgg ttgagagtgc ttatgaggtg atcaaactca aaggctacac | 840 |
| atcctgggct attggactct ctgtagcaga tttggcagag agtataatga gaatcttag | 900 |
| gcgggtgcac ccagtttcca ccatgattaa gggtctttac ggaataaagg atgatgtctt | 960 |
| ccttagtgtt ccttgcattt tgggacagaa tggaatctca gaccttgtga aggtgactct | 1020 |
| gacttctgag gaagaggccc gtttgaagaa gagtgcagat acactttggg ggatccaaaa | 1080 |
| ggagctgcaa ttttaaagtc ttctgatgtc atatcatttc actgtctagg ctacaacagg | 1140 |
| attctaggtg gaggttgtgc atgttgtcct ttttatctga tctgtgatta aagcagtaat | 1200 |

```
attttaagat ggactgggaa aaacatcaac tcctgaagtt agaaataaga atggtttgta    1260
aaatccacag ctatatcctg atgctggatg gtattaatct tgtgtagtct tcaactggtt    1320
agtgtgaaat agttctgcca cctctgacgc accactgcca atgctgtacg tactgcattt    1380 gcccettgag ccaggtggat gtttaccgtg tgttatataa cttcctggct ccttcactga    1440
acatgcctag tccaacattt tttcccagtg agtcacatcc tgggatccag tgtataaatc    1500
caatatcatg tcttgtgcat aattcttcca aaggatctta ttttgtgaac tatatcagta    1560
gtgtacatta ccatataatg taaaaagatc tacatacaaa caatgcaacc aactatccaa    1620
gtgttatacc aactaaaacc cccaataaac cttgaacagt g                        1661
```

<210> SEQ ID NO 69
<211> LENGTH: 3655
<212> TYPE: DNA
<213> ORGANISM: Homo sapiens

<400> SEQUENCE: 69

```
cttcagatag attatatctg gagtgaagga tcctgccacc tacgtatctg gcatagtatt      60
ctgtgtagtg ggatgagcag agaacaaaaa caaaataatc cagtgagaaa agcccgtaaa     120
taaaccttca gaccagagat ctattctcca gcttatttta agctcaactt aaaaagaaga     180
actgttctct gattcttttc gccttcaata cacttaatga tttaactcca ccctccttca     240
aaagaaacag catttcctac ttttatactg tctatatgat tgatttgcac agctcatctg     300
gccagaagag ctgagacatc cgttccccta caagaaactc tccccgggtg aacaagatg      360 gattatcaag tgtcaagtcc aatctatgac atcaattatt atacatcgga gccctgccaa     420
aaaatcaatg tgaagcaaat cgcagcccgc ctcctgcctc cgctctactc actggtgttc     480
atctttggtt ttgtgggcaa catgctggtc atcctcatcc tgataaactg caaaaggctg     540
aagagcatga ctgacatcta cctgctcaac ctggccatct ctgacctgtt tttccttctt     600
actgtcccct tctgggctca ctatgctgcc gcccagtggg actttggaaa tacaatgtgt     660
caactcttga caggggctcta ttttataggc ttcttctctg gaatcttctt catcatcctc     720
ctgacaatcg ataggtacct ggctgtcgtc catgctgtgt ttgctttaaa agccaggacg     780
gtcacctttg gggtggtgac aagtgtgatc acttgggtgg tggctgtgtt tgcgtctctc     840
ccaggaatca tctttaccag atctcaaaaa gaaggtcttc attacacctg cagctctcat     900
tttccataca gtcagtatca attctggaag aatttccaga cattaaagat agtcatcttg     960
gggctggtcc tgccgctgct tgtcatggtc atctgctact cgggaatcct aaaaactctg    1020
cttcggtgtc gaaatgagaa aagaggcac agggctgtga ggcttatctt caccatcatg    1080
attgtttatt ttctcttctg ggctccctac aacattgtcc ttctcctgaa cacctccag    1140 gaattctttg gcctgaataa ttgcagtagc tctaacaggt tggaccaagc tatgcaggtg    1200
acagagactc ttgggatgac gcactgctgc atcaaccca tcatctatgc ctttgtcggg    1260
gagaagttca gaaactacct cttagtcttc ttccaaaagc acattgccaa acgcttctgc    1320
aaatgctgtt ctattttcca gcaagaggct cccgagcgag caagctcagt ttacacccga    1380
tccactgggg agcaggaaat atctgtgggc ttgtgacacg gactcaagtg ggctggtgac    1440
ccagtcagag ttgtgcacat ggcttagttt tcatacacag cctgggctgg ggtggggtg    1500 ggagaggtct tttttaaaag gaagttactg ttatagaggg tctaagattc atccatttat    1560
ttggcatctg tttaaagtag attagatctt ttaagcccat caattataga agccaaatc    1620 aaaatatgtt gatgaaaaat agcaacctttt ttatctcccc ttcacatgca tcaagttatt    1680
```

```
gacaaactct cccttcactc cgaaagttcc ttatgtatat ttaaaagaaa gcctcagaga    1740
attgctgatt cttgagttta gtgatctgaa cagaaatacc aaaattattt cagaaatgta    1800
caacttttta cctagtacaa ggcaacatat aggttgtaaa tgtgtttaaa acaggtcttt    1860
gtcttgctat ggggagaaaa gacatgaata tgattagtaa agaaatgaca cttttcatgt    1920
gtgatttccc ctccaaggta tggttaataa gtttcactga cttagaacca ggcgagagac    1980
ttgtggcctg ggagagctgg ggaagcttct taaatgagaa ggaatttgag ttggatcatc    2040
tattgctggc aaagacagaa gcctcactgc aagcactgca tgggcaagct ggctgtaga     2100
aggagacaga gctggttggg aagacatggg aggaaggac aaggctagat catgaagaac     2160
cttgacggca ttgctccgtc taagtcatga gctgagcagg gagatcctgg ttggtgttgc    2220
agaaggttta ctctgtggcc aaaggagggt caggaaggat gagcatttag ggcaaggaga    2280
ccaccaacag ccctcaggtc agggtgagga tggcctctgc taagctcaag gcgtgaggat    2340
gggaaggagg gaggtattcg taaggatggg aaggagggag gtattcgtgc agcatatgag    2400
gatgcagagt cagcagaact ggggtggatt tggtttggaa gtgagggtca gagaggagtc    2460
agagagaatc cctagtcttc aagcagattg agaaaccct tgaaaagaca tcaagcacag     2520
aaggaggagg aggaggttta ggtcaagaag aagatggatt ggtgtaaaag gatgggtctg    2580
gtttgcagag cttgaacaca gtctcaccca gactccaggc tgtctttcac tgaatgcttc    2640
tgacttcata gatttccttc ccatcccagc tgaaatactg aggggtctcc aggaggagac    2700
tagatttatg aatacacgag gtatgaggtc taggaacata cttcagctca cacatgagat    2760
ctaggtgagg attgattacc tagtagtcat ttcatgggtt gttgggagga ttctatgagg    2820
caaccacagg cagcatttag cacatactac acattcaata agcatcaaac tcttagttac    2880
tcattcaggg atagcactga gcaaagcatt gagcaaaggg gtcccatata ggtgagggaa    2940
gcctgaaaaa ctaagatgct gcctgcccag tgcacacaag tgtaggtatc attttctgca    3000
tttaaccgtc aataggcaaa ggggggaagg gacatattca tttggaaata agctgccttg    3060
agccttaaaa cccacaaaag tacaatttac cagcctccgt atttcagact gaatgggggt    3120
ggggggggcg ccttaggtac ttattccaga tgccttctcc agacaaacca gaagcaacag    3180
aaaaaatcgt ctctccctcc ctttgaaatg aatatacccc ttagtgtttg ggtatattca    3240
tttcaaaggg agagagagag gttttttttct gttctttctc atatgattgt gcacatactt   3300
gagactgttt tgaatttggg ggatggctaa aaccatcata gtacaggtaa ggtgagggaa    3360
tagtaagtgg tgagaactac tcagggaatg aaggtgtcag aataataaga ggtgctactg    3420
actttctcag cctctgaata tgaacggtga gcattgtggc tgtcagcagg aagcaacgaa    3480
gggaaatgtc tttccttttg ctcttaagtt gtggagagtg caacagtagc ataggaccct    3540
accctctggg ccaagtcaaa gacattctga catcttagta tttgcatatt cttatgtatg    3600
tgaaagttac aaattgcttg aaagaaaata tgcatctaat aaaaaacacc ttcta          3655
```

<210> SEQ ID NO 70  
<211> LENGTH: 1320  
<212> TYPE: DNA  
<213> ORGANISM: Homo sapiens

<400> SEQUENCE: 70

```
cggaagggga aggggtgga ggttgctgct atgagagaga aaaaaaaaac agccacaata      60
gagattctgc cttcaaaggt tggcttgcca cctgaagcag ccactgccca gggggtgcaa    120
```

| | |
|---|---|
| agaagagaca gcagcgccca gcttggaggt gctaactcca gaggccagca tcagcaactg | 180 |
| ggcacagaaa ggagccgcct gggcagggac catggcacgg ccacatccct ggtggctgtg | 240 |
| cgttctgggg accctggtgg ggctctcagc tactccagcc cccaagagct gcccagagag | 300 |
| gcactactgg gctcagggaa agctgtgctg ccagatgtgt gagccaggaa cattcctcgt | 360 |
| gaaggactgt gaccagcata gaaaggctgc tcagtgtgat ccttgcatac cgggggtctc | 420 |
| cttctctcct gaccaccaca cccggcccca ctgtgagagc tgtcggcact gtaactctgg | 480 |
| tcttctcgtt cgcaactgca ccatcactgc caatgctgag tgtgcctgtc gcaatggctg | 540 |
| gcagtgcagg gacaaggagt gcaccgagtg tgatcctctt ccaaacccctt cgctgaccgc | 600 |
| tcggtcgtct caggccctga gcccacaccc tcagcccacc cacttacctt atgtcagtga | 660 |
| gatgctggag gccaggacag ctgggcacat gcagactctg gctgacttca ggcagctgcc | 720 |
| tgcccggact ctctctaccc actggccacc ccaaagatcc ctgtgcagct ccgatttat | 780 |
| tcgcatcctt gtgatcttct ctggaatgtt ccttgttttc accctggccg gggccctgtt | 840 |
| cctccatcaa cgaaggaaat atagatcaaa caaaggagaa agtcctgtgg agcctgcaga | 900 |
| gccttgtcgt tacagctgcc caggggagga ggagggcagc accatcccca tccaggagga | 960 |
| ttaccgaaaa ccggagcctg cctgctcccc ctgagccagc acctgcggga gctgcactac | 1020 |
| agccctggcc tccaccccca ccccgccgac catccaaggg agagtgagac ctggcagcca | 1080 |
| caactgcagt cccatcctct tgtcagggcc cttttcctgtg tacacgtgac agagtgcctt | 1140 |
| ttcgagactg gcaggacga ggacaaatat ggatgaggtg gagagtggga agcaggagcc | 1200 |
| cagccagctg cgcctgcgct gcaggagggc ggggctctg gttgtaaaac acacttcctg | 1260 |
| ctgcgaaaga cccacatgct acaagacggg caaaataaag tgacagatga ccaccctgca | 1320 |

<210> SEQ ID NO 71
<211> LENGTH: 1310
<212> TYPE: DNA
<213> ORGANISM: Homo sapiens

<400> SEQUENCE: 71

| | |
|---|---|
| aaattgagcc cgcagcctcc cgcttcgctc tctgctcctc ctgttcgaca gtcagccgca | 60 |
| tcttcttttg cgtcgccagc cgagccacat cgctcagaca ccatggggaa ggtgaaggtc | 120 |
| ggagtcaacg gatttggtcg tattgggcgc ctggtcacca gggctgcttt taactctggt | 180 |
| aaagtggata ttgttgccat caatgacccc ttcattgacc tcaactacat ggtttacatg | 240 |
| ttccaatatg attccaccca tggcaaattc catggcaccg tcaaggctga gaacgggaag | 300 |
| cttgtcatca atggaaatcc catcaccatc ttccaggagc gagatccctc caaaatcaag | 360 |
| tgggggcgatg ctggcgctga gtacgtcgtg gagtccactg gcgtcttcac caccatggag | 420 |
| aaggctgggg ctcatttgca ggggggagcc aaaagggtca tcatctctgc ccctctgct | 480 |
| gatgcccca tgttcgtcat gggtgtgaac catgagaagt atgacaacag cctcaagatc | 540 |
| atcagcaatg cctcctgcac caccaactgc ttagcacccc tggccaaggt catccatgac | 600 |
| aactttggta tcgtggaagg actcatgacc acagtccatg ccatcactgc acccagaag | 660 |
| actgtggatg cccctccgg gaaactgtgg cgtgatggcc gcggggctct ccagaacatc | 720 |
| atccctgcct ctactggcgc tgccaaggct gtgggcaagg tcatccctga ctgaacggg | 780 |
| aagctcactg gcatggcctt ccgtgtcccc actgccaacg tgtcagtggt ggacctgacc | 840 |
| tgccgtctag aaaaacctgc caaatatgat gacatcaaga aggtggtgaa gcaggcgtcg | 900 |
| gagggccccc tcaagggcat cctgggctac actgagcacc aggtggtctc ctctgacttc | 960 |

| | |
|---|---|
| aacagcgaca cccactcctc cacctttgac gctggggctg gcattgccct caacgaccac | 1020 |
| tttgtcaagc tcatttcctg gtatgacaac gaatttggct acagcaacag ggtggtggac | 1080 |
| ctcatggccc acatggcctc caaggagtaa gacccctgga ccaccagccc cagcaagagc | 1140 |
| acaagaggaa gagagagacc ctcactgctg gggagtccct gccacactca gtcccccacc | 1200 |
| acactgaatc tcccctcctc acagttgcca tgtagacccc ttgaagaggg gaggggccta | 1260 |
| gggagccgca ccttgtcatg taccatcaat aaagtaccct gtgctcaacc | 1310 |

<210> SEQ ID NO 72
<211> LENGTH: 2510
<212> TYPE: DNA
<213> ORGANISM: Homo sapiens

<400> SEQUENCE: 72

| | |
|---|---|
| gcacctcgct gctccagcct ctggggcgca ttccaacctt ccagcctgcg acctgcggag | 60 |
| aaaaaaaatt acttatttc ttgccccata cataccttga ggcgagcaaa aaaattaaat | 120 |
| tttaaccatg agggaaatcg tgcacatcca ggctggtcag tgtggcaacc agatcggtgc | 180 |
| caagttctgg gaggtgatca gtgatgaaca tggcatcgac cccaccggca cctaccacgg | 240 |
| ggacagcgac ctgcagctgg accgcatctc tgtgtactac aatgaagcca caggtggcaa | 300 |
| atatgttcct cgtgccatcc tggtggatct agaacctggg accatggact ctgttcgctc | 360 |
| aggtcctttt ggccagatct ttagaccaga caactttgta tttggtcagt ctggggcagg | 420 |
| taacaactgg gccaaaggcc actacacaga gggcgccgag ctggttgatt ctgtcctgga | 480 |
| tgtggtacgg aaggaggcag agagctgtga ctgcctgcag ggcttccagc tgacccactc | 540 |
| actgggcggg ggcacaggct ctggaatggg cactctcctt atcagcaaga tccgagaaga | 600 |
| ataccctgat cgcatcatga atacctcag tgtggtgcct tcacccaaag tgtctgacac | 660 |
| cgtggtcgag ccctacaatg ccaccctctc cgtccatcag ttggtagaga atactgatga | 720 |
| gacctattgc attgacaacg aggccctcta tgatatctgc ttccgcactc tgaagctgac | 780 |
| cacaccaacc tacggggatc tgaaccacct tgtctcagcc accatgagtg gtgtcaccac | 840 |
| ctgcctccgt ttccctggcc agctcaatgc tgacctccgc aagttggcag tcaacatggt | 900 |
| ccccttccca cgtctccatt tctttatgcc tggctttgcc cctctcacca gccgtggaag | 960 |
| ccagcagtat cgagctctca cagtgccgga actcacccag caggtcttcg atgccaagaa | 1020 |
| catgatggct gcctgtgacc cccgccacgg ccgataccttc accgtggctg ctgtcttccg | 1080 |
| tggtcgatg tccatgaagg aggtcgatga gcagatgctt aacgtgcaga acaagaacag | 1140 |
| cagctacttt gtggaatgga tccccaacaa tgtcaagaca gccgtctgtg acatcccacc | 1200 |
| tcgtggcctc aagatggcag tcaccttcat tggcaatagc acagccatcc aggagctctt | 1260 |
| caagcgcatc tcggagcagt tcactgccat gttccgccgg aaggccttcc tccactggta | 1320 |
| cacaggcgag ggcatggacg agatggagtt caccgaggct gagagcaaca tgaacgacct | 1380 |
| cgtctctgag tatcagcagt accaggatgc caccgcagaa gaggaggagg atttcggtga | 1440 |
| ggaggccgaa gaggaggcct aaggcagagc cccatcacc tcaggcttct cagttccctt | 1500 |
| agccgtctta ctcaactgcc cctttcctct ccctcagaat ttgtgtttgc tgcctctatc | 1560 |
| ttgttttttg ttttttcttc tgggggggt ctagaacagt gcctggcaca tagtaggcgc | 1620 |
| tcaataaata cttgtttgtt gaatgtctcc tctctctttc cactctggga aacctaggtt | 1680 |
| tctgccattc tgggtgaccc tgtatttctt tctggtgcca attccatttg tccagttaat | 1740 |

| | | |
|---|---|---|
| acttcctctt aaaaatctcc aagaagctgg gtctccagat cccatttaga accaaccagg | 1800 | |
| tgctgaaaac acatgtagat aatggccatc atcctaagcc caaagtagaa aatggtagaa | 1860 | |
| ggtagtgggt agaagtcact atataaggaa ggggatggga ttttccattc taaaagtttt | 1920 | |
| ggagagggaa atccaggcta ttaaagtcac taaatttcta agtatgtcca tttcccatct | 1980 | |
| cagcttcaag ggaggtgtca gcagtattat ctccactttc aatctccctc caagctctac | 2040 | |
| tctggaggag tctgtcccac tctgtcaagt ggaatccttc cctttccaac tctacctccc | 2100 | |
| tcactcagct cctttcccct gatcagagaa agggatcaag ggggttggga ggggggaaag | 2160 | |
| agaccagcct tggtccctaa gcctccagaa acgtcttctt aatccccacc tttcttact | 2220 | |
| cccaaaaaag aatgaacacc cctgactctg gagtggtgta tactgccaca tcagtgtttg | 2280 | |
| agtcagtccc cagaggagag gggaaccctc ctccatcttt tttgcaacat ctcatttctt | 2340 | |
| ccttttgctg ttgcttcccc cctcacacac ttggttttgt tctatcctac atttgagatt | 2400 | |
| tctattttat gttgaacttg ctgcttttt tcatattgaa agatgacat cgccccaaga | 2460 | |
| gccaaaaata aatgggaatt gaaaaaaaaa aaaaaaaaa aaaaaaaaa | 2510 | |

<210> SEQ ID NO 73
<211> LENGTH: 1867
<212> TYPE: DNA
<213> ORGANISM: Homo sapiens

<400> SEQUENCE: 73

| | | |
|---|---|---|
| ggttcgctgt ggcgggcgcc tgggccgccg gctgtttaac ttcgcttccg ctggcccata | 60 | |
| gtgatctttg cagtgaccca gcagcatcac tgtttcttgg cgtgtgaaga taacccaagg | 120 | |
| aattgaggaa gttgctgaga agagtgtgct ggagatgctc taggaaaaaa ttgaatagtg | 180 | |
| agacgagttc cagcgcaagg gtttctggtt tgccaagaag aaagtgaaca tcatggatca | 240 | |
| gaacaacagc ctgccacctt acgctcaggg cttggcctcc cctcagggtg ccatgactcc | 300 | |
| cggaatccct atctttagtc caatgatgcc ttatggcact ggactgaccc cacagcctat | 360 | |
| tcagaacacc aatagtctgt ctattttgga agagcaacaa aggcagcagc agcaacaaca | 420 | |
| acagcagcag cagcagcagc agcagcaaca gcaacagcag cagcagcagc agcagcagca | 480 | |
| gcagcagcag cagcagcagc agcagcagca gcaacaggca gtggcagctg cagccgttca | 540 | |
| gcagtcaacg tcccagcagg caacacaggg aacctcaggc caggcaccac agctcttcca | 600 | |
| ctcacagact ctcacaactg caccttgcc gggcaccact ccactgtatc cctcccccat | 660 | |
| gactcccatg acccccatca ctcctgccac gccagcttcg gagagttctg ggattgtacc | 720 | |
| gcagctgcaa aatattgtat ccacagtgaa tcttggttgt aaacttgacc taaagaccat | 780 | |
| tgcacttcgt gcccgaaacg ccgaatataa tcccaagcgg tttgctgcgg taatcatgag | 840 | |
| gataagagag ccacgaacca cggcactgat tttcagttct gggaaaatgg tgtgcacagg | 900 | |
| agccaagagt gaagaacagt ccagactggc agcaagaaaa tatgctagag ttgtacagaa | 960 | |
| gttgggtttt ccagctaagt tcttggactt caagattcag aatatggtgg ggagctgtga | 1020 | |
| tgtgaagttt cctataaggt tagaaggcct tgtgctcacc caccaacaat ttagtagtta | 1080 | |
| tgagccagag ttatttcctg gtttaatcta cagaatgatc aaaccccagaa ttgttctcct | 1140 | |
| tattttttgtt tctggaaaag ttgtattaac aggtgctaaa gtcagagcag aaatttatga | 1200 | |
| agcatttgaa aacatctacc ctattctaaa gggattcagg aagacgacgt aatggctctc | 1260 | |
| atgtacccctt gcctccccca cccccttctt tttttttttt taaacaaatc agtttgtttt | 1320 | |
| ggtacccttta aatggtggtg ttgtgagaag atggatgttg agttgcaggg tgtggcacca | 1380 | |

```
ggtgatgccc ttctgtaagt gcccaccgcg ggatgccggg aagggggcatt atttgtgcac   1440 tgagaacacc gcgcagcgtg actgtgagtt gctcataccg tgctgctatc tgggcagcgc   1500
tgcccattta tttatatgta gattttaaac actgctgttg acaagttggt ttgagggaga   1560
aaactttaag tgttaaagcc acctctataa ttgattggac tttttaattt taatgttttt   1620
ccccatgaac cacagttttt atatttctac cagaaaagta aaaatctttt ttaaaagtgt   1680
tgttttctca atttataact cctaggggtt atttctgtgc cagacacatt ccacctctcc   1740
agtattgcag gacagaatat atgtgttaat gaaaatgaat ggctgtacat attttttct    1800 ttcttcagag tactctgtac aataaatgca gtttataaaa gtgttaaaaa aaaaaaaaa    1860 aaaaaaa                                                             1867

<210> SEQ ID NO 74
<211> LENGTH: 748
<212> TYPE: DNA
<213> ORGANISM: Homo sapiens

<400> SEQUENCE: 74
gcagataatg ggaggagccg ggcccgagcg agctctttcc tttcgctgct gcggccgcag     60
ccatgagtat gctcaggctt cagaagaggc tcgcctctag tgtcctccgc tgtggcaaga    120
agaaggtctg gttagacccc aatgagacca atgaaatcgc caatgccaac tcccgtcagc    180
agatccggaa gctcatcaaa gatgggctga tcatccgcaa gcctgtgacg gtccattccc    240
gggctcgatg ccggaaaaac accttggccc gccggaaggg caggcacatg gcataggta    300 agcggaaggg tacagccaat gcccgaatgc cagagaaggt cacatggatg aggagaatga    360
ggattttgcg ccggctgctc agaagatacc gtgaatctaa aagatcgat cgccacatgt    420 atcacagcct gtacctgaag gtgaagggga atgtgttcaa aaacaagcgg attctcatgg    480
aacacatcca caagctgaag gcagacaagg cccgcaagaa gctcctggct gaccaggctg    540
aggcccgcag gtctaagacc aaggaagcac gcaagcgccg tgaagagcgc ctccaggcca    600
agaaggagga gatcatcaag actttatcca aggaggaaga gaccaagaaa taaaacctcc    660
cactttgtct gtacatactg gcctctgtga ttacatagat cagccattaa aataaaacaa    720
gccttaatct gcaaaaaaaa aaaaaaaa                                       748

<210> SEQ ID NO 75
<211> LENGTH: 1331
<212> TYPE: DNA
<213> ORGANISM: Homo sapiens

<400> SEQUENCE: 75
tcttgctgcg cctccgcctc ctcctctgct ccgccaccgg cttcctcctc ctgagcagtc     60
agcccgcgcg ccggccggct ccgttatggc gacccgcagc cctggcgtcg tgattagtga    120
tgatgaacca ggttatgacc ttgatttatt ttgcatacct aatcattatg ctgaggattt    180
ggaaagggtg tttattcctc atggactaat tatggacagg actgaacgtc ttgctcgaga    240
tgtgatgaag gagatgggag gccatcacat tgtagccctc tgtgtgctca agggggggcta    300 taaattcttt gctgacctgc tggattacat caaagcactg aatagaaata gtgatagatc    360
cattcctatg actgtagatt ttatcagact gaagagctat tgtaatgacc agtcaacagg    420
ggacataaaa gtaattggtg gagatgatct ctcaacttta actggaaaga atgtcttgat    480
tgtggaagat ataattgaca ctggcaaaac aatgcagact ttgctttcct tggtcaggca    540
```

```
gtataatcca aagatggtca aggtcgcaag cttgctggtg aaaaggaccc cacgaagtgt    600
tggatataag ccagactttg ttggatttga aattccagac aagtttgttg taggatatgc    660
ccttgactat aatgaatact tcagggattt gaatcatgtt tgtgtcatta gtgaaactgg    720
aaaagcaaaa tacaaagcct aagatgagag ttcaagttga gtttggaaac atctggagtc    780
ctattgacat cgccagtaaa attatcaatg ttctagttct gtggccatct gcttagtaga    840
gcttttgca  tgtatcttct aagaatttta tctgttttgt actttagaaa tgtcagttgc     900
tgcattccta aactgtttat ttgcactatg agcctataga ctatcagttc cctttgggcg    960
gattgttgtt taacttgtaa atgaaaaaat tctcttaaac cacagcacta ttgagtgaaa   1020
cattgaactc atatctgtaa gaaataaaga gaagatatat tagtttttta attggtattt   1080
taattttat  atatgcagga aagaatagaa gtgattgaat attgttaatt ataccaccgt   1140
gtgttagaaa agtaagaagc agtcaatttt cacatcaaag acagcatcta agaagttttg   1200
ttctgtcctg gaattatttt agtagtgttt cagtaatgtt gactgtattt tccaacttgt   1260
tcaaattatt accagtgaat ctttgtcagc agttcccttt taaatgcaaa tcaataaatt   1320
cccaaaaatt t                                                        1331

<210> SEQ ID NO 76
<211> LENGTH: 2407
<212> TYPE: DNA
<213> ORGANISM: Homo sapiens

<400> SEQUENCE: 76
ctgtatatta aggcgccggc gatcgcggcc tgaggctgct cccggacaag ggcaacgagc     60
gtttcgtttg gacttctcga cttgagtgcc cgcctccttc gccgccgcct ctgcagtcct    120
cagcgcagtt atgcccagtt cttcccgctg tggggacacg accacggagg aatccttgct    180
tcagggactc gggaccctgc tggaccccct cctcgggttt aggggatgtg gggaccagga    240
gaaagtcagg atccctaaga gtcttccctg cctggatgga tgagtggctt cttctccacc    300
tagattcttt ccacaggagc cagcatactt cctgaacatg gagagtgttg ttcgccgctg    360
cccattctta tcccgagtcc cccaggcctt tctgcagaaa gcaggcaaat ctctgttgtt    420
ctatgcccaa aactgcccca agatgatgga agttggggcc aagccagccc ctcgggcatt    480
gtccactgca gcagtacact accaacagat caaagaaacc cctccggcca gtgagaaaga    540
caaaactgct aaggccaagg tccaacagac tcctgatgga tcccagcaga gtccagatgg    600
cacacagctt ccgtctggac accccttgcc tgccacaagc cagggcactg caagcaaatg    660
cccttccctg gcagcacaga tgaatcagag aggcagcagt gtcttctgca aagccagtct    720
tgagcttcag gaggatgtgc aggaaatgaa tgccgtgagg aaagaggttg ctgaaacctc    780
agcaggcccc agtgtggtta gtgtgaaaac cgatggaggg gatcccagtg gactgctgaa    840
gaacttccag gacatcatgc aaaagcaaag accagaaaga gtgtctcatc ttcttcaaga    900
taacttgcca aaatctgttt ccactttca gtatgatcgt ttctttgaga aaaaattga     960
tgagaaaaag aatgaccaca cctatcgagt ttttaaaact gtgaaccggc gagcacacat   1020
cttccccatg gcagatgact attcagactc cctcatcacc aaaaagcaag tgtcagtctg   1080
gtgcagtaat gactacctag gaatgagtcg ccacccacgg gtgtgtgggg cagttatgga   1140
cactttgaaa caacatggtg ctggggcagg tggtactaga aatatttctg gaactagtaa   1200
attccatgtg gacttagagc gggagctggc agacctccat gggaaagatg ccgcactctt   1260
gttttcctcg tgctttgtgg ccaatgactc aaccctcttc accctggcta agatgatgcc   1320
```

```
aggctgtgag atttactctg attctgggaa ccatgcctcc atgatccaag ggattcgaaa    1380
cagccgagtg ccaaagtaca tcttccgcca caatgatgtc agccacctca gagaactgct    1440
gcaaagatct gacccctcag tccccaagat tgtggcattt gaaactgtcc attcaatgga    1500
tggggcggtg tgcccactgg aagagctgtg tgatgtggcc catgagtttg gagcaatcac    1560
cttcgtggat gaggtccacg cagtggggct ttatggggct cgaggcggag ggattgggga    1620
tcgggatgga gtcatgccaa aaatggacat catttctgga acacttggca aagcctttgg    1680
ttgtgttgga gggtacatcg ccagcacgag ttctctgatt gacaccgtac ggtcctatgc    1740
tgctggcttc atcttcacca cctctctgcc acccatgctg ctggctggag ccctggagtc    1800
tgtgcggatc ctgaagagcg ctgagggacg ggtgcttcgc cgccagcacc agcgcaacgt    1860
caaactcatg agacagatgc taatggatgc cggcctccct gttgtccact gcccagcca    1920 catcatccct gtgcgggttg cagatgctgc taaaaacaca gaagtctgtg atgaactaat    1980
gagcagacat aacatctacg tgcaagcaat caattaccct acggtgcccc ggggagaaga    2040
gctcctacgg attgccccca cccctcacca cacaccccag atgatgaact acttccttga    2100
gaatctgcta gtcacatgga agcaagtggg gctggaactg aagcctcatt cctcagctga    2160
gtgcaacttc tgcaggaggc cactgcattt tgaagtgatg agtgaaagag agaagtccta    2220
tttctcaggc ttgagcaagt tggtatctgc tcaggcctga gcatgacctc aattatttca    2280
cttaacccca ggccattatc atatccagat ggtcttcaga gttgtcttta tatgtgaatt    2340
aagttatatt aaattttaat ctatagtaaa aacatagtcc tggaaataaa ttcttgctta    2400
aatggtg                                                              2407

<210> SEQ ID NO 77
<211> LENGTH: 6732
<212> TYPE: DNA
<213> ORGANISM: Homo sapiens

<400> SEQUENCE: 77
gagagcgcgg ccgggacggt tggagaagaa ggcggctccc cggaaggggg agagacaaac     60
tgccgtaacc tctgccgttc aggaacccgg ttacttattt attcgttacc cttttcttc    120 ttcctccccc aaaaaccttt tcctttccc ttctttttt ttccttttg ggagctgaaa      180 aatttccggt aagggaaaga agggctcctt tcgctcctta tttcgccgcc tccttccctc    240
cgccaccttc ccctcctccg gcttttcct cccaactcgg ggaggtcctt ccggtggcc     300 gccctgacga ggtctgagca cctaggcgga ggcggcgcag gcttttgta gtgaggtttg    360 cgcctgcgca ggcgcctgcc tccgccatgc acggggtgg cccccctcg ggggacagcg    420 catgcccgct gcgcaccatc aagagagtcc agttcggagt cctgagtccg gatgaactga    480
agcgaatgtc tgtgacggag ggtggcatca atacccaga gacgactgag ggaggccgcc    540
ccaagcttgg ggggctgatg gacccgaggc aggggtgat tgagcggact ggccgctgcc    600
aaacatgtgc aggaaacatg acagagtgtc ctggccactt tggccacatt gaactggcca    660
agcctgtgtt tcacgtgggc ttcctggtga agacaatgaa agttttgcgc tgtgtctgct    720
tcttctgctc caaactgctt gtggactcta caacccaaa gatcaaggat atcctggcta    780
agtccaaggg acagcccaag aagcggctca cacatgtcta cgacctttgc aagggcaaaa    840
acatatgcga gggtgggag gagatggaca caagttcgg tgtggaacaa cctgagggtg    900
acgaggatct gaccaaagaa aagggccatg gtggctgtgg gcggtaccag cccaggatcc    960
```

```
ggcgttctgg cctagagctg tatgcggaat ggaagcacgt taatgaggac tctcaggaga    1020
agaagatcct gctgagtcca gagcgagtgc atgagatctt caaacgcatc tcagatgagg    1080
agtgttttgt gctgggcatg gagcccgct atgcacggcc agagtggatg attgtcacag     1140
tgctgcctgt gcccccgctc tccgtgcggc ctgctgttgt gatgcagggc tctgcccgta    1200
accaggatga cctgactcac aaactggctg acatcgtgaa gatcaacaat cagctgcggc    1260
gcaatgagca gaacggcgca gcggcccatg tcattgcaga ggatgtgaag ctcctccagt    1320
tccatgtggc caccatggtg acaatgagc tgcctggctt gccccgtgcc atgcagaagt     1380
ctgggcgtcc cctcaagtcc ctgaagcagc ggttgaaggg caaggaaggc cgggtgcgag    1440
ggaacctgat gggcaaaaga gtggacttct cggcccgtac tgtcatcacc cccgacccca    1500
acctctccat tgaccaggtt ggcgtgcccc gctccattgc tgccaacatg acctttgcgg    1560
agattgtcac ccccttcaac attgacagac ttcaagaact agtgcgcagg gggaacagtc    1620
agtacccagg cgccaagtac atcatccgag acaatggtga tcgcattgac ttgcgtttcc    1680
accccaagcc cagtgaccTT cacctgcaga ccggctataa ggtggaacgg cacatgtgtg    1740
atggggacat tgttatcttc aaccggcagc caactctgca caaaatgtcc atgatggggc    1800
atcgggtccg cattctccca tggtctacct ttcgcttgaa tcttagcgtg caactccgt     1860 acaatgcaga ctttgacggg gatgagatga acttgcacct gccacagtct ctggagacgc    1920
gagcagagat ccaggagctg gccatggttc ctcgcatgat tgtcaccccc cagagcaatc    1980
ggcctgtcat gggtattgtg caggacacac tcacagcagt gcgcaaattc accaagagag    2040
acgtcttcct ggagcggggt gaagtgatga acctcctgat gttcctgtcg acgtgggatg    2100
ggaaggtccc acagccggcc atcctaaagc cccggcccct gtggacaggc aagcaaatct    2160
tctccctcat catacctggt cacatcaatt gtatccgtac ccacagcacc atcccgatg     2220 atgaagacag tggcccttac aagcacatct ctcctgggga caccaaggtg gtggtggaga    2280
atggggagct gatcatgggc atcctgtgta agaagtctct gggcacgtca gctggctccc    2340
tggtccacat ctcctacctg agatgggtc atgacatcac tcgcctcttc tactccaaca    2400
ttcagactgt cattaacaac tggctcctca tcgagggtca tactattggc attggggact    2460
ccattgctga ttctaagact taccaggaca ttcagaacac tattaagaag gccaagcagg    2520
acgtaataga ggtcatcgag aaggcacaca caatgagctg gagcccacc ccagggaaca    2580 ctctgcggca gacgtttgag aatcaggtga accgcattct taacgatgcc cgagacaaga    2640
ctggctcctc tgctcagaaa tccctgtctg aatacaacaa cttcaagtct atggtcgtgt    2700
ccggagctaa aggttccaag attaacatct cccaggtcat tgctgtcgtt ggacagcaga    2760
acgtcgaggg caagcggatt ccatttggct tcaagcaccg gactctgcct cacttcatca    2820
aggatgacta cgggcctgag agccgtggct tgtggagaa ctcctaccta gccggcctca    2880
cacccactga gttctttttc cacgccatgg ggggtcgtga ggggctcatt gacacggctg    2940
tcaagactgc tgagactgga tacatccagc ggcggctgat caagtccatg gagtcagtga    3000
tggtgaagta cgacgcgact gtgcggaact ccatcaacca ggtggtgcag ctgcgctacg    3060
gcgaagacgg cctggcaggc gagagcgttg agttccagaa cctggctacg cttaagcctt    3120
ccaacaaggc tttttgagaag aagttccgct ttgattatac caatgagagg gccctgcggc    3180
gcactctgca ggaggacctg gtgaaggacg tgctgagcaa cgcacacatc cagaacgagt    3240
tggagcggga atttgagcgg atgcgggagg atcggggagg gctcagggtc atcttcccaa    3300
ctggagacag caaggtcgtc ctcccctgta acctgctgcg gatgatctgg aatgctcaga    3360
```

```
aaatcttcca catcaaccca cgccttccct ccgacctgca ccccatcaaa gtggtggagg   3420
gagtcaagga attgagcaag aagctggtga ttgtgaatgg ggatgaccca ctaagtcgac   3480
aggcccagga aaatgccacg ctgctcttca acatccacct gcggtccacg ttgtgttccc   3540
gccgcatggc agaggagttt cggctcagtg gggaggcctt cgactggctg cttggggaga   3600
ttgagtccaa gttcaaccaa gccattgcgc atcccgggga aatggtgggg gctctggctg   3660
cgcagtccct tggagaacct gccacccaga tgaccttgaa taccttccac tatgctggtg   3720
tgtctgccaa gaatgtgacg ctgggtgtgc ccgacttaa ggagctcatc aacatttcca    3780
agaagccaaa gactccttcg cttactgtct tcctgttggg ccagtccgct cgagatgctg   3840
agagagccaa ggatattctg tgccgtctgg agcatacaac gttgaggaag gtgactgcca   3900
acacagccat ctactatgac cccaaccccc agagcacggt ggtggcagag gatcaggaat   3960
gggtgaatgt ctactatgaa atgcctgact ttgatgtggc ccgaatctcc ccctggctgt   4020
tgcgggtgga gctggatcgg aagcacatga ctgaccggaa gctcaccatg gagcagattg   4080
ctgaaaagat caatgctggt tttggtgacg acttgaactg catctttaat gatgacaatg   4140
cagagaagct ggtgctccgt attcgcatca tgaacagcga tgagaacaag atgcaagagg   4200
aggaagaggt ggtggacaag atggatgatg atgtcttcct gcgctgcatc gagtccaaca   4260
tgctgacaga tatgaccctg cagggcatcg agcagatcag caaggtgtac atgcacttgc   4320
cacagacaga caacaagaag aagatcatca tcacggagga tggggaattc aaggccctgc   4380
aggagtggat cctggagacg gacggcgtga gcttgatgcg ggtgctgagt gagaaggacg   4440
tggaccccgt acgcaccacg tccaatgaca ttgtggagat cttcacggtg ctgggcattg   4500
aagccgtgcg gaaggccctg gagcgggagc tgtaccacgt catctccttt gatggctcct   4560
atgtcaatta ccgacacttg gctctcttgt gtgataccat gacctgtcgt ggccacttga   4620
tggccatcac ccgacacgga gtcaaccgcc aggacacagg accactcatg aagtgttcct   4680
ttgaggaaac ggtggacgtg cttatggaag cagccgcaca cggtgagagt gaccccatga   4740 aggggggtctc tgagaatatc atgctgggcc agctggctcc ggccggcact ggctgctttg   4800
acctcctgct tgatgcagag aagtgcaagt atggcatgga gatccccacc aatatccccg   4860
gcctgggggc tgctggaccc accggcatgt tctttggttc agcacccagt cccatgggtg   4920
gaatctctcc tgccatgaca ccttggaacc agggtgcaac cctgcctat ggcgcctggt    4980 cccccagtgt tgggagtgga atgaccccag gggcagccgg cttctctccc agtgctgcgt   5040
cagatgccag cggcttcagc ccaggttact cccctgcctg gtctcccaca ccgggctccc   5100
cggggtcccc aggtccctca agcccctaca tcccttcacc aggtggtgcc atgtctccca   5160
gctactcgcc aacgtcacct gcctacgagc cccgctctcc tgggggctac acacccagga   5220
gtccctctta ttcccccact tcaccctcct actcccctac ctctccatcc tattctccaa   5280
ccagtcccaa ctatagtccc acatcaccca gctattcgcc aacgtcaccc agctactcac   5340
cgacctctcc cagctactca cccacctctc ccagctactc gcccacctct cccagctatt   5400
cgcccacctc tcccagctac tcacccactt cccctagcta ttcgcccact tccccctagct   5460 actcgccaac gtctcccagc tactcgccga catctcccag ctactcgcca acttcaccca   5520
gctattctcc cacttctccc agctactcac ctacctctcc aagctattca cccacctccc   5580
ccagctactc acccacttcc ccaagttact cacccaccag cccgaactat tctccaacca   5640
gtcccaatta caccccaaca tcacccagct acagcccgac atcacccagc tattccccta   5700
```

| | |
|---|---|
| ctagtcccaa ctacacacct accagccctactacagccc aacctctcca agctactctc | 5760 |
| caacatcacc cagctattcc ccgacctcac caagttactc cccttccagc ccacgataca | 5820 |
| caccacagtc tccaacctat accccaagct cacccagcta cagccccagt tcgcccagct | 5880 |
| acagcccaac ctcacccaag tacacccaa ccagtccttc ttatagtccc agctccccag | 5940 |
| agtataccccc aacctctccc aagtactcac ctaccagtcc caatattca cccacctctc | 6000 |
| ccaagtactc gcctaccagt cccacctatt cacccaccac cccaaaatac tccccaacat | 6060 |
| ctcctactta ttccccaacc tctccagtct acaccccaac ctctcccaag tactcaccta | 6120 |
| ctagccccac ttactcgccc acttccccca agtactcgcc caccagcccc acctactcgc | 6180 |
| ccacctcccc caaaggctca acctactctc ccacttcccc tggttactcg cccaccagcc | 6240 |
| ccacctacag tctcacaagc ccggctatca gcccggatga cagtgacgag agaactgag | 6300 |
| ggcacgtggg gtgcggcagc gggctagggc ccagggcagc ttgcccgtgc tgccgtgcag | 6360 |
| ttcttgcctc cctcacgggg cgtcaccccc agcccagctc cgttgtacat aaataccttg | 6420 |
| tgacagagct cccggtgaac ttctggatcc cgtttctgat gcagattctt gtcttgttct | 6480 |
| ccacttgtgc tgttagaact cactggccca gtggtgttct acctcctacc ccacccaccc | 6540 |
| cctgcctgtc cccaaattga agatcctccc ttgcctgtgg cttgatgcgg ggcgggtaaa | 6600 |
| gggtatttta acttaggggt agttcctgct gtgagtggtt acagctgatc ctcgggaaga | 6660 |
| acaaagctaa agctgccttt tgtctgttat tttattttt tgaagtttaa ataaagttta | 6720 |
| ctaattttga cc | 6732 |

<210> SEQ ID NO 78
<211> LENGTH: 2191
<212> TYPE: DNA
<213> ORGANISM: Homo sapiens

<400> SEQUENCE: 78

| | |
|---|---|
| ggtggccgag cggggaccg ggaagcatgg cccgggggtc ggcggttgcc tgggcggcgc | 60 |
| tcgggccgtt gttgtggggc tgcgcgctgg ggctgcaggg cgggatgctg taccccccagg | 120 |
| agagcccgtc gcgggagtgc aaggagctgg acggcctctg gagcttccgc gccgacttct | 180 |
| ctgacaaccg acgccggggc ttcgaggagc agtggtaccg gcggccgctg tgggagtcag | 240 |
| gccccaccgt ggacatgcca gttccctcca gcttcaatga catcagccag gactggcgtc | 300 |
| tgcggcattt tgtcggctgg gtgtggtacg aacgggaggt gatcctgccg gagcgatgga | 360 |
| cccaggacct cgcgcacaaga gtggtgctga ggattgcag tgcccattcc tatgccatcg | 420 |
| tgtgggtgaa tggggtcgac acgctagagc atgagggggg ctacctcccc ttcgaggccg | 480 |
| acatcagcaa cctggtccag gtggggcccc tgccctcccg gctccgaatc actatcgcca | 540 |
| tcaacaacac actcaccccc accaccctgc caccagggac catccaatac ctgactgaca | 600 |
| cctccaagta tccaagggt tactttgtcc agaacacata ttttgactt ttcaactacg | 660 |
| ctggactgca gcggtctgta cttctgtaca cgacacccac cacctacatc gatgacatca | 720 |
| ccgtcaccac cagcgtggag caagacagtg ggctggtgaa ttaccagatc tctgtcaagg | 780 |
| gcagtaacct gttcaagttg gaagtgcgtc tttggatgc agaaaacaaa gtcgtggcga | 840 |
| atgggactgg gacccagggc caacttaagg tgccaggtgt cagcctctgg tggccgtacc | 900 |
| tgatgcacga acgccctgcc tatctgtatt cattggaggt gcagctgact gcacagacgt | 960 |
| cactggggcc tgtgtctgac ttctacacac tccctgtggg gatccgcact gtggctgtca | 1020 |
| ccaagagcca gttcctcatc aatgggaaac ctttctattt ccacggtgtc aacaagcatg | 1080 |

```
aggatgcgga catccgaggg aagggcttcg actggccgct gctggtgaag gacttcaacc    1140
tgcttcgctg gcttggtgcc aacgctttcc gtaccagcca ctaccctat gcagaggaag     1200 tgatgcagat gtgtgaccgc tatgggattg tggtcatcga tgagtgtccc ggcgtgggcc    1260
tggcgctgcc gcagttcttc aacaacgttt ctctgcatca ccacatgcag gtgatgaag    1320 aagtggtgcg tagggacaag aaccaccccg cggtcgtgat gtggtctgtg gccaacgagc    1380
ctgcgtccca cctagaatct gctggctact acttgaagat ggtgatcgct cacaccaaat    1440
ccttggaccc ctcccggcct gtgacctttg tgagcaactc taactatgca gcagacaagg    1500
gggctccgta tgtggatgtg atctgtttga acagctacta ctcttggtat cacgactacg    1560
ggcacctgga gttgattcag ctgcagctgg ccacccagtt tgagaactgg tataagaagt    1620
atcagaagcc cattattcag agcgagtatg agcagaaaac gattgcaggg tttcaccagg    1680
atccacctct gatgttcact gaagagtacc agaaaagtct gctagagcag taccatctgg    1740
gtctggatca aaaacgcaga aaatatgtgg ttggagagct catttggaat tttgccgatt    1800
tcatgactga acagtcaccg acgagagtgc tggggaataa aaagggggatc ttcactcggc    1860 agagacaacc aaaaagtgca gcgttccttt tgcgagagag atactggaag attgccaatg    1920
aaaccaggta tccccactca gtagccaagt cacaatgttt ggaaaacagc ccgtttactt    1980
gagcaagact gataccacct gcgtgtccct tcctccccga gtcagggcga cttccacagc    2040
agcagaacaa gtgcctcctg gactgttcac ggcagaccag aacgtttctg gcctgggttt    2100
tgtggtcatc tattctagca gggaacacta aaggtggaaa taaagatttt tctattatgg    2160
aaataaagag ttggcatgaa agtcgctact g                                  2191
```

<210> SEQ ID NO 79
<211> LENGTH: 3360
<212> TYPE: DNA
<213> ORGANISM: Homo sapiens

<400> SEQUENCE: 79

```
gcgccagctt ggagagccag ccccatcggg gttccccgcc gccggaagcg gaaatagcac      60
cgggcgccgc cacagtagct gtaactgcca ccgcgatgcc gaaggcgccc aagcagcagc    120
cgccggagcc cgagtggatc ggggacggag agagcacgag cccatcagac aaagtggtga    180
agaaagggaa gaaggacaag aagatcaaaa aaacgttctt tgaagagctg gcagtagaag    240
ataaacaggc tggggaagaa gagaaagtgc tcaaggagaa ggagcagcag cagcagcaac    300
agcaacagca gcaaaaaaaa aagcgagata cccgaaaagg caggcggaag aaggatgtgg    360
atgatgatgg agaagagaaa gagctcatgg agcgtcttaa gaagctctca gtgccaacca    420
gtgatgagga ggatgaagta cccgccccaa aaccccgcgg agggaagaaa accaagggtg    480
gtaatgtttt tgcagccctg attcaggatc agagtgagga agaggaggag gaagaaaaac    540
atcctcctaa gcctgccaag ccggagaaga tcggatcaa taaggccgta tctgaggaac    600
agcagcctgc actcaagggc aaaaagggaa aggaagagaa gtcaaaaggg aaggctaagc    660
ctcaaaataa attcgctgct ctggacaatg aagaggagga taagaagaa gaaattataa    720 aggaaaagga gcctcccaaa caaggaagg agaaggccaa gaaggcagag cagatggagt    780
atgagcgcca agtggcttca ttaaaagcag ccaatgcagc tgaaaatgac ttctccgtgt    840
cccaggcgga gatgtcctcc cgccaagcca tgttagaaaa tgcatctgac atcaagctgg    900
agaagttcag catctccgct catggcaagg agctgttcgt caatgcagac ctgtacattg    960
```

```
tagccggccg ccgctacggg ctggtaggac ccaatggcaa gggcaagacc acactcctca   1020
agcacattgc caaccgagcc ctgagcatcc ctcccaacat tgatgtgttg ctgtgtgagc   1080
aggaggtggt agcagatgag acaccagcag tccaggctgt tcttcgagct gacaccaagc   1140
gattgaagct gctggaagag gagcggcggc ttcaggaca gctggaacaa ggggatgaca    1200
cagctgctga gaggctagag aaggtgtatg aggaattgcg ggccactggg gcggcagctg   1260
cagaggccaa agcacggcgg atcctggctg gcctgggctt tgaccctgaa atgcagaatc   1320
gacccacaca gaagttctca gggggctggc gcatgcgtgt ctccctggcc agggcactgt   1380
tcatggagcc cacactgctg atgctggatg agcccaccaa ccacctggac ctcaacgctg   1440
tcatctggct taataactac ctccagggct ggcggaagac cttgctgatc gtctcccatg   1500
accagggctt cttggatgat gtctgcactg atatcatcca cctcgatgcc cagcggctcc   1560
actactatag gggcaattac atgaccttca aaaagatgta ccagcagaag cagaaagaac   1620
tgctgaaaca gtatgagaag caagagaaaa agctgaagga gctgaaggca ggcgggaagt   1680
ccaccaagca ggcggaaaaa caaacgaagg aagccctgac tcggaagcag cagaaatgcc   1740
gacggaaaaa ccaagatgag gaatcccagg aggcccctga gctcctgaag cgccctaagg   1800
agtacactgt gcgcttcact tttccagacc ccccaccact cagccctcca gtgctgggtc   1860
tgcatggtgt gacattcggc taccagggac agaaaccact cttttaagaac ttggattttg   1920 gcatcgacat ggattcaagg atttgcattg tgggccctaa tggtgtgggg aagagtacgc   1980
tactcctgct gctgactggc aagctgacac cgacccatgg ggaaatgaga aagaaccacc   2040
ggctgaaaat tggcttcttc aaccagcagt atgcagagca gctgcgcatg gaggagacgc   2100
ccactgagta cctgcagcgg ggcttcaacc tgccctacca ggatgcccgc aagtgcctgg   2160
gccgcttcgg cctggagagt cacgcccaca ccatccagat ctgcaaactc tctggtggtc   2220
agaaggcgcg agttgtgttt gctgagctgg cctgtcggga acctgatgtc ctcatcttgg   2280
acgagccaac caataacctg gacatagagt ctattgatgc tctaggggag gccatcaatg   2340
aatacaaggg tgctgtgatc gttgtcagcc atgatgcccg actcatcaca gaaaccaatt   2400
gccagctgtg ggtggtggag gagcagagtg ttagccaaat cgatggtgac tttgaagact   2460
acaagcggga ggtgttggag gccctgggtg aagtcatggt cagccggccc cgagagtgag   2520 cttttccttcc cagaagtctc ccgagagaca tatttgtgtg gcctagaagt cctctgtggt   2580
ctcccctcct ctgaagactg cctctggcct gcagctgacc tggcaaccat tcaggcacat   2640
gaaggtggag tgtgaccttg atgtgaccgg gatcccactc tgattgcatc catttctctg   2700
aaagacttgt ttgttctgct tctcttcata taactgagct ggccttatcc ttggcatccc   2760
cctaaacaaa caagaggtga ccaccttatt gtgaggttcc atccagccaa gtttatgtgg   2820
cctattgtct caggactctc atcactcaga agcctgcctc tgatttaccc tacagcttca   2880 ggccagctg ccccccagtc tttgggtggt gctgttcttt tctggtggat ttaatgctga    2940
ctcactggta caaacagctg ttgaagctca gagctggagg tgagcttctg aggcctttgc   3000
cattatccag cccaagattt ggtgcctgca gcctcttgtc tggttgagga cttggggcag   3060
gaaaggaatg ctgctgaact tgaatttccc tttacaaggg gaagaaataa aggaaaggag   3120
ttgctgccga cctgtcactg tttggagatt gatgggagtt ggaactgttc tcagtcttga   3180
tttgctttat tcagtttttct agcagctttt aatagtcccc tcttcccca taaatggatc    3240 ttgtttgcag tcttgctgac agtgtttgct gtttaaggat cataggattc ctttccccca   3300
acccttcacg caaggaaaaa gcaaagtgat tcataccttc tatcttggaa aaaaaaaaa    3360
```

<210> SEQ ID NO 80
<211> LENGTH: 2725
<212> TYPE: DNA
<213> ORGANISM: Homo sapiens

<400> SEQUENCE: 80

| | | | | | |
|---|---|---|---|---|---|
| agaatgctga | gcagtcaaca | gcatttcttg | ttccaagatc | acccttctga | gtacctctct | 60 |
| ggctgccaaa | ttgccagggc | cttcacagtt | tgattccatt | tctcagctcc | aagcattagg | 120 |
| taaacccacc | aagcaatcct | agcctgtgat | ggcgtttgac | gtcagctgct | tcttttgggt | 180 |
| ggtgctgttt | tctgccggct | gtaaagtcat | cacctcctgg | gatcagatgt | gcattgagaa | 240 |
| agaagccaac | aaaacatata | actgtgaaaa | tttaggtctc | agtgaaatcc | ctgacactct | 300 |
| accaaacaca | acagaatttt | tggaattcag | ctttaatttt | ttgcctacaa | ttcacaatag | 360 |
| aaccttcagc | agactcatga | atcttacctt | tttggattta | actaggtgcc | agattaactg | 420 |
| gatacatgaa | gacactttc | aaagccatca | tcaattaagc | acacttgtgt | taactggaaa | 480 |
| tccctgata | ttcatggcag | aaacatcgct | taatgggccc | aagtcactga | agcatctttt | 540 |
| cttaatccaa | acgggaatat | ccaatctcga | gtttattcca | gtgcacaatc | tggaaaactt | 600 |
| ggaaagcttg | tatcttggaa | gcaaccatat | ttcctccatt | aagttcccca | aagacttccc | 660 |
| agcacggaat | ctgaaagtac | tggattttca | gaataatgct | atacactaca | tctctagaga | 720 |
| agacatgagg | tctctggagc | aggccatcaa | cctaagcctg | aacttcaatg | gcaataatgt | 780 |
| taaaggtatt | gagcttgggg | cttttgattc | aacgatcttc | caaagtttga | actttggagg | 840 |
| aactccaaat | ttgtctgtta | tattcaatgg | tctgcagaac | tctactactc | agtctctctg | 900 |
| gctgggaaca | tttgaggaca | ttgatgacga | agatattagt | tcagccatgc | tcaagggact | 960 |
| ctgtgaaatg | tctgttgaga | gcctcaacct | gcaggaacac | cgcttctctg | acatctcatc | 1020 |
| caccacattt | cagtgcttca | cccaactcca | agaattggat | ctgacagcaa | ctcacttgaa | 1080 |
| agggttaccc | tctgggatga | agggtctgaa | cttgctcaag | aaattagttc | tcagtgtaaa | 1140 |
| tcatttcgat | caattgtgtc | aaatcagtgc | tgccaatttc | ccctccctta | cacacctcta | 1200 |
| catcagaggc | aacgtgaaga | aacttcacct | tggtgttggc | tgcttggaga | aactaggaaa | 1260 |
| ccttcagaca | cttgatttaa | gccataatga | catagaggct | tctgactgct | gcagtctgca | 1320 |
| actcaaaaac | ctgtcccact | tgcaaacctt | aaacctgagc | acaatgagc | ctcttggtct | 1380 |
| ccagagtcag | gcattcaaag | aatgtcctca | gctagaactc | ctcgatttgg | catttacccg | 1440 |
| cttacacatt | aatgctccac | aaagtcccct | ccaaaacctc | catttccttc | aggttctgaa | 1500 |
| tctcacttac | tgcttccttg | ataccagcaa | tcagcatctt | ctagcaggcc | taccagttct | 1560 |
| ccggcatctc | aacttaaaag | ggaatcactt | tcaagatggg | actatcacga | agaccaacct | 1620 |
| acttcagacc | gtgggcagct | tggaggttct | gattttgtcc | tcttgtggtc | tcctctctat | 1680 |
| agaccagcaa | gcattccaca | gcttgggaaa | aatgagccat | gtagacttaa | gccacaacag | 1740 |
| cctgacatgc | gacagcattg | attctcttag | ccatcttaag | ggaatctacc | tcaatctggc | 1800 |
| tgccaacagc | attaacatca | tctcaccccg | tctcctccct | atcttgtccc | agcagagcac | 1860 |
| cattaattta | agtcataacc | ccctggactg | cacttgctcg | aatattcatt | tcttaacatg | 1920 |
| gtacaaagaa | aacctgcaca | aacttgaagg | ctcggaggag | accacgtgtg | caaacccgcc | 1980 |
| atctctaagg | ggagttaagc | tatctgatgt | caagctttcc | tgtgggatta | cagccatagg | 2040 |
| cattttcttt | ctccatagtat | ttctattatt | gttggctatt | ctgctatttt | ttgcagttaa | 2100 |

-continued

```
ataccttctc aggtggaaat accaacacat ttagtgctga aggtttccag agaaagcaaa    2160
taagtgtgct tagcaaaatt gctctaagtg aaagaactgt catctgctgg tgaccagacc    2220
agacttttca gattgcttcc tggaactggg cagggactca ctgtgctttt ctgagcttct    2280
tactcctgtg agtcccagag ctaaagaacc ttctaggcaa gtacaccgaa tgactcagtc    2340
cagagggtca gatgctgctg tgagaggcac agagcccttt ccgcatgtgg aagagtggga    2400
ggaagcagag ggagggactg ggcagggact gccggccccg gagtctccca cagggaggcc    2460 attcccttc tactcaccga catccctccc agcaccacac accccgcccc tgaaaggaga     2520
tcatcagccc ccacaatttg tcagagctga agccagccca ctacccaccc ccactacagc    2580
attgtgcttg ggtctgggtt ctcagtaatg tagccatttg agaaacttac ttggggacaa    2640
agtctcaatc cttattttaa atgaaaaaag aaaagaaaag cataataaat ttaaaagaaa    2700
aggctgagaa atgaaaaaaa aaaaa                                          2725
```

BIOMARKER ASSOCIATED WITH RISK OF MELANOMA REOCCURRENCE

CROSS-REFERENCE TO RELATED APPLICATIONS

This application is a § 371 national stage of PCT International Application No. PCT/US2013/053511, filed Aug. 2, 2013, claiming the benefit of U.S. Provisional Application No. 61/679,394, filed Aug. 3, 2012, the contents of each of which are hereby incorporated by reference in their entirety.

REFERENCE TO A SEQUENCE LISTING

This application incorporates-by-reference nucleotide and/or amino acid sequences which are present in the file named "150203_0028_84006_A_PCT_US_Substitute_Sequence_Listing_JR.txt" which is 258 kilobytes in size, and which was created Jan. 12, 2015 in the IBM-PC machine format, having an operating system compatibility with MS-Windows, which is contained in the text file filed Feb. 3, 2015 as part of this application.

Throughout this application, various publications are referenced. Full citations for these publications may be found at the end of the specification immediately preceding the claims. The disclosures of these publications in their entireties are hereby incorporated by reference into this application in order to more fully describe the state of the art to which this invention pertains.

BACKGROUND OF INVENTION

Melanoma is an aggressive malignancy associated with five-year survival rates under 5% in patients with metastatic disease.[1] Despite successful excision of the primary lesion, a five-year survival of only 68% is expected in cases of primary melanoma greater than 2 mm in thickness.[5, 6] Increasing depth of the primary tumor and the presence of high risk histopathology are predictive of recurrence across populations, but do not accurately assess risk in individual patients.[7] Sentinel lymph node biopsy (SLNB) is an invasive procedure that offers limited prognostic information and has no proven survival benefit.[8] Improved biomarkers are needed to identify patients at high risk for recurrence and death.

Expression profiling has never been systematically performed in formalin-fixed, paraffin-embedded (FFPE) primary melanoma.[9] In contrast, Oncotype DX measures the expression of a 21-gene panel and offers prognostic information for patients with breast cancer.[10] The development of similar biomarkers in melanoma has been limited due in part to the clinical standard of entire tumor fixation in formalin which leads to low yields of extractable RNA and limits the quality of RNA available for molecular studies. As a result, studies of primary melanoma have relied on cell lines, limited supplies of frozen tissue, or focused on profiling microRNA, which is less subject to degradation.[11-17] Even in rare cases where frozen tissue is available, RNA extraction is difficult due to the fibrous nature of cutaneous tissues.[9, 12]

Thus, there is a need for suitable methods and markers for providing prognostic information related to melanoma.

SUMMARY OF THE INVENTION

The present invention provides a method of predicting the risk of reoccurrence of melanoma in a patient from whom melanoma tissue was previously removed which comprises the following:

a. obtaining a RNA-containing sample of the previously removed melanoma tissue containing RNA from the patient;
b. treating the sample to determine from the RNA contained in the sample the level of expression of a plurality of preselected genes; and
c. comparing the level of expression of each gene of the plurality of pre-selected genes to a predetermined reference level of expression for each such gene;
wherein a higher level of expression of the plurality of pre-selected genes in the sample as compared with the predetermined reference level of expression of such genes indicates that the patient has a reduced risk of reoccurrence of melanoma, and
wherein the plurality of pre-selected genes comprises the following genes:
a. CD2;
b. KLRK1;
c. ITK; and
d. HLAE.

The present invention also provides a method of treating a patient from whom melanoma tissue was previously removed, and which patient was determined to not have a reduced risk of reoccurrence of melanoma by a method of the invention, comprising administering an immunotherapy to the patient.

The present invention also provides a method of treating a patient from whom melanoma tissue was previously removed, and which patient was determined to not have a reduced risk of reoccurrence of melanoma by a method of the invention, comprising testing the human patient for recurrence of melanoma more frequently than a corresponding patient who was determined to have a reduced risk of reoccurrence of melanoma would be tested for recurrence.

The present invention also provides a method of treating a patient afflicted with melanoma which comprises the following:

a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and
d. administering a therapy to the patient if there is a higher level of expression of the plurality of pre-selected genes in the sample as compared with the predetermined reference level of expression of such genes, and
wherein the plurality of pre-selected genes comprises the following genes:
a. CD2;
b. KLRK1;
c. ITK; and
d. HLAE.

The present invention also provides a method of treating a patient afflicted with melanoma which comprises the following:

a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and d. administering a therapy to the patient if there is a lower level of expression of the plurality of pre-selected genes in the sample as compared with the predetermined reference level of expression of such genes, and wherein the plurality of pre-selected genes comprises the following genes:
a. CD2;
b. KLRK1;
c. ITK; and
d. HLAE.

The present invention also provides a method of treating a patient afflicted with melanoma which comprises the following:
a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and
d. administering a therapy to the patient if the level of expression of the plurality of pre-selected genes in the sample is i) lower as compared with the predetermined reference upper level of expression of such genes and ii) higher as compared with the predetermined reference lower level of expression of such genes, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a higher level of expression of the plurality of pre-selected genes in the sample as compared with the predetermined reference level of expression of such genes indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of the melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a lower level of expression of the plurality of pre-selected genes in the sample as compared with the predetermined reference level of expression of such genes indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of the melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a level of expression of the plurality of pre-selected genes in the sample is i) lower as compared with the predetermined reference upper level of expression of such genes and ii) higher as compared with the predetermined reference lower level of expression of such genes, indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of determining whether a therapy is effective for treating patients afflicted with melanoma which comprises the following:
a. obtaining a RNA-containing sample of the melanoma tissue containing RNA from at least one patient afflicted with melanoma, which at least one patient was administered the therapy for treatment of the melanoma previous to collection of the sample;
b. treating the sample to determine from the RNA contained in the sample the level of expression of a plurality of preselected genes; and
c. comparing the levels of expression of each gene of the plurality of pre-selected genes to the levels of expression of the plurality of pre-selected genes to the expression level of each such gene in a corresponding at least one patient not administered the therapy;

wherein a higher level of expression of the plurality of pre-selected genes in the sample of step a) as compared with the level of expression of such genes in a corresponding at least one patient not administered the treatment indicates that the therapy is effective for treating patients afflicted with melanoma, and wherein the plurality of pre-selected genes comprises the following genes:
a. CD2;
b. KLRK1;
c. ITK; and
d. HLAE.

The present invention also provides a method of determining whether a patient afflicted with melanoma and which patient was administered a therapy has exhibited a positive clinical response to the therapy which comprises the following:
a. obtaining a RNA-containing sample of the melanoma tissue containing RNA from the patient, which RNA-containing sample was removed from the patient who was administered the therapy;
b. treating the sample to determine from the RNA contained in the sample the level of expression of a plurality of preselected genes; and
c. comparing the levels of expression of each gene of the plurality of pre-selected genes to a predetermined reference level of expression for each such gene;
wherein a higher level of expression of the plurality of pre-selected genes in the sample as compared with the predetermined reference level of expression of such genes indicates that the patient has exhibited a positive clinical response to the therapy, and wherein the plurality of pre-selected genes comprises the following genes:
a. CD2;
b. KLRK1;
c. ITK; and
d. HLAE.

The present invention also provides a method of determining whether a treatment should be administered to patients afflicted with melanoma as an adjuvant or a neoadjuvant therapy which comprises the following:
a. obtaining a RNA-containing sample of the melanoma tissue containing RNA from at least one patient afflicted with melanoma;
b. treating the sample to determine from the RNA contained in the sample the level of expression of a plurality of preselected genes; and
c. comparing the levels of expression of each gene of the plurality of pre-selected genes to a predetermined reference level of expression for each such gene;
wherein a higher level of expression of the plurality of pre-selected genes in the sample as compared with the predetermined reference level of expression of such genes indicates that the treatment should be administered to patients afflicted with melanoma as a neoadjuvant therapy, and a lower level of expression of the plurality of pre-selected genes in the sample as compared with the predetermined reference level of expression of such genes indicates that the treatment should be administered to patients afflicted with melanoma as an adjuvant therapy, and
wherein the plurality of pre-selected genes comprises the following genes:
a. CD2;
b. KLRK1;
c. ITK; and
d. HLAE.

The present invention provides a method of predicting the risk of reoccurrence of melanoma in a patient from whom melanoma tissue was previously removed which comprises the following:
a. obtaining a sample of the previously removed melanoma tissue from the patient;
b. treating the sample to determine the level of an expression product of a gene or each of two or more genes in the sample; and
c. comparing the level of the expression product of the gene or each of the two or more genes to a predetermined reference level of the expression product for each such gene,
wherein a higher level of expression product of the gene or each of the two or more genes in the sample as compared with the predetermined reference level of the expression product for each such gene indicates that the patient has a reduced risk of reoccurrence of melanoma.

The present invention provides a method of treating a patient afflicted with melanoma which comprises the following:
a. obtaining a sample of melanoma tissue from the patient;
b. treating the sample to determine the level of an expression product of a gene or each of two or more genes in the sample;
c. comparing the level of the expression product of the gene or each of the two or more genes to a predetermined reference level of the expression product for each such gene; and
d. administering a therapy to the patient if there is a higher level of expression of the expression product of the gene or each of the two or more genes in the sample as compared with the predetermined reference level of the expression product for each such gene.

The present invention provides a method of treating a patient afflicted with melanoma which comprises the following:
a. obtaining a sample of melanoma tissue from the patient;
b. treating the sample to determine the level of an expression product of a gene or each of two or more genes in the sample;
c. comparing the level of the expression product of the gene or each of the two or more genes to a predetermined reference level of the expression product for each such gene; and
d. administering a therapy to the patient if there is a lower level of expression of the expression product of the gene or each of the two or more genes in the sample as compared with the predetermined reference level of the expression product for each such gene.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of a gene or each of two or more genes in the sample; and
c. comparing the level of the expression product of the gene or the each of two or more genes to a predetermined reference level of the expression product for each such gene,
wherein a higher level of expression product of the gene or each of the two or more genes in the sample as compared with the predetermined reference level of the expression product for each such gene indicates that the patient is likely to exhibit a positive clinical response to treatment with the therapy.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of the gene or each of the two or more genes in the sample; and
c. comparing the level of the expression product of the gene or each of the two or more genes to a predetermined reference level of the expression product for each such gene, wherein a lower level of expression product of the gene or each of the two or more genes in the sample as compared with the predetermined reference level of the expression product for each such gene indicates that the patient is likely to exhibit a positive clinical response to treatment with the therapy.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of a gene or each of two or more genes in the sample; and
c. comparing the level of the expression product of the gene or each of the two or more genes to a predetermined reference level of the expression product for each such gene,
wherein a level of the expression product of the gene or each of the two or more genes that is i) lower as compared with a predetermined reference upper level of expression for each such gene and ii) higher as compared with a predetermined reference lower level of expression for each such gene, indicates that the patient is likely to exhibit a positive clinical response to treatment with the therapy.

The present invention provides a method of determining whether a therapy is effective for treating patients afflicted with melanoma which comprises the following:
a. obtaining a sample of melanoma tissue from at least one patient afflicted with melanoma, which at least one patient was administered the therapy;
b. treating the sample to determine the level of an expression product of the gene or each of two or more genes in the sample; and
c. comparing the level of the expression product of the gene or each of the two or more genes to the level of the expression product of the gene or each of the two or more genes in a corresponding at least one patient not administered the treatment,
wherein a higher level of expression product of the gene or each of the two or more genes in the sample of step (a) as compared with the level of expression product of the gene or each of the two or more genes in the corresponding at least one patient not administered the treatment indicates that the therapy is effective for treating patients afflicted with melanoma.

The present invention provides a method of determining whether a patient afflicted with melanoma and which patient was administered a therapy has exhibited a positive clinical response to the therapy which comprises the following:
a. obtaining a sample of melanoma tissue from the patient;
b. treating the sample to determine the level of an expression product of a gene or each of two or more genes in the sample; and
c. comparing the level of the expression product of the gene or each of the two or more genes to a predetermined reference level for each such gene,
wherein a higher level of expression the expression product of the gene or each of the two or more genes as compared to the predetermined reference level of the expression product of each such gene indicates that the patient has exhibited a positive clinical response to the therapy.

The present invention provides a method of determining whether a treatment should be administered to patients afflicted with melanoma as an adjuvant or a neoadjuvant therapy which comprises the following:
a. obtaining a sample of melanoma tissue from at least one patient afflicted with melanoma;
b. treating the sample to determine the level of an expression product of a gene or each of two or more genes in the sample; and
c. comparing the level of the expression product of the gene or each of the two or more genes to a predetermined reference level for each such gene,
wherein a higher level of the expression product of the gene or each of the two or more genes in the sample as compared with the predetermined reference level of expression for each such gene indicates that the treatment should be administered to patients afflicted with melanoma as a neoadjuvant therapy, and a lower level of the expression product of the gene or each of the two or more genes in the sample as compared with the predetermined reference level of the expression product for each such gene indicates that the treatment should be administered to patients afflicted with melanoma as an adjuvant therapy.

The present invention provides a method of predicting the risk of reoccurrence of melanoma in a patient from whom melanoma tissue was previously removed which comprises the following:
a. obtaining a sample of the previously removed melanoma tissue from the patient;
b. treating the sample to determine the level of the expression product of the CD2 gene in the melanoma tissue sample; and
c. comparing the level of the expression product of the CD2 gene to a predetermined reference level of the expression product of the CD2 gene,
wherein a higher level of expression product of the CD2 gene in the sample as compared with the predetermined reference level of the expression product of the CD2 gene indicates that the patient has a reduced risk of reoccurrence of melanoma.

The present invention provides a method of predicting the risk of reoccurrence of melanoma in a patient from whom melanoma tissue was previously removed which comprises the following:
a. obtaining a sample of the previously removed melanoma tissue from the patient;
b. treating the sample to determine the level of the expression product of the X gene in the melanoma tissue sample; and
c. comparing the level of the expression product of the X gene to a predetermined reference level of the expression product of the X gene,
wherein a higher level of expression product of the X gene in the sample as compared with the predetermined reference level of the expression product of the X gene indicates that the patient has a reduced risk of reoccurrence of melanoma.

BRIEF DESCRIPTION OF THE DRAWINGS

FIG. 1. RNA was extracted from FFPE primary melanomas and analyzed using NanoString Technology. Relative levels of mRNA expression for each sample are depicted according to the color scale shown, with each column representing a patient sample and each row representing a gene. Genes are arranged in the heatmap and listed in this order on the right from most differentially expressed (top) to least (bottom). Panel A shows the relative expression of 92 inflammatory genes found to be differentially expressed between 21 recurrent (light grey) and 23 non-recurrent (dark grey) patient samples. Of these 92 genes, 90 were up-regulated in melanomas which did not recur (see, e.g., Table 4 and 5 for fold change). In panel B, validation of these findings in 37 melanomas is shown. 41 genes out of 63 tested were differentially expressed between recurrent and non-recurrent melanomas, all of which were up-regulated in the non-recurrent group.

* Inadequate tissue in FFPE block to make slides for IHC in 6 recurrent patients and 2 non-recurrent patients in the validation cohort.

Figure 2:
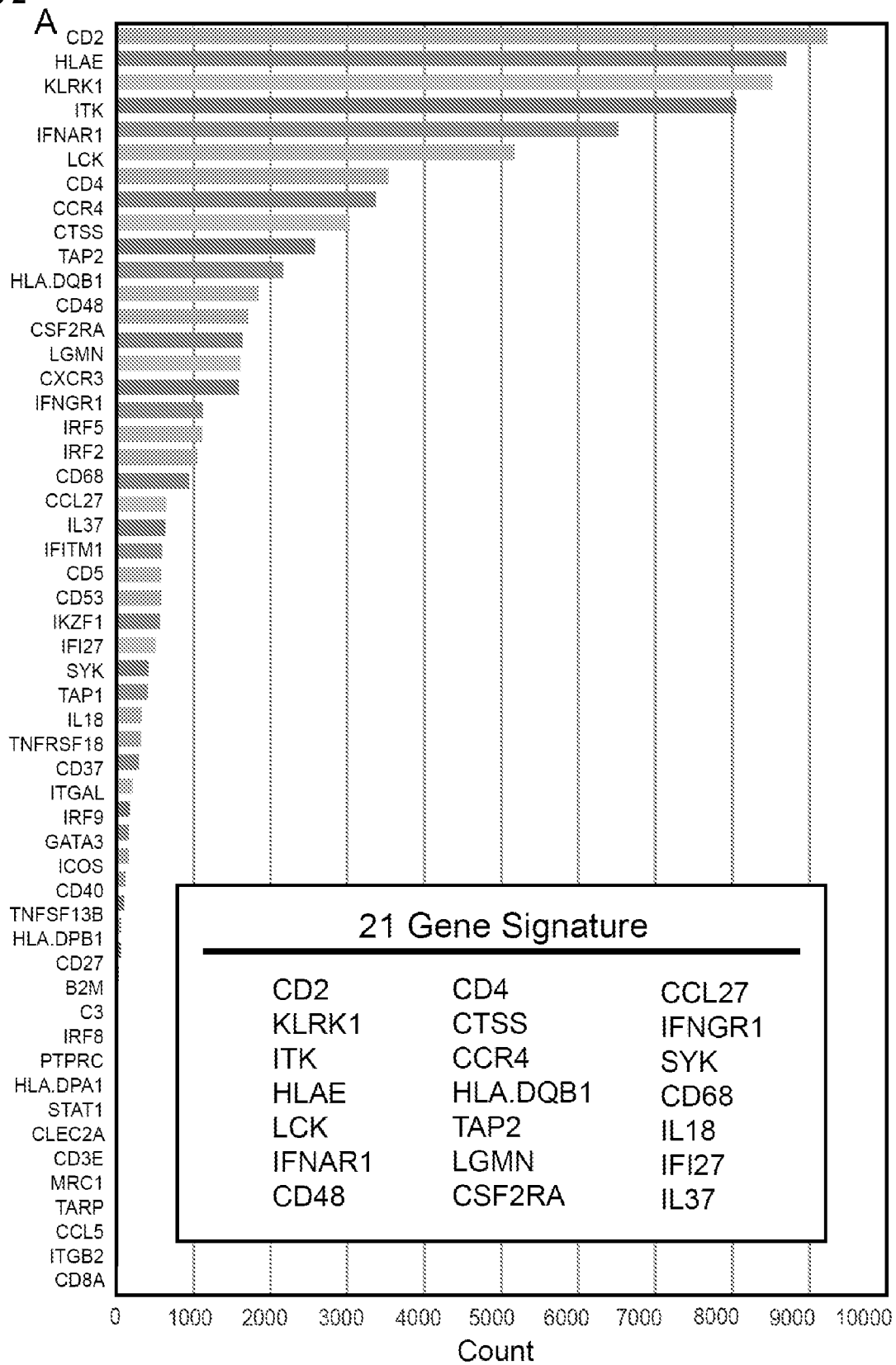
FIG. 2. A 21-gene signature able to predict melanoma recurrence is proposed. Panel A shows a bar graph representing the number of times each gene was selected in a leave-4-out cross-validation module. From this cross validation, a compact list of genes was selected using a linear regression model to compose a 21-gene signature, listed in the inset. In panel B, the receiver operating characteristic (ROC) curves for the statistical model using these 21 genes is shown in the training (left) and validation (right) cohorts. By definition, random classification of a sample as recurrent or non-recurrent provides an AUC of 50% (dotted line). The AUC for the proposed gene signature was 0.983 and 0.794 in the training and validation cohorts respectively. In panel C, the coefficient of determination ($R^2$) was calculated using a linear model for each characteristic with and without the gene signature for both training and validations sets. When combined with the gene signature, the $R^2$ value drastically increases for each characteristic, indicating improved ability to predict recurrence. Values are provided in the Table 7.

FIG. 4. Kaplan-Meier curves of overall survival are shown. In panel A, patients in the training and validation cohorts were classified as either signature + (red) or signature − (black) based on expression of the 21-gene panel defined in FIG. 2. Patients with a positive gene signature had a higher overall survival compared to those with a negative signature (p<0.0001). In panel B, patients were classified according to depth as either <4 mm or >4 mm. Depth trends towards but does not reach statistical significance in predicting survival for the same cohort (p=0.0509).

Figure 5:
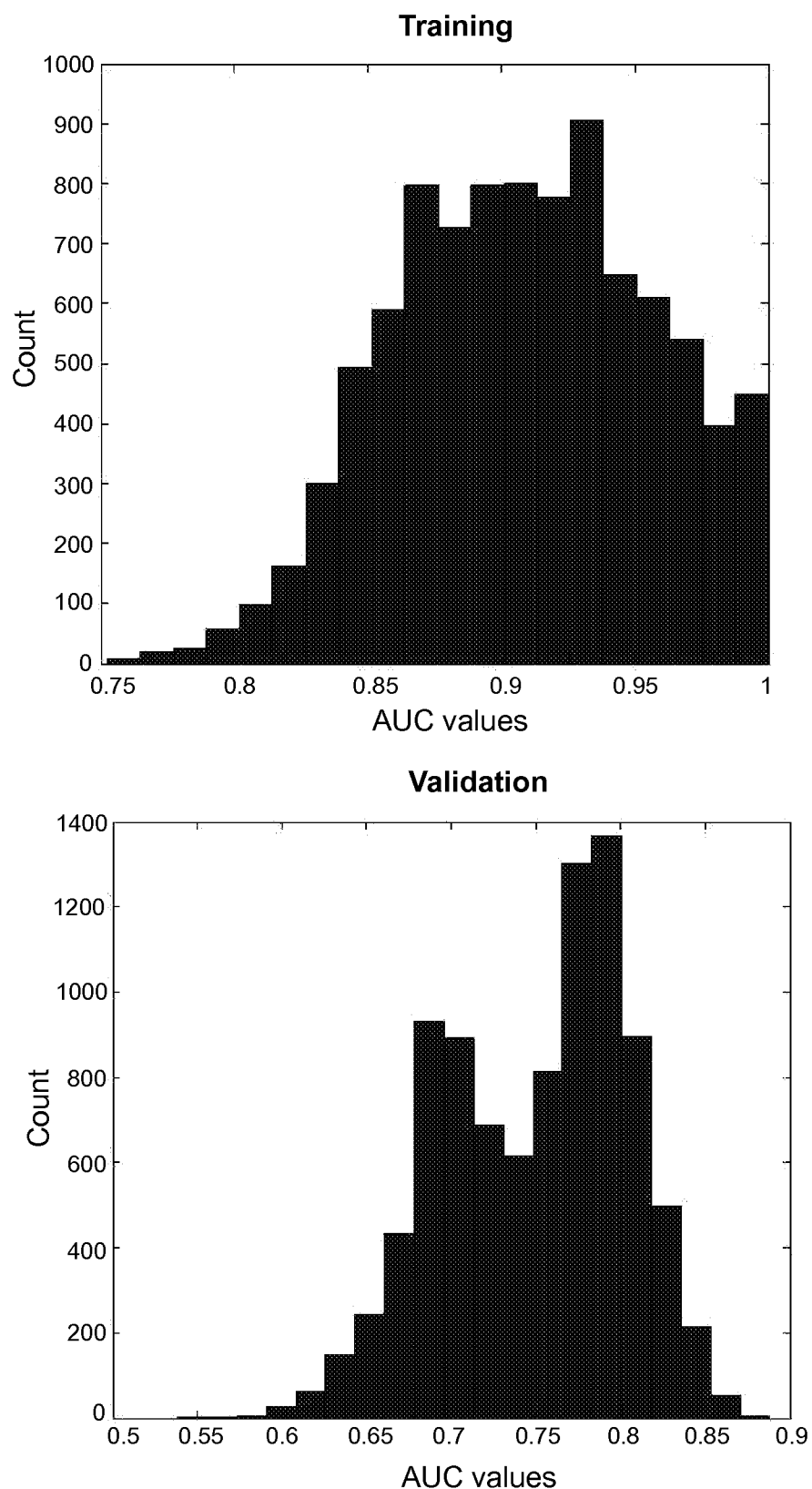

FIG. 5. The distribution of the AUC values for the 900 cross validation iterations, using a leave-4-out approach, are shown in the training (A) and validation (B) sets. Distribution of AUC values in training and validation sets during cross-validation.

FIG. 6. Normalized mRNA count of the 21 gene signature in training and validation sets. Analysis of a gene signature for predicting melanoma recurrence using NanoString is shown. Panels A displays the differential in mRNA counts between recurrent and non-recurrent patients for 21 genes composing the proposed signature. Values represent the number of mRNA transcripts counted by the nCounter® Analysis System of NanoString Technology. For every gene, a marked upregulation in mRNA expression is demonstrated in patients with non-recurrent melanoma when compared with patients with recurrent disease. These 21 genes were validated by NanoString in an independent set of samples displayed in Panel B. With the exception of IFNAR1, all genes were upregulated in the non-recurrent group with 14 out of 21 genes found to be differentially expressed to a statistically significant degree (p<0.05) in the validation cohort.

Figure 7:
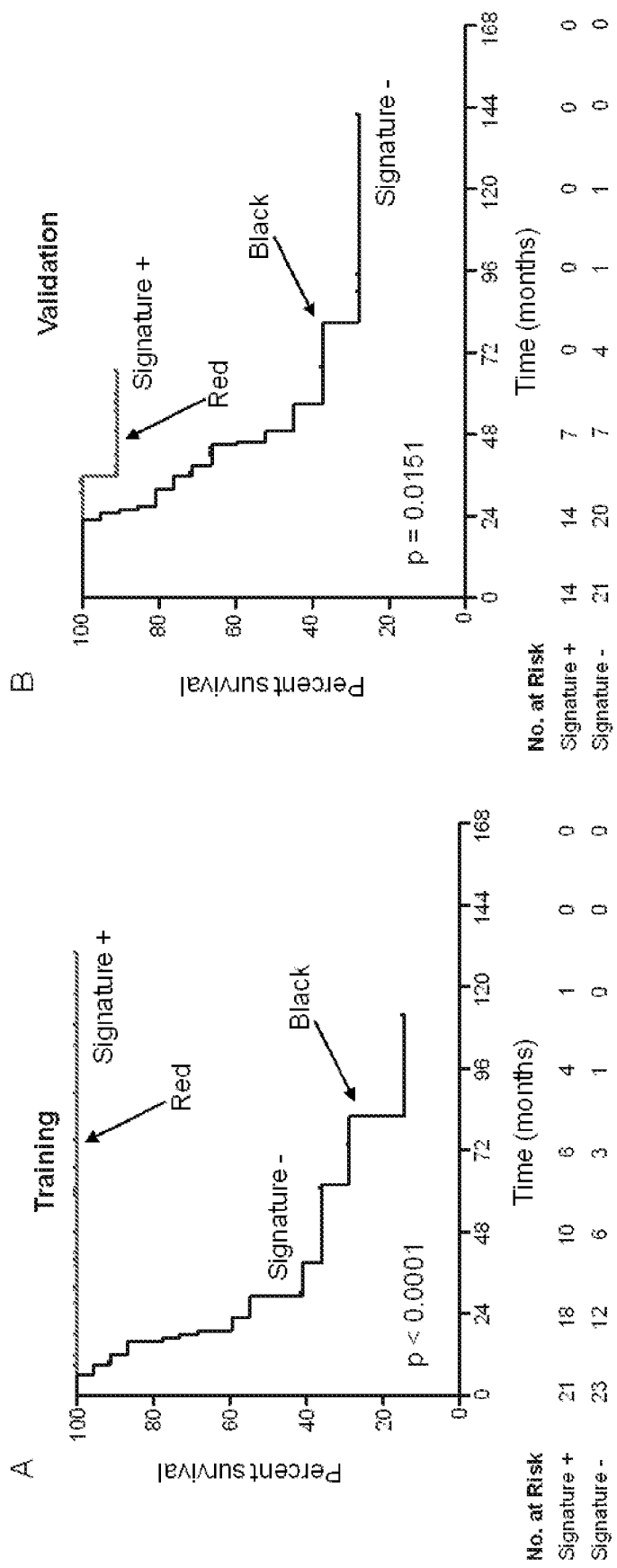

FIG. 7. Percent survival for signature positive and negative groups in training and validation cohorts. Kaplan-Meier curves of survival based on a 21-gene signature are shown for the training and validation cohorts. Patients were classified as either signature + (red) or signature − (black). In both the training (A) and validation (B) cohorts, patients with a positive gene signature had a higher overall survival compared to those with a negative signature, which conferred a poor prognosis (Training: p<0.0001, Validation: p=0.0151).

Figure 8:
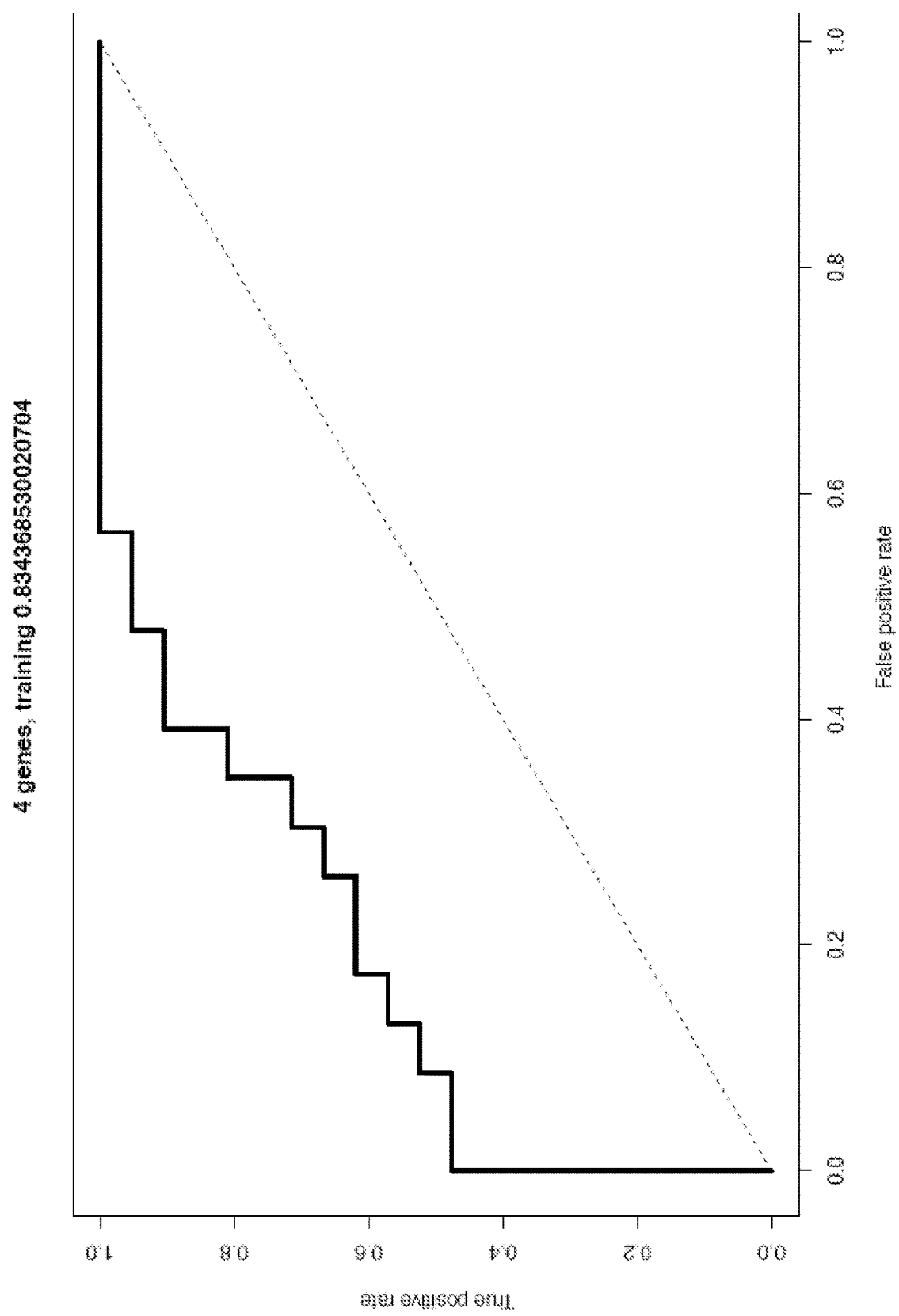

FIG. 8. The receiver operating characteristic (ROC) curves for the statistical model using the 4 core genes is shown in the training cohort. By definition, random classification of a sample as recurrent or non-recurrent provides an AUC of 50% (dotted line). The AUC for the proposed gene signature was 0.834.

Figure 9:
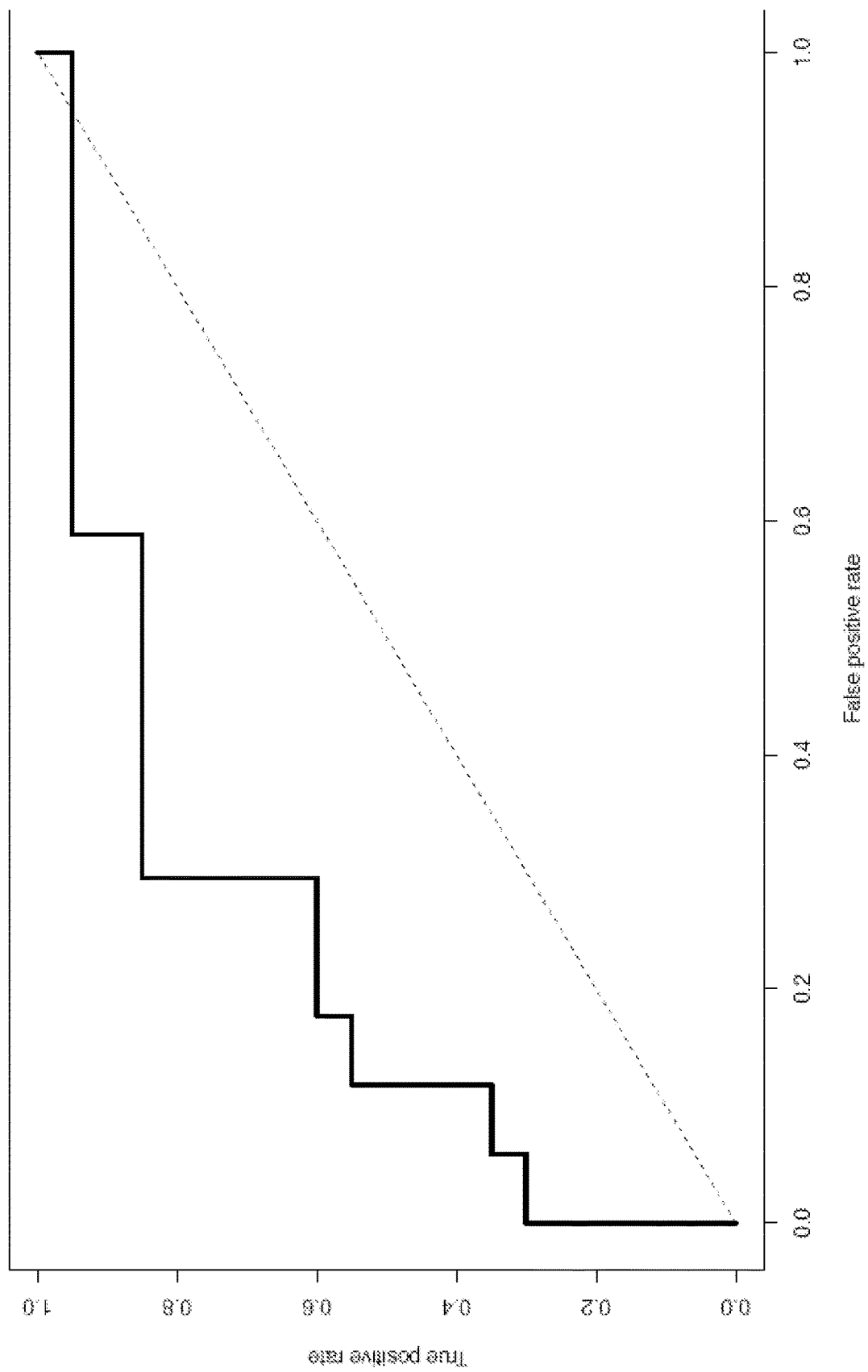

FIG. 9. The receiver operating characteristic (ROC) curves for the statistical model using the 4 core genes is shown in the validation cohort. By definition, random classification of a sample as recurrent or non-recurrent provides an AUC of 50% (dotted line). The AUC for the proposed gene signature was 0.782.

Figure 10:
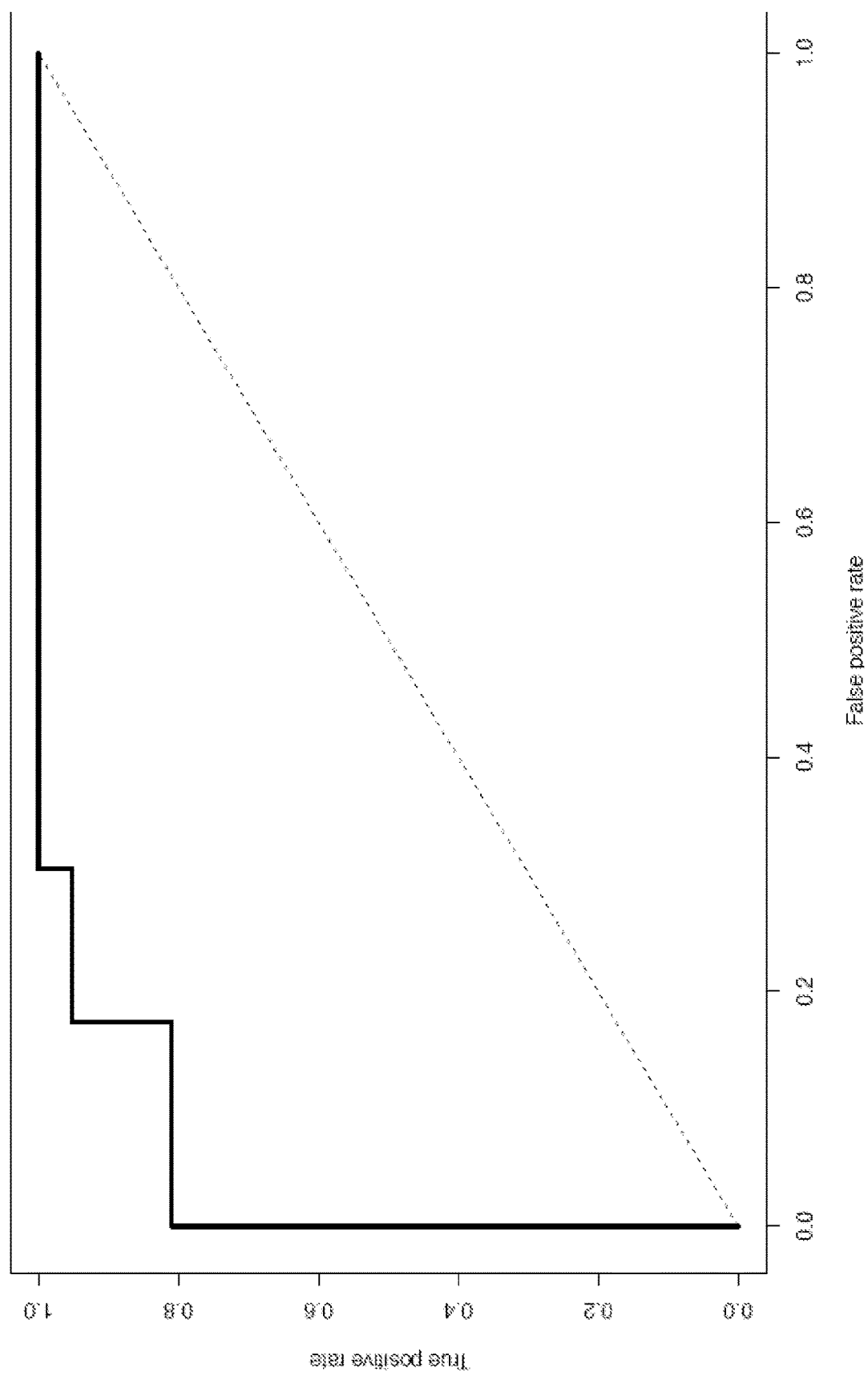

FIG. 10. The receiver operating characteristic (ROC) curves for the statistical model using the 15 core genes is shown in the training cohort. By definition, random classification of a sample as recurrent or non-recurrent provides an AUC of 50% (dotted line). The AUC for the proposed gene signature was 0.961.

Figure 11:
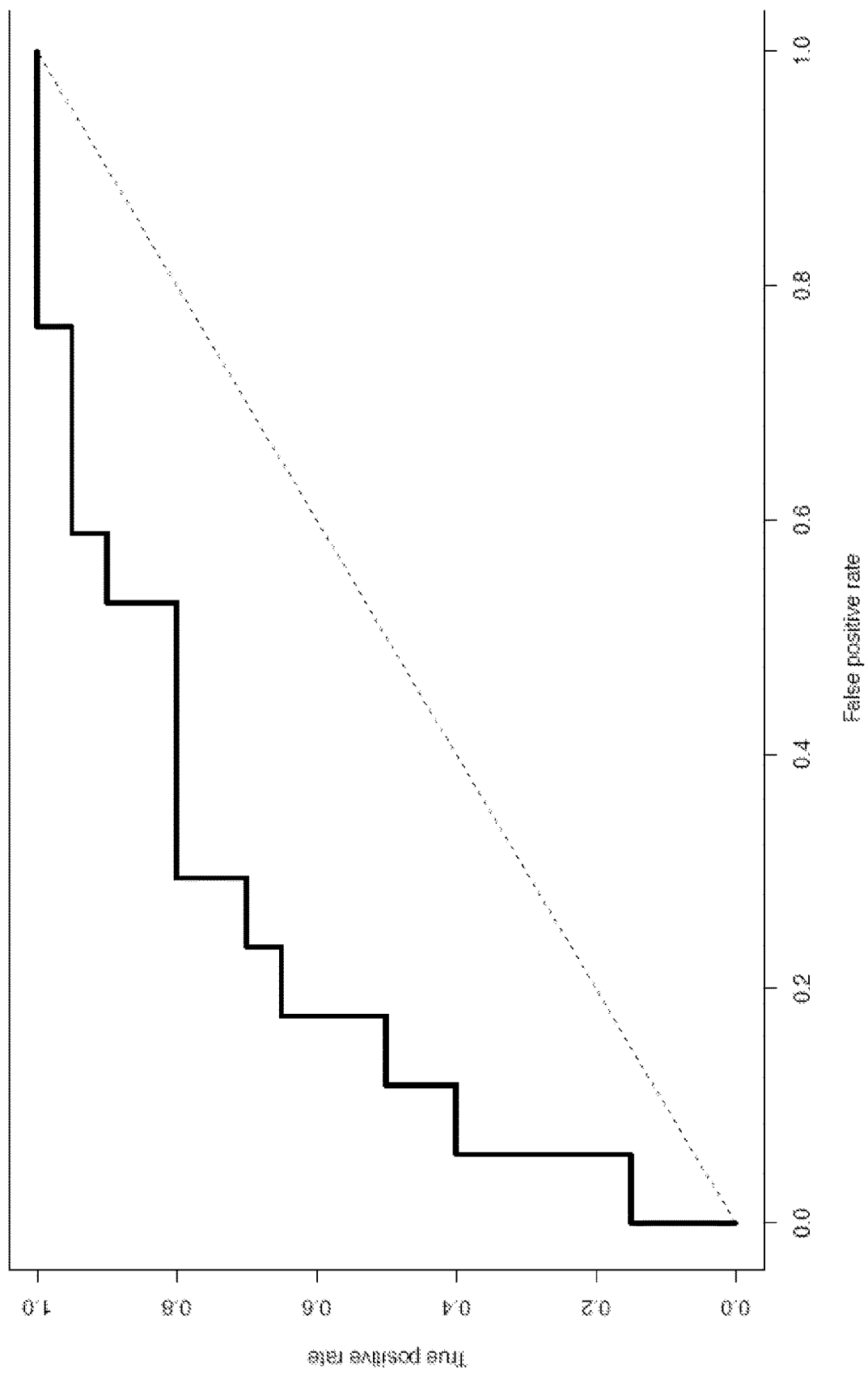

FIG. 11. The receiver operating characteristic (ROC) curves for the statistical model using the 15 core genes is shown in the validation cohort. By definition, random classification of a sample as recurrent or non-recurrent provides an AUC of 50% (dotted line). The AUC for the proposed gene signature was 0.785.

Figure 12:
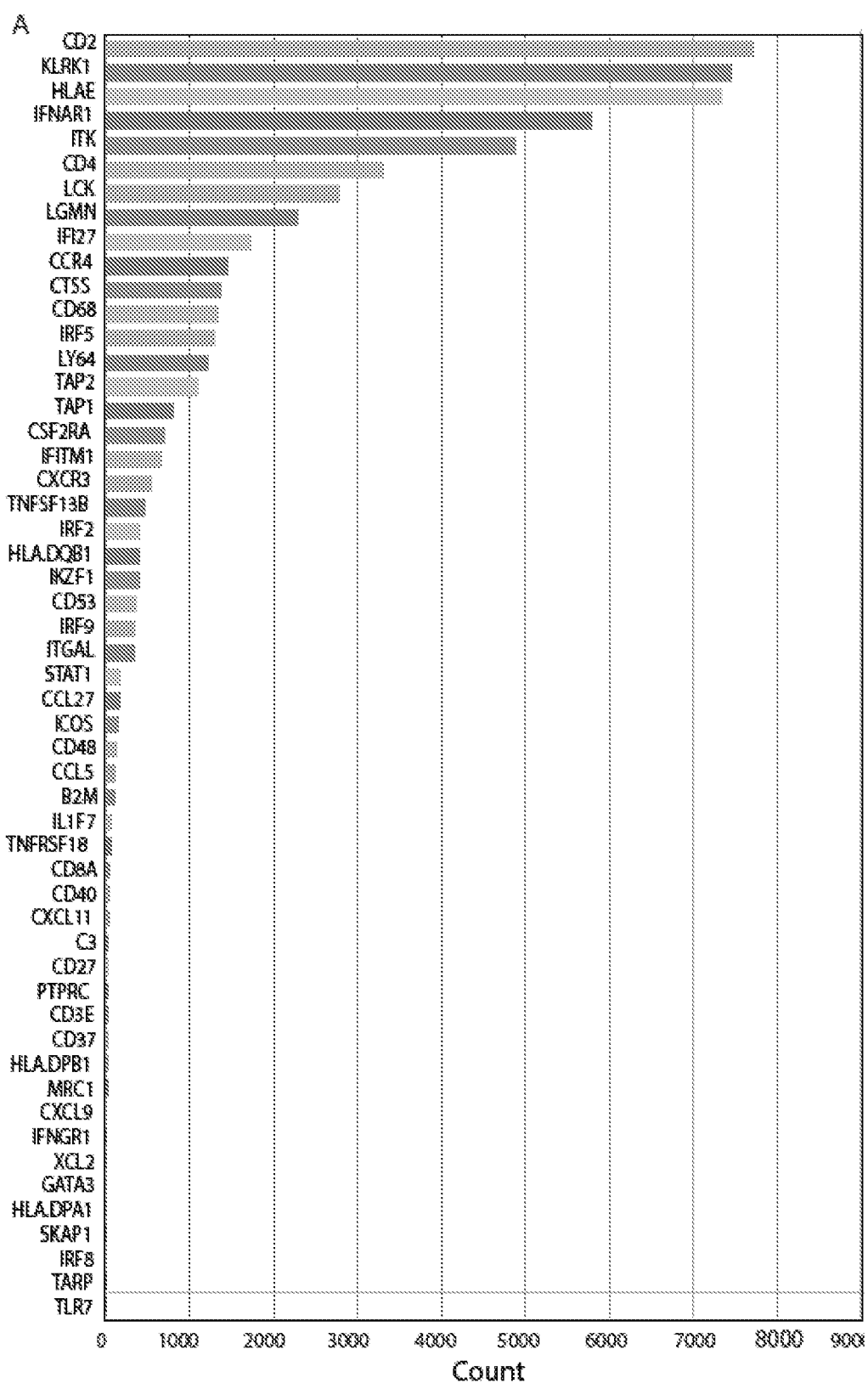

FIG. 12. RNA was extracted from 40 FFPE stage II-III primary melanoma specimens and analyzed using NanoString Technology and 53 genes predictive of melanoma progression were identified using elastic net and random forest classifiers. In (A), a bar graph depicts the number of times each of the 53 genes was selected using a leave-4-out cross-validation. ROC curve to predict melanoma progression is shown in (B), AUC=1.000, p<0.001. In (C), relative levels of mRNA expression for each sample are depicted according to the color scale shown, with each column representing a different patient sample and each row representing one of the 53 genes. Unsupervised hierarchical clustering was performed on both genes and samples. Patient who progressed are labeled in dark gray and patients who did not progress are labeled in dark gray.

Figure 13:
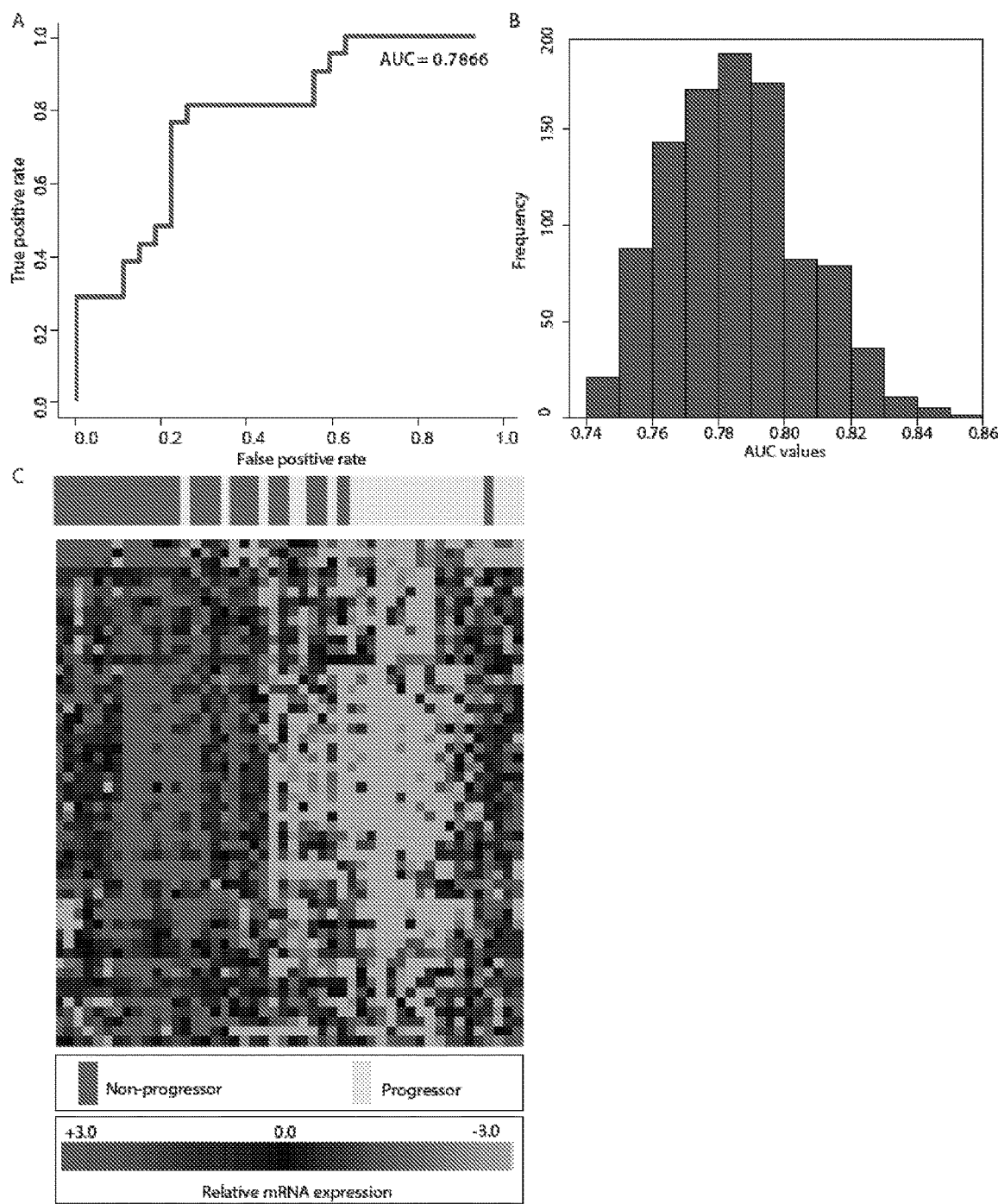

FIG. 13. RNA was extracted from 48 FFPE stage II-III primary melanoma specimens and analyzed using NanoString Technology. ROC curve to predict melanoma progression is shown in (A), AUC=0.787, p<0.001. In (B), distribution of AUC values using a leave-4-out cross-validation test is shown. In (C), relative levels of mRNA expression for each sample are depicted according to the color scale shown, with each column representing a different patient sample and each row representing one of the 53 genes. Unsupervised hierarchical clustering was performed on both genes and samples. Patient who progressed are labeled in dark gray and patients who did not progress are labeled in light gray.

Figure 14:
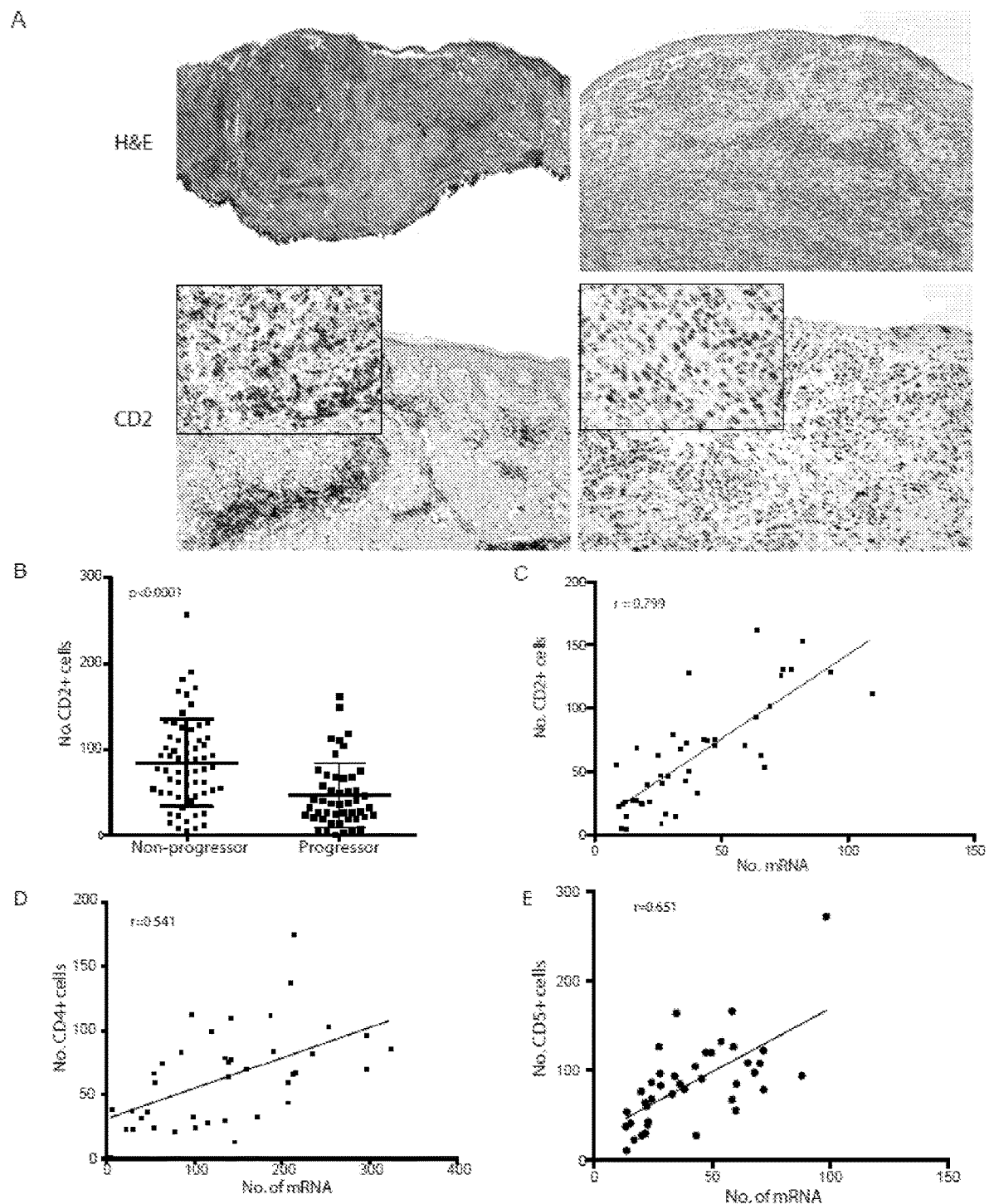

FIG. 14. IHC using anti-CD2 monoclonal antibody was performed to assess risk of disease progression. (A) Photographs of a tumor expressing low levels of CD2 which did progress (left) and a tumor with high levels of CD2 from a patient who remained disease free are shown (right). A brisk peri-tumoral in!ltrate is seen at 4× magnification on H&E in the tumor that did not progress. (B) The average number of CD2 positive cells counted at 40× magnification in 8 random HPFs for patients in the validation test set is shown. A linear regression model is used to assess correlation in Nanostring with IHC for CD2 (C), CD4 (D), and CD5 (E) in the training set.

Figure 15:
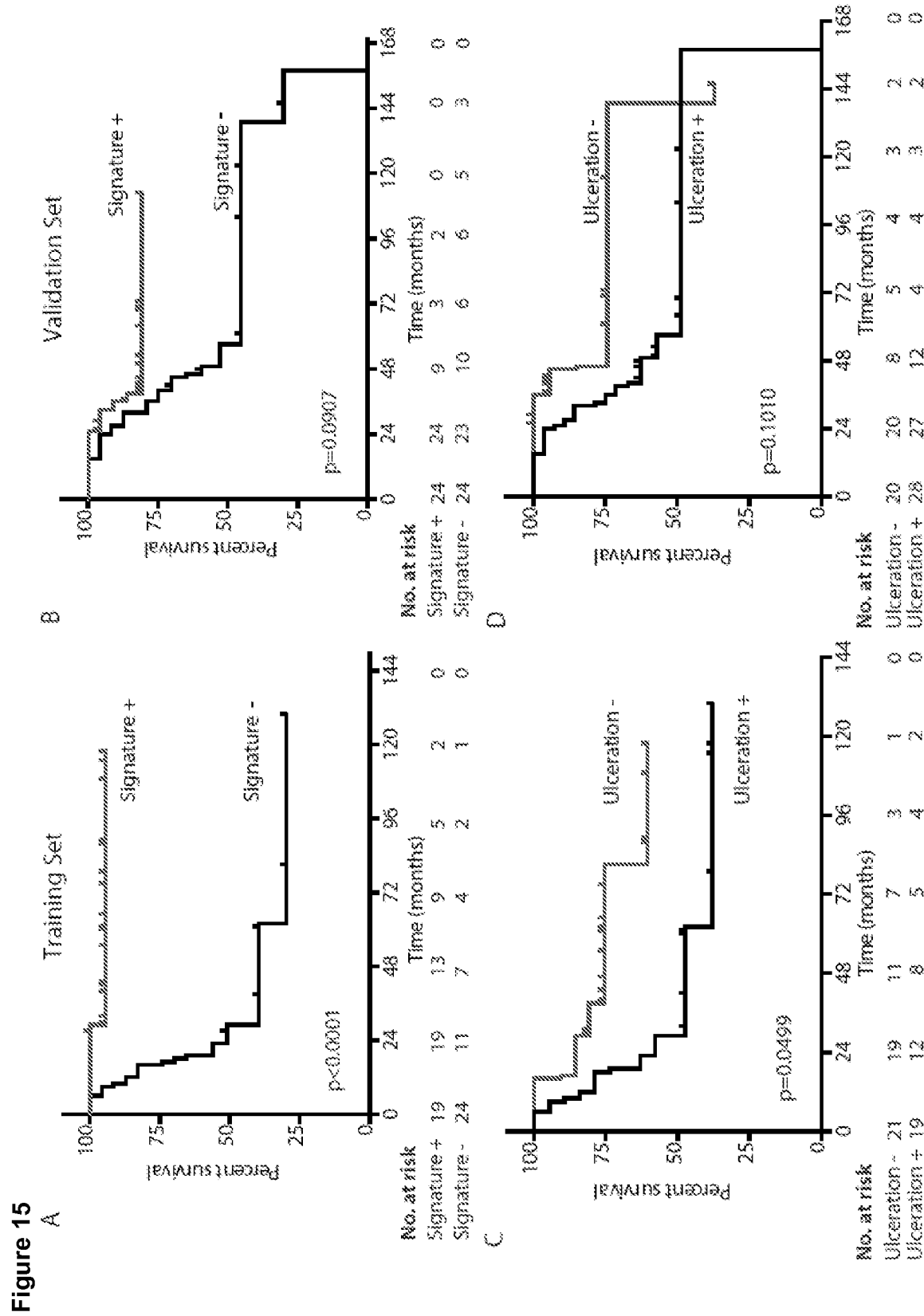

FIG. 15. Kaplan-Meier curves of survival based on a 21-gene signature and ulceration using a log rank Mantel-Cox test are shown for the training (A,C,E) and validation (B,D,F) populations. In both the training (A) and validation (B), patients were classified as either signature + (gray) or signature − (black) based on median score. In the training set, a negative gene signature conferred inferior survival ($p<0.001$) while there was a strong trend for an ulcerated tumor ($p=0.050$), while patients with both negative indicators also had decreased survival ($p<0.001$). In the validation population, there was a trend towards shortened survival in patients with a negative gene signature ($p=0.091$) or an ulcerated tumor ($p=0.101$), while patients with both features had significantly diminished survival ($p=0.044$).

Figure 16:
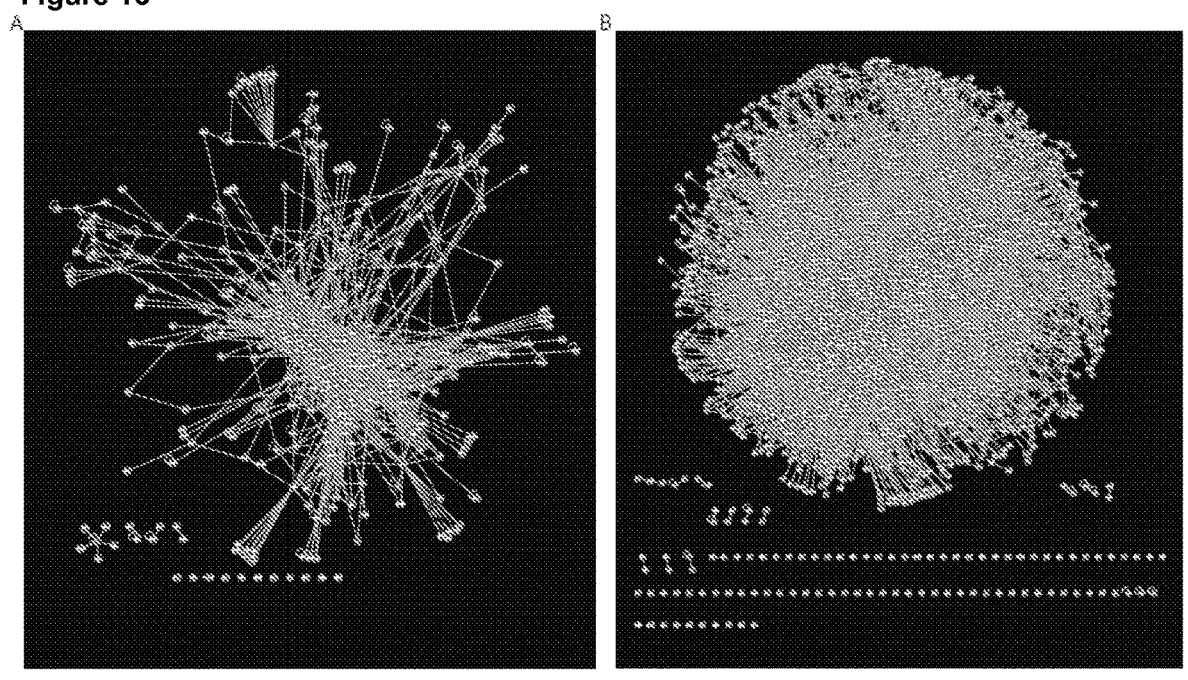

FIG. 16. (A) Gene-protein interaction network surrounding the 53-gene panel. The 53-gene panel (pink) forms a denser network of gene-protein or protein-protein interactions (green) than the network surrounding the original 446-gene panel tested as shown in (B). (C) Network attributes of the 53-gene panel and 446-gene panel networks. Av. local CC and local cc SE represents the mean local clustering coefficient and standard error. Global CC denotes the global clustering coefficient. Local CC Average P-value and Global CC P-value represents the p-values associated with Local CC Average P-value and Global CC.

Figure 17:
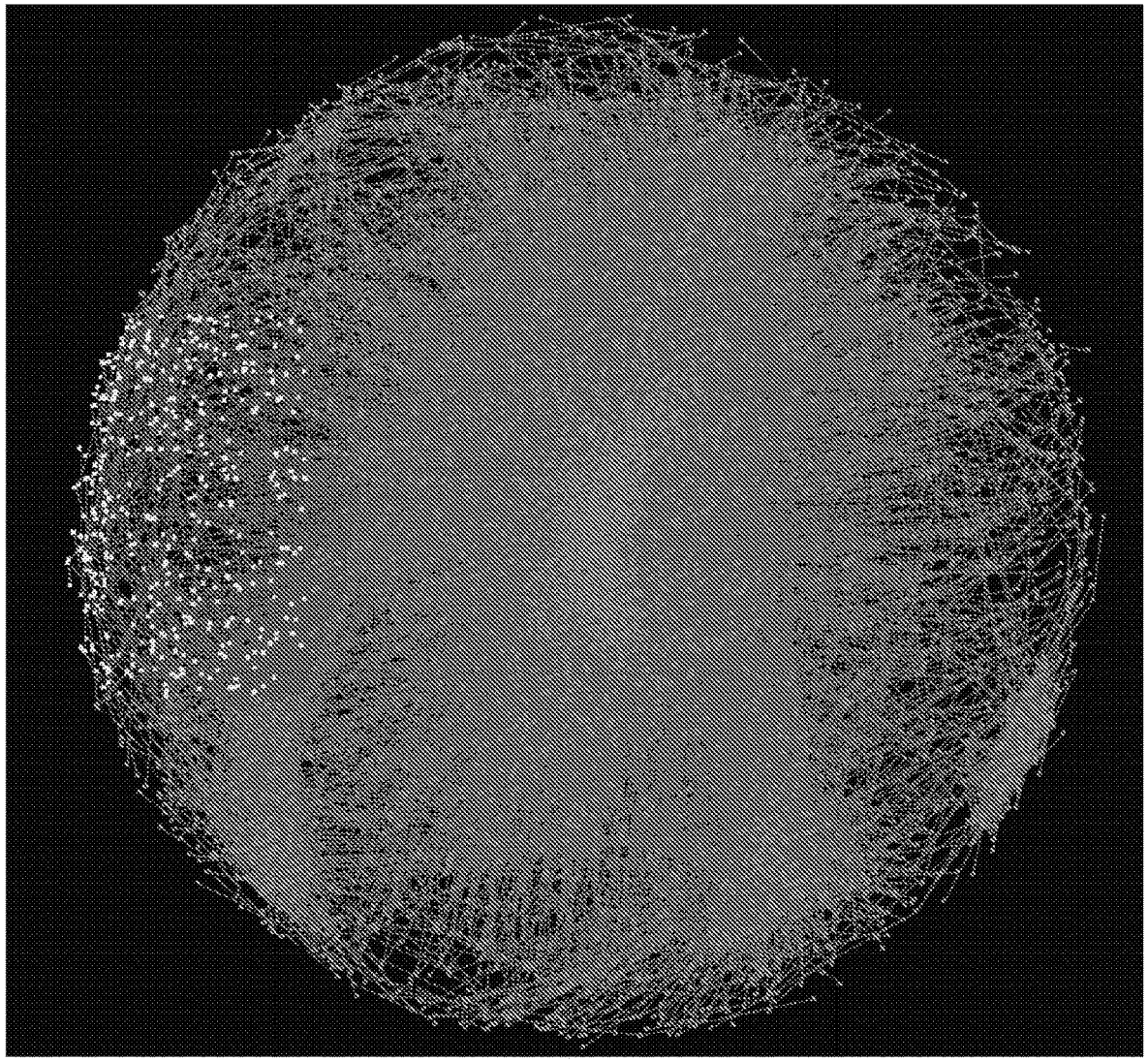

FIG. 17. Co-expression network using WGCNA27 on 46 gene expression profiles in primary melanoma patients (GEO accession ID: GSE15605). The yellow dots compose a 758-gene module within the entire gene genome (pink). Red lines denote interactions between nodes involving nodes within the module.

Figure 18:
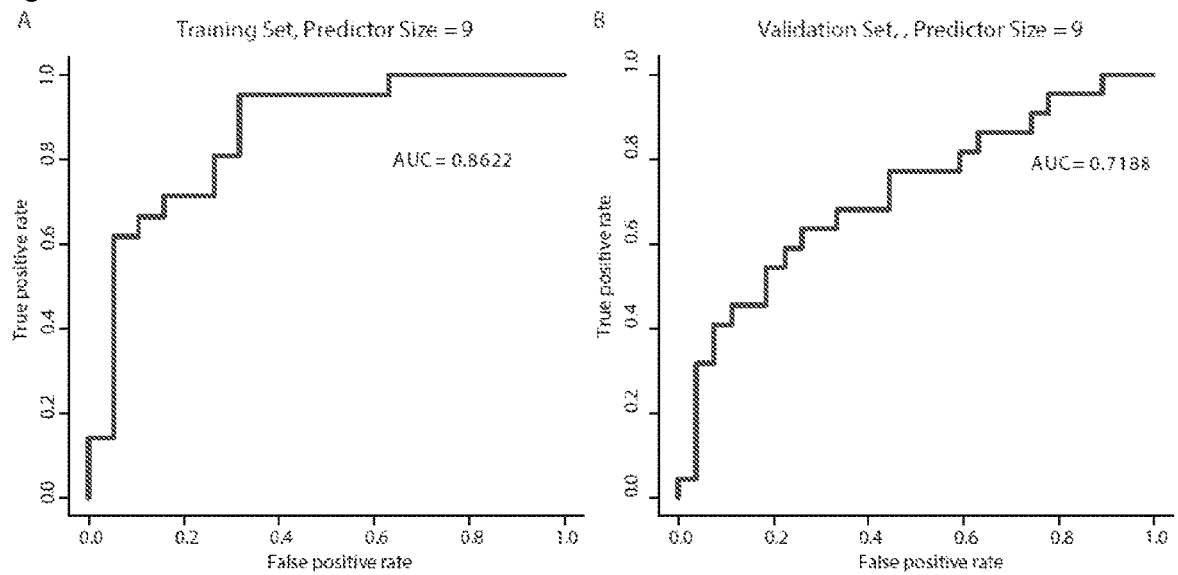

FIG. 18. ROC curves were generated for the refined 9 gene signatures on the training (A) and validation data set (B).

Figure 19:
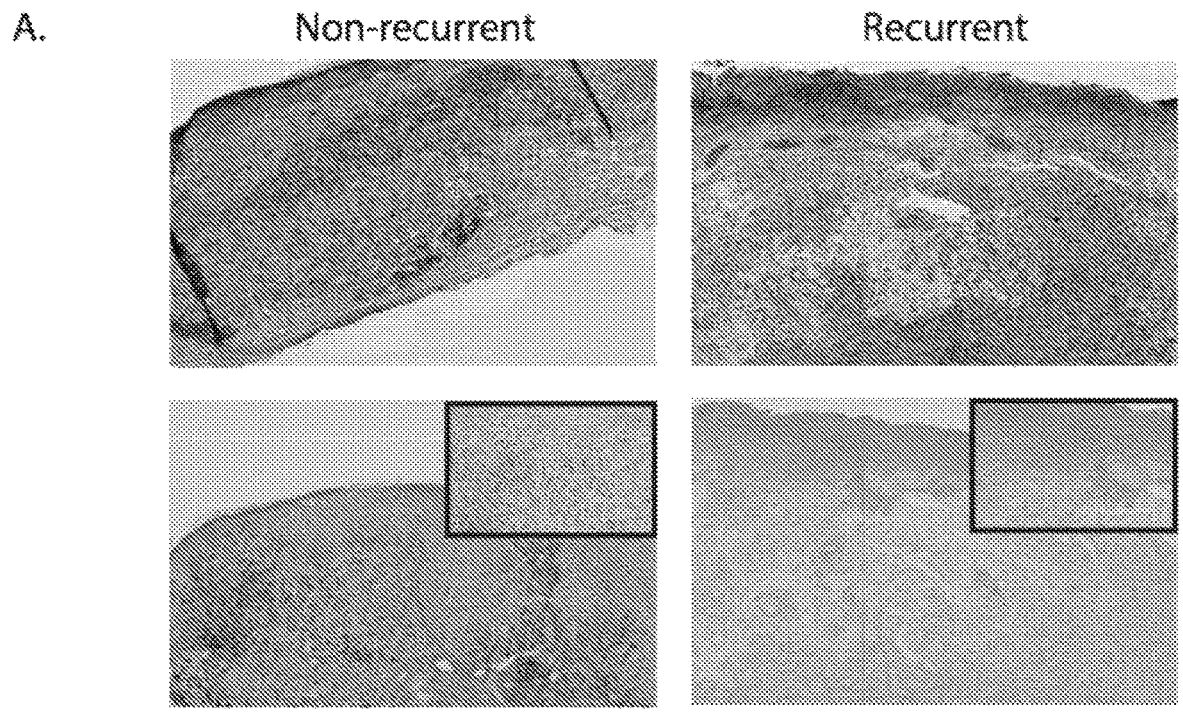

FIG. 19. Cutaneous melanoma. CD2 Immunohistochemistry and disease recurrence Immunohistochemistry (IHC) using anti-CD2 monoclonal antibody was performed to examine differential expression of this protein in recurrent and non-recurrent patients. In panel A, photographs of non-recurrent (left) and recurrent (right) patient melanoma tumors are shown. In the non-recurrent patient sample, a representative field at 40× magnification stained with H&E is shown (top left). The tumor contained many CD2-positive cells (bottom left), shown at 40× and 100× power (inset). The recurrent patient sample is shown at 40× power stained with H&E (top right), with few corresponding cells staining positive for CD2 (bottom right) at 40× and 100× magnification (inset). Panel B displays the average number of cells counted at 400× magnification in 8 random HPFs for 90 patients with primary melanoma. Significantly more CD2 positive cells were counted in patients with non-recurrent disease in comparison to patients who experienced recurrent disease ($p=0.0003$). Panel C shows the Kaplan-Meier survival curves for patients with high- and low-CD2 counts. Patients with a higher number of CD2 positive cells in their primary tumor showed superior overall survival ($p=0.004$).

FIG. 20. Cutaneous melanoma. Cell surface expression of CD2

A. Charged slides from six melanoma tumors were co-stained using immunoflourescence with an anti-CD3 antibody, a pan T-cell marker, and an anti-CD2 antibody. Patterns of staining, shown at 100×, were similar for CD3 and CD2. B. Serially-sectioned charged slides from three tumors were stained with an anti-CD16 antibody, expressed on Natural Killer cells, and an anti-CD2 antibody. Patterns of staining, shown at 100×, were dissimilar with a small amount of overlap.

Figure 21:
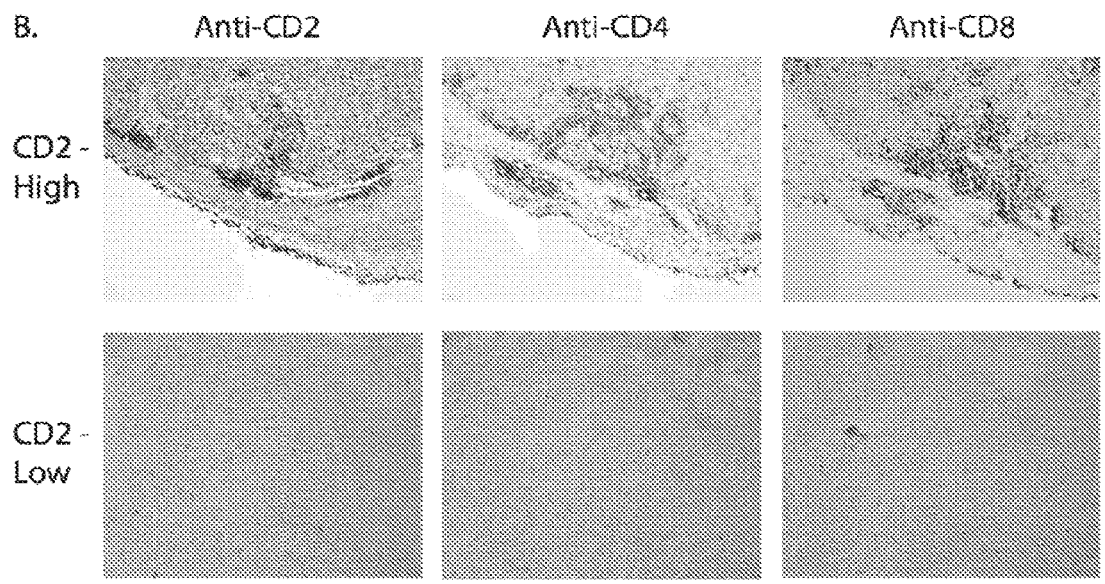

FIG. 21. Cutaneous melanoma. T-cell subtypes and CD2 expression

A. Tumors were co-stained with either anti-CD2 and anti-CD4 or anti-CD2 and anti-CD8 using immunoflourescence. Co-expression of CD2 and CD4, as well as CD2 and CD8, is shown. Images at 200× magnification. B. Immunohistochemistry (IHC) using anti-CD2, anti-CD4 and anti-CD8 monoclonal antibodies was performed to classify the T-cell subtype expressing CD2 in primary melanoma tumors. In panel A (top), a tumor found to contain high levels of CD2-positive cells was found to contain both CD4-positive (top left) and CD8-positive (top right) T-cells. CD2 staining is seen to overlap with CD4 and CD8 staining. Images shown at 40× magnification. A tumor found to contain low levels of CD2-positive cells (bottom) was shown to contain low levels of CD4-positive (bottom left) and CD8-positive cells (bottom right). Images shown at 40× magnification. In Panel C, a comparison of the number of CD4-positive cells to the number of CD8-positive cells within the same tumor is shown for four tumors expressing high levels of CD2 and four tumors expressing low levels of CD2. The distribution of CD4 and CD8-positive cells is not different between the high CD2 and low CD2 groups ($p=0.5152$).

Figure 22:
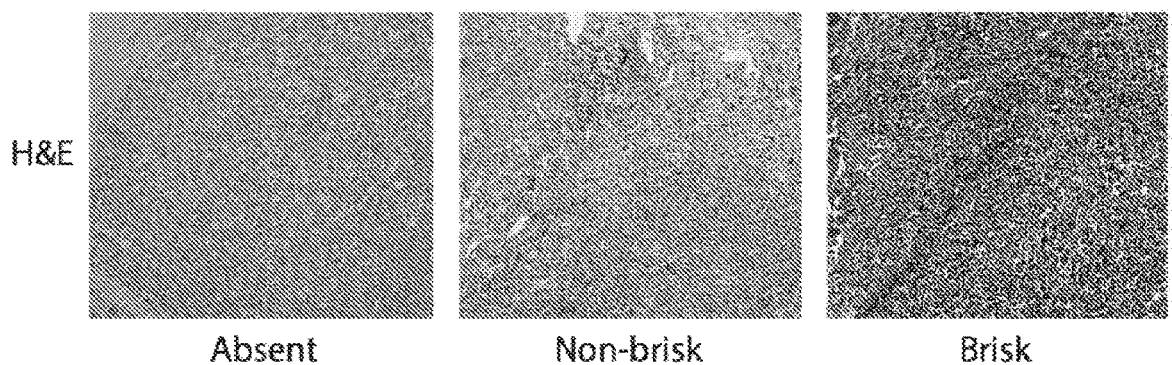

FIG. 22. Cutaneous melanoma. CD2 Count and TIL Characterization

A subset of slides available for analysis were examined by the Department of Dermatopathology (RGP) and tumor-infiltrating lymphocytes were characterized as absent, non-brisk, or brisk using established criteria. Panel A demonstrates representative images of (from left to right) absent, non-brisk and brisk tumor-infiltrating lymphocytes stained with H&E at 88× magnification. Panel B demonstrates the number of CD2 positive cells by IHC seen in tumors with absent, non-brisk and brisk tumor-infiltrating lymphocytes. CD2 count increases from absent to non-brisk to brisk infiltrates ($p=0.0004$). In Panel C, the number of CD2 positive cells in recurrent (right) and non-recurrent (left) tumors is shown for tumors containing non-brisk infiltrates. Among this large subset of patients, CD2 count remains significantly elevated in non-recurrent patients, compared to recurrent patients ($p=0.0006$), and a high CD2 count correlates with improved overall survival (Panel D; $p=0.0318$).

FIG. 23. Cutaneous melanoma. CD2 and CD3 immunohistochemistry, disease recurrence and overall survival. Immunohistochemistry (IHC) using anti-CD2 and anti-CD3 monoclonal antibodies was performed to examine differential expression of these proteins in a subset of recurrent and non-recurrent patients (n=21). Significantly more CD2 positive cells were counted in patients with non-recurrent disease in comparison to patients who experienced recurrent disease (Panel A (left), p=0.041). CD2 also significantly correlated with improved overall survival (Panel A (right), p=0.0123). Panel B demonstrates the relationship between CD3 immunohistochemistry, disease recurrence and overall survival. (Left) CD3 immunohistochemistry did not significantly differ between recurrent and non-recurrent patient populations (p=0.0514). (Right) CD3 immunohistochemistry did not significantly correlate with improved overall survival (p=0.0873).

FIG. 24. Cutaneous melanoma. Tumor-infiltrating lymphocyte topography and intensity.

Fifty-five primary tumor specimens were determined to have non-brisk tumor-infiltrating lymphocytes. A. Subclassification of non-brisk TILs in terms of topography (central, peripheral or both) did not distinguish recurrent and non-recurrent patients in this group. B. Subclassification of non-brisk TILs in terms of intensity (focal, multifocal, or segmental) did not distinguish recurrent from non-recurrent patients in this group.

FIG. 25. The figure shows the list of all 446 genes selected for NanoString analysis in training cohort, with housekeeping genes highlighted. The genes were identified via a PubMed literature review.

FIG. 26. The figure shows the R2 values obtained using a linear model for each characteristic with and without the gene signature for both the training and validation sets.

FIG. 27. The figure shows the core gene picks.

FIG. 28. The figure shows the official names of all 446 genes selected for NanoString analysis in training cohort, with 17 housekeeping genes highlighted. The genes were identified via a PubMed literature review.

DETAILED DESCRIPTION OF THE INVENTION

The present invention provides a method of predicting the risk of reoccurrence of melanoma in a patient from whom melanoma tissue was previously removed which comprises the following:
a. obtaining a RNA-containing sample of the previously removed melanoma tissue containing RNA from the patient;
b. treating the sample to determine from the RNA contained in the sample the level of expression of a plurality of preselected genes; and
c. comparing the level of expression of each gene of the plurality of pre-selected genes to a predetermined reference level of expression for each such gene;
wherein a higher level of expression of the plurality of pre-selected genes in the sample as compared with the predetermined reference level of expression of such genes indicates that the patient has a reduced risk of reoccurrence of melanoma, and
wherein the plurality of pre-selected genes comprises the following genes:
a. CD2;
b. KLRK1;
c. ITK; and
d. HLAE.

In some embodiments, the method further comprises the step of creating a report summarizing said prediction.

In some embodiments, the expression level of each gene of the plurality of pre-selected genes is normalized relative to the expression level of one or more reference genes.

In some embodiments, the expression level of each such gene is normalized relative to the expression level of the following genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the expression level of each such gene is normalized relative to the expression level of one or more of, or each of the following genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the predetermined reference level of expression is the expression level of the one or more reference genes.

The present invention also provides a method of treating a patient from whom melanoma tissue was previously removed, and which patient was determined to not have a reduced risk of reoccurrence of melanoma by a method of the invention, comprising administering an immunotherapy to the patient.

The present invention also provides a method of treating a patient from whom melanoma tissue was previously removed, and which patient was determined to not have a reduced risk of reoccurrence of melanoma by a method of the invention, comprising testing the human patient for recurrence of melanoma more frequently than a corresponding patient who was determined to have a reduced risk of reoccurrence of melanoma would be tested for recurrence.

The present invention also provides a method of treating a patient afflicted with melanoma which comprises the following:
a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and
d. administering a therapy to the patient if there is a higher level of expression of the plurality of pre-selected genes in the sample as compared with the predetermined reference level of expression of such genes, and
wherein the plurality of pre-selected genes comprises the following genes:
a. CD2;
b. KLRK1;
c. ITK; and
d. HLAE.

The present invention also provides a method of treating a patient afflicted with melanoma which comprises the following:
a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and
d. administering a therapy to the patient if there is a lower level of expression of the plurality of pre-selected genes in the sample as compared with the predetermined reference level of expression of such genes, and wherein the plurality of pre-selected genes comprises the following genes:
a. CD2;
b. KLRK1;
c. ITK; and
d. HLAE.

The present invention also provides a method of treating a patient afflicted with melanoma which comprises the following:
a. obtaining a RNA-containing sample of the melanoma tissue containing RNA from the patient;
b. treating the sample to determine from the RNA contained in the sample the level of expression of a plurality of preselected genes;
c. comparing the levels of expression of each gene of the plurality of pre-selected genes to a predetermined reference level of expression for each such gene; and
d. administering a therapy to the patient if the level of expression of the plurality of pre-selected genes in the sample is i) lower as compared with the predetermined reference upper level of expression of such genes and ii) higher as compared with the predetermined reference lower level of expression of such genes, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a higher level of expression of the plurality of pre-selected genes in the sample as compared with the predetermined reference level of expression of such genes indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of the melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a lower level of expression of the plurality of pre-selected genes in the sample as compared with the predetermined reference level of expression of such genes indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of predicting whether a patient afflicted with melanoma is likely to exhibit a positive clinical response to treatment with a therapy which comprises the following:
a. obtaining a RNA-containing sample of the melanoma tissue containing RNA from the patient;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a level of expression of the plurality of pre-selected genes in the sample is i) lower as compared with the predetermined reference upper level of expression of such genes and ii) higher as compared with the predetermined reference lower level of expression of such genes, indicates that the patient is likely to exhibit a positive clinical response to treatment with the therapy, and wherein the plurality of pre-selected genes comprises the following genes:
a. CD2;
b. KLRK1;
c. ITK; and
d. HLAE.

The present invention also provides a method of determining whether a therapy is effective for treating patients afflicted with melanoma which comprises the following:
a. obtaining a RNA-containing sample of the melanoma tissue containing RNA from at least one patient afflicted with melanoma, which at least one patient was administered the therapy for treatment of the melanoma previous to collection of the sample;
b. treating the sample to determine from the RNA contained in the sample the level of expression of a plurality of preselected genes; and
c. comparing the levels of expression of each gene of the plurality of pre-selected genes to the levels of expression of the plurality of pre-selected genes to the expression level of each such gene in a corresponding at least one patient not administered the therapy;

wherein a higher level of expression of the plurality of pre-selected genes in the sample of step a) as compared with the level of expression of such genes in a corresponding at least one patient not administered the treatment indicates that the therapy is effective for treating patients afflicted with melanoma, and wherein the plurality of pre-selected genes comprises the following genes:
a. CD2;
b. KLRK1;
c. ITK; and
d. HLAE.

The present invention also provides a method of determining whether a patient afflicted with melanoma and which patient was administered a therapy has exhibited a positive clinical response to the therapy which comprises the following:

a. obtaining a RNA-containing sample of the melanoma tissue containing RNA from the patient, which RNA-containing sample was removed from the patient who was administered the therapy;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a higher level of expression of the plurality of pre-selected genes in the sample as compared with the predetermined reference level of expression of such genes indicates that the patient has exhibited a positive clinical response to the therapy, and wherein the plurality of pre-selected genes comprises the following genes:
a. CD2;
b. KLRK1;
c. ITK; and
d. HLAE.

The present invention also provides a method of determining whether a treatment should be administered to patients afflicted with melanoma as an adjuvant or a neoadjuvant therapy which comprises the following:
a. obtaining a RNA-containing sample of the melanoma tissue containing RNA from at least one patient afflicted with melanoma;
b. treating the sample to determine from the RNA contained in the sample the level of expression of a plurality of preselected genes; and
c. comparing the levels of expression of each gene of the plurality of pre-selected genes to a predetermined reference level of expression for each such gene;

wherein a higher level of expression of the plurality of pre-selected genes in the sample as compared with the predetermined reference level of expression of such genes indicates that the treatment should be administered to patients afflicted with melanoma as a neoadjuvant therapy, and a lower level of expression of the plurality of pre-selected genes in the sample as compared with the predetermined reference level of expression of such genes indicates that the treatment should be administered to patients afflicted with melanoma as an adjuvant therapy, and wherein the plurality of pre-selected genes comprises the following genes:
a. CD2;
b. KLRK1;
c. ITK; and
d. HLAE.

In some embodiments, the plurality of pre-selected genes further comprises at least one of the following genes:
a. IFNAR1;
b. LCK;
c. CD4;
d. LGMN; and
e. IFI27.

In some embodiments, the plurality of pre-selected genes comprises the following genes:
a. CD2;
b. KLRK1;
c. ITK;
d. HLAE;
e. IFNAR1;
f. LCK;
g. CD4;
h. LGMN; and
i. IFI27.

In some embodiments, the plurality of pre-selected genes further comprises at least one of the following genes:
a. CCL27;
b. SYK;
c. CD68;
d. IL18; and
f. IL1F7.

In some embodiments, the plurality of pre-selected genes comprises the following genes:
a. CD2;
b. KLRK1;
c. ITK;
d. HLAE;
e. LCK;
f. IFNAR1;
g. CD48;
h. CD4;
i. CTSS;
j. CCR4;
k. HLA-DQB1;
l. TAP2;
m. LGMN;
n. CSF2RA;
o. IFNGR1;
p. CCL27;
q. SYK;
r. CD68;
s. IL18;
t. IFI27; and
u. IL1F7.

In some embodiments, the plurality of pre-selected genes further comprises at least one of the following genes:
a. LCK;
b. IFNAR1;
c. CD48;
d. CD4;
e. CTSS;
f. CCR4;
g. HLA-DQB1;
h. TAP2;
i. LGMN;
j. CSF2RA; and
k. IFNGR1.

In some embodiments, the plurality of pre-selected genes further comprises at least two, three, four, five, six, seven, eight, nine, ten, or eleven of the following genes:
a. LCK;
b. IFNAR1;
c. CD48;
d. CD4;
e. CTSS;
f. CCR4;
g. HLA-DQB1;
h. TAP2;
i. LGMN;
j. CSF2RA; and
k. IFNGR1.

In some embodiments, the plurality of pre-selected genes comprises the following genes:
a. CD2;
b. KLRK1;
c. ITK;
d. HLAE;
e. LCK;
f. IFNAR1;
g. CD48;

h. CD4;
i. CTSS;
j. CCR4;
k. HLA-DQB1;
l. TAP2;
m. LGMN;
n. CSF2RA; and
o. IFNGR1.

In some embodiments, the plurality of pre-selected genes further comprises at least one of the following genes:
a. CCL27;
b. SYK;
c. CD68;
d. IL18;
e. IFI27; and
f. IL1F7.

In some embodiments, the plurality of pre-selected genes further comprises at least two, three, four or five of the following genes:
a. CCL27;
b. SYK;
c. CD68;
d. IL18;
e. IFI27; and
f. IL1F7.

In some embodiments, the plurality of pre-selected genes comprises the following genes:
a. CD2;
b. KLRK1;
c. ITK;
d. HLAE;
e. LCK;
f. IFNAR1;
g. CD48;
h. CD4;
i. CTSS;
j. CCR4;
k. HLA-DQB1;
l. TAP2;
m. LGMN;
n. CSF2RA;
o. IFNGR1;
p. CCL27;
q. SYK;
r. CD68;
s. IL18;
t. IFI27; and
u. IL1F7.

In some embodiments, the plurality of pre-selected genes consists of less than about 10, 20, 30, 40, 50, 100, 200, 300, 400, 500, 1000, or 10,000 genes.

In some embodiments, the expression level is assayed by NanoString gene expression analysis.

In some embodiments, the RNA transcripts of the plurality of pre-selected genes in the sample are fragmented.

The present invention provides a method of predicting the risk of reoccurrence of melanoma in a patient from whom melanoma tissue was previously removed which comprises the following:
a. obtaining a sample of the previously removed melanoma tissue from the patient;
b. treating the sample to determine the level of an expression product of a gene or each of two or more genes in the sample; and
c. comparing the level of the expression product of the gene or each of the two or more genes to a predetermined reference level of the expression product for each such gene,
wherein a higher level of expression product of the gene or each of the two or more genes in the sample as compared with the predetermined reference level of the expression product for each such gene indicates that the patient has a reduced risk of reoccurrence of melanoma.

In some embodiments, the method further comprises the step of creating a report summarizing said prediction.

In some embodiments, the expression level of the expression product of the gene or the each of two or more genes is normalized relative to the expression level of the expression product of one or more of the following genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the predetermined reference level of expression of the expression product is the expression level of the expression product the one or more reference genes.

The present invention provides a method of treating a patient from whom melanoma tissue was previously removed, and which patient was determined to not have a reduced risk of reoccurrence of melanoma by the method of the invention, comprising administering an immunotherapy to the patient.

The present invention provides a method of treating a patient from whom melanoma tissue was previously removed, and which patient was determined to not have a reduced risk of reoccurrence of melanoma by the method of the invention, comprising testing the human patient for recurrence of melanoma more frequently than a corresponding patient who was determined to have a reduced risk of reoccurrence of melanoma would be tested for recurrence.

The present invention provides a method of treating a patient afflicted with melanoma which comprises the following:
a. obtaining a sample of melanoma tissue from the patient;
b. treating the sample to determine the level of an expression product of a gene or each of two or more genes in the sample;
c. comparing the level of the expression product of the gene or each of the two or more genes to a predetermined reference level of the expression product for each such gene; and
d. administering a therapy to the patient if there is a higher level of expression of the expression product of the gene or each of the two or more genes in the sample as compared with the predetermined reference level of the expression product for each such gene.

The present invention provides a method of treating a patient afflicted with melanoma which comprises the following:
a. obtaining a sample of melanoma tissue from the patient;
b. treating the sample to determine the level of an expression product of a gene or each of two or more genes in the sample;
c. comparing the level of the expression product of the gene or each of the two or more genes to a predetermined reference level of the expression product for each such gene; and
d. administering a therapy to the patient if there is a lower level of expression of the expression product of the gene or each of the two or more genes in the sample as compared with the predetermined reference level of the expression product for each such gene.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of a gene or each of two or more genes in the sample; and
c. comparing the level of the expression product of the gene or the each of two or more genes to a predetermined reference level of the expression product for each such gene, wherein a higher level of expression product of the gene or each of the two or more genes in the sample as compared with the predetermined reference level of the expression product for each such gene indicates that the patient is likely to exhibit a positive clinical response to treatment with the therapy.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of the gene or each of the two or more genes in the sample; and
c. comparing the level of the expression product of the gene or each of the two or more genes to a predetermined reference level of the expression product for each such gene, wherein a lower level of expression product of the gene or each of the two or more genes in the sample as compared with the predetermined reference level of the expression product for each such gene indicates that the patient is likely to exhibit a positive clinical response to treatment with the therapy.

The present invention provides a method of predicting whether a patient afflicted with melanoma is likely to exhibit a positive clinical response to treatment with a therapy which comprises the following:
a. obtaining a sample of melanoma tissue from the patient;
b. treating the sample to determine the level of an expression product of a gene or each of two or more genes in the sample; and
c. comparing the level of the expression product of the gene or each of the two or more genes to a predetermined reference level of the expression product for each such gene, wherein a level of the expression product of the gene or each of the two or more genes that is i) lower as compared with a predetermined reference upper level of expression for each such gene and ii) higher as compared with a predetermined reference lower level of expression for each such gene, indicates that the patient is likely to exhibit a positive clinical response to treatment with the therapy.

The present invention provides a method of determining whether a therapy is effective for treating patients afflicted with melanoma which comprises the following:
a. obtaining a sample of melanoma tissue from at least one patient afflicted with melanoma, which at least one patient was administered the therapy;
b. treating the sample to determine the level of an expression product of the gene or each of two or more genes in the sample; and
c. comparing the level of the expression product of the gene or each of the two or more genes to the level of the expression product of the gene or each of the two or more genes in a corresponding at least one patient not administered the treatment, wherein a higher level of expression product of the gene or each of the two or more genes in the sample of step (a) as compared with the level of expression product of the gene or each of the two or more genes in the corresponding at least one patient not administered the treatment indicates that the therapy is effective for treating patients afflicted with melanoma.

The present invention provides a method of determining whether a patient afflicted with melanoma and which patient was administered a therapy has exhibited a positive clinical response to the therapy which comprises the following:
a. obtaining a sample of melanoma tissue from the patient;
b. treating the sample to determine the level of an expression product of a gene or each of two or more genes in the sample; and
c. comparing the level of the expression product of the gene or each of the two or more genes to a predetermined reference level for each such gene, wherein a higher level of expression the expression product of the gene or each of the two or more genes as compared to the predetermined reference level of the expression product of each such gene indicates that the patient has exhibited a positive clinical response to the therapy.

The present invention provides a method of determining whether a treatment should be administered to patients afflicted with melanoma as an adjuvant or a neoadjuvant therapy which comprises the following:
a. obtaining a sample of melanoma tissue from at least one patient afflicted with melanoma;
b. treating the sample to determine the level of an expression product of a gene or each of two or more genes in the sample; and
c. comparing the level of the expression product of the gene or each of the two or more genes to a predetermined reference level for each such gene, wherein a higher level of the expression product of the gene or each of the two or more genes in the sample as compared with the predetermined reference level of expression for each such gene indicates that the treatment should be administered to patients afflicted with melanoma as a neoadjuvant therapy, and a lower level of the expression product of the gene or each of the two or more genes in the sample as compared with the predetermined reference level of the expression product for each such gene indicates that the treatment should be administered to patients afflicted with melanoma as an adjuvant therapy.

The present invention provides a method of predicting the risk of reoccurrence of melanoma in a patient from whom melanoma tissue was previously removed which comprises the following:
a. obtaining a sample of the previously removed melanoma tissue from the patient;
b. treating the sample to determine the level of the expression product of the CD2 gene in the melanoma tissue sample; and
c. comparing the level of the expression product of the CD2 gene to a predetermined reference level of the expression product of the CD2 gene, wherein a higher level of expression product of the CD2 gene in the sample as compared with the predetermined reference level of the expression product of the CD2 gene indicates that the patient has a reduced risk of reoccurrence of melanoma.

The present invention provides a method of predicting the risk of reoccurrence of melanoma in a patient from whom melanoma tissue was previously removed which comprises the following:

a. obtaining a sample of the previously removed melanoma tissue from the patient;
b. treating the sample to determine the level of the expression product of the X gene in the melanoma tissue sample; and
c. comparing the level of the expression product of the X gene to a predetermined reference level of the expression product of the X gene, wherein a higher level of expression product of the X gene in the sample as compared with the predetermined reference level of the expression product of the X gene indicates that the patient has a reduced risk of reoccurrence of melanoma.

In some embodiments, the sample was previously removed from the patient.

In some embodiments, the sample is a fixed, wax-embedded tissue specimen.

In some embodiments, the sample is at least one week old.

In some embodiments, the sample is at least one month old.

In some embodiments, the sample is at least six months old.

In some embodiments, the sample is at least one year old.

In some embodiments, the sample is at least ten years old.

In some embodiments, a method of the invention further comprises identifying a treatment option for the patient based on the expression level of the plurality of pre-selected genes.

In some embodiments, the expression level is determined by immunohistochemistry or proteomics technology.

In some embodiments, the therapy is chemotherapy.

In some embodiments, the chemotherapy comprises dacarbazine, temozolomide, paclitaxel, cisplatin, carmustine, fotemustine, vindesine, vincristine, and bleomycin, or vemurafenib.

In some embodiments, the therapy is radiation therapy.

In some embodiments, the therapy is immunotherapy.

In some embodiments, the immunotherapy comprises an interferon (IFN).

In some embodiments, the immunotherapy comprises IFN-α.

In some embodiments, the IFN-α is IFN-α2b.

In some embodiments, the IFN-α2b is PEGylated IFN-α2b.

In some embodiments, the PEGylated IFN-α2b is Sylatron.

In some embodiments, the immunotherapy comprises an interleukin.

In some embodiments, the interleukin is IL-2.

In some embodiments, the IL-2 is aldesleukin.

In some embodiments, the immunotherapy comprises an antibody.

In some embodiments, the antibody is a monoclonal antibody.

In some embodiments, the monoclonal antibody is a humanized monoclonal antibody.

In some embodiments, the monoclonal antibody is a fully human monoclonal antibody.

In some embodiments, the antibody is an anti-PD-1 antibody.

In some embodiments, the anti-PD-1 antibody is BMS-936558.

In some embodiments, the antibody is an anti-CTLA-4 antibody.

In some embodiments, the antibody is ipilimumab.

In some embodiments, the immunotherapy is an oncolytic immunotherapy.

In some embodiments, the oncolytic immunotherapy comprises a virus.

In some embodiments, the virus is derived from HSV-1.

In some embodiments, the oncolytic immunotherapy is a vaccine.

In some embodiments, the vaccine is talimogene laherparepvec (T-VEC).

In some embodiments, the level of an expression product is determined for one gene.

In some embodiments, the one gene is CD2.

In some embodiments, each of the two or more genes comprises two, three, four, five, six, seven, nine, ten or more of CD2, KLRK1, ITK, HLAE, LCK, IFNAR1, CD48, CD4, CTSS, CCR4, HLA-DQB1, TAP2, LGMN, CSF2RA, IFNGR1, CCL27, SYK, CD68, IL18, IFI27 or IL1F7 gene.

In some embodiments, each of the two or more genes consists of less than about 10, 20, 30, 40, 50, 100, 200, 300, 400, 500, 1000, or 10,000 genes.

In some embodiments, the expression product is a protein encoded by the gene or is the expression product of each of the two or more genes.

In some embodiments, the expression product of each gene is a protein encoded by the gene.

In some embodiments, the X gene is the CD2, KLRK1, ITK, HLAE, LCK, IFNAR1, CD48, CD4, CTSS, CCR4, HLA-DQB1, TAP2, LGMN, CSF2RA, IFNGR1, CCL27, SYK, CD68, IL18, IFI27 or IL1F7 gene.

In some embodiments, the sample is treated to determine the level of the expression product of each of two, three, four, five, six, seven, eight nine, ten or more genes in the melanoma tissue sample.

In some embodiments, the two, three, four, five, six, seven, eight nine, ten or more genes are two, three, four, five, six, seven, eight nine, ten or more of CD2, KLRK1, ITK, HLAE, LCK, IFNAR1, CD48, CD4, CTSS, CCR4, HLA-DQB1, TAP2, LGMN, CSF2RA, IFNGR1, CCL27, SYK, CD68, IL18, IFI27 or IL1F7 gene.

In some embodiments, the patient is afflicted with sentinel lymph node positive melanoma when the melanoma tissue was removed.

In some embodiments, the patient was afflicted a melanoma deeper than 2 mm or deeper than 1 mm and ulcerated when the melanoma tissue was removed.

In some embodiments, the melanoma is sentinel lymph node positive melanoma.

In some embodiments, the melanoma is deeper than 2 mm or deeper than 1 mm and ulcerated.

In some embodiments, the method further comprises the step of creating a report summarizing said prediction.

In some embodiments, the expression product is a protein encoded by the X gene.

In some embodiments, the level of the expression product of each gene is determined by immunohistochemistry or proteomics technology.

In some embodiments, the level of the expression product of each gene is determined by immunohistochemistry.

In some embodiments, the melanoma tissue is stage II or III primary melanoma tissue.

In some embodiments, the melanoma is stage II or III melanoma.

In some embodiments, the expression level of each gene of the plurality of pre-selected genes is normalized relative to the expression level of one or more reference genes.

In some embodiments, the expression level of each such gene is normalized relative to the expression level of the following genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the predetermined reference level of expression is the expression level of one or more reference genes.

In some embodiments, the predetermined reference level of expression is
i) the expression level of each such gene in normal tissue; or
ii) the expression level of one or more of the following reference genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the predetermined reference level of the expression product is
i) the level of the expression product of each such gene in normal tissue; or
ii) the level of the expression product of one or more of the following reference genes: ABCF1, ACTB, ALAS1, CLTC, G6PD, GAPDH, GUSB, HPRT1, LDHA, PGK1, POLR1B, POLR2A, RPL19, RPLP0, SDHA, TBP and TUBB.

In some embodiments, the normal tissue is normal skin tissue.

In some embodiments of the present invention the patient is a human patient.

Each embodiment disclosed herein is contemplated as being applicable to each of the other disclosed embodiments. Thus, all combinations of the various elements described herein are within the scope of the invention.

It is understood that where a parameter range is provided, all integers within that range. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

"About" in the context of a numerical value or range means ±10% of the numerical value or range recited or claimed, unless the context requires a more limited range.

The term "melanoma" is used in the broadest sense and refers to all stages and all forms of cancer arising from melanocytes. Melanoma is typically a malignant tumor associated with skin cancer.

The term "prediction" is used herein to refer to the likelihood that a patient will have a particular clinical outcome, whether positive or negative. For instance, the term "prediction" may refer to the likelihood that a patient will respond either favorably or unfavorably to a drug or set of drugs, and also the extent of those responses, or that a patient will survive, following surgical removal of the primary tumor and/or therapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, therapy with a given drug or drug combination, and/or radiation therapy, or whether long-term survival of the patient, following surgery and/or termination of therapy is likely. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as a chemotherapy, an immunotherapy, or radiation.

The term "positive clinical response" means an improvement in any measure of patient status, including but not limited to those measures ordinarily used in the art, such as an increase in the duration of Recurrence-Free Interval (RFI), an increase in the time of Overall Survival (OS), an increase in the time of Disease-Free Survival (DFS), an increase in the duration of Distant Recurrence-Free Interval (DRFI), and the like. In a non-limiting example, an increase in the likelihood of positive clinical response corresponds to a decrease in the likelihood of cancer recurrence.

The term "Recurrence-Free Interval (RFI)" is used herein to refer to time to first melanoma cancer recurrence censoring for second primary cancer as a first event or death without evidence of recurrence. The time may be in months or years. For instance, in some embodiments, the time may be at least 1, 2, 3, 4, 5, 6, 7, 8, 9, 10, 11, 12 or more, or at least 1, 2, 3, 4, 5, 6, 7, 8, 9, 10 or more years.

The term "Overall Survival (OS)" is used herein to refer to time from surgery to death from any cause. For instance, in some embodiments, the time may be at least 1, 2, 3, 4, 5, 6, 7, 8, 9, 10, 11, 12 or more, or at least 1, 2, 3, 4, 5, 6, 7, 8, 9, 10 or more years.

The term "Disease-Free Survival (DFS)" is used herein to refer to time to melanoma recurrence or death from any cause. For instance, in some embodiments, the time may be at least 1, 2, 3, 4, 5, 6, 7, 8, 9, 10, 11, 12 or more, or at least 1, 2, 3, 4, 5, 6, 7, 8, 9, 10 or more years.

The term "Distant Recurrence-Free Interval (DRFI)" is used herein to refer to the time from surgery to the first anatomically distant cancer recurrence. For instance, in some embodiments, the time may be at least 1, 2, 3, 4, 5, 6, 7, 8, 9, 10, 11, 12 or more, or at least 1, 2, 3, 4, 5, 6, 7, 8, 9, 10 or more years.

Normalization of Data

Aspects of the present invention relate to the use of the measured expression of certain genes by melanoma tissue to provide predictive information. In some embodiments, it is necessary to correct for (normalize away) differences in the amount of RNA assayed and/or variability in the quality of the RNA used. Therefore, assays and methods of the invention may measure and incorporate the expression of certain normalizing genes, including well known housekeeping genes. Non-limiting examples of normalizing genes include ABCF1, ACTB, ALAS1, CLTC, G6PD, GAPDH, GUSB, HPRT1, LDHA, PGK1, POLR1B, POLR2A, RPL19, RPLP0, SDHA, TBP, and/or TUBB. In some embodiments, a combination of two or more normalizing genes may be used. In some embodiments, normalization can be based on the mean or median signal (Ct) of all of the assayed genes or a large subset thereof (global normalization approach).

In some embodiments, sample-specific normalization factors are used to normalize raw mRNA counts in order to account for slight differences in assay efficiency such as hybridization, purification, and binding. In some embodiments, normalization for sample RNA quantity and quality differences are applied to spike-normalized values using sample-specific normalization factors calculated from the geometric mean of the counts from reporters targeting the reference genes, including but not limited to any one of or all of the following reference genes: ABCF1, ACTB, ALAS1, CLTC, G6PD, GAPDH, GUSB, HPRT1, LDHA, PGK1, POLR1B, POLR2A, RPL19, RPLP0, SDHA, TBP, and TUBB. The resulting normalized counts may be used in downstream analyses.

General Description and Non-Limiting Examples of mRNA Isolation, Purification and Amplification The steps of a representative protocol for profiling gene expression using fixed, paraffin-embedded tissues as the RNA source, including mRNA isolation, purification, primer extension and amplification are provided in various published journal articles (for example: T. E. Godfrey et al., J. Malec. Diagnostics 2: 84-91 (2000); K. Specht et al., Am. J. Pathol. 158: 419-29 (2001)). Briefly, a representative process starts with cutting about 10 or 20 µm thick sections of paraffin-embedded tumor tissue samples. The RNA is then extracted, and protein and DNA are removed. Another representative method for extracting RNA from a sample, such as from a fixed, paraffin-embedded tissue sample includes the Ambion® RecoverAll Total Nucleic Acid Isolation Kit (Life Technologies, Carlsbad, Calif.).

Gene Expression Profiling

NanoString Gene Expression Analysis

In embodiments of the invention, gene expression may be determined using melanoma samples by NanoString gene expression analysis. As a clinical standard in melanoma all of the tumor has to be formalin fixed to preserve it for morphology assessment by the pathologist. The terms "NanoString gene expression analysis" and "NanoString" are used interchangeably herein, and refer to the nCounter® Analysis System of NanoString Technology (Seattle, Wash., USA). NanoString does not require amplification of RNA, has low sample requirements and is effective for evaluating the level of gene expression in FFPE samples, such as melanoma FFPE samples. Furthermore, NanoString is a multiplexed method for detecting gene expression and provides a method for direct measurement of mRNAs without the use of transcription or amplification. The RNA extracted from formalin fixed melanoma specimens may be of very poor quality and until recently no such analysis was possible. NanoString, however, allows for analysis of these specimens. With a sensitivity of 500 attomolar NanoString can detect as little as one copy of RNA per cell using 100 nanograms of total RNA as input.

NanoString and aspects thereof are described in Geiss et al., "Direct multiplexed measurement of gene expression with color-coded probe pairs" Nature Biotechnology 26, 317-325 (2008); in U.S. Pat. Nos. 7,473,767, 7,941,279 and 7,919,237, and in U.S. Patent Application Publication No. 2010/0112710, the entire contents of each of which are hereby incorporated by reference. NanoString is also discussed in: Payton et al., "High throughput digital quantification of mRNA abundance in primary human acute myeloid leukemia samples" The Journal of Clinical Investigation 119(6): 1714-1726 (2009); and Vladislav et al. "Multiplexed measurements of gene signatures in different analytes using the NanoString nCounter Assay System" BMC Research Notes 2: 80 (2009), the entire contents of each of which are hereby incorporated by reference.

Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase.

Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Methods of gene expression profiling include methods based on hybridization analysis of polynucleotides, methods based on sequencing of polynucleotides, and proteomics based methods. The commonly used methods known in the art for the quantification of mRNA expression in a sample include NanoString (Geiss et al., Nature Biotechnology 26, 317-325 (2008)), northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription polymerase chain reaction (RT-PCR) (Weis et al., Trends in Genetics 8:263-264 (1992)). Alternatively, antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). Methods of Gene Expression Profiling, including SAGE; MPSS; proteomics based methods; RT-PCT and other PCR based methods; microarray analysis; and Promoter Methylation Analysis are discussed in U.S. Pat. Nos. 8,067,178 and 8,034,565. The entire contents of each of which are hereby incorporated herein in their entireties.

Antibodies

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., Nature 352:624-28 (1991) and Marks et al., J. Mol. Biol. 222(3): 581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art [Kozbor et al., *Immunol. Today* 4:72 (1983); Cole et al., in *Monoclonal Antibodies and Cancer Therapy*, Alan R. Liss, Inc. 77-96 (1985)].

The term "epitope" refers to a portion of a molecule (the antigen) that is capable of being bound by a binding agent, e.g., an antibody, at one or more of the binding agent's antigen binding regions. Epitopes usually consist of specific three-dimensional structural characteristics, as well as specific charge characteristics.

As used herein, "fully human antibody" is an antibody that is completely human. Fully human antibodies may be generated by, e.g., phage display, or in animals (such as mice) which have been genetically engineered to produce human antibodies. Exemplary methods of producing fully human antibodies are described in U.S. Pat. Nos. 7,414,170; 7,803,981; in U.S. Patent Application No. 2008/0248531, and in McCafferty et al., "Phage antibodies: filamentous phage displaying antibody variable domains" Nature (1990) 348 (6301): 552-554; Osbourn J K, "Proximity-guided (ProxiMol) antibody selection" Methods Mol. Biol. (2002) 178: 201-5; and Lonberg et al., "Human antibodies from transgenic mice" Int. Rev. Immunol. (1995) 13(1):65-93, the contents of each of which are hereby incorporated by reference in their entireties.

"Humanized antibodies" means antibodies that contain minimal sequence derived from non-human immunoglobulin sequences. For the most part, humanized antibodies are human immunoglobulins (recipient antibody) in which residues from a hyper variable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., *Nature* 332:323-27 (1988); and Presta, *Curro Opin. Struct. Biol.* 2:593-96 (1992), each of which is incorporated herein by reference.

Antibodies of the invention also include antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598, the entire contents of which are incorporated herein by reference.

Those skilled in the art will be aware of how to produce antibody molecules of the present invention. For example, polyclonal antisera or monoclonal antibodies can be made using standard methods. A mammal, (e.g., a mouse, hamster, or rabbit) can be immunized with an immunogenic form of the protein which elicits an antibody response in the mammal. For instance, a mammal can be immunized with irradiated cells that were transfected with a nucleic acid encoding the protein such that high levels of the protein were expressed on the cell surface. The progress of immunization can be monitored by detection of antibody titers in plasma or serum. Standard ELISA or other immunoassay can be used with the immunogen as antigen to assess the levels of antibodies. Following immunization, antisera can be obtained, and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

Immunotherapy

As used herein, "immunotherapy" is a treatment that induces or enhances the immune system to reject cancer in a patient. In some embodiments of the invention an immunotherapy comprises at least one cytokine. In some embodiments, an immunotherapy comprises a vaccine that causes a patient's immune system to reject a cancer. In some embodiments, an immunotherapy comprises an antibody that binds to an antigen on the surface of cancer cells. Non-limiting examples of immunotherapies include high-dose interleukin-2 (IL-2); PEGylated IL-2 and interferon-α2b (IFN-α2b); ipilimumab; BMS-936558; and vaccines such as talimogene laherparepvec (T-VEC).

Recombinant interleukin-2 (IL-2) is sold under the trade name Proleukin, and is also known as aldesleukin. Aldesleukin is available from Prometheus, Inc. (San Diego, Calif., USA)

PEGylated IFN-α2b is also known as Peginterferon alfa-2b and Sylatron, and is available from Merck (Whitehouse Station, N.J., USA).

Ipilimumab is a fully human anti-CTLA-4 antibody which is marketed as Yervoy. Yervoy is available from Bristol-Myers Squibb (New York, N.Y., USA).

BMS-936558 is a fully human anti-PD-1 antibody which is also known as MDX 1106. BMS-936558 is available from Bristol-Myers Squibb (New York, N.Y., USA).

Talimogene laherparepvec (T-VEC) is an oncolytic immunotherapy derived from HSV-1, and is also known as Oncovex. T-VEC is available from Amgen Inc. (Thousand Oaks, Calif., USA).

Chemotherapy

Chemotherapies of the invention include but are not limited to any agent which specifically kills or reduces the proliferation of cancer cells in a patient afflicted with cancer. Non-limiting examples of chemotherapeutic agents which may be used in aspects of the invention are dacarbazine (DTIC-Dome), temozolomide (Temodar, Temodal), paclitaxel (Taxol), cisplatin (Paraplatin), carmustine (BCNU), fotemustine, vindesine (Eldisine, Fildesin), vincristine (Oncovin, Vincasar), and bleomycin (Blenoxane).

Another non-limiting example of a chemotherapeutic agent for the treatment of melanoma is vemurafenib, which is useful for the treatment of patients with a V600E BRAF mutation. The CAS number for vemurafenib is 1029872-54-5. Vemurafenib is also known as Zelboraf, PLX4032, RG7204, 805185426, has the formula: $C_{23}H_{18}C_1F_2N_3O_3S$, and is available from Plexxikon, Inc. (Berkeley, Calif., USA).

In some embodiments, chemotherapy may be combined with an immunotherapy and/or radiation. In some embodiments, vemurafenib is combined with an immunotherapy.

Administration

"Administering" the therapies described herein can be effected or performed using any of the various methods and delivery systems known to those skilled in the art. The administering can be, for example, intravenous, oral, intramuscular, intravascular, intra-arterial, intracoronary, intramyocardial, intraperitoneal, and subcutaneous. Other non-limiting examples include topical administration, or coating of a device to be placed within the subject. In embodiments, administration is effected by injection or via a catheter.

Injectable drug delivery systems may be employed in the methods described herein include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

The administration of therapies and compounds described herein may be by way of compositions containing one of the antagonists and a pharmaceutically acceptable carrier. As used herein, a "pharmaceutical acceptable carrier" is a pharmaceutically acceptable solvent, suspending agent or vehicle, for delivering an active compound to a mammal, including humans. The carrier may be liquid, aerosol, gel or solid and is selected with the planned manner of administration in mind. In some embodiments, the pharmaceutical carrier is a sterile pharmaceutically acceptable solvent suitable for intravenous administration. In an embodiment, the pharmaceutical carrier is a pharmaceutically acceptable solid suitable for oral administration.

As used herein, the term "effective amount" refers to the quantity of a component that is sufficient to treat a subject without undue adverse side effects (such as toxicity, irritation, or allergic response) commensurate with a reasonable benefit/risk ratio when used in the manner of this invention, i.e. a therapeutically effective amount. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

By treating the patient there are multiple possible outcomes. For instance, treating a subject may comprise substantially reducing, slowing, stopping, preventing or reversing the progression of a disease, particularly melanoma. Additionally, treating a patient may comprise substantially reducing, slowing, stopping, preventing or reversing a symptom of a disease. In some embodiments, an outcome of treating the patient is substantially reducing, slowing, stopping, preventing, or reversing metastasis, wherein the patient has, or has been treated for, a solid tumor. In some embodiments, treating the patient comprises reducing the likelihood of metastasis in the patient. In some embodiments the patient is treated after melanoma tissue has been removed from the patient. In some embodiments, a therapy is used for prevention and treatment of melanoma metastasis or recurrence. In the most favorable case, reduction is equivalent to prevention.

The methods provided by the present invention may also be automated in whole or in part.

The following abbreviated gene names are used herein:
IFI27: interferon, alpha-inducible protein 27
HLA-DPB1: major histocompatibility complex, class II, DP beta 1
STAT1: signal transducer and activator of transcription 1, 91 kDa
MRC1: mannose receptor, C type 1
B2M: beta-2-microglobulin
IL18: interleukin 18 (interferon-gamma-inducing factor)
IFNGR1: interferon gamma receptor 1
CXCL11: chemokine (C—X—C motif) ligand 11
TAP2: transporter 2, ATP-binding cassette, sub-family B (MDR/TAP)
CXCL9: chemokine (C—X—C motif) ligand 9
CLEC2A: C-type lectin domain family 2, member A
HLA-DPA1: major histocompatibility complex, class II, DP alpha 1
XCL2: chemokine (C motif) ligand 2
CTSS: cathepsin S
CCL27: chemokine (C—C motif) ligand 27
ICOS: inducible T-cell co-stimulator
IRF8: interferon regulatory factor 8
IFITM1: interferon induced transmembrane protein 1
HLAE: major histocompatibility complex, class I, E
GATA3: GATA binding protein 3
TAP1: transporter 1, ATP-binding cassette, sub-family B (MDR/TAP)
CD2: CD2 molecule
CD37: CD37 molecule
KLRK1: killer cell lectin-like receptor subfamily K, member 1
CD5: CD5 molecule
LY9: lymphocyte antigen 9
CXCR3: chemokine (C—X—C motif) receptor 3
CD3E: CD3e molecule, epsilon (CD3-TCR complex)
TNFSF13B: tumor necrosis factor (ligand) superfamily, member 13b
LCK: lymphocyte-specific protein tyrosine kinase
IL1F7: interleukin 37
XCR1: chemokine (C motif) receptor 1
C3: complement component 3
CD4: CD4 molecule
CD48: CD48 molecule
LGMN: legumain
TNFRSF18: tumor necrosis factor receptor superfamily, member 18
IRF9: interferon regulatory factor 9
SKAP1: src kinase associated phosphoprotein 1
TARP: TCR gamma alternate reading frame protein
GZMK: granzyme K (granzyme 3; tryptase II)
ITK: IL2-inducible T-cell kinase CSF2RA: colony stimulating factor 2 receptor, alpha, low-affinity (granulocyte-macrophage)
PGK1: phosphoglycerate kinase 1
HLA-DQB1: major histocompatibility complex, class II, DQ beta 1
CD40: CD40 molecule, TNF receptor superfamily member 5
CYBB: cytochrome b-245, beta polypeptide
CCL5: chemokine (C—C motif) ligand 5
PTPRC: protein tyrosine phosphatase, receptor type, C
ITGAL: integrin, alpha L (antigen CD11A (p180), lymphocyte function-associated antigen 1; alpha polypeptide)
IRF2: interferon regulatory factor 2
CD68: CD68 molecule
TLR7: toll-like receptor 7
CD53: CD53 molecule
SDHA: succinate dehydrogenase complex, subunit A, flavoprotein (Fp)
CD8A: CD8a molecule
POLR1B: polymerase (RNA) I polypeptide B, 128 kDa
IKZF1: IKAROS family zinc finger 1 (Ikaros)
ITGB2: integrin, beta 2 (complement component 3 receptor 3 and 4 subunit)
ACTB: actin, beta
CLTC: clathrin, heavy polypeptide (Hc)
CCR4: chemokine (C—C motif) receptor 4
IFNAR1: interferon (alpha, beta and omega) receptor 1
SYK: spleen tyrosine kinase
G6PD: glucose-6-phosphate dehydrogenase
IRF5: interferon regulatory factor 5
RPLP0: ribosomal protein, large, P0
LDHA: lactate dehydrogenase A
CCR5: chemokine (C—C motif) receptor 5
CD27: CD27 molecule
GAPDH: glyceraldehyde-3-phosphate dehydrogenase
TUBB: tubulin, beta class I
TBP: TATA box binding protein
RPL19: ribosomal protein L19
HPRT1: hypoxanthine phosphoribosyltransferase 1
ALAS1: aminolevulinate, delta-, synthase 1
POLR2A: polymerase (RNA) II (DNA directed) polypeptide A, 220 kDa
GUSB: glucuronidase, beta
ABCF1: ATP-binding cassette, sub-family F (GCN20), member 1
LY64: Lymphocyte Antigen-64
LY64 is also known as: CD180 molecule (CD180).

All publications and other references mentioned herein are incorporated by reference in their entirety, as if each individual publication or reference were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Methods
Patients and Samples
The training set included FFPE primary melanomas from 44 consecutive patients with tumors either ≥2 mm or ≥1 mm with one of the following high-risk features: ulceration, satellite lesions, and/or a positive sentinel lymph node. Thirty-four specimens were obtained from Geisinger Health System (Danville, Pa.) and 10 from Mount Sinai School of Medicine and affiliates (New York, N.Y.). The validation set included 30 FFPE melanomas obtained from NYU Medical Center (New York, N.Y.), 6 from Mount Sinai School of Medicine and affiliates, and 1 from Geisinger Health System. Recurrence was defined as metastatic melanoma beyond the local lymph node basin (stage IV) or the development of unresectable stage III disease. Non-recurrence was defined as no further evidence of melanoma following excision of the primary lesion. Minimal follow up for non-recurrent patients in the validation cohort was 2 years. All samples and clinical information were obtained following approval by local institutional review boards (IRBs).

Dermatopathology
Primary and recurrent melanomas were selected from the Tamtron PowerPath database at the Mount Sinai Medical Center (New York, N.Y.), the Cerner CoPathPlus database at Geisinger Heath System (Danville, Pa.), the Oracle Clinical RDC 4i database at NYU Medical Center (New York, N.Y.), as well as the NovoPath database at Englewood Hospital and Medical Center (Englewood, N.J.). Combined, the databases consisted of over 2,500,000 specimens collected since 1985 and derived from surgical pathology, dermatopathology, neuropathology and cytology. Criteria for inclusion were primary melanoma specimens measuring ≥2 mm without ulceration or ≥1 mm with ulceration. Selected slides and paraffin blocks were reviewed by two of the study participants (RGP and SS). Each sample was evaluated for histogenetic type, extent and type of inflammatory infiltrate, thickness, and ulceration.

Analysis of Gene Expression
RNA was extracted using the Ambion® RecoverAll Total Nucleic Acid Isolation Kit (Life Technologies, Carlsbad, Calif.). 446 genes were selected based on a PubMed literature review (FIG. 25). The nCounter platform (NanoString Technologies, Seattle, Wash.) was used to quantify relative gene expression (described below).[31]

NanoString
Gene Expression Analysis
Using the nCounter® platform (NanoString Technologies, Seattle, Wash.), relative gene expression was quantified in a multiplex reaction. A custom CodeSet, designated MtSinai0511, was synthesized by NanoString for the 446 selected genes as well as 17 housekeeping genes and 14 controls in a 477-plex reaction (listed in the supplemental reference file). Hybridizations were carried out according to the supplier protocols.[40] In a total reaction volume of 30 µl, 100 ng of each RNA sample in 5 µl H$_2$O was mixed with 10 µl nCounter Reporter probes, 10 µl hybridization buffer (1× hybridization buffer=5×SSPE, 0.1% Tween-20), and 5 µl of nCounter Capture probes. Hybridizations were incubated at 65° C. for approximately 16-20 hours. Following hybridization, the samples were processed in a PrepStation and counted in a DigitalAnalyzer (Nanostring Technologies) according to standard protocol recommended by NanoString Technologies.

Normalization of Data
Calculated from the sum counts of reporters of 6 positive control RNA spikes, sample-specific normalization factors were used to normalize raw mRNA counts in order to account for slight differences in assay efficiency such as hybridization, purification, and binding. Concentrations of the control RNA spikes range from 0.125-128 fM. Normalization for sample RNA quantity and quality differences were applied to the spike-normalized values using sample-specific normalization factors calculated from the geometric mean of the counts from reporters targeting the following reference genes: ABCF1, ACTB, ALAS1, CLTC, G6PD, GAPDH, GUSB, HPRT1, LDHA, PGK1, POLR1B, POLR2A, RPL19, RPLP0, SDHA, TBP, and TUBB. The resulting normalized counts were used in downstream analyses.

RNA Extraction

FFPE tissue blocks were cut into four 20 μm sections and treated with 100% xylene (Fisher Scientific, Pittsburgh, Pa.) to deparaffinize. Samples were washed twice with 100% ethanol (Absolute Ethanol Molecular Biology Grade 200 proof, Fisher Scientific, Pittsburgh, Pa.) and dried via vacuum centrifugation at 40° C. Tissue was then incubated in Digestion Buffer and Protease (Ambion® RecoverAll, Life Technologies, Carlsbad, Calif.) at 50° C. for 3 hours, followed by a 15-minute incubation at 80° C. RNA was separated using an Isolation Additive/Ethanol mixture (Ambion® RecoverAll, Life Technologies, Carlsbad, Calif.), and filtered by centrifugation at 10,000 rpm. The sample was rinsed with Wash 1 and Wash 2 (Ambion® RecoverAll, Life Technologies, Carlsbad, Calif.), before and after incubation with DNase for 30 minutes at RT. RNA was eluted with 60 μl of Elution Solution (Ambion® RecoverAll, Life Technologies, Carlsbad, Calif.) at RT.

Immunohistochemistry

IHC was performed on 5-μm charged slides using anti-CD2 monoclonal antibody (MRQ-11, Ventana Medical Systems, Tucson, Ariz.). Sections were deparaffinized and stained using a Ventana BenchMark XT immunostainer. Slides were evaluated by two of the study authors (SGB & MMM) in a blinded manner in 8 random High Powered Fields (HPFs) using an ocular micrometer with a 1 mm$^2$ grid (Nikon Eclipse E400®).

Five μm sections of the same paraffin-embedded tissue samples analyzed by NanoString were prepared for immunophenotypic analysis. Immunohistochemistry (IHC) was performed using primary, pre-diluted anti-CD2 (MRQ-11, mouse anti-human, Ventana Medical Systems, Tucson, Ariz.). Sections were deparaffinized, stained according to standard protocol using a Ventana BenchMark XT immunostainer and manually counterstained.[40] The immunohistochemical slides were evaluated and interpreted by two of the study authors (SGB & MMM) in a blinded manner without knowledge of corresponding clinical data. For each sample, cells with circumferential membrane staining were counted and averaged in 8 random HPFs using an ocular micrometer with a 1 mm$^2$ grid (Nikon Eclipse E400®).

Statistics

Ensemble Classification/Regression Method and ROC Curves

Classification was performed using two standard linear regression classifiers: random forest and elastic net. The 446 genes from the training experiment were ranked based on prediction of melanoma recurrence in the training cohort and sequentially reduced using a nested cross-validation procedure. Selected genes were then further reduced to eliminate redundant genes with α=0.2 and an optimal value of λ selected by an internal leave-one-out cross-validation yielding a final list of 21 genes. ROC curves were generated and the area under the curve (AUC) with class labels was defined for each sample to maximize prediction accuracy.

Survival and Demographic Analysis

Kaplan-Meier analysis and Log-Rank (Mantel Cox) tests were performed. Mann-Whitney U tests generated p values for age and depth. Other non-continuous characteristics were analyzed using a two-tailed Fisher's exact test. Graphpad Prism version 5.0 was used (San Diego Calif. USA) and statistical significance was defined as p<0.05. Detailed description of the above methods is included below.

Cross-Validation 900 iterations of an 11-fold cross-validation on the training dataset were simulated with random sample reordering in each iteration to strengthen the robustness of the final classifier model disclosed herein. Going from the top of the list to the bottom of the training cohort, every 4 samples were removed. These sample sets were then used as training data to fit a statistical model. 10,000 model training tasks were performed. The trained model and gene predictors selected were recorded in each task yielding 10,000 models and 10,000 lists of gene predictors based on randomly sub-sampled training samples. For each model, a classification was performed for the entire training (44 samples) and validation datasets (37 samples). To derive a robust list of gene hits by these models, the 10,000 gene lists were pooled and the statistical count of each gene (out of 446 genes) was selected by these models using the training cohort only. A higher count value for a given gene indicates that it is frequently selected as a predictor during the cross-validation process. Finally, all genes selected at least once in the 10,000 cross-validation were put into a final model training task to yield an optimal, compact predictor gene list of 24 genes. Three genes (IFNG, TNFSF18, and CREB1) were excluded from the signature because the p value did not meet the cutoff in the preliminary analysis of the training data and levels were therefore not tested in the validation set.

Ensemble Classification/Regression Method

A two-step sequential ensemble classification scheme, that sequentially concatenated two widely applied classifiers: random forest and elastic net, was employed. Random forest itself is an ensemble classifier consisting of many decision trees that generates the mode of individual classes yielded by independent trees. A powerful variable selector and classification/regression method, elastic net integrates a linear regression model with Lasso and Ridge regularization. Elastic net is particularly useful when there are many more predictors than samples, serving to further exclude genes that are only correlated with, but not most predictive, of recurrence. This two-step ensemble classification scheme was applied to the cross-validated training data for the outer loop of the 900, 11-fold training cross-validation data points.

Random Forest

With 446 genes as an initial set of features and 40 samples from the cross-validation used as training data, a random forest model was fit. Initially, random forest was run without feature selection to determine the importance of all 446 genes based on various metrics in the RandomForest R package.[41] Next, an independent run was started that incorporated feature selection into random forest by sequentially reducing a certain number of predictors, ranked by variable importance, by employing a nested cross-validation procedure. In the simulation, a leave-one-out strategy was used. In each internal cross-validation, (step=30%) the least important genes/features, ranked by variable importance, was removed from the last cross-validation iteration. Next, (Ntree=50 k) bootstrap samples from the original data (40 samples) were drawn. For each of the bootstrap samples, an untrimmed classification/regression tree with randomly selected (mtry=22) genes was generated from the pool of genes leftover following removal. Following cross-validation, the number of genes that resulted in the lowest error rate among all the cross-validation runs was selected. This number represents the number of genes ($N_{RF}$) selected by random forest after cross-validation. Next, the top $N_{RF}$ genes based on the averaged gene rank were selected from the initial run without feature selection, yielding the final gene selections by random forest. The selected genes $G_{RF}$ were used as input for an elastic net model in order to identify the constituents of a gene signature predictive of melanoma recurrence.

Elastic Net

A powerful variable selector and classification/regression method, elastic net integrates a linear regression model with Lasso and Ridge regularization.[42] Elastic net is particularly useful when there are many more predictors than samples, serving to further exclude genes that are only correlated with, but not most predictive of recurrence. In each round of 11-fold cross-validation on the training data, there were 40 training samples. The number of genes selected by random forest varied from 50 to 446 depending on both the leave-one-out training data and randomized feature selection used during decision tree growth. Elastic net extends the basic form of linear/logistic regression via L1 and L2-regularization. $\lambda$ controls the model complexity with higher values resulting in a less complex model (less number of genes). $\alpha$ controls the balance between two types of model complexity penalties, including the ridge-regression penalty ($\alpha=0$) and the lasso penalty ($\alpha=1$). The Ridge penalty is particularly useful when there are more genes and fewer samples. Ridge regression is known to shrink the coefficients of correlated predictors towards each other. In contrast, lasso tends to pick one out of an entire set and ignore the rest. In this study, we set $\alpha=0.2$ and used an internal leave-one-out cross-validation to select an optimal value of $\lambda$.[4] The input training data was a subset of the original training data based on the gene lists $G_{RF}$ determined by random forest. The output gene lists by elastic net with non-zero coefficients is our final gene list $G_{EN}$ for the cross-validation run.

Final Gene List Generation

Employing the two-step ensemble classification method outlined above, the gene list $G_{EN}$ was recorded for each of the 11-fold data cross-validation runs. After more than 900 runs, 10,000 lists of final genes were selected from the cross-validation training data. The number of times each gene was selected among the 10,000 lists was counted and the p-value for the count distribution against otherwise random selection was calculated. Since this combined gene list compressed 10 k lists in the cross-validation based on different subsampled training data, it may contain correlated genes from different runs. Therefore, to filter these out and obtain our final gene signature, elastic net was used again with the same parameter configurations outlined previously ($\alpha=0.2$, $\lambda$ retrained based on the cross-validation of the 56-gene subset training data) for all 44 training samples. This yielded the gene signature composed of 21 genes described herein.

Results

Patient Demographics

The populations used are representative of patients with high-risk primary melanomas in the United States (Table 1). Patients in the training set had melanomas either ≥2 mm thick or ≥1 mm thick with ulceration, satellite lesions, and/or a positive sentinel node. With the exception of 4 patients in the training cohort who received adjuvant interferon alpha, patients were not treated unless they recurred.

No significant correlation between known prognostic factors and disease recurrence was observed in the training cohort, but a significant correlation with lesion depth was found in the validation cohort (p=0.044). This is consistent with prior observations that prognostic factors may not necessarily predict risk in smaller groups of melanoma patients. There were no statistically significant differences between demographics of the training and validation cohorts with the exception of immune infiltrate, which closely correlated with the institution where the pathology was interpreted (Table 2).

Immune Gene Expression is Increased in Non-Recurrent Patients.

To test the hypothesis that the immune system limits progression of early-stage melanoma, mRNA transcripts for 446 genes were measured using NanoString technology. RNA of sufficient quality for NanoString analysis was obtained in 44 out of 59 samples. Ninety-two of these 446 genes were differentially (p<0.05) expressed between recurrent and non-recurrent groups. Of these 92 genes, 90 were upregulated in the non-recurrent group (Table 4). A heat map clustered according to expression of these 92 genes (FIG. 1A) demonstrates that non-recurrent samples cluster at higher extremes of expression while recurrent samples cluster at lower extremes. These findings establish that immune gene expression is predictive of non-recurrence in the training cohort.

Identification of an Immune Gene Expression Signature Protective Against Melanoma Recurrence Next, a panel of genes for clinical application was defined. 53 genes selected at least once using a leave-4-out cross-validation on the training data set (FIG. 2A) were refined by linear regression to select a 21-gene panel (FIG. 2A, inset). This panel predicted recurrence with an area under the curve (AUC) of 0.983 in the training cohort (FIG. 2B top). The best correlation with melanoma recurrence was found using the gene signature in combination with clinical predictors ($R^2=0.794$). Alone, these clinical predictors yielded a correlation of 0.318. Thus, expression of 21 immune-associated genes showed a strong correlation with recurrence in the training cohort.

Identification of CD2 as an Immunohistochemical Marker of Favorable Prognosis

Figure 3:
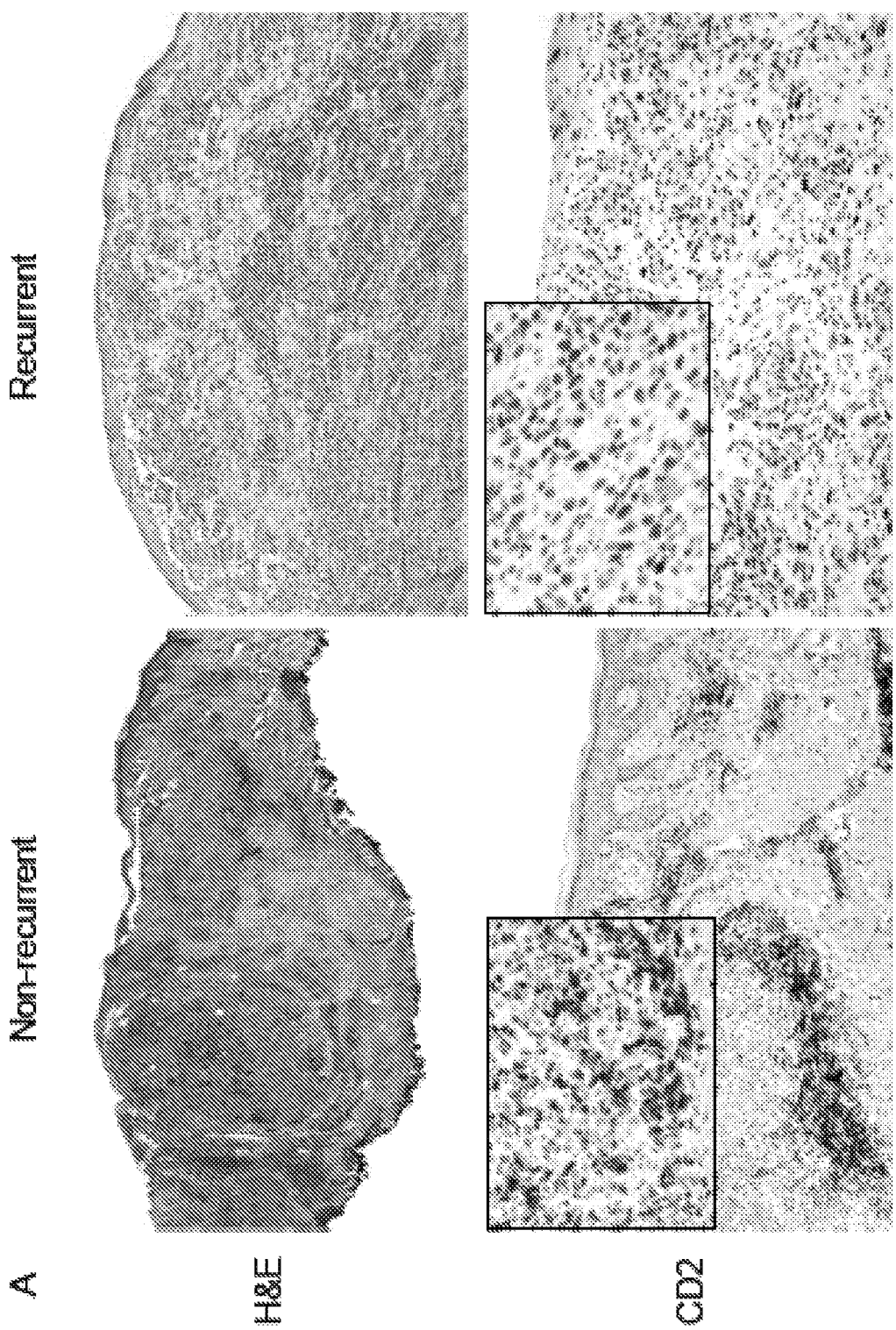
FIG. 3. Immunohistochemistry (IHC) using anti-CD2 monoclonal antibody was performed to assess risk of disease recurrence. In panel A, photographs of non-recurrent (left) and recurrent (right) patient specimens are shown. In the non-recurrent patient sample, a brisk peritumoral infiltrate is seen at 4× magnification on H&E (top left) corresponding with cells staining positive for CD2 at 10× and 40× power (bottom left). In the recurrent patient sample, no such infiltrate is seen at 4× power on H&E (top right) with few corresponding cells positive for CD2 at 10× and 40× magnification (bottom right). Panel B displays the average number of cells counted at 40× magnification in 8 random HPFs for patients in the training and validation groups.* Significantly more CD2 positive cells were found in non-recurrent, as compared to recurrent, melanomas in the training (left, p=0.0172) and validation (right, p=0.0032) cohorts. In Panel C, linear regression is used to assess correlation of NanoString with IHC for CD2 in the training (left) and validation (right) groups. The two methods correlate with one another with r values of 0.847 and 0.538 for the training (p<0.0001) and validation (p=0.0026) cohorts respectively.

CD2 was the most differentially expressed gene between the recurrent and non-recurrent groups in the training cohort (p<0.001). In order to validate NanoString findings at the protein level, tumors were stained for CD2 (FIG. 3A). Low number of CD2 positive staining by IHC correlated with melanoma recurrence (p=0.017). These findings were concordant with NanoString results as determined by linear regression (r=0.847, p<0.001) (FIGS. 3B and 3C left).

Validation of an Immune Gene Signature Protective Against Disease Recurrence

Next, the above findings were validated in an independent set of tissue samples. RNA of sufficient quality for NanoString analysis was obtained in 37 out of 51 samples. Based on preliminary analysis, the 63 immune-associated genes most differentially expressed by p value between recurrent and non-recurrent samples in the training cohort were measured in the validation cohort (FIG. 1B). Of these genes, 41 were upregulated in the non-recurrent group (Table 5). A 21-gene signature was able to predict recurrence in the validation cohort with an AUC of 0.794 (p=0.002, FIG. 2B). When combined with clinical factors, the gene signature correlated with recurrence with a coefficient of determination of 0.947 (FIG. 3C). Cross-validation using a leave-4-out approach demonstrated that this signature was statistically robust (Table 7). Corresponding slides were then stained for CD2 in the validation cohort and expression of this protein was found to correlate with recurrence (p=0.003) (FIG. 3B, right). These data show that immune gene expression profiling predicts recurrence in primary melanoma with an accuracy exceeding those of standard clinical predictors.

Correlation of Immune Gene Expression Signature with Survival

To investigate correlation between the proposed 21-gene signature and survival, a Kaplan-Meier analysis was performed, yielding a precise prediction of overall survival (p<0.001, FIG. 4A). By comparison, the American Joint Committee on Cancer (AJCC) standard of 4 mm was less accurate in predicting survival (p=0.084, FIG. 4B). The 21-gene signature was derived from the training cohort, and therefore may only reflect survival benefit in this group. To exclude this possibility, the 21-gene signature was applied to the validation cohort alone and found patients with a positive gene signature survived longer (p=0.015, Table 2).

TABLE 1

Clinical Characteristics of Patients with Primary Melanoma in the Training and Validation Cohorts

| Characteristic | Training | | | Validation | | |
|---|---|---|---|---|---|---|
| | Non-recurrent (N = 23) | Recurrent (N = 21) | P Value | Non-recurrent (N = 17) | Recurrent (N = 20) | P Value |
| Sex | | | 1 | | | 0.193 |
| Male -- no.(%) | 16 (70) | 15 (71) | | 8 (47) | 14 (70) | |
| Female -- no. (%) | 7 (30) | 6 (29) | | 9 (53) | 6 (30) | |
| Age | | | 1 | | | 1 |
| Median -- no. | 66 | 69 | | 68 | 73.5 | |
| Clinical Stage of Disease | | | 0.225 | | | 0.288 |
| Stage I/II -- no. (%) | 15 (65) | 9 (43) | | 14 (82) | 13 (65) | |
| Stage III -- no. (%) | 8 (35) | 12 (57) | | 3 (18) | 7 (35) | |
| Location of Tumor | | | 0.136 | | | 0.31 |
| Trunk -- no. (%) | 11 (48) | 15 (71) | | 8 (47) | 10 (50) | |
| Extremity -- no. (%) | 12 (52) | 6 (29) | | 9 (53) | 10 (50) | |
| Pathological characteristics | | | | | | |
| Depth (mm) -- avg ± CI | 2.81 ± 0.62 | 4.72 ± 1.51 | 0.074 | 4.26 ± 2.54 | 6.94 ± 2.87 | 0.044 |
| Ulceration | | | 0.227 | | | 0.512 |
| Absent -- no. (%) | 14 (61) | 8 (38) | | 7 (41) | 6 (30) | |
| Present -- no. (%) | 9 (39) | 13 (62) | | 10 (59) | 14 (70) | |
| Inflammatory Infiltrate | | | 1 | | | 0.169 |
| Absent -- no. (%) | 17 (74) | 15 (74) | | 3 (17) | 8 (40) | |
| Present -- no. (%) | 6 (26) | 6 (26) | | 14 (82) | 12 (60) | |
| Patient Outcome (Months) | | | | | | |
| Time to recurrence -- avg ± CI | — | 16.8 ± 5.5 | | — | 28.6 ± 12.0 | |
| Death from melanoma -- no. (%) | 0 (0) | 16 (76) | | 0 (0) | 13 (65) | |
| Time to death -- avg ± CI | — | 26.6 ± 9.8 | | — | 48.6 ± 19.1 | |
| Time to follow-up -- avg ± CI* | 55.7 ± 13.5 | 60.4 ± 34.6 | | 52.1 ± 8.0 | 79 ± 39.1 | |

*Data for living patients only

TABLE 2

Clinical Characteristics of Patients in the Training and Validation Cohorts.

| Characteristic | Training (N = 44) | Validation (N = 37) | P Value |
|---|---|---|---|
| Sex | | | 0.487 |
| Male - no.(%) | 31 (70) | 22 (60) | |
| Female - no. (%) | 14 (31) | 15 (40) | |
| Age | | | 0.3775 |
| Median - no. | 67 | 69 | |
| Clinical Stage of Disease | | | 0.109 |
| Stage I/II - no. (%) | 24 (55) | 27 (73) | |
| Stage III - no. (%) | 20 (45) | 10 (27) | |
| Location of Tumor | | | 0.378 |
| Trunk - no. (%) | 26 (60) | 18 (49) | |
| Extremity - no. (%) | 18 (41) | 19 (51) | |
| Pathological characteristics | | | |
| Depth (mm) - avg ± CI | 3.72 ± 0.83 | 5.71 ± 1.94 | 0.0975 |
| Ulceration | | | 0.26 |
| Absent - no. (%) | 22 (50) | 13 (35) | |
| Present - no. (%) | 22 (50) | 24 (65) | |
| Inflammatory Infiltrate | | | 0.0001 |
| Absent - no. (%) | 32 (73) | 11 (30) | |
| Present - no. (%) | 12 (27) | 26 (70) | |
| Patient Outcome (Months) | | | |
| Time to recurrence- avg ± CI | 16.8 ± 5.45 | 28.6 ± 12.02 | |
| Death from melanoma- no. (%) | 16 (36) | 13 (35) | |
| Time to death- avg ± CI | 26.6 ± 9.77 | 48.6 ± 19.06 | |
| Time to follow-up- avg ± CI* | 56.5 ± 12.7 | 60.3 ± 13.3 | |

TABLE 3

Cross Validation on Clinical Characteristics of Patients in the Training Cohort*

| Characteristic - no. [range] | Training | | |
|---|---|---|---|
| | Non-recurrent (N = 23) | Recurrent (N = 21) | P Value |
| Sex | | | 1 |
| Male | 15 [12-16] | 14 [11-15] | |
| Female | 6 [3-7] | 6 [3-6] | |
| Age | | | |
| Median | 66 [57-72] | 69 [67-72] | |
| Clinical Stage of Disease | | | 0.203 |
| Stage I/II | 14 [11-15] | 8 [5-9] | |

TABLE 3-continued

Cross Validation on Clinical Characteristics of Patients in the Training Cohort*

| Characteristic - no. [range] | Training | | P Value |
|---|---|---|---|
| | Non-recurrent (N = 23) | Recurrent (N = 21) | |
| Stage III | 7 [4-8] | 11 [8-12] | |
| Location of Tumor | | | 0.208 |
| Trunk | 10 [7-11] | 14 [11-15] | |
| Extremity | 11 [8-12] | 6 [2-6] | |
| Pathological characteristics | | | |
| Depth (mm) | 225 [2.2-2.5] | 3 [2.8-3.75] | 0.035 |
| Ulceration | | | |
| Absent | 13 [10-14] | 7 [4-8] | |
| Present | 8 [5-9] | 12 [9-13] | |
| Inflammatory Infiltrate | | | 1 |
| Absent | 15 [13-17] | 14 [11-15] | |
| Present | 6 [2-6] | 6 [3-6] | |
| Number of Samples | | | |
| Median | 21 [19-23] | 19 [17-21] | |

*Using a leave-4-out approach

TABLE 4

Gene Function of Statistically Significant Genes in Training Set

| Official Symbol | Fold Change (Non-reccurent/ Recurrent) | P-value | Gene Function |
|---|---|---|---|
| CD2 | 2.015246 | 0.000296 | CD2 is a surface antigen of the human T-lymphocyte lineage that is expressed on all peripheral blood T cells. It is one of the earliest T-cell markers, being present on more than 95% of thymocytes; it is also found on some natural killer cells but not on B lymphocytes. |
| KLRK1 | 1.907905 | 0.000752 | KLRK1 encodes for a member of the NKG2 family which is located within the NK complex, a region that contains several C-type lectin genes preferentially expressed in NK cells. It binds to a diverse family of ligands that can result in the activation of NK and T cells. This protein and its ligands are therapeutic targets for the treatment of immune diseases and cancers. |
| ITK | 1.841831 | 0.000823 | ITK encodes an intracellular tyrosine kinase expressed in T-cells. It is thought to play a role in. T-cell proliferation and differentiation. |
| HLAE | 1.545037 | 0.001147 | HLA-E binds a restricted subset of peptides derived from the leader peptides of other class I molecules. |
| LCK | 1.998149 | 0.001462 | LCK is a member of the Src family of protein tyrosine kinases (PTKs).The encoded protein localizes to the plasma membrane where it binds to cell surface receptors, including CD4 and CD8, and is a key signaling molecule in the selection and maturation of developing T-cells. |

TABLE 4-continued

Gene Function of Statistically Significant Genes in Training Set

| Official Symbol | Fold Change (Non-reccurent/ Recurrent) | P-value | Gene Function |
|---|---|---|---|
| CREB1 | 1.267037 | 0.001947 | CREB1 encodes for a transcription factor that is phosphorylated by several protein kinases, and induces transcription of genes in response to hormonal stimulation of the cAMP pathway. |
| IFNAR1 | 1.248822 | 0.002154 | The protein encoded by IFNAR1 forms one of the two chains of a receptor for interferons alpha and beta. Binding and activation of the receptor stimulates Janus protein kinases, which in turn phosphorylate several proteins, including STAT1 and STAT2. The encoded protein also functions as an antiviral factor. |
| CD48 | 1.774847 | 0.002713 | CD48 encodes a member of the CD2 subfamily of immunoglobulin-like receptors which includes SLAM (signaling lymphocyte activation molecules) proteins. The encoded protein is found on the surface of lymphocytes and other immune cells, dendritic cells and endothelial cells, participating in activation and differentiation pathways in these cells. |
| CXCR3 | 1.794847 | 0.002995 | This gene encodes a G protein-coupled receptor with selectivity for three chemokines, termed CXCL9/Mig, CXCL10/IP10, and CXCL11/I-TAC. Binding of chemokines to this protein induces cellular responses that are involved in leukocyte traffic, most notably integrin activation, cytoskeletal changes and chemotactic migration. |
| CD4 | 1.590889 | 0.003089 | CD4 encodes a membrane glycoprotein of T lymphocytes that interacts with major histocompatibility complex class II antigens. CD4 is expressed in T lymphocytes, B cells, macrophages, and granulocytes. The protein functions to initiate or augment the early phase of T-cell activation. |
| IFNG | 1.620499 | 0.003532 | IFNG encodes a member of the type II interferon family. The protein encoded is a soluble cytokine with antiviral, immunoregulatory and anti-tumor properties and is a potent activator of macrophages. |
| CTSS | 2.012265 | 0.003876 | The protein encoded by CTSS is a member of the peptidase C1 family and a lysosomal cysteine proteinase that may participate in the degradation of antigenic proteins to peptides for presentation on MHC class II molecules. |
| CCR4 | 1.372039 | 0.004007 | The protein encoded by CCR4 is a receptor for the CC |

TABLE 4-continued

Gene Function of Statistically Significant Genes in Training Set

| Official Symbol | Fold Change (Non-reccurent/ Recurrent) | P-value | Gene Function |
|---|---|---|---|
| HLA-DQB1 | 2.09166 | 0.004592 | chemokine-MIP-1, RANTES, TARC and MCP-1. HLA-DQB1 plays a central role in the immune system by presenting peptides derived from extracellular proteins. Class II molecules are expressed in antigen presenting cells such as B lymphocytes, dendritic cells, macrophages. |
| TAP2 | 1.444613 | 0.004638 | The membrane-associated protein encoded by TAP2 is a member of the superfamily of ATP-binding cassette (ABC) transporters. The protein encoded by this gene is involved in antigen presentation. |
| CD37 | 1.681894 | 0.005394 | The protein encoded by CD37 is a member of the tetraspanin family, most of which are cell-surface proteins that mediate signal transduction events that play a role in the regulation of cell development, activation, growth and motility. It may play a role in T-cell-B-cell interactions. |
| IRF2 | 1.247296 | 0.005432 | IRF2 encodes interferon regulatory factor 2, a member of the interferon regulatory transcription factor (IRF) family. It competitively inhibits the IRF1-mediated transcriptional activation of interferons alpha and beta, and presumably other genes that employ IRF1 for transcription activation. |
| TNFSF18 | 1.604035 | 0.00557 | The protein encoded by TNFSF18 is a cytokine that belongs to the tumor necrosis factor (TNF) ligand family. It has been shown to modulate T lymphocyte survival in peripheral tissues. This cytokine is also found to be expressed in endothelial cells, and is thought to be important for interaction between T lymphocytes and endothelial cells. |
| LGMN | 1.652632 | 0.006518 | LGMN encodes a cysteine protease that may be involved in the processing of bacterial peptides and endogenous proteins for MHC class II presentation in the lysosomal/endosomal systems. Overexpression of this gene may be associated with the majority of solid tumor types. |
| CCL5 | 1.943322 | 0.006747 | CCL5 is one of several CC cytokine genes that functions as a chemoattractant for blood monocytes, memory T helper cells and eosinophils. It causes the release of histamine from basophils and activates eosinophils. |
| CSF2RA | 1.523143 | 0.006915 | The protein encoded by CSF2RA is the alpha subunit of the heterodimeric receptor for |

TABLE 4-continued

Gene Function of Statistically Significant Genes in Training Set

| Official Symbol | Fold Change (Non-reccurent/ Recurrent) | P-value | Gene Function |
|---|---|---|---|
| | | | colony stimulating factor 2, a cytokine which controls the production, differentiation, and function of granulocytes and macrophages. |
| ITGAL | 1.675467 | 0.006919 | ITGAL encodes the integrin alpha L chain. This I-domain containing alpha integrin combines with the beta 2 chain (ITGB2) to form the integrin lymphocyte function-associated antigen-1 (LFA-1), which is expressed on all leukocytes. LFA-1 plays a central role in leukocyte intercellular adhesion. |
| BTK | 1.389055 | 0.007196 | BTK plays a crucial role in B-cell development. Mutations in this gene cause X-linked agammaglobulinemia type 1. |
| CD53 | 1.512738 | 0.007369 | The protein encoded by CD53 is a member of the tetraspanin family, most of which serve to mediate signal transduction events that play a role in the regulation of cell development, activation, growth and motility. It contributes to the transduction of CD2-generated signals in T cells and natural killer cells and has been suggested to play a role in growth regulation. |
| IRF5 | 1.403363 | 0.007497 | IRF5 encodes a member of the interferon regulatory factor (IRF) family, a group of transcription factors with diverse roles, including modulation of cell growth, differentiation, apoptosis, and immune system activity. |
| IL17RA | 1.292772 | 0.00885 | The protein encoded by IL17RA binds with low affinity to interleukin 17A which is a pro-inflammatory cytokine secreted by activated T-lymphocytes. It is a potent inducer of the maturation of CD34-positive hematopoietic precursors into neutrophils. |
| HLA-DPB1 | 1.725111 | 0.009152 | HLA-DPB belongs to the HLA class II beta chain paralogues that plays a central role in the immune system by presenting peptides derived from extracellular proteins. |
| CCL27 | 2.459453 | 0.009421 | The protein encoded by CCL27 is chemotactic for skin-associated memory T lymphocytes and may also play a role in mediating the homing of lymphocytes to cutaneous sites. |
| IFNGR1 | 1.288055 | 0.009535 | IFNGR1 encodes the ligand-binding chain (alpha) of the gamma interferon receptor. |
| SYK | 1.401605 | 0.01008 | SYC encodes a member of the family of non-receptor type Tyr protein kinases that is widely expressed in hematopoietic cells and is involved in coupling activated immunoreceptors to downstream |

TABLE 4-continued

Gene Function of Statistically Significant Genes in Training Set

| Official Symbol | Fold Change (Non-reccurent/ Recurrent) | P-value | Gene Function |
|---|---|---|---|
| | | | signaling events that mediate diverse cellular responses, including proliferation, differentiation, and phagocytosis. It is thought to be a modulator of epithelial cell growth and a potential tumor suppressor in human breast carcinomas. |
| CD180 | 1.435879 | 0.010121 | CD180 is a cell surface molecule whose interactions serve to control B cell recognition and signaling of lipopolysaccharide (LPS). |
| CD68 | 1.605002 | 0.01036 | CD68 encodes a transmembrane glycoprotein that is highly expressed by human monocytes and tissue macrophages. The protein is a member of the scavenger receptor family. that typically functions to clear cellular debris, promote phagocytosis, and mediate the recruitment and activation of macrophages. |
| B2M | 1.66008 | 0.011068 | B2M encodes a serum protein found in association with the major histocompatibility complex (MHC) class I heavy chain on the surface of nearly all nucleated cells. |
| IRF9 | 1.310939 | 0.011403 | IRF9 encodes for interferon regulatory factor 9. |
| CD27 | 1.836914 | 0.011584 | The protein encoded by CD27 is a member of the TNF-receptor superfamily and is required for generation and long-term maintenance of T cell immunity. It plays a key role in regulating B-cell activation and immunoglobulin synthesis. |
| KLRD1 | 1.614182 | 0.011947 | KLRD1 is an antigen preferentially expressed on NK cells which are a distinct lineage of lymphocytes that mediate cytotoxic activity and secrete cytokines upon immune stimulation. |
| CD40 | 1.340179 | 0.012885 | The protein encoded by CD40 is a member of the TNF-receptor superfamily and has been found to be essential in mediating a broad variety of immune and inflammatory responses including T cell-dependent immunoglobulin class switching, memory B cell development, and germinal center formation. |
| PTPRC | 1.518673 | 0.012959 | The protein encoded by PTPRC is a member of the protein tyrosine phosphatase (PTP) family which are signaling molecules that regulate a variety of cellular processes including cell growth, differentiation, mitotic cycle, and oncogenic transformation. |
| NFATC3 | 1.284201 | 0.013039 | The product of NFATC3 plays a role in the regulation of gene expression in T cells and immature thymocytes. |

TABLE 4-continued

Gene Function of Statistically Significant Genes in Training Set

| Official Symbol | Fold Change (Non-reccurent/ Recurrent) | P-value | Gene Function |
|---|---|---|---|
| C3 | 2.335095 | 0.013304 | Complement component C3 plays a central role in the activation of complement system. Its activation is required for both classical and alternative complement activation pathways. |
| CD8A | 1.847047 | 0.013679 | The CD8 antigen is a cell surface glycoprotein found on most cytotoxic T lymphocytes that mediates efficient cell-cell interactions within the immune system. |
| IKZF1 | 1.493992 | 0.013683 | IKZF1 encodes a transcription factor associated with chromatin remodeling that functions as a regulator of lymphocyte differentiation. Overexpression of some dominant-negative isoforms have been associated with B-cell malignancies, such as acute lymphoblastic leukemia (ALL). |
| IL18 | 1.537873 | 0.014344 | The protein encoded by IL18 is a proinflammatory cytokine that augments natural killer cell activity in spleen cells and stimulates interferon gamma production in T-helper type I cells. |
| HLA-DPA1 | 1.605975 | 0.014775 | HLA-DPA1 belongs to the HLA class II alpha chain paralogues that plays a central role in the immune system by presenting peptides derived from extracellular proteins. |
| TAP1 | 1.420407 | 0.014927 | The protein encoded by TAP1 is involved in the pumping of degraded cytosolic peptides across the endoplasmic reticulum into the membrane-bound compartment where class I molecules assemble. |
| ITGB2 | 1.557211 | 0.016195 | The product of ITGB2 belongs to the integrin beta chain family of proteins which are known to participate in cell adhesion as well as cell-surface mediated signalling. |
| 1F127 | 1.679386 | 0.016642 | Encodes for the protein interferon alpha-inducible protein 27. |
| STAT1 | 1.601101 | 0.018416 | The protein encoded by STAT1 can be activated by various ligands such as interferon-alpha, interferon-gamma, EGF, PDGF, and IL6. It mediates the expression of a variety of genes and is thought to be important for cell viability in response to different cell stimuli and pathogens. |
| CD3E | 1.558632 | 0.01849 | The protein encoded by CD3E plays an important role in coupling antigen recognition to several intracellular signal-transduction pathways. The epsilon polypeptide plays an essential role in T-cell development. |
| TBX21 | 1.504635 | 0.018557 | Expression of TBX21 has been shown to correlate with IFNG |

TABLE 4-continued

Gene Function of Statistically Significant Genes in Training Set

| Official Symbol | Fold Change (Non-reccurent/ Recurrent) | P-value | Gene Function |
|---|---|---|---|
| | | | expression in Th1 and natural killer cells, suggesting a role for this gene in initiating Th1 lineage development from naive Th precursor cells. |
| CD5 | 1.478656 | 0.019625 | CD5 is a cluster of differentiation found on a subset of IgM-secreting B cells known as B-1 cells as well as T cells. |
| PLCG2 | 1.346729 | 0.020213 | The protein encoded by PLCG2 is a transmembrane signaling enzyme that plays an important role in the synthesis of IP3 and DAG which are important for transmitting signals from growth factor receptors and immune system receptors across the cell membrane. |
| TNFSF13B | 1.563995 | 0.021075 | The protein encoded by TNFSF13B belongs to the tumor necrosis factor (TNF) ligand family that has been shown to play an important role in the proliferation and differentiation of B cells. |
| LAMP1 | 1.21012 | 0.022709 | The protein encoded by LAMP1 is a glycoprotein that provides selectins with carbohydrate ligands. It may also play a role in tumor cell metastasis. |
| IL37 | 1.753289 | 0.022796 | The protein encoded by IL37 is a member of the interleukin 1 cytokine family that can bind to, and may be a ligand for interleukin 18 receptor (IL18R1/IL-1Rrp) as well as interleukin 18 binding protein (IL18BP). |
| GATA3 | 1.495402 | 0.023877 | GATA3 encodes a protein that is an important regulator of T-cell development and plays an important role in endothelial cell biology. |
| LTA | 1.722909 | 0.02389 | LTA encodes for a cytokine produced by lymphocytes that is highly inducible, secreted, and forms heterotrimers with lymphotoxin-beta which anchor lymphotoxin-alpha to the cell surface. This protein also mediates a large variety of inflammatory and immunostimulatory responses and plays a role in apoptosis. |
| CLEC2A | 1.945567 | 0.026066 | CLEC2A belongs to the CLEC2 family of activation-induced, natural killer gene complex-encoded C-type lectin-like receptors. |
| IKZF5 | 1.239951 | 0.026122 | IKZF5 is expressed in lymphocytes and is implicated in the control of lymphoid development. |
| XCL2 | 1.459574 | 0.026267 | XCL2 is a cytokine related to XCL1 that is predominantly expressed in activated T cells which induces chemotaxis of cells expressing the chemokine receptor XCR1. |
| ZAP70 | 1.631185 | 0.026582 | ZAP70 encodes an enzyme that plays a role in T-cell |

TABLE 4-continued

Gene Function of Statistically Significant Genes in Training Set

| Official Symbol | Fold Change (Non-reccurent/ Recurrent) | P-value | Gene Function |
| --- | --- | --- | --- |
| | | | development and lymphocyte activation. This enzyme functions in the initial step of TCR-mediated signal transduction in combination with the Src family kinases, Lck and Fyn. |
| PILRA | 1.367106 | 0.026666 | PILRA encodes for an ITIM-bearing member and serves an inhibitory function that is central to the regulation of several cell signaling pathways. |
| GZMK | 2.111418 | 0.027669 | GZMK is a member of a group of related serine proteases from the cytoplasmic granules of cytotoxic lymphocytes. |
| IRF8 | 1.543724 | 0.0279 | The IRF family proteins bind to the IFN-stimulated response element (ISRE) and regulate expression of genes stimulated by type I IFNs, namely IFN-alpha and IFN-beta. |
| TNFRSF18 | 1.444177 | 0.02993 | TNFRSF18 is thought to play a key role in dominant immunological self-tolerance maintained by CD25 (+) CD4 (+) regulatory T cells. Knockout studies in mice also suggest the role of this receptor is in the regulation of CD3-driven T-cell activation and programmed cell death. |
| CLECL1 | 1.461028 | 0.030971 | CLECL1 encodes a C-type lectin-like protein that is highly expressed on dendritic and B cells. It may act as a T-cell costimulatory molecule that enhances interleukin-4 production, and maybe involved in the regulation of the immune response. |
| MST1R | 1.522389 | 0.032201 | MST1R encodes a cell surface receptor for macrophage-stimulating protein (MSP) with tyrosine kinase activity. It is expressed on the ciliated epithelia of the mucociliary transport apparatus of the lung, and together with MSP, thought to be involved in host defense. |
| TARP | 1.446441 | 0.032526 | In some non-lymphoid tissues, the unrearranged T cell receptor gamma (TRG@) locus is expressed. The resulting transcript contains a subset of the TRG@ gene segments and is shorter than TRG@ transcripts expressed in lymphoid tissues. |
| IFITM1 | 1.609253 | 0.032627 | IFITM1 codes for an intrinsic membrane protein that is induced by interferon and is part of the interferon signaling pathway. |
| MFGE8 | 1.422697 | 0.033878 | MFGE9 contains a phosphatidylserine (PS) binding domain that allows it to bind to PS on the surface of apoptotic cells. This helps facilitate opsonization of apoptotic cells. |

TABLE 4-continued

Gene Function of Statistically Significant Genes in Training Set

| Official Symbol | Fold Change (Non-reccurent/ Recurrent) | P-value | Gene Function |
|---|---|---|---|
| CYBB | 1.455351 | 0.034018 | CYBB is the beta chain of Cytochrome b which has been proposed as a primary component of the microbicidal oxidase system of phagocytes. |
| NFKB1 | 1.250284 | 0.034122 | NFKB1 encodes a protein that can undergo cotranslational processing that forms a DNA binding subunit of the NF-kappa-B (NFKB) protein complex. Inappropriate activation of NFKB has been associated with a number of inflammatory diseases while persistent inhibition of NFKB leads to inappropriate immune cell development or delayed cell growth. |
| LY9 | 1.422617 | 0.035493 | LY9 belongs to the SLAM family of immunomodulatory receptors and interacts with the adaptor molecule SAP. |
| STAT2 | 1.284081 | 0.035692 | The protein encoded by STAT2 is phosphorylated In response to cytokines and growth factors. In response to interferon (IFN), it forms a complex with STAT1 and IFN regulatory factor family protein p48 (ISGF3G). |
| XCR1 | 1.403745 | 0.037724 | The protein encoded by XCR1 is a chemokine receptor most closely related to RBS11 and the MIP1-alpha/RANTES receptor. It transduces a signal by increasing the intracellular calcium ions level. |
| MRC1 | 1.45079 | 0.03779 | The protein encoded by MRC1 mediates the endocytosis of glycoproteins by macrophages. |
| CCR5 | 1.479252 | 0.038168 | CCR5 is expressed by T cells and macrophages. Its expression has also been detected in a promyeloblastic cell line, suggesting that this protein may play a role in granulocyte lineage proliferation and differentiation. |
| CXCL9 | 1.893082 | 0.038221 | While the exact function of CXCL9 has not been specifically defined, it is thought to be involved in T cell trafficking. |
| SKAP1 | 1.776735 | 0.038853 | SKAP1 encodes a protein that plays a critical role in inside-out signaling by coupling T-cell antigen receptor stimulation to the activation of integrins. |
| CD1C | 1.43729 | 0.039292 | CD1C encodes a protein that mediates the presentation of primarily lipid and glycolipid antigens of self or microbial origin to T cells. |
| SP110 | 1.257066 | 0.039624 | SP110 encodes a leukocyte-specific nuclear body component that can function as an activator of gene transcription and may play a role in ribosome biogenesis as well as the induction of myeloid cell differentiation. |

TABLE 4-continued

Gene Function of Statistically Significant Genes in Training Set

| Official Symbol | Fold Change (Non-reccurent/ Recurrent) | P-value | Gene Function |
| --- | --- | --- | --- |
| IFNGR2 | 1.170558 | 0.040199 | IFNGR2 encodes the non-ligand-binding beta chain of the gamma interferon receptor which is a heterodimer of IFNGR1 and IFNGR2. |
| MAP3K7 | 1.213028 | 0.040203 | The protein encoded by MAP3K7 mediates the signaling transduction induced by TGF beta and morphogenetic protein (BMP). It controls a variety of cell functions including transcription regulation and apoptosis. |
| CEBPA | 1.545808 | 0.041975 | The protein encoded by CEBPA can bind as a homodimer to certain promoters and enhancers. It can interact with CDK2 and CDK4, thereby inhibiting these kinases and causing growth arrest in cultured cells. |
| NLRC5 | 1.439237 | 0.044939 | NLRC5 plays a role in cytokine response and antiviral immunity through its inhibition of NF-kappa-B activation and negative regulation of type I interferon signaling pathways. |
| CXCL11 | 1.584466 | 0.04521 | CXCL11 encodes a protein that induces a chemotactic response in activated T-cells and is the dominant ligand for CXC receptor-3. IFN-gamma is a potent inducer of transcription of this gene. |
| ICOS | 1.415572 | 0.045259 | The protein encoded by ICOS belongs to the CD28 and CTLA-4 cell-surface receptor family and plays an important role in cell-cell signaling, immune responses, and regulation of cell proliferation. |
| CTLA4 | 1.644172 | 0.04539 | CTLA4 encodes a protein that transmits an inhibitory signal to T cells. |
| BIRC5 | 0.67022 | 0.045418 | BIRC5 is a member of the inhibitor of apoptosis (IAP) gene family which encodes negative regulatory proteins that prevent apoptotic cell death. Gene expression is high during fetal development and in most tumors, yet low in adult tissues. |
| TLR6 | 1.561918 | 0.04578 | The protein encoded by TLR6 is a member of the Toll-like receptor (TLR) family and plays a fundamental role in pathogen recognition and activation of innate immunity. |
| IL10RA | 1.408962 | 0.048235 | The protein encoded by IL10RA has been shown to mediate the immunosuppressive signal of interleukin 10, thus serving to inhibit the synthesis of proinflammatory cytokines. This receptor is reported to promote survival of progenitor myeloid cells through the insulin receptor substrate-2/PI 3-kinase/AKT pathway. |
| CXCL6 | 0.559425 | 0.048912 | CXCL6 encodes a protein that serves as a chemoattractant for neutrophilic granulocytes |

TABLE 4-continued

Gene Function of Statistically Significant Genes in Training Set

| Official Symbol | Fold Change (Non-reccurent/Recurrent) | P-value | Gene Function |
|---|---|---|---|
| | | | by interacting with the chemokine receptors CXCR1 and CXCR2. |

TABLE 5

Statistically Significant Genes in Validation Set

| Official Symbol | Fold Change (Non-reccurent/Recurrent) | P-value |
|---|---|---|
| IFI27 | 1.977386 | 0.000887 |
| HLA-DPB1 | 1.649143 | 0.00097 |
| STAT1 | 1.805251 | 0.000972 |
| MRC1 | 1.563158 | 0.001282 |
| B2M | 1.584912 | 0.002027 |
| IL18 | 1.864116 | 0.002164 |
| IFNGR1 | 1.350452 | 0.002413 |
| CXCL11 | 2.850672 | 0.002644 |
| TAP2 | 1.489447 | 0.003244 |
| CXCL9 | 3.114418 | 0.003475 |
| CLEC2A | 3.20643 | 0.003833 |
| HLA-DPA1 | 1.603543 | 0.005165 |
| XCL2 | 1.431471 | 0.005597 |
| CTSS | 1.59295 | 0.005937 |
| CCL27 | 3.513776 | 0.006878 |
| ICOS | 1.399578 | 0.011073 |
| IRF8 | 1.435517 | 0.011883 |
| IFITM1 | 1.391794 | 0.012035 |
| HLAE | 1.356181 | 0.012934 |
| GATA3 | 1.6531 | 0.014346 |
| TAPI | 1.707536 | 0.014598 |
| CD2 | 1.487405 | 0.015139 |
| CD37 | 1.347055 | 0.016238 |
| KLRK1 | 1.612816 | 0.018172 |
| CD5 | 1.300416 | 0.018254 |
| LY9 | 1.282556 | 0.018897 |
| CXCR3 | 1.334443 | 0.020895 |
| CD3E | 1.400876 | 0.02122 |
| TNFSF13B | 1.42329 | 0.021607 |
| LCK | 1.325899 | 0.021821 |
| IL37 | 1.935279 | 0.027492 |
| XCR1 | 1.29547 | 0.032381 |
| C3 | 1.392606 | 0.035138 |
| CD4 | 1.19348 | 0.037494 |
| CD48 | 1.224441 | 0.038406 |
| LGMN | 1.186092 | 0.039788 |
| TNFRSF18 | 1.323574 | 0.04165 |
| IRF9 | 1.220289 | 0.043863 |
| SKAP1 | 1.221685 | 0.044579 |
| TARP | 1.49682 | 0.045214 |
| GZMK | 1.412444 | 0.046383 |

TABLE 9

Gene Accession Numbers

| Gene Name | Accession # |
|---|---|
| IFI27 | NM_005532.3 (SEQ ID NO: 1) |
| HLA-DPB1 | NM_002121.4 (SEQ ID NO: 2) |
| STAT1 | NM_007315.2 (SEQ ID NO: 3) |
| MRC1 | NM_002438.2 (SEQ ID NO: 4) |
| B2M | NM_004048.2 (SEQ ID NO: 5) |
| IL18 | NM_001562.2 (SEQ ID NO: 6) |
| IFNGR1 | NM_000416.1 (SEQ ID NO: 7) |
| CXCL11 | NM_005409.3 (SEQ ID NO: 8) |
| TAP2 | NM_000544.3 (SEQ ID NO: 9) |
| CXCL9 | NM_002416.1 (SEQ ID NO: 10) |
| CLEC2A | NM_207375.1 (SEQ ID NO: 11) |
| HLA-DPA1 | NM_033554.2 (SEQ ID NO: 12) |
| XCL2 | NM_003175.3 (SEQ ID NO: 13) |
| CTSS | NM_004079.3 (SEQ ID NO: 14) |
| CCL27 | NM_006664.2 (SEQ ID NO: 15) |
| ICOS | NM_012092.2 (SEQ ID NO: 16) |
| IRF8 | NM_002163.2 (SEQ ID NO: 17) |
| IFITM1 | NM_003641.3 (SEQ ID NO: 18) |
| HLAE | NM_005516.4 (SEQ ID NO: 19) |
| GATA3 | NM_001002295.1 (SEQ ID NO: 20) |
| TAP1 | NM_000593.5 (SEQ ID NO: 21) |
| CD2 | NM_001767.2 (SEQ ID NO: 22) |
| CD37 | NM_001774.2 (SEQ ID NO: 23) |
| KLRK1 | NM_007360.3 (SEQ ID NO: 24) |
| CD5 | NM_014207.2 (SEQ ID NO: 25) |
| LY9 | NM_001033667.1 (SEQ ID NO: 26) |
| CXCR3 | NM_001504.1 (SEQ ID NO: 27) |
| CD3E | NM_000733.2 (SEQ ID NO: 28) |
| TNFSF13B | NM_006573.3 (SEQ ID NO: 29) |
| LCK | NM_005356.2 (SEQ ID NO: 30) |
| IL1F7 | NM_014439.3 (SEQ ID NO: 31) |
| XCR1 | NM_005283.2 (SEQ ID NO: 32) |
| C3 | NM_000064.2 (SEQ ID NO: 33) |
| CD4 | NM_000616.3 (SEQ ID NO: 34) |
| CD48 | NM_001778.2 (SEQ ID NO: 35) |

TABLE 9-continued

Gene Accession Numbers

| Gene Name | Accession # |
|---|---|
| LGMN | NM_001008530.1 (SEQ ID NO: 36) |
| TNFRSF18 | NM_004195.2 (SEQ ID NO: 37) |
| IRF9 | NM_006084.4 (SEQ ID NO: 38) |
| SKAP1 | NM_003726.3 (SEQ ID NO: 39) |
| TARP | NM_001003799.1 (SEQ ID NO: 40) |
| GZMK | NM_002104.2 (SEQ ID NO: 41) |
| ITK | NM_005546.3 (SEQ ID NO: 42) |
| CSF2RA | NM_006140.3 (SEQ ID NO: 43) |
| PGK1 | NM_000291.2 (SEQ ID NO: 44) |
| HLA-DQB1 | NM_002123.2 (SEQ ID NO: 45) |
| CD40 | NM_001250.4 (SEQ ID NO: 46) |
| CYBB | NM_000397.3 (SEQ ID NO: 47) |
| CCL5 | NM_002985.2 (SEQ ID NO: 48) |
| PTPRC | NM_002838.2 (SEQ ID NO: 49) |
| ITGAL | NM_002209.2 (SEQ ID NO: 50) |
| IRF2 | NM_002199.2 (SEQ ID NO: 51) |
| CD68 | NM_001251.2 (SEQ ID NO: 52) |
| TLR7 | NM_016562.3 (SEQ ID NO: 53) |
| CD53 | NM_000560.3 (SEQ ID NO: 54) |
| SDHA | NM_004168.1 (SEQ ID NO: 55) |
| CDBA | NM_001765.5 (SEQ ID NO: 56) |
| POLR18 | NM_019014.3 (SEQ ID NO: 57) |
| IK2F1 | NM_006060.3 (SEQ ID NO: 58) |
| ITGB2 | NM_000211.2 (SEQ ID NO: 59) |
| ACT8 | NM_001101.2 (SEQ ID NO: 60) |
| CLTC | NM_004859.2 (SEQ ID NO: 61) |
| CCR4 | NM_005508.4 (SEQ ID NO: 62) |
| IFNAR1 | NM_000629.2 (SEQ ID NO: 63) |
| SYK | NM_003177.3 (SEQ ID NO: 64) |
| G6PD | NM_000402.2 (SEQ ID NO: 65) |
| IRF5 | NM_002200.3 (SEQ ID NO: 66) |
| RPLP0 | NM_001002.3 (SEQ ID NO: 67) |
| LDHA | NM_005566.1 (SEQ ID NO: 68) |
| CCR5 | NM_000579.1 (SEQ ID NO: 69) |
| CD27 | NM_001242.4 (SEQ ID NO: 70) |
| GAPDH | NM_002046.3 (SEQ ID NO: 71) |
| TUBB | NM_178014.2 (SEQ ID NO: 72) |
| TBP | NM_003194.3 (SEQ ID NO: 73) |
| RPL19 | NM_000981.3 (SEQ ID NO: 74) |
| HPRT1 | NM_000194.1 (SEQ ID NO: 75) |
| ALAS1 | NM_000688.4 (SEQ ID NO: 76) |
| POLR2A | NM_000937.2 (SEQ ID NO: 77) |
| GUSB | NM_000181.1 (SEQ ID NO: 78) |
| ABCF1 | NM_001090.2 (SEQ ID NO: 79) |
| LY64 | NM_005582.2 (SEQ ID NO: 80) |

The entire sequence of each accession number provided in Table 9 above is incorporated herein by reference in its entirety.

Example 2

Abstract

Melanoma is a devastating form of skin cancer that is rarely curative in advanced stages of the disease. Even early stage melanomas can metastasize and accurate diagnosis and clinical staging is vitally important. Evidence shows that the host immune system plays a determinative role in clinical outcomes in cancer. Studies in liver cancer, lung cancer, prostate cancer, and advanced melanoma have revealed that the expression of inflammatory genes by "normal" host cells correlates with survival. Prognostic information in cancer can therefore be learned from study of the host immunologic milieu. Characterization of the immune signature of melanoma is clearly an important step in disease staging, prognostication, and therapeutics. Primary melanomas have been inadequately studied to date because clinical standards require that the entire specimen be fixed in formalin to preserve morphology for pathology diagnosis. This process is damaging to RNA, hindering analysis of gene expression signatures. Novel technologies recently developed, however, allow for analysis of partially degraded RNA derived from formalin fixed paraffin embedded (FFPE) tissue blocks. Pure RNA extracted from these FFPE tissue blocks can be analyzed using an nCounter system (NanoString) which is capable of detecting as little as 0.5 fM of a specific mRNA. This has opened a new avenue for high throughput research in this area. In this study such cutting-edge technologies are used to create a gene signature for recurrent melanoma. Specifically this study has three aims: screen the dermatopathology database at Mount Sinai and identify melanoma specimens from patients who subsequently recurred and matched specimens from patients who did not recur; establish a protocol for extraction of RNA from paraffin embedded primary melanoma tissues; and establish an inflammatory signature for early stage melanoma at high risk of recurrence. Characterization of the immune signature of melanoma is clearly an important step in disease staging, prognostication, and therapeutics of this devastating disease.

Introduction

Melanoma is the deadliest form of skin cancer. Over 160,000 new cases of melanoma are diagnosed annually worldwide with 40,800 deaths per year from advanced (stage IV) melanoma.[69] The median survival time in stage IV melanoma is six months and few effective therapies exist to treat this disease. A meta-analysis of all phase II cooperative group trials in stage IV melanoma demonstrated a median survival time of 6.2 months with 25.5% of patients alive at one year.[70] A review of 35 immunotherapy trials involving 765 patients demonstrated an overall response rate of 3.3%.[71] Clearly, a better way is needed to identify patients at risk or not at risk for progression to metastatic disease so as to guide therapeutic decisions and enable one to tailor therapeutic approaches. There are several important examples in cancer of how gene signatures have affected management and the course of disease. In breast cancer, a prognostic tool called Oncotype DX was developed to identify patients whose prognosis was sufficiently good that they may not require chemotherapy in addition to hormonal therapy.[72] HER2 (tyrosine kinase receptor) amplification is a predictive signature for those patients who will benefit from trastuzumab.[72] The KRAS mutation in colorectal cancer is a predictive signature for patients who will benefit from the EGFR inhibitors and the EGFR mutation in non small lung cancer is a predictive signature for patients who would benefit from first line treatment with erlotinib.[73] Systematic, well designed trials have shown that gene signatures are effective for prediction or prognostication in a variety of malignancies.

Gene signature studies in melanoma have been hampered by several factors including the need for fresh tissue to perform RNA extractions, restrictions to studying metastatic lesions in order to preserve primary biopsies for clinical use, and the descriptive nature of most studies with few clinical endpoints being utilized. Additionally, melanoma studies are particularly difficult given how small the specimens are and the need to preserve some tissue for clinical use. Two key studies have evaluated gene expression in primary melanomas. Kauffman et al evaluated 60 primary fresh frozen melanoma lesions (17 in the validation set) with four years of follow-up. They specifically reviewed only DNA repair/replication genes and found a 48 gene signature associated with metastatic progression.[74] Winnepenninckx et al evaluated 234 primary melanoma lesions with at least 4 years of follow up and found a 254 gene signature associated with distant metastases free survival. These genes were mainly involved in DNA replication; a subsequent studies have not shown this gene signature to be of utility in the clinical setting.[75]

Melanoma has classically been regarded as an immune mediated disease. Pathological studies have demonstrated that skin melanomas are characterized by lymphoid infiltrates to various degrees with brisk infiltrates being a good prognostic indicator. Regression of primary melanoma due to heavy lymphoid infiltrates is a common clinicopathologic feature. Tumor infiltrating cells in melanomas contain T cells, B cells, dendritic cells, and macrophages.[75] Several gene signature studies have demonstrated immune gene upregulation in several settings. Metastatic melanoma in comparison to benign nevi had increased expression of immune related genes such as HLA-B, HLA-H, and STAT1.[76] Bogunovic et al. found that in metastatic melanoma, upregulation of a gene signature profile reflective of immune activation was associated with improved survival while cell proliferation genes negatively impacted survival.[77] Evidence suggests that the host immune system plays a determinative role in clinical outcomes in melanoma. Therefore, prognostic information in melanoma can possibly be informed by examining the expression of genes involved in the host immunologic response milieu.

This study establishes an immune signature for Stage II cutaneous melanoma at high risk of recurrence. Such an immune signature helps identify which subset of stage II melanoma patients benefits from earlier therapeutic interventions. Although, research in this field has been hampered by the need for cell lines or fresh tissue to conduct functional genomics newer technologies are used that allow RNA extraction from formalin fixed paraffinized melanoma samples in conjunction with microarray assays designed specifically to assay to degraded RNA have opened a new avenue for large volume research in this area.

Specific Aims:

Specific Aim 1: To screen the dermatopathology database at Mount Sinai and identify melanoma specimens from patients who recurred and specimens from patients who did not recur; and to create a database of clinical and pathologic characteristics (obtained from electronic and paper medical records as well as patient surveys) for each patient.
  A. Evaluate stage II melanomas from the dermatopathology database and examine the clinical record to identify 24 patients who recurred
  B. Identify lesions from 24 patients who did not recur matched for stage, age, gender and ethnicity.

Specific Aim 2: To extract RNA from paraffin embedded primary melanoma tissues using the Ambion RecoverAll Total Nucleic Acid Isolation kit.
  A. To optimize a standard protocol for extraction of RNA (Ambion RecoverAll Total Nucleic Acid Isolation kit) from paraffinized tissue, for use with small amounts of previously archived tissue samples.

Specific Aim 3: To establish an inflammatory immune signature for early stage melanoma at high risk of recurrence
  A. To identify a panel of 500 inflammatory and cancer genes based on a systematic search of the literature for genes that are significant in both melanoma and other malignancies
  B. To employ NanoString technology to screen 24 melanomas which recurred and 24 melanomas (discovery set) that did not recur for expression of a panel of 500 inflammatory markers to identify candidate genes. A gene signature is created from these genes
  C. To validate a gene signature from the discovery set in a training set of recurrent and non recurrent melanomas and determine whether differential expression of inflammatory genes provides prognostic information beyond pathological markers of prognostication Methods Patient Selection:

Stage II melanoma is defined as a tumor greater than 2 mm in depth or a tumor between 1-2 mm with ulceration. Stage II melanomas are chosen as they are the melanomas at highest risk of recurrence or progression to metastatic disease. The Mount Sinai Hospital pathology department has all melanoma related pathology stored from 1999-2009. An electronic database is queried to identify all patients diagnosed with melanoma and then each pathology report is reviewed by the investigators to determine if they fit the criteria of either stage II melanoma. A 10 year time period is examined as the FFPE extraction kit has been validated for samples up to 10 years old. As melanoma is most likely to recur in the first two years after diagnosis, the patient must have at least two years of follow up to be included in this study. Each pathology specimen is reviewed with Dr. Robert Phelps, the head of dermatopathology. As part of this study a database that stores both pathologic and clinical characteristics of every specimen in the study is created. Pathologic characteristics (as reviewed by Dr. Phelps) including depth of lesion, ulceration, immune infiltration, number of mitoses, degree of sun damage, pathologic subtype, Clarks level, satellite lesions, blood vessel invasion, and lymphatic invasion, and lymph node involvement are recorded.

As the dermatopathology database does not contain any clinical information about patient outcomes, it is created. A systematic review of the electronic medical records (2 existing databases at Mount Sinai) and paper charts (Main medical records, Dermatology records, Oncology records) is conducted on every patient in the study. Clinical characteristics that are recorded include recurrence status, gender, ethnicity, alive/deceased, cause of death if applicable, metastatic sites, treatments (chemotherapy, surgery, radiation), other skin tumors, other cancers, a family history of melanoma, a history of immune disease, site of recurrence, how many months since primary melanoma did the recurrence happen, and what treatment did the patient receive for the recurrence.

Additionally, in cases where the medical record is incomplete, a patient phone questionnaire is administered (Table 10). Patients are mailed a cover letter explaining the project as well as a consent form. A follow up phone call by one of the investigators is conducted to administer the questionnaire to consenting patients. The phone survey attempts to gather the following information: does the patient receive regular dermatology follow up, how many moles do they have, what is there hair and skin color, do they have freckles, when they are exposed to the sun how frequently do the burn versus tan, how many blistering sunburns have they had in the past, what is there occupation, how many hours do they spend outside for their occupation, how many hours do they spend outside for their leisure activities, do they wear sunscreen of protective clothing on a daily basis.

RNA Extraction:

For extraction of RNA from FFPE tissues, several commercially available kits were tested. The best yield of total RNA came from the RecoverAll Total Nucleic Acid Isolation Kit which is optimized for and can only be used in FFPE samples. Historically, the chemicals used in preserving tissue in paraffin have made the samples unusable in molecular analysis. The paraffinization process made the RNA from these samples too fragmented to be compatible with molecular techniques. The RecoverAll Total Nucleic Acid Isolation kit uses a protease digestion process that releases the maximal amount of RNA, of all sizes, as possible. RNA from frozen tissue are extracted using a four step protocol that involves: 1. Phase separation (uses Trizol based reagents, homogenization); 2. RNA precipitation and incubation; 3. RNA wash; 4. Redisolving the RNA in Rnase free water. The microarray requires no more than 5 uL of sample with a concentration of 20 ng/ul. More than 33-50% of the samples should be greater than 300 base pairs.

Immune Assay:

NanoString is a gene expression assay that directly captures and counts individual mRNA transcripts. It is uniquely suited for measuring partially degraded RNA as found in FFPE tissues. Total RNA is mixed with a pool of probes bound to strings of fluorophores. The color sequence encoded by each nanostring is specific to a given probe. Experimentally, 100 ng of total RNA is mixed with a mixture of up to 550 unique DNA/fluorophore and a hybridization step follows. The reporter probe is a 50 mer oligonucleotide. As a result partially fragmented samples can be detected using this technology without affecting the quality of the results. After hybridization the excess reporter probes are washed off. The transcripts present in the total RNA sample are identified by binding the hybridized RNA/probe to a substrate and scanning the substrate with a laser device. The surface is imaged by a CCD camera and the signal processed by software which determines total counts for each reporter probe. With a sensitivity of 500 attomolar this assay can detect as little as one copy of RNA per cell using 100 nanograms of total RNA as input. 500 genes can be evaluated using the NanoString assay. To identify these genes a PubMed literature search for gene expression profiling in melanoma, gene signatures in melanoma, immune/inflammatory genes in melanoma, and immune signatures in other malignancies (eg. prostate, breast, liver, lung) was conducted. Additionally, commercially available inflammatory panels were screened for possible candidate genes.

A discovery set of at least 24 recurrent and at least 24 non recurrent melanomas is evaluated to identify genes for the immune signature. The gene signature from the discovery set is then be applied to the validation set of samples (obtained from the dermatopathology database) to estimate prediction accuracy. To demonstrate that the new signature is significant it is compared to standard prognostic factors (depth, ulceration).

Sample Size:

The number of samples necessary for the identification of a robust biomarker signature is variable. Sample size depends on the amplitude of the difference between and variability within study groups. Little consensus exists for the calculation of sample size for microarray experiments.[78-79] Best practices utilize independent sets of samples for the purpose of validating candidate signatures. Thus the robustness of the signature relies on a statistically significant association between the predicted and true phenotypic class in the sample sets. In the discovery set, this is indicated by the Fisher's Exact Test result, as well as the estimates for sensitivity and specificity and their corresponding exact 95% confidence intervals. In this study, results obtained from the discovery set are used for power calculations for the validation set.

Statistical Analysis:

Continuous variables (e.g. depth) are described by their frequency of observations, mean, median, standard deviation, minimum, and maximum values. Categorical variables (e.g. recurrence) are described by their frequency and percentage. In addition to the previously mentioned microarray analysis techniques, other inferential statistics are used to assess the association between transcripts based variables and clinical outcomes. Appropriate methods are chosen depending on the specific outcome's level of measurement and whether or not observations are independent. For continuous variables with independent observations comparisons of central tendency are made using ANOVA or Kruskal-Wallis test. For dependent observations (e.g. clustered or longitudinal data), linear mixed model analyses is used. For categorical variables with independent observations likelihood-ratio chi-square tests are used to univariately test for differences among groups. For dependent observations McNemar's or Cochran's Q (for tables larger than 2 by 2) test is used. For multivariate analyses of binary outcomes generalized linear mixed models (assuming a binomially distributed outcome and using the logit link function) are used to account for correlated observations. For time to event (e.g. survival and disease progression) analysis, the Cox proportional hazards model is used. The Benjamini and Hochberg method for controlling the false discovery rate are used to account for multiple testing. Descriptive statistics for clinical and demographic variables are given overall and by appropriate classifications (e.g. disease stage).

Preliminary Results:

Clinical Database: To date 70 patients with stage II melanoma have been identified for the database. Obtaining the corresponding clinical information and recurrence status is ongoing and currently 12 recurrent and 12 non recurrent patients have been identified that can be used for the discovery set. This information was initially collected utilizing excel and is currently being converted to an access database.

Phone Questionnaire to ascertain additional clinical information: Ten patients were consented for administration of the questionnaire as seen in Table 10. The questionnaire is used to supplement clinical information that is often not found in the patients clinical record but is relevant to their dermatology and oncology history. The clinical information that is abstracted from the patient's medical record includes: recurrence status, gender, ethnicity, alive/deceased, cause of death if applicable, metastatic sites, treatments (chemotherapy, surgery, radiation), other skin tumors, other cancers, a family history of melanoma, a history of immune disease, site of recurrence, how months since primary melanoma did the recurrence happen, what treatment did the patient receive for the recurrence, does the patient receive regular dermatology follow up, how many moles do they have, what is there hair and skin color, do they have freckles, when they are exposed to the sun how frequently do they burn versus tan, how many blistering sunburns have they had in the past, what is there occupation, how many hours do they spend outside for their occupation, how many hours do they spend outside for their leisure activities, and do they wear sunscreen of protective clothing on a daily basis.

RNA extraction and custom immune gene assay: RNA has been successfully and repeatedly been extracted from FFPE specimens using the Ambion RecoverAll Total Nucleic Acid Isolation kit. This commercial protocol was optimized in the Saenger Lab for extraction of RNA from skin tissue. Over several months this commercial protocol was adjusted to increase RNA yield from cutaneous tissue. The commercial protocol involves four major steps—deparaffinization, protease digestion, nucleic acid isolation, and nuclease digestion and final nucleic acid purification. Two major modifications were made. During the deparaffinization step four 20 micron sections are deparaffinized in one tube which is the maximum number of sections the protocol allows for. It was found that given the small size of the melanoma samples, using less than this amount gave RNA yields unsuitable for nanostring analysis. Additionally, when incubating the samples in 100% xylene, extending the incubation period to a maximum of 30 minutes at 50 degrees Celsius rather than 3 minutes resulted in higher RNA yields, presumably secondary to more complete deparaffinization. The second major step of the protocol requires digestion of the melanoma tissue with digestion buffer and protease. This step allows for release of the RNA from the deparaffinized melanoma tissue. The commercial protocol recommends incubation at 50 degrees for 15 minutes followed by 15 minutes at 80 degrees Celsius. It was found that this incubation time did not produce yields high enough to utilize for nanostring analysis. In the literature, RNA extraction from fresh skin tissue has been historically difficult because the tissue is tough, hard to homogenize, and contains many RNAases. Some of these issues may be similar in extraction from paraffin. It was found that extending the digestion time to three hours at 50 degrees Celsius followed by 15 minutes at 80 degrees Celsius increased the yield of RNA to sufficient amounts suitable for nanostring analysis. This is the maximum recommended time per the commercial protocol. This has been demonstrated by using an Agilent Bioanalyzer for total RNA. A 500 gene immune panel has been assembled for the nanostring assay. A PubMed literature using the following key phrases were used to identify relevant genes: gene expression profiling in melanoma; gene signatures in melanoma; immune/inflammatory genes in melanoma; and immune signatures in other malignancies (eg. prostate, breast, liver, lung). Additionally, commercially available inflammatory panels were screened for possible candidate genes. Genes from the following functional categories were chosen—macrophages, neutrophils, natural killer cells, dendritic cells, cytokines, chemokines, adhesion molecules, toll like receptors, complement, t cells, b cells, cell death, cell signaling, major histocompatability complex I and II, immunoglobulins, NF kappa B, and the JAK-STAT pathway. These genes were mainly chosen because of their relevance to cancer surveillance or progression in melanoma or other malignancies as found in our literature search. This gene set that was created has not been used, in any other studies. The gene set being used can be viewed in FIG. 25.

Ongoing Work 12 recurrent and 12 non recurrent patients were identified that can be used for the discovery set and have extracted RNA on these specimens. These have been sent to NanoString Technologies for analysis on a custom immune gene assay that created with NanoString Technologies. These results are obtained and a gene signature from the discovery set is applied to the validation set of samples (obtained from the dermatopathlogy database) to estimate prediction accuracy. To maximize the sample number, Tammie Ferringer M. D., a dermatopathologist in the Geisinger Health Network is collaborated with.

Summary of Novel Findings to Date:
1. Establishment of a new database linking clinical and pathological information on patients with early stage melanoma with recurrent verses non recurrent disease
2. Adaption, modification, and optimization of an RNA extraction procedure for extraction of RNA from a small sample of archived tissue material previously embedded in paraffin.
3. Development of a new phone survey to capture important clinical information
4. Development & utilization of a customized & novel 500 immune gene panel (Nanostring immune gene set).

TABLE 10

Institutional Review Board (IRB) approved phone questionnaire administered to study subjects with incomplete clinical records 1) Have you been diagnosed with melanoma? When and how many times?
2) Do you have any melanoma in your body currently as far as you know?
3) Did any of your melanomas spread beyond the skin?
4) Did any of your melanomas reoccur again in the skin after it was removed? How long after?
5) Have you had any other melanomas that were diagnosed by a doctor not associated with Mount Sinai Hospital? If so, where was the melanoma located, when were you diagnosed, and did you receive any treatment for this melanoma?
6) Do you get regular follow up for your melanoma? How often do you visit your dermatologist?
7) Do you have more than 10 moles?
8) What would you describe as your race?
9) Do you have red hair? Freckles?
10) Does anyone in your family have melanoma
11) Have you ever been diagnosed with a cancer other than melanoma, if so what cancer, when, and are you receiving active treatment?
12) When you are exposed to the sun do you always burn? Burn sometimes? Always tan? Tan sometimes? Never tan? Never burn?

TABLE 10-continued

Institutional Review Board (IRB) approved phone questionnaire administered to study subjects with incomplete clinical records 13) As a child/young adult how many blistering sunburns did you get?
14) What type of work do you do and how many hours a day are your exposed to the sun in your job?
15) What kind of leisure activities do you do and how many hours a day to those activities expose you to the sun?
16) How often do you use sunscreen and/or where sun-protective clothing such as hats, long sleeves, and/or long pants?
17) What is your ethnicity?
18) Have you been diagnosed with any other skin tumors Example 3

1) There are 70,000 cases of melanoma a year in the US of which approximately 25,000 are deep primary melanomas. Early stage 3 melanomas (sentinel lymph node positive) and late stage 2 melanomas (deeper than 2 mm or deeper than 1 mm and ulcerated) are included. These melanomas are at high risk of recurrence, causing advanced disease and death Depth provides some prognostic information but generally only allows the estimation of mortality risk to between 25-50%. Therefore there is a need for better information to guide patient and physician choices.

In order to define a better biomarker for melanoma recurrence, RNA was isolated from primary melanoma tumors and measured expression of inflammatory genes. This has not been done yet because primary melanomas are preserved in paraffin and this affects RNA quality, making the RNA difficult to analyze. A specialized technology, NanoString, was used to analyze the degraded RNA. Excitingly, of the 33 genes that were significantly different between recurrent and non-recurrent groups, all of them were up-regulated in the non-recurrent patients, suggesting that inflammation is protective.

More importantly, a 10 gene signature was determined, similar to Oncotype Dx for breast cancer, which allows for determination of risk of recurrence for breast cancer. This signature, in our test sample, allows for detection of recurrence risk with 90% specificity and 80% sensitivity. Genes included in this signature make biologic sense as they correlate with markers of T cell infiltration. Current morphologic assays of T cell infiltration are crude and do not allow for any phenotypic differentiation between lymphocyte population so our genetic screen would add a great deal of information to current clinical parameters.

Notably this approach may have application beyond the primary melanoma setting. Inflammatory markers may be predictive of prognosis as well as response to immunotherapy in the metastatic setting. The same genes permitting the tumor to escape the immune system early on in disease may also be operative at more advanced stages. This technology could therefore be applied to patients with metastatic disease to predict survival and also to predict response to immunotherapy such as ipilimumab, anti-PD1, oncovex treatments, or potentially conventional or targeted therapies resulting in antigen release and potential immune response. NanoString would have great application here because, although it is theoretically possible to preserve frozen tumor specimens, most samples available in clinical practice are paraffin embedded. An identical or similar panel of genes may have utility here.

The 10 relevant genes are: HLAE, CD2, ITK, KLRK1, CCR4, LCK, CD48, CD4, CXCR3, CD53

CD2 is particularly intriguing because CD53 and CD48 are both implicated as having interactions with CD2. CD2 is a co-stimulatory marker on T cells and also implicated in NK cell and dendritic cell function. These genes are associated with T cell responses and with the recruitment of inflammatory cells to the skin.

2) Patients can have the test done to determine their risk of recurrence. This helps define monitoring as far as whether they need regular imaging tests and also help patients to assess their own risk and decide whether to take adjuvant therapies which can be very toxic. Patients want to know this information.

3) Oncotype Dx

There is currently no biomarker for recurrence of primary melanoma based on gene expression and there is no biomarker for cancer recurrence based exclusively on inflammatory gene expression, and no biomarker related specifically to T cell genes and interferon response genes or to any of the genes listed above.

Example 4

Abstract

Improved biomarkers are needed for patients with resected stage II-III melanoma. Clinico-pathologic features such depth, ulceration, and sentinel lymph node status, while essential to clinical practice, often fail to predict progression in individual patients. Biomarker development has been hindered by clinical standards dictating that the entire specimen be formalin fixed and paraffin embedded (FFPE) for morphology evaluation, a process damaging to RNA. To define a biomarker for melanoma progression, mRNA copy number of 446 genes was measured in completely resected stage II-III FFPE primary melanoma using NanoString, a hybridization assay suited for analysis of partially degraded RNA. A 53-gene biomarker of progression was defined using receiver operating characteristic (ROC) curves in a test population (N=40). Prediction power of this panel was tested in a second independent population (N=48, AUC=0.787, p<0.001). Protein levels of the most differentially expressed gene, CD2, associated with non-progression by immunohistochemistry. In the validation population, multivariable analysis identified gene signature score as an independent predictors of progression (p<0.001) and survival (p=0.03 Analysis of publicly available expression data in primary melanoma identified a co-expression network and a module enriched for the 53-gene panel and immune response.). Signaling pathway analysis revealed the 53 genes to form a dense network enriched in T and NK cell signaling pathways. mRNA levels of 53 genes with immune-surveillance function are co-regulated in primary FFPE melanoma, predict non-progression, and should be evaluated in larger studies as a biomarker.

Introduction

Metastatic melanoma is a devastating illness, taking the lives of over 48,000 people worldwide per year.[106] Newer immune therapies are bringing hope to patients with advanced disease. Nonetheless, mortality rates remain very high for patients with stage IV melanoma where the estimated survival rate at 5 years is less than 20%.[107] Surgery, for decades, has been the only reliably curative therapy for this cancer, and, unfortunately, despite significant advances, medical treatments remain non-curative at the present time for the majority of patients.[108]

Patients who have had a stage II or stage III melanoma surgically removed remain at high risk for progression and death because micro-metastasis may have spread to other body sites prior to resection. No highly effective therapy is available to prevent progression. While interferon is FDA approved in patients with stage IIB-III melanoma, it has limited benefit and a difficult toxicity profile, and therefore is inconsistently prescribed in oncology practices across the United States.[109-111]

Critical prognostic features in the pathology report describing a newly resected primary melanoma are depth and ulceration, and these are incorporated into the AJCC melanoma staging system, with stage II melanoma defined as a lesion 2 mm or greater, or 1 mm or greater with ulceration.[112,113] The best test available to further estimate risk is the sentinel lymph node biopsy procedure, and stage III disease is defined by a positive sentinel lymph node.[114,115] Stage III disease, however is highly heterogeneous. Five year survival ranges from 87% for stage III patients with one nodal micro-metastasis and a primary lesion less than 2 mm down to 36% for stage III patients with four or more involved nodes.[116]

Meanwhile, patients with a clean sentinel lymph node (Stage II) are not safe from progression either as patients with IIC disease (primary lesion 4 mm or greater, or 2 mm with ulceration and a negative node) have a five year survival of only 48%.[112] Thus, a primary melanoma greater than 4 mm in depth confers a worse prognosis than a microscopic focus of melanoma in the sentinel node, likely due to hematogenous spread.[112] There is a clear need for accurately, broadly applicable prognostic tools for patients with resectable stage II-III melanoma, both for clinical care, and because improved prognostication would greatly enhance stratification for study of adjuvant therapies.

Evidence is growing that the phenomenon of immuno-surveillance, originally defined in mice, plays a key role in human solid tumors.[117-119] Thus, the immunoscore, has recently been developed as a biomarker for cancer progression.[120] In melanoma, it has long been known that tumor infiltrating lymphocytes (TILs) can confer a more favorable prognosis, and this has recently been validated in patients with stage I-III melanoma.[121,122] Two factors, however, limit the widespread clinical application of TIL quantification. First, TIL quantification is subjective and subject to observer variability.[123] Second, the majority of patients have "non-brisk" TILs, an intermediate category which offers little further clarification of the prognosis.[122] More objective, molecular immune markers are needed.

A major barrier to the development of molecular markers in primary melanoma tumors in particular is the fact that most clinical treatment centers require that the entire specimen be formalin fixed and paraffin embedded (FFPE). This is because the tumors are very small and key features including depth and ulceration can be accurately determined only in FFPE specimens.[124] Thus only those markers which can be assayed in FFPE tissues are applicable to the vast majority of stage I-III melanoma patients in the United States. Genomic markers of inflammation have shown promise in more advanced cases where frozen tissue can be obtained from larger metastatic lesions.[125-127] In melanoma, however, most of the uncertainty exists in the clinical setting before these large metastatic lesions develop. Furthermore, the immune-surveillance hypothesis suggests that it is precisely at the earlier stages of tumor growth, that the determinative balance between tumor and immune system is established.[128]

In order to address the need for an FFPE based immune biomarker in primary melanoma, we tested the ability of NanoString, a technology developed to quantify mRNA transcripts in partially degraded samples, to distinguish patients with a good prognosis from patients with a poor one.[129] We find that expression levels within the original biopsy specimen of an 53 gene panel comprised of genes implicated in immune surveillance predicts clinically non-progression and prolonged survival in two independent sets of patients with resectable melanoma. Herein we present, to our knowledge, the first genomic based immune biomarker based on analysis of FFPE primary melanoma. Large scale prospective studies should be initiated to define the role of mRNA quantification of genes with immune function using NanoString in primary tumors of patients with resectable melanoma.

Materials and Methods

Patients and Samples

The training set included FFPE primary melanoma tumors from 40 patients with completely resected stage II/III melanoma identified by screening dermatopathology databases between January 2001 and January of 2011 at Geisinger Medical Center (GMC, Danville Pa., 32 patients) and Mount Sinai School of Medicine (MSSM. New York, N.Y., 8 patients). Following approval by the local institutional review board (IRB), authorized personnel obtained clinical information at each institution. Progression was defined as biopsy proven melanoma which had spread beyond the local lymph node basin (stage IV) or was no longer amenable to surgical resection. Non-progression was defined as no further evidence of melanoma following excision of the primary lesion with a minimum follow up of 24 months. Patients with incomplete clinical follow-up were contacted by mail and telephone under an IRB-approved protocol. The validation set included additional patients from GHS (15) and MSSM (7) as well as 25 patients meeting criteria defined above from New York University Medical Center (New York, N.Y.). A complete review of all patient records was performed on Dec. 31, 2011 for the training set and Dec. 31, 2012 for the validation set and living patients were censured.

Analysis of Gene Expression

RNA was extracted from primary melanoma specimens using the Ambion® RecoverAll Total Nucleic Acid Isolation Kit (Life Technologies, Carlsbad, Calif.). 446 genes were selected based on a PubMed literature review (Table 13). The nCounter platform (NanoString Technologies, Seattle, Wash.) was used to quantify relative mRNA copy number.[130]

Immunohistochemistry

IHC was performed on 5-µm charged slides using anti-CD2 monoclonal antibody (MRQ-11, Ventana Medical Systems, Tucson, Ariz.). Sections were deparaffinized and stained using a Ventana BenchMark XT immunostainer. Slides were evaluated by two of the study authors (SGB & MMM) in a blinded manner in 8 random High Powered Fields (HPFs) using an ocular micrometer with a 1 mm² grid (Nikon Eclipse E400®).

Statistics

Ensemble Classification/Regression Method and ROC Curves

Classification was performed using an ensemble feature selection method encapsulating two standard classifiers: random forest and elastic net, both embedded in data bootstrapping to boost the robustness of the final gene panel. The starting 446 genes from the training experiment were ranked and filtered based on prediction power of melanoma progression in the training cohort and a subset of 53 genes was selected as final gene panel. ROC curves were generated and the area under the curve (AUC) was calculated on both training and test datasets. Detailed methods are included in the below.

Demographic, Survival and Multivariable Analysis

Two tailed student T tests generated p values for continuous variables including age, depth, and mitotic rate. Other non-continuous characteristics were analyzed using a two-tailed Fisher's exact test or, in the case of TILs, a chi square test. For survival analysis, Kaplan-Meier analysis and Log-Rank (Mantel Cox) tests were performed. Graphpad Prism version 5.0 was used (San Diego Calif. USA) and statistical significance was defined as p<0.05 without correction for multiple comparisons. Standard multivariable logistic and Cox proportional hazards analysis were performed using XLSTAT (Addinsoft) software.

Co-Expression Network Analysis

From the NIH GEO database, 46 samples of gene expression data identified based on origin in primary melanoma tissue and expression platform (Table 14) were collected (GEO accession ID: GSE15605)[131]. Co-expression network analysis was performed using Weighted Gene Co-expression Network Analysis (WGCNA)[132] to identify highly correlated gene modules among whole-genome genes in early stage melanoma patients. Let N denote the total number of genes in the whole-genome. For an overlap of m genes between a module of size M and a panel of genes of size n, an enrichment fold was computed using the ratio of the proportion of panel genes contained in the module (m/n) to the proportion of whole genome genes contained in the module (M/N). That is, enrichment fold=(m/n)/(M/N). The p-value of this enrichment fold is calculated by using Fisher exact test.

Physical Interaction Network Analysis

To analyze the enrichment of the 53-gene panel from both a network perspective and a functional perspective, a gene network was constructed using the gene network tool VisAnt 4.0.[133,134] A reference network was similarly constructed using the original 446-gene panel. For a detailed description of the network construction, see supplemental appendix methods. Density, clustering coefficients, and other network statistics were compared across networks. Furthermore P-values associated with clustering coefficients on each network were generated by randomizing networks of the same size and density.

Pathway and Gene Ontology Enrichment

Gene panels were annotated using the functional database and tool DAVID.[135,136] The default list of whole-genome was chosen as the background gene set, and each network gene list was tested for enrichment of KEGG pathways or GO term biological process (BP) or GO term molecular function (MF).

RNA Extraction

FFPE tissue blocks were cut into four 20 µm sections and treated with 100% xylene (Fisher Scientific, Pittsburgh, Pa.) to deparaffinize. Samples were washed twice with 100% ethanol (Absolute Ethanol Molecular Biology Grade 200 proof, Fisher Scientific, Pittsburgh, Pa.) and dried via vacuum centrifugation at 40° C. Tissue was then incubated in Digestion Buffer and Protease (Ambion® RecoverAll, Life Technologies, Carlsbad, Calif.) at 50° C. for 3 hours, followed by a 15-minute incubation at 80° C. RNA was separated using an Isolation Additive/Ethanol mixture (Ambion® RecoverAll, Life Technologies, Carlsbad, Calif.), and filtered by centrifugation at 10,000 rpm. The sample was rinsed with Wash 1 and Wash 2 (Ambion® RecoverAll, Life Technologies, Carlsbad, Calif.), before and after incubation with DNase for 30 minutes at RT. RNA was eluted with 60 µl of Elution Solution (Ambion® RecoverAll, Life Technologies, Carlsbad, Calif.) at RT.

Dermatopathology

Primary and recurrent melanomas were selected from the Tamtron PowerPath database at the Mount Sinai Medical Center (New York, N.Y.), the Cerner CoPathPlus database at Geisinger Heath System (Danville, Pa.), the Oracle Clinical RDC 4i database at NYU Medical Center (New York, N.Y.), as well as the NovoPath database at Englewood Hospital and Medical Center (Englewood, N.J.). Combined, the databases contained more than 2,500,000 specimens collected since 1985 and derived from surgical pathology, dermatopathology, neuropathology and cytology. Criteria for inclusion were: completely resected stage I-III melanoma, adequate clinical follow-up for all variables listed in the demographic table, and availability of tissue of sufficient quality to extract RNA. Selected slides and paraffin blocks were reviewed by two of the study authors (RGP and SS). Each sample was evaluated for histogenetic type, extent and type of inflammatory infiltrate, thickness, and ulceration.

Tumor infiltrating lymphocytes (TILs) were defined as ones that percolated between and around tumor cells, as previously described by Rao et al.[1] High magnification images of H&E stained tumor specimens were evaluated for TILs by a dermatopathologist. Brisk refers to lymphocytes present throughout the substance or infiltrating the entire base of the vertical growth phase; non-brisk refers to lymphocytes in one focus or more of the vertical growth phase, either dispersed throughout or situated focally in the periphery; and absent if there were no lymphocytes or if they were present but did not infiltrate the melanoma.[107]

Immunohistochemistry

Five micron sections of the same paraffin-embedded tissue samples analyzed by Nanostring were prepared for immunophenotypic analysis. Immunohistochemistry (IHC) was performed using primary, pre-diluted anti-CD2 (MRQ-11, mouse anti-human, Ventana Medical Systems, Tucson, Ariz.). Sections were deparaffinized, stained according to standard protocol using a Ventana BenchMark XT immunostainer and manually counterstained.[108] The immunohistochemical slides were evaluated and interpreted by two of the study authors (SGB & MMM) in a blinded manner without knowledge of corresponding clinical data. For each sample, cells with circumferential membrane staining were counted and averaged in 8 random HPFs using an ocular micrometer with a 1 $mm^2$ grid (Nikon Eclipse E400®).

Statistical Analysis

Cross-Validation

We simulated 900 iterations of a 11-fold cross-validation on the training dataset with random sample reordering in each iteration to strengthen the robustness of our final classifier model. 4 samples were removed at random. These sample sets were then used as training data to fit a statistical model. 10,000 model training tasks were performed. The trained model and gene predictors selected were recorded in each task yielding 10,000 models and 10,000 lists of gene predictors based on randomly sub-sampled training samples. For each model, we performed a classification for the entire training (44 samples) and validation datasets (37 samples). To derive a robust list of gene hits by these models, the 10,000 gene lists were pooled and the statistical count of each gene (out of 446 genes) was selected by these models using the training cohort only. A higher count value for a given gene indicates that it is frequently selected as a predictor during the cross-validation process. Three genes (IFNG, TNFSF18, and CREB1) were excluded from the signature because the p value did not meet the cutoff in the preliminary analysis of the training data and levels were therefore not tested in the validation set. Finally, all genes selected at least once in the 10,000 cross-validation were put into a final model training task to yield an optimal, compact predictor gene list of 53 genes.

Ensemble Classification/Regression Method

We employed a two-step sequential ensemble classification scheme that sequentially concatenated two widely applied classifiers: random forest and elastic net. Random forest itself is an ensemble classifier consisting of many decision trees that generates the mode of individual classes yielded by independent trees. A powerful variable selector and classification/regression method, elastic net integrates a linear regression model with Lasso and Ridge regularization. Elastic net is particularly useful when there are many more predictors than samples, serving to further exclude genes that are only correlated with, but not most predictive, of recurrence. We applied this two-step ensemble classification scheme to the cross-validated training data for the outer loop of the 900, 11-fold training cross-validation data points.

Random Forest

With 446 genes as an initial set of features and 40 samples from the cross-validation used as training data, a random forest model was fit. Initially, random forest was run without feature selection to determine the importance of all 446 genes based on various metrics in the RandomForest R package.[109] Next, an independent run was started that incorporated feature selection into random forest by sequentially reducing a certain number of predictors, ranked by variable importance, by employing a nested cross-validation procedure. In our simulation, a leave-one-out strategy was used. In each internal cross-validation, we removed (step=30%) the least important genes/features, ranked by variable importance, from the last cross-validation iteration. Next, we drew (Ntree=50 k) bootstrap samples from the original data (40 samples). For each of the bootstrap samples, we generated an untrimmed classification/regression tree with randomly selected (mtry=22) genes from the pool of genes leftover following removal. Following cross-validation, we selected the number of genes that resulted in the lowest error rate among all the cross-validation runs. This number represents the number of genes ($N_{RF}$) selected by random forest after cross-validation. Next, we selected the top $N_{RF}$ genes based on the averaged gene rank from the initial run without feature selection, yielding our final gene selections by random forest. The selected genes $G_{RF}$ were used as input for an elastic net model in order to identify the constituents of a gene signature predictive of melanoma recurrence.

Elastic Net

A powerful variable selector and classification/regression method, elastic net integrates a linear regression model with Lasso and Ridge regularization.[110] Elastic net is particularly useful when there are many more predictors than samples, serving to further exclude genes that are only correlated with, but not most predictive of recurrence. In each round of 11-fold cross-validation on the training data, there were 40 training samples. The number of genes selected by random forest varied from 50 to 446 depending on both the leave-one-out training data and randomized feature selection used during decision tree growth. Elastic net extends the basic form of linear/logistic regression via L1 and L2-regularization. $\lambda$ controls the model complexity with higher values resulting in a less complex model (less number of genes). $\alpha$ controls the balance between two types of model complexity penalties, including the ridge-regression penalty ($\alpha$=0) and the lasso penalty ($\alpha$=1). The Ridge penalty is particularly useful when there are more genes and fewer samples. Ridge regression is known to shrink the coefficients of correlated predictors towards each other. In contrast, lasso tends to pick one out of an entire set and ignore the rest. In our study, we set $\alpha$=0.2 and used an internal leave-one-out cross-validation to select an optimal value of $\lambda$.[111] Our input training data was a subset of the original training data based on the gene lists $G_{RF}$ determined by random forest. The output gene lists by elastic net with non-zero coefficients is our final gene list $G_{EN}$ for the cross-validation run.

NanoString

Gene Expression Analysis 446 candidate genes were selected based on a PubMed literature search using the reference terms: melanoma, biomarker, immune, and gene signature[112-135]. The nCounter® platform (NanoString Technologies, Seattle, Wash.), was used to quantify relative gene expression in a multiplex reaction. A custom CodeSet, designated MtSinai0511, was synthesized by NanoString for the 446 selected genes as well as 17 housekeeping genes and 14 controls in a 477-plex reaction (listed in the supplemental reference file). Hybridizations were carried out according to the supplier protocols.[108] In a total reaction volume of 30 μl, 100 ng of each RNA sample in 5 μl H$_2$O was mixed with 10 μl nCounter Reporter probes, 10 μl hybridization buffer (1× hybridization buffer=5×SSPE, 0.1% Tween-20), and 5 μl of nCounter Capture probes. Hybridizations were incubated at 65° C. for approximately 16-20 hours. Following hybridization, the samples were processed in a PrepStation and counted in a DigitalAnalyzer (Nanostring Technologies) according to standard protocol recommended by NanoString Technologies.

Normalization of Data

Calculated from the sum counts of reporters of 6 positive control RNA spikes, sample-specific normalization factors were used to normalize raw mRNA counts in order to account for slight differences in assay efficiency such as hybridization, purification, and binding. Concentrations of the control RNA spikes range from 0.125-128 fM. Normalization for sample RNA quantity and quality differences were applied to the spike-normalized values using sample-specific normalization factors calculated from the geometric mean of the counts from reporters targeting reference genes: ABCF1, ACTB, ALAS1, GAPDH, GUSB, HPRT1, LDHA, PGK1, POLR1B, POLR2A, RPLP0, SDHA, and TUBB. The resulting normalized counts were used in downstream analyses. For the validation set data was run in two batches, with some common samples between them (technical replicates). In order to account for batch effect, the ratio of probe counts between each of the replicate samples tested in both codesets (excluding the 22$^{nd}$ replicate (M87) which was removed at the beginning of this process due to normalization flag). Standard ratios were then calculated for each probe and then used to adjust the two data sets so they could be analyzed together.

Results

Patient Populations

To test the hypothesis that the immune system limits progression of completely resected localized melanoma, mRNA transcripts for immune genes were measured using NanoString technology in melanoma tissues of patients with documented clinical follow up. All tumor tissue was from the initial primary lesion and no patient received any treatment for melanoma prior to tissue harvesting. Patients were scored as "progressors" if they presented with unresectable and/or systemic (stage IV) disease. Patients were scored as "non-progressors," if they remained free of melanoma with a minimum follow up of 24 months. Based on these criteria, an initial test set of 47 patients with completely resected stage II-III primary melanoma was identified for whom sufficient tissue and clinical follow up was available. RNA of sufficient quality for NanoString analysis was obtained in 40 of these cases (85%). A validation test set of 57 patients was identified using identical criteria and RNA was successfully extracted from 48 melanomas (84%). Thus out of a total of 104 patients identified, RNA could be extracted from 88 for an overall success rate of 85%. The 16 patients from whom RNA could not be extracted had significantly thinner melanomas (p=0.024) and a lower mitotic rate (p=0.0067) and were not significantly different in terms of any other clinical characteristics (Table 15).

Clinical characteristics of the two test populations are shown in Table 11. There was no statistically significant difference between demographics of the training and validation populations with the exception of mitosis that were higher in the training population (p=0.002, and all others p>0.05 without correcting for multiple comparisons). 52% of patients in the training cohort and 44% in the validation cohort progressed. Univariate logistic regression showed that ulceration (p=0.003), depth (p=0.005), and age (p=0.016) associated significantly with progression. TILs, mitotic rate, location of the primary tumor and stage of disease (II A-C vs III A-C) did not significantly associate with progression.[112] Death rates were 43% and 36% in each test population, generally consistent with expected death rates based on AJCC staging over the follow up time (median 61 months in test set 1 and 45 months in test set 2).[112]

TABLE 11

Clinical Characteristics of Patients with Primary Melanoma in Test Set 1 and Test Set 2.

| Characteristic | Test Set 1 (N = 40) | Test Set 2 (N = 48) | P Value |
|---|---|---|---|
| Sex | | | |
| Male -- no. (%) | 28 (70) | 26 (54) | 0.187 |
| Female -- no. (%) | 12 (30) | 22 (46) | |
| Age | | | |
| Median (range) -- no. | 67 (29-87) | 65 (27-90) | 0.531 |
| Location of Tumor | | | |
| Trunk -- no. (%) | 24 (60) | 25 (52) | 0.521 |
| Extremity -- no. (%) | 16 (40) | 23 (48) | |
| Pathological characteristics | | | |
| Depth (mm) -- median (range) | 2.65 (1.2-13) | 3.47 (1-30) | 0.179 |
| Ulceration | | | |
| Absent -- no. (%) | 21 (52) | 20 (42) | 0.392 |
| Present -- no. (%) | 19 (48) | 28 (58) | |
| Tumor-infiltrating lymphocytes[+] | | | |
| Absent -- no. (%) | 7 (17) | 0 (0) | 0.071 |
| Non-brisk -- no. (%) | 29 (73) | 24 (89) | |
| Brisk -- no. (%) | 4 (10) | 3 (11) | |
| Mitoses -- median (range) | 6.5 (0-26) | 3 (0-20) | 0.00204 |

TABLE 11-continued

Clinical Characteristics of Patients with Primary Melanoma in Test Set 1 and Test Set 2.

| Characteristic | Test Set 1 (N = 40) | Test Set 2 (N = 48) | P Value |
|---|---|---|---|
| Stage | | | |
| II - no. (%) | 12 (30) | 25 (52) | 0.051 |
| III - no. (%) | 28 (70) | 23 (48) | |
| Patient Outcome (months) | | | |
| Disease Progression | | | |
| Yes -- no. (%) | 21 (52) | 22 (46) | 0.669 |
| No -- no. (%) | 19 (48) | 26 (54) | |
| Time to Recurrence -- median (range) | 14 (2-72) | 20 (2-130) | 0.885 |
| Died from Melanoma -- no. (%) | 17 (43) | 18 (38) | 0.667 |
| Time to death -- median (range) | 19 (6-82) | 42 (25-160) | 0.036 |
| Time to censoring -- median (range) | 61 (27-130) | 47 (31-160) | 0.159 |

[+]Tumor-infiltrating lymphocytes assessed for 27 set 2 patients

Definition of a 53 Immune Gene Panel Predictive of Melanoma Progression Based on the Training Population 446 genes of interest were identified based on a pubmed search of the literature using the search terms "gene signature," "inflammatory," "immune," "melanoma," and "biomarker." The list of 446 genes is provided in the supplement, along with a list of these genes. The starting 446 genes from the training experiment were ranked and filtered based on prediction power of melanoma progression in the training cohort using two standard classifiers, random forest and elastic net. A subset of 53 genes was selected as final gene panel (FIG. 12A). ROC curves were generated and the area under the curve (AUC) was calculated on the training data (FIG. 13B). A heat map clustered according to expression of these 53 genes (FIG. 12C) shows that these genes differentiate between patients who progress and those who do not. Furthermore, all 53 genes were up-regulated in the non-progressors as shown, a distribution which was significantly not random (p<0.0001).

Next, the ability of the gene signature to predict progression was evaluated in the context of known clinic-pathologic predictors. Within the training population depth (p=0.022) and age (p=0.014) significantly correlated with progression by logistic regression, while there was a strong trend for ulceration (p=0.053). Mitotic rate, TILs, gender, stage, and location of the primary tumor did not significantly correlate with progression. Multivariable logistic regression showed that gene signature score alone was the best predictive model of progression (p<0.001) and that clinico-pathologic features did not enhance the gene signature.

Survival analysis was then performed on the training set. Cox proportional hazards showed that the gene signature also correlated with prolonged survival (p<0.001). Multivariable cox proportional hazards analysis showed that the best model to predict survival included age and gene signature (p<0.001). Thus, the immune signature correlated strongly with progression and survival in the context of clinic-pathologic predictors in the training patient population.

Validation of the Immune Gene Signature of Melanoma Progression in a Second Independent Cohort.

Next, experiments were conducted that sought to validate the above findings in an independent set of tissue samples. Demographics for this group are shown in Table 11. To test whether immune-associated genes in the panel were reproducibly up-regulated in tumor that did not progress, the 53 genes included in the signature were measured (FIG. 12A). Notably, the proposed 53-gene signature was able to predict progression in the validation cohort with an AUC of 0.787 (p<0.001, FIG. 13B). Cross-validation using a leave-4-out approach to rule out the possibility that individual samples were biasing the final result demonstrated that this signature was statistically robust (FIG. 12B). Heat map of expression of these 53 genes in the training set confirms that these genes discriminate between progressing and non-progressing patients, with notable higher expression levels seen again in non-progressors (FIG. 12C).

When the gene signature was evaluated in the validation test set in the context of clinic-pathologic predictors, it was noted that, within the validation population univariate logistic analysis showed that depth (p=0.044) and ulceration (p=0.013) correlated with progression. Multivariable logistic regression showed that the best model predictive of progression included gene signature and ulceration (p<0.0001).

The gene signature was then examined in terms of survival in the validation cohort. The gene signature correlated with survival by cox proportional hazards (p=0.037). Multivariable analysis showed that the best model to predict survival within the validation included gene signature and ulceration (p=0.028). Ulceration and an unfavorable immune signature identified a population at high risk of death with median survival of 49 months as compared to 139 months in patients with one or none of these risk factors (FIG. 15, p=0.044). Thus, the immune gene signature enhances the ability of established clinical-pathologic features to predict progression and survival in a second independent patient population.

Validation of Expression Data at the Protein Level and Identification of CD2 as an Immunohistochemical (IHC) Marker of Favorable Prognosis In order to validate mRNA data obtained by NanoString, CD2 staining, IHC was performed for top genes for which antibodies in clinical use were readily available. Results were concordant with NanoString results as determined by linear regression for CD2, the most differentially expressed gene between the patients who progressed and those who did not. (r=0.799; FIG. 14C). Tumors from the training cohort were also stained for CD4 and CD5, and findings correlated with the NanoString data, validating expression of these genes at the protein level (r=0.543 and r=0.666; FIGS. 14D and 14E respectively). Thus, immunohistochemistry correlated with the mRNA results from NanoString.

CD2 was the most differentially expressed gene between the tumors that progressed and those that did not within the training cohort (p=0.002). Low number of CD2 positive staining by IHC correlated with melanoma progression in the second independent population (p<0.001; FIG. 14B). Thus, the NanoString analysis allowed for the identification of a novel IHC stain that may be predictive of progression in patients with completely resected stage II/III melanoma.

Physical Interaction Network Analysis Results.

Next, experiments were conducted that sought to determine whether there were any factors distinguishing the final 53 genes from the original 446 candidates (Table 13). To analyze the density of physical interactions among the 53-gene panel relative to the original 446-gene panel, gene/protein physical interaction networks were constructed using VisAnt[133,434] (see methods). FIG. 16 is a visualization (using the software Cytoscape[137]) of the gene networks induced by the 53-gene panel (16A), and the original 446 genes (16B). Descriptive statistics across each network (e.g. size, density, average local clustering coefficient, global clustering coefficient) are listed below (16C). Interestingly, the density of the networks is higher with the smaller 53-gene panel network, indicating that the induced subgraph (from the 53-gene panel) is proportionally more connected. That is, genes within the 53-gene panel network are interacting at a greater level than the genes in the broader 446-gene panel network. There is a 4.81 density fold change of the 53-gene panel network to the 446-gene panel network. Importantly, the P-values associated with average local CC was significant for the 53-gene panel network but not for the 446-gene panel network (FIG. 5). Therefore, a significant difference in the connectivity was observed when the 446-gene panel was refined to the 53-gene panel of predictive genes.

TABLE 12a

Top 10 enriched KEGG and GO terms (using DAVID) in the 53-gene module relative to the whole genome.

| Category | Term | P Value | Fold Enrichment | Bonferroni | Benjamini | FDR |
|---|---|---|---|---|---|---|
| GOTERM_BP_FAT | GO:0006955~immune response | 2.34E−57 | 5.987716412 | 5.76E−54 | 5.76E−54 | 4.12E−54 |
| GOTERM_BP_FAT | GO:0002684~positive regulation of immune system process | 1.48E−42 | 9.524596866 | 3.65E−39 | 1.82E−39 | 2.61E−39 |
| GOTERM_BP_FAT | GO:0048584~positive regulation of response to stimulus | 9.87E−33 | 8.210994045 | 2.43E−29 | 8.11E−30 | 1.74E−29 |
| GOTERM_BP_FAT | GO:0045321~leukocyte activation | 4.12E−31 | 7.856332365 | 1.02E−27 | 2.54E−28 | 7.26E−28 |
| GOTERM_BP_FAT | GO:0050778~positive regulation of immune response | 1.39E−30 | 10.59041938 | 3.43E−27 | 6.86E−28 | 2.45E−27 |
| GOTERM_BP_FAT | GO:0001775~cell activation | 2.75E−30 | 7.006686129 | 6.79E−27 | 1.13E−27 | 4.85E−27 |
| GOTERM_BP_FAT | GO:0046649~lymphocyte activation | 6.60E−29 | 8.451555073 | 1.63E−25 | 2.32E−26 | 1.16E−25 |
| KEGG_PATHWAY | hsa04650: Natural killer cell mediated cytotoxicity | 1.68E−28 | 7.031371532 | 1.78E−26 | 1.78E−26 | 1.88E−25 |
| GOTERM_BP_FAT | GO:0042110~T cell activation | 2.44E−28 | 11.02668383 | 6.01E−25 | 7.51E−26 | 4.29E−25 |
| KEGG_PATHWAY | hsa04660: T cell receptor signaling pathway | 1.91E−27 | 7.757024266 | 2.02E−25 | 1.01E−25 | 2.14E−24 |

TABLE 12b

Top 10 enriched KEGG and GO terms (using DAVID) in the 446-gene module relative to the whole genome.

| Module | Category | Term | P Value | Fold Enrichment | Bonferroni | Benjamini | FDR |
|---|---|---|---|---|---|---|---|
| 446 gene | GOTERM_BP_FAT | GO:0006955~immune response | 2.92E−104 | 3.130862049 | 1.44E−100 | 1.44E−100 | 5.55E−101 |
| | GOTERM_BP_FAT | GO:0010941~regulation of cell death | 3.14E−85 | 2.726186103 | 1.55E−81 | 7.73E−82 | 5.96E−82 |
| | GOTERM_BP_FAT | GO:0043067~regulation of programmed cell death | 4.09E−85 | 2.728678557 | 2.01E−81 | 6.71E−82 | 7.77E−82 |
| | KEGG_PATHWAY | hsa04060: Cytokine-cytokine receptor interaction | 1.05E−84 | 3.192464986 | 1.72E−82 | 1.72E−82 | 1.28E−81 |
| | GOTERM_BP_FAT | GO:0042981~regulation of apoptosis | 3.02E−83 | 2.717554176 | 1.49E−79 | 3.72E−80 | 5.74E−80 |
| | GOTERM_BP_FAT | GO:0006952~defense response | 1.35E−74 | 2.892202076 | 6.63E−71 | 1.33E−71 | 2.56E−71 |
| | GOTERM_BP_FAT | GO:0010604~positive regulation of macromolecule metabolic process | 1.87E−73 | 2.542309068 | 9.19E−70 | 1.53E−70 | 3.55E−70 |
| | GOTERM_BP_FAT | GO:0009611~response to wounding | 1.49E−69 | 2.984442117 | 7.36E−66 | 1.05E−66 | 2.84E−66 |
| | GOTERM_BP_FAT | GO:0007243~protein kinase cascade | 4.28E−67 | 3.393394486 | 2.11E−63 | 2.63E−64 | 8.13E−64 |
| | GOTERM_BP_FAT | GO:0002684~posttive regulation of immune system process | 1.50E−66 | 4.06002401 | 7.40E−63 | 8.22E−64 | 2.86E−63 |

TABLE 12c

Top 10 enriched KEGG and GO terms (using DAVID) in the 758 gene module relative to the whole genome.

| Category | Term | P Value | Fold Enrichment | Bonferroni | Benjamini | FDR |
|---|---|---|---|---|---|---|
| GOTERM_BP_FAT | GO:0006955~immune response | 2.92E−104 | 3.130862049 | 1.44E−100 | 1.44E−100 | 5.55E−101 |
| GOTERM_BP_FAT | GO:0010941~regulation of cell death | 3.14E−85 | 2.726186103 | 1.55E−81 | 7.73E−82 | 5.96E−82 |
| GOTERM_BP_FAT | GO:0043067~regulation of programmed cell death | 4.09E−85 | 2.728678557 | 2.01E−81 | 6.71E−82 | 7.77E−82 |
| KEGG_PATHWAY | hsa04060: Cytokine-cytokine receptor interaction | 1.05E−84 | 3.192464986 | 1.72E−82 | 1.72E−82 | 1.28E−81 |
| GOTERM_BP_FAT | GO:0042981~regulation of apoptosis | 3.02E−83 | 2.717554176 | 1.49E−79 | 3.72E−80 | 5.74E−80 |
| GOTERM_BP_FAT | GO:0006952~defense response | 1.35E−74 | 2.892202076 | 6.63E−71 | 1.33E−71 | 2.56E−71 |
| GOTERM_BP_FAT | GO:0010604~positive regulation of macromolecule metabolic process | 1.87E−73 | 2.542309068 | 9.19E−70 | 1.53E−70 | 3.55E−70 |
| GOTERM_BP_FAT | GO:0009611~response to wounding | 1.49E−69 | 2.984442117 | 7.36E−66 | 1.05E−66 | 2.84E−66 |
| GOTERM_BP_FAT | GO:0007243~protein kinase cascade | 4.28E−67 | 3.393394486 | 2.11E−63 | 2.63E−64 | 8.13E−64 |
| GOTERM_BP_FAT | GO:0002684~positive regulation of immune system process | 1.50324E−66 | 4.06002401 | 7.40198E−63 | 8.22442E−64 | 2.85615E−63 |

Co-Expression Network Analysis

In order to further assess the applicability of the findings herein to patients diagnosed with primary melanoma, a co-expression network, consisting of 16,745 genes, (FIG. 17) was reconstructed using the 46 samples of gene expression data in primary melanoma patients (GEO accession ID: GSE15605)[26]. A 758-gene module (highlighted in yellow in FIG. 17) was found to be the most enriched for both the 53-gene panel and 446-gene panel. For the 53-gene panel, there was an enrichment fold of 13.75 with a p-value of 1.985e-31. An enrichment fold was similarly computed for the same module against the 446-gene panel, yielding an enrichment fold of 7.03 with p-value of 3.99e-80. The enrichment fold increased almost two times in the more refined set of genes, which indicates a higher correlation among the selected 53 genes than the original 446 genes. This data shows that the 53 gene panel is closely related to a module of genes with immune function discovered though unbiased network analysis of publicly available data from primary melanoma tumor samples.

Physical Interaction Network and Co-Expression Network Pathway Enrichment Analyses Next, experiments were conducted that sought to determine which functional pathways were enriched in our 53-gene panel. The gene lists generated by both the 53 and 446 gene networks were annotated with Pathway and GO molecular function. The top 10 most significant enriched pathways or GO terms are shown in Tables 12a and 12b, for the 446-gene panel network genes and the 53-gene panel network genes, respectively. Interestingly, the smaller network surrounding the 53 genes shows a higher enrichment of biological processes that characterize lymphocyte function and immune-surveillance. Moreover, the enrichment fold change (Table 12a) in the top enriched terms for the 53-gene panel network ranges from 5 to 11 fold whereas the enrichment fold change of the top 10 terms corresponding to the 446-gene panel network (Table 12b) ranges from just 2 to 4 fold. Therefore, there a higher functional enrichment was observed in the network induced by the 53-gene panel.

Finally, experiments were conducted that sought to determine whether the module identified in publicly available samples on GEO, correlated well functionally with our proposed 53-gene signature. The functional pathways enriched by the yellow module derived from the GEO model (FIG. 17) are listed in Table 12c. The top 10 terms are listed in Table 12c. Immune processes enriched for include T cell and NK cell related functions. These findings show that a module enriched for immune processes known to be implicated in immune surveillance is identified both in two independent melanoma patient populations of matched stage and also in publicly available primary melanoma data from GEO. These experiments find that, in the two populations for which clinical follow up is available, including a training set and a test set, higher expression of this immune surveillance module associates with non-progression.

TABLE 14

Gene expression samples in Primary melanoma patients from GEO (GSE15605)

| GEO sample | Phenotype |
| --- | --- |
| GSM390224 | Primary_melanoma MEL101 |
| GSM390225 | Primary_melanoma MEL128 |
| GSM390226 | Primary_melanoma MEL131 |
| GSM390227 | Primary_melanoma MEL135 |
| GSM390228 | Primary_melanoma MEL142 |
| GSM390229 | Primary_melanoma MEL145 |
| GSM390230 | Primary_melanoma MEL157 |
| GSM390231 | Primary_melanoma MEL173 |
| GSM390232 | Primary_melanoma MEL176 |
| GSM390233 | Primary_melanoma MEL185 |
| GSM390234 | Primary_melanoma MEL190 |
| GSM390235 | Primary_melanoma MEL197 |
| GSM390236 | Primary_melanoma MEL209 |
| GSM390237 | Primary_melanoma MEL213 |
| GSM390238 | Primary_melanoma MEL233 |
| GSM390239 | Primary_melanoma MEL236 |
| GSM390240 | Primary_melanoma MEL243 |
| GSM390241 | Primary_melanoma MEL244 |
| GSM390242 | Primary_melanoma MEL250 |
| GSM390243 | Primary_melanoma MEL257 |
| GSM390244 | Primary_melanoma MEL258 |
| GSM390245 | Primary_melanoma MEL272 |
| GSM390246 | Primary_melanoma MEL275 |
| GSM390247 | Primary_melanoma MEL276 |
| GSM390248 | Primary_melanoma MEL280 |
| GSM390249 | Primary_melanoma MEL282 |
| GSM390250 | Primary_melanoma MEL283 |
| GSM390251 | Primary_melanoma MEL287 |
| GSM390252 | Primary_melanoma MEL290 |
| GSM390253 | Primary_melanoma MEL294 |
| GSM390254 | Primary_melanoma MEL298 |
| GSM390255 | Primary_melanoma MEL307 |
| GSM390256 | Primary_melanoma MEL310 |
| GSM390257 | Primary_melanoma MEL326 |
| GSM390258 | Primary_melanoma MEL339 |
| GSM390259 | Primary_melanoma MEL340 |
| GSM390260 | Primary_melanoma MEL356 |
| GSM390261 | Primary_melanoma MEL362 |
| GSM390262 | Primary_melanoma MEL364 |
| GSM390263 | Primary_melanoma MEL375 |

TABLE 14-continued

Gene expression samples in Primary melanoma patients from GEO (GSE15605)

| GEO sample | Phenotype |
| --- | --- |
| GSM390264 | Primary_melanoma MEL380 |
| GSM390265 | Primary_melanoma MEL385 |
| GSM390266 | Primary_melanoma MEL395 |
| GSM390267 | Primary_melanoma MEL420 |
| GSM390268 | Primary_melanoma MEL429 |
| GSM390269 | Primary_melanoma MEL430 |

TABLE 15

Clinical Characteristics of Patients with Primary Melanoma (Extracted Vs. Non-Extracted)

| Characteristic | Extracted (N = 88) | Unextracted (N = 16) | P Value |
| --- | --- | --- | --- |
| Sex | | | |
| Male -- no. (%) | 54 (61) | 11 (69) | 0.78 |
| female -- no. (%) | 34 (39) | 5 (31) | |
| Age* | | | |
| Median (range) -- no. | 66 (27-90) | 71.5 (46-77) | 0.645 |
| Location of Tumor | | | |
| Trunk -- no. (%) | 49 (56) | 12 (75) | 0.177 |
| Extremity -- no. (%) | 39 (44) | 4 (25) | |
| Pathological characteristics** | | | |
| Depth (mm) -- median (range) | 3 (1-30) | 2.45 (1-8) | 0.024 |
| Ulceration | | | |
| Absent -- no. (%) | 41 (47) | 10 (62) | 0.285 |
| Present -- no. (%) | 47 (53) | 6 (38) | |
| Mitoses -- median (range) | 4 (0-26) | 1 (0-10) | 0.0067 |
| Stage | | | |
| II -- no. (%) | 37 (42) | 9 (56) | 0.413 |
| III -- no. (%) | 51 (58) | 7 (44) | |
| Patient Outcome | | | |
| Development of Recurrent Disease | | | |
| Yes -- no. (%) | 43 (49) | 4 (25) | 0.103 |
| No -- no. (%) | 45 (51) | 12 (75) | |

*Age assessed for 8 patients in non-extracted set
**Mitosis assessed for 86 patients in extracted set and 14 patients in non-extracted set Example 5

Defining a Key 9 Gene Subnetwork Predictive of Melanoma Progression

In order to define key genes predictive of melanoma progression the 53 gene network was further refined to a smaller network. This smaller network was then validated in a larger validation set including patients with completely resected stage I-III melanoma and known progression status. Thus, the difference between this validation set and the earlier one for the 53 gene set is that patients with completely resected stage I disease which were provided to us by NYU and Geisinger Health Systems were also tested to test whether the more compact panel would also be applicable to stage I patients. The 9 genes resulting from this algorithm include: CD2, KLRK1, IFNAR1, HLAE, ITK, LCK, CD4, LGMN, IFI27.

ROC curves showing the predictive accuracy of this panel in the training and validation set are shown in FIG. 18 for the training set (A) and the validation set (B).

Statistical Methods:

In order to refine the 53 gene panel a cross-validation procedure was performed. We simulated 900 iterations of an 11-fold cross-validation on the training dataset with random sample reordering in each iteration to strengthen the robustness of our final classifier model. Going from the top of the list to the bottom of the training cohort, every 4 samples were removed. These sample sets were then used as training data to fit a statistical model. 10,000 model training tasks were performed. The trained model and gene predictors selected were recorded in each task yielding 10,000 models and 10,000 lists of gene predictors based on randomly sub-sampled training samples. For each model, a classification was performed for the entire training (40 samples) and validation datasets (70 samples).

To derive a robust list of gene hits by these models, the 10,000 gene lists were pooled and the statistical count of each gene (out of 446 genes) was selected by these models using the training cohort only. A higher count value for a given gene indicates that it is frequently selected as a predictor during the cross-validation process. Finally, all genes selected at least once in the 10,000 cross-validation were put into a final model training task to yield an optimal, compact predictor gene list of 9 genes.

Ensemble Classification/Regression Method

A two-step sequential ensemble classification scheme that sequentially concatenated two widely applied classifiers: random forest and elastic net, was employed. Random forest itself is an ensemble classifier consisting of many decision trees that generates the mode of individual classes yielded by independent trees. A powerful variable selector and classification/regression method, elastic net integrates a linear regression model with Lasso and Ridge regularization. Elastic net is particularly useful when there are many more predictors than samples, serving to further exclude genes that are only correlated with, but not most predictive, of recurrence. This two-step ensemble classification scheme was applied to the cross-validated training data for the outer loop of the 900, 11-fold training cross-validation data points.

Random Forest

With 446 genes as an initial set of features and 40 samples from the cross-validation used as training data, a random forest model was fit. Initially, random forest was run without feature selection to determine the importance of all 446 genes based on various metrics in the RandomForest R package.[2] Next, an independent run was started that incorporated feature selection into random forest by sequentially reducing a certain number of predictors, ranked by variable importance, by employing a nested cross-validation procedure. In the simulation, a leave-one-out strategy was used. In each internal cross-validation, we removed (step=30%) the least important genes/features, ranked by variable importance, from the last cross-validation iteration. Next, we drew (Ntree=50 k) bootstrap samples from the original data (40 samples). For each of the bootstrap samples, an untrimmed classification/regression tree with randomly selected (mtry=22) genes was generated from the pool of genes leftover following removal. Following cross-validation, the number of genes that resulted in the lowest error rate among all the cross-validation runs was selected. This number represents the number of genes ($N_{RF}$) selected by random forest after cross-validation. Next, we selected the top $N_{RF}$ genes based on the averaged gene rank from the initial run without feature selection, yielding the final gene selections by random forest. The selected genes $G_{RF}$ were used as input for an elastic net model in order to identify the constituents of a gene signature predictive of melanoma recurrence.

Elastic Net

A powerful variable selector and classification/regression method, elastic net integrates a linear regression model with Lasso and Ridge regularization.[3] Elastic net is particularly useful when there are many more predictors than samples, serving to further exclude genes that are only correlated with, but not most predictive of recurrence. In each round of 11-fold cross-validation on the training data, there were 40 training samples. The number of genes selected by random forest varied from 50 to 446 depending on both the leave-one-out training data and randomized feature selection used during decision tree growth. Elastic net extends the basic form of linear/logistic regression via L1 and L2-regularization. $\lambda$ controls the model complexity with higher values resulting in a less complex model (less number of genes). $\alpha$ controls the balance between two types of model complexity penalties, including the ridge-regression penalty ($\alpha=0$) and the lasso penalty ($\alpha=1$). The Ridge penalty is particularly useful when there are more genes and fewer samples. Ridge regression is known to shrink the coefficients of correlated predictors towards each other. In contrast, lasso tends to pick one out of an entire set and ignore the rest. In our study, we set $\alpha=0.2$ and used an internal leave-one-out cross-validation to select an optimal value of $\lambda$.[4] The input training data was a subset of the original training data based on the gene lists $G_{RF}$ determined by random forest. The output gene lists by elastic net with non-zero coefficients is our final gene list $G_{EN}$ for the cross-validation run.

Final Gene List Generation

Employing the two-step ensemble classification method outlined above, the gene list $G_{EN}$ was recorded for each of the 11-fold data cross-validation runs. After more than 900 runs, we collected 10,000 lists of final genes were from the cross-validation training data. We counted the number of times each gene was selected among the 10,000 lists and calculated the p-value for the count distribution against otherwise random selection. Since this combined gene list compressed 10 k lists in the cross-validation based on different subsampled training data, it may contain correlated genes from different runs. Therefore, to filter these out and obtain the final gene signature, elastic net was used again with the same parameter configurations outlined previously ($\alpha=0.2$, $\lambda$ retrained based on the cross-validation of the 53-gene subset training data) for all 44 training samples. This yielded the 9 genes composing our gene signature.

Defining a Key 4 Gene Subnetwork Predictive of Melanoma Progression

A 4 gene subnetwork with predictive value was identified in the two independent populations. These genes are: CD2, KLRK1, HLAE, and ITK and AUC curves are shown in FIGS. 18 C and D for the training and validation sets respectively.

Example 6

Defining the Role of CD2 in Disease Progression and Overall Survival Among Patients with Completely Resected Stage II-III Cutaneous Melanoma Abstract Background: Accurate assessment of prognosis remains clinically challenging in stage II-III cutaneous melanoma. Studies have implicated CD2 in immune surveillance, T-cell activation and anti-tumor immunity, but its role in melanoma progression warrants further investigation.

Objective: To investigate the prognostic role of CD2 in primary cutaneous melanoma Methods: Patients with American Joint Committee on Cancer Stage II and III cutaneous melanoma were identified by retrospective review of dermatopathology databases from 2001-2010 at Mount Sinai Medical Center and Geisinger Medical Center. Additional patients were provided by New York University Medical Center based on tissue availability. Immunohistochemistry was performed on tumors from 90 patients with known recurrence status and documented follow-up.

Results: Primary tumors from patients who developed recurrent disease had fewer CD2-positive cells (p=0.0003). In multivariable analyses including standard clinicopathologic predictors, CD2 was an independent predictor of disease recurrence (p=0.008) and overall survival (p=0.007). CD2 count correlated with characterization of tumor infiltrating lymphocytes (TILs) (p=0.0004). Among the intermediate prognosis group of patients with non-brisk TILs, CD2 count was predictive of disease recurrence (p=0.0006) and overall survival (p=0.0318).

Limitations: The retrospective design of this study may have resulted in incomplete representation of patients lacking documented follow-up.

Conclusions: CD2 may be an independent predictor of disease recurrence and overall survival among patients with primary cutaneous melanoma.

Abbreviations and Acronyms:
AJCC—American Joint Committee on Cancer
IHC—Immunohistochemistry
TILs—Tumor-infiltrating lymphocytes
Ig—Immunoglobulin
NK—Natural killer
IRB—institutional review board
HPF—high-powered fields Capsule Summary:
  Melanoma is the deadliest form of skin cancer and accurate prognostication remains clinically challenging
  CD2 immunohistochemistry correlates with non-recurrence and improved overall survival among patients with Stage II-III cutaneous melanoma
  CD2 immunohistochemistry may inform clinician and patient decision-making regarding treatment and follow-up Introduction Melanoma is a devastating disease that is steadily increasing in incidence. An estimated 1 million survivors are living in the United States, and an additional 76,250 individuals will be diagnosed in 2012 alone[80]. The current American Joint Committee on Cancer (AJCC) staging system, revised in 2009, emphasizes the importance of tumor thickness, ulceration and mitotic rate in predicting prognosis. Further, the presence of a single melanoma cell by immunohistochemistry (IHC) within a lymph node is considered stage III disease[81]. While survival generally correlates with AJCC staging, the subgroup of stage II and stage III patients has a variable prognosis, with 5-year survival rates ranging from 24%-70%[81,82]. Further, while surgical resection is often curative, patients who develop recurrent disease are at a high-risk for unfavorable outcomes. Though rates vary widely with depth of the primary lesion, some studies report that up to one-third of all patients treated for primary cutaneous melanoma will experience disease recurrence[83-85]. Thus there is a need for additional biomarkers capable of enhancing prognostication and guiding clinical follow-up for these high-risk patients.

For many years, studies have demonstrated the critical role of the host immune system in the development or progression of melanoma. Interestingly, the evolving interaction between the immune system and tumor cells can result in elimination of malignant cells—a phenomenon known as immune-surveillance[86]. When elimination is incomplete, the tumor and immune cell microenvironment enter a state of equilibrium, where tumor growth is controlled by the immune system. Ultimately, however, continuous selection pressure by infiltrating immune cells can lead to an escape phase, where tumor cells are unrecognized by the immune system or induce an immunosuppressive microenvironment[86]. The presence of tumor-infiltrating lymphocytes has been associated with decreased lymphatic spread and improved survival in patients with cutaneous melanoma though studies have demonstrated inconsistencies in TIL characterization, limiting its use in clinical practice[87,88]. Additional immune based markers might add to the predictive value of TILs.

CD2 is a member of the immunoglobulin (Ig) superfamily shown to be present on T-cells, thymocytes and natural-killer (NK) cells. Various studies have implicated CD2 in immune surveillance, T-cell activation and anti-tumor immunity[89-91]. CD2 is expressed at much higher levels on activated and memory T cells than on naïve T cells, and it binds LFA3 expressed by antigen presenting cells[97,98]. The interaction between CD2 and LFA3 enhances IL-2 production in response to antigen stimulation[92,93]. CD2 polymorphisms have been associated with systemic auto-immunity, and, more recently gene expression studies in stage II-IV melanoma have implicated CD2, among other immune genes, in prognostic molecular signatures[94-96]. CD2 has also been implicated in the adhesion of T cells to their target including tumor cells[97,98]. Examples herein examine the role of CD2 as a biomarker in cutaneous melanoma and its ability to enhance the predictive power of infiltrating lymphocyte characterization.

Results

Patients

Unstained charged slides were obtained from 90 patients with Stage II or Stage III primary melanoma with documented follow-up and available tissue. These included 25 patients from MSMC, 39 patients from GMS and 26 patients from NYU. Patient demographics are shown in Table 16. The majority of patients were male (59 patients) and elderly, with a median age of 69 years (range 27-90). The median depth of primary melanoma was 3 mm (range 1.2-30). 59 patients presented with American Joint Committee on Cancer (AJCC) Stage II disease, while 31 presented with AJCC stage III disease. Patient and tumor characteristics were consistent across the three contributing institutions with the exception of greater depth in the NYU cases and shorter follow-up in the non-recurrent MSMC cases (Table 19).

TABLE 16

Clinicopathologic Characteristics of 90 Patients with Cutaneous Melanoma

| Characteristic | Value |
| --- | --- |
| Age (years), median (range) | 69 (27-90) |
| Gender--no. (%) | |
| Male | 59 (66) |
| Female | 31 (34) |

TABLE 16-continued

Clinicopathologic Characteristics of 90 Patients with Cutaneous Melanoma

| Characteristic | Value |
|---|---|
| Site of Primary Lesion--no. (%) | |
| Axial | 52 (58) |
| Extremity | 38 (42) |
| Thickness (mm) | |
| Mean | 4.19 |
| Median (range) | 3 (1.2-30) |
| Ulceration--no. (%) | |
| Yes | 51 (57) |
| No | 39 (43) |
| Stage, no. (%) | |
| Stage IIA | 27 (30) |
| Stage IIB | 18 (20) |
| Stage IIC | 14 (16) |
| Stage III | 31 (34) |
| Sentinel Lymph Node (SLN) Status--no. (%) | |
| Positive | 31 (34) |
| Negative | 59 (66) |
| Number of mitoses--median (range) | 4 (0-30) |
| Development of Recurrent Disease--no. (%) | |
| Yes | 45 (50) |
| No | 45 (50) |

Half of all patients experienced disease recurrence (45 patients). Known clinicopathologic predictors of poor prognosis, including tumor depth, patient age and AJCC Stage, significantly differed between recurrent and non-recurrent patients (Table 17). Among patients developing recurrent disease, the median time to recurrence was 13.5 months (range 2-72 months). Non-recurrent patients remaining disease-free had a median follow-up of 54 months (range 26-132 months).

TABLE 17

Comparison of Clincopathologic Characteristics of Recurrent and Non-recurrent Patients

| Characteristic | Recurrent (n = 45) | Non-recurrent (n = 45) | P-value |
|---|---|---|---|
| Age (years)--median (range) | 71 (28-87) | 64.5 (27-90) | 0.0281 |
| Gender--no. (%) | | | 1.0000 |
| Male | 30 (67) | 29 (64) | |
| Female | 15 (33) | 16 (36) | |
| Site of Primary Lesion--no. (%) | | | 0.8312 |
| Axial | 27 (60) | 25 (56) | |
| Extremity | 18 (40) | 20 (44) | |
| Thickness (mm) | | | 0.0085 |
| Mean | 5.25 | 3.12 | |
| Median (range) | 3.5 (1.4-30) | 2.6 (1.2-8.5) | |
| Ulceration- no. (%) | | | 0.0882 |
| Yes | 30 (67) | 21 (47) | |
| No | 15 (33) | 24 (53) | |
| Stage-no. (%) | | | 0.0246 |
| Stage IIA | 7 (16) | 20 (44) | |
| Stage IIB | 10 (22) | 8 (18) | |
| Stage IIC | 8 (18) | 6 (13) | |
| Stage III | 20 (44) | 11 (24) | |
| Sentinel Lymph Node Status--no. (%) | | | 0.0751 |
| Positive | 20 (44) | 11 (24) | |
| Negative | 25 (56) | 34 (76) | |
| Number of mitoses--median (range) | 4 (0-30) | 4 (0-17) | |
| Time to recurrence (months)--median (range) | 13.5 (2-72) | — | |
| Follow-up for non-recurrence (months)--median (range) | — | 54 (26-132) | |

CD2 Immunohistochemistry

Quantification of the number of CD2 positive cells per HPF was reproducible with good inter rater reliability (r=0.880, p<0.0001). The number of CD2 positive cells was significantly increased in primary melanomas from non-recurrent patients compared with recurrent patients (FIG. 19A+B, p=0.0003). Among recurrent patients, the median number of CD2 positive cells was 75.6 cells per HPF, compared with 37.5 cells per HPF for patients who subsequently developed recurrent disease. The number of CD2 positive cells per HPF was inversely correlated with SLN positivity, and positively correlated with improved overall survival (p=0.004 and p=0.003, respectively). CD2 did not significantly vary within Stage II substages (p=0.569), however there was a decrease in CD2 expression in stage III patients compared with stage II patients (FIG. 19C, p=0.0039). Additionally, using the median CD2 count to stratify the cohort into two groups, the high-CD2 group demonstrated superior overall survival (p=0.0065; FIG. 19D). After the inclusion of clinicopathologic predictors, the CD2 count was found to be an independent predictor of disease recurrence and overall survival (p=0.008 and p=0.007, respectively; Table 18). In a stepwise Cox Proportional Hazards analysis, the CD2 count significantly improved the ability of clinicopathologic variables to predict overall survival (p=0.004).

TABLE 18

Predictors of Disease Recurrence and Overall Survival

| | Predictors of Disease recurrence | | Predictors of overall Survival | |
|---|---|---|---|---|
| | Univariate | Multivariate | Univariate | Multivariate |
| Gender | 0.767 | 0.954 | 0.567 | 0.939 |
| Age | 0.028 | 0.020 | 0.014 | 0.011 |
| Site of Disease | 0.762 | 0.912 | 0.097 | 0.204 |
| Depth | 0.007 | 0.020 | 0.037 | 0.391 |
| Ulceration | 0.048 | 0.274 | 0.086 | 0.286 |
| Number of mitoses | 0.141 | 0.164 | 0.024 | 0.036 |
| SLN | 0.036 | 0.128 | 0.505 | 0.993 |
| CD2 count | 0.001 | 0.008 | 0.003 | 0.007 |

CD2 Expression on T-Cells and Natural Killer (NK)-Cells

Serial sections stained with antibodies for CD2 and CD3, a pan T-cell marker, demonstrated similar patterns of membrane staining within primary melanoma tumors (FIG. 20A). However, when quantified in the same manner, CD2 immunohistochemistry was a superior predictor of overall survival compared with CD3 immunohistochemistry (FIG. 23). Further, sections stained with antibodies against CD2 and CD16, a marker expressed by NK-cells, demonstrated dissimilar patterns of membrane staining but with slight overlap (FIG. 20B).

Immunoflourescent co-staining with antibodies against CD4, present on the subset of helper T-cells, and CD8, present of the subset of cytotoxic T-cells, demonstrated CD2 expression by both cell types (FIG. 21A). Further, serial sections demonstrated similar patterns of CD4, CD8 and CD2 staining by immunohistochemistry (FIG. 21B). To assess whether CD2 surface expression correlated with a change in the distribution of T-cell subtype, the ratio of CD4 to CD8 staining was compared in a subset of tumors with high CD2 expression and a subset with low CD2 expression. While ratios within individual tumors varied, overall the ratio of CD4 to CD8-positive T-cells was similar within tumors demonstrating high and low levels of CD2 staining (p=0.5167; FIG. 21B).

CD2 and Tumor Infiltrating Lymphocytes (TILs)

The number of CD2-positive cells significantly correlated with the characterization of TILs as absent, non-brisk and brisk (p=0.0004, FIG. 22B). The majority of the 70 cases evaluated (55 patients, 79%) were classified as having non-brisk TILs. Among this large group with non-brisk TILs, further classification in terms of topography (central, peripheral, both) and intensity (focal, multifocal, segmental) failed to distinguish recurrent from non-recurrent patients (FIG. 24). The CD2 count did not correlate with topography or intensity of TILs. However, the CD2 count remained predictive of disease recurrence and overall survival among patients with non-brisk TILs (p=0.0006 and p=0.0318, respectively; FIG. 22C-D).

were classified as regionally advanced recurrences. Non-recurrence was defined as no further evidence of melanoma following excision of the primary lesion. A minimum follow-up of two years was required for all non-recurrent patients. Additional patient samples meeting clinical criteria were contributed by New York University Medical Center in March 2012 based on tissue availability. All living patients were censored on Mar. 31, 2012 or on the last date of documented clinical follow-up if they were lost to follow-up prior to that date.

Patient demographics, tumor histopathologic features and clinical follow-up were extracted from electronic medical records by authorized personnel at each institution following approval by the institutional review board (IRB). Due to the retrospective nature of the study, treatment and monitoring following the diagnosis of primary melanoma were dictated by each patients' dermatologist and/or oncologist. Information was obtained from physician records of these visits. MSMC patients with incomplete clinical records were contacted by mail and telephone under an IRB approved protocol by authorized personnel to obtain clinical follow-up.

Immunohistochemistry

Immunohistochemistry (IHC) was performed on 5-micron charged slides obtained from eligible patients with known clinical follow-up. Cut sections from each tumor specimen were deparaffinized in xylene, rehydrated in ethanol and stained with an anti-CD2 monoclonal antibody (pre-diluted, Ventana Medical Systems, Tucson, Ariz.) using

TABLE 19

Comparison of Clincopathologic Characteristics Among Contributing Institutions

| Characteristic | GMS (n = 39) | MSSM (n = 25) | NYU (n = 26) | P-value |
| --- | --- | --- | --- | --- |
| Age (years), median (range) | 66.5 (29-86) | 71 (27-87) | 67 (28-90) | 0.3230 |
| Gender--no. (%) | | | | |
| Male | 27 (69) | 16 (64) | 16 (62) | 0.8002 |
| Female | 12 (31) | 9 (36) | 10 (38) | |
| Site of Primary Lesion--no. (%) | | | | 0.4217 |
| Axial | 25 (64) | 12 (48) | 14 (54) | |
| Extremity | 14 (36) | 13 (52) | 12 (46) | |
| Thickness (mm) | | | | 0.0006* |
| Mean | 3.07 | 4.16 | 5.89* | |
| Median (range) | 2.6 (1.2-13) | 3.25 (1.7-11) | 4.15 (1.4-30) | |
| Ulceration--no. (%) | | | | 0.0894 |
| Yes | 17 (44) | 17 (68) | 17 (65) | |
| No | 22 (56) | 8 (32) | 9 (35) | |
| Number of mitoses, median (range) | 6 (0-26)* | 3 (0-30) | 3 (0-14) | 0.0260* |
| Stage--no. (%) | | | | 0.1622 |
| Stage II | 21 (54) | 20 (80) | 17 (65) | |
| Stage III | 18 (46) | 5 (20) | 9 (35) | |
| Time to recurrence (months), median (range) | 12 (3-72) | 9 (2-36) | 15 (7-35) | 0.3232 |
| Follow-up for non-recurrence (months), median (range) | 70 (30-132) | 32 (27-71)* | 55 (26-110) | 0.0006* |
| CD2 Count (cells per HPF), median (range) | 46.3 (4.13-161.9) | 70.9 (7.1-171.5) | 52.3 (0.63-118.5) | 0.1977 |

Materials and Methods

Patient Selection

A retrospective review of dermatopathology database records from 2001-2010 at The Mount Sinai Medical Center (MSMC) and Geisinger Medical Center (GMC) was conducted between July 2010 and July 2011. Patients with American Joint Committee on Cancer (AJCC) Stage II or Stage III primary melanoma were selected for possible inclusion[81]. Disease recurrence was defined as local, regionally advanced or systemic. Local recurrences were those occurring within the scar of the primary resection. Cutaneous lesions beyond the resection scar, as well as clinically palpable lymph nodes found to contain malignant melanoma the Ventana BenchMark XT immunostainer. Staining was visualized using the i-View DAB kit solutions (Ventana Medical Systems, Tucson, Ariz.). Each slide set included a negative control without the addition of primary antibody to confirm specificity of the stain. Once stained, each slide was evaluated twice independently by blinded investigators using an ocular micrometer with a 1 mm$^2$ 130 grid (Nikon Eclipse E400®) and the number of CD2 positive cells in 8 high-powered fields (HPF) per slide was counted. Scores for each slide were averaged to yield a single score for use in subsequent analyses. A subset of tumors with available tissue were stained and quantified in an identical manner using anti-CD3 monoclonal antibody (pre-diluted, Ventana Medical Systems, Tucson, Ariz.).

IHC was also performed on serial 5-micron sections cut from a subset of tumors. Serially sectioned slides were stained with anti-CD4 (pre-diluted, Ventana Medical Systems, Tucson, Ariz.) and anti-CD8 (pre-diluted, Ventana Medical Systems, Tucson, Ariz.) as described above. One adjacent section was stained with anti-CD16 monoclonal antibody (2H7, 1:20 dilution, Thermo Scientific Lab Vision, Kalamazoo, Mich.). Slides were deparaffinized in xylene and rehydrated in ethanol. Following antigen retrieval in 10 mmol/L citrate solution, endogenous peroxidase activity was blocked with 3% hydrogen peroxide in phosphate buffered saline. Following blocking for non-specific binding, slides were incubated with anti-CD16 antibody overnight at 4° C. Staining was detected using diaminobenzine (Sigma-Aldrich, Saint Louis, Mo.) and slides were counterstained with Mayer's hematoxylin. As CD16 146 is also expressed on the surface of macrophages, membrane staining was evaluated by a dermatopathologist to ensure its expression on NK-cells.

Immunofluorescence

Charged slides from a subset of tumors were deparaffinized in xylene, rehydrated in ethanol and heated in ethylenediaminetetraacetic acid (EDTA) pH 9.0 for antigen retrieval. Slides were then co-stained with anti-CD2 (1:40 dilution, Dako, Glostrup, Denmark) and anti-CD3 (pre-diluted, Ventana Medical Systems, Tucson, Ariz.) monoclonal antibodies. Staining was visualized using fluorochrome-conjugated secondary antibodies. Slides were sealed using mounting media with 4',6-diamidino-2-phenylindole (DAPI). Additional slides were co-stained in the same manner using anti-CD2 (1:40 dilution) and anti-CD4 (1:100 dilution, Abcam, Cambridge, Mass., USA) or anti-CD2 and anti-CD8 (1:100 dilution, Abcam, Cambridge, Mass., USA).

Tumor-Infiltrating Lymphocyte Characterization

Additional slides were stained with hematoxylin and eosin and reviewed by Dr. Robert G. Phelps, Director of the Department of Dermatopathology at MSMC. TILs were characterized as brisk, non-brisk and absent according to published criteria[99]. Brisk lymphocytic infiltration was used to describe lymphocyte density greater than 20 lymphocytes per high-powered field throughout the lesion. Non-brisk was used to describe collections of a few lymphoctyes per high-powered field. Non-brisk tumor-infiltrating lymphocytes were further characterized in terms of their topography and intensity within the tumor. TIL topography was classified as central, peripheral or both and intensity was classified as focal, multifocal or segmental. Focal infiltration was used to describe a single collection of a few lymphocytes. Multifocal describes multiple collections of a few lymphocytes. Segmental describes a large collection 170 of lymphocytes occupying a substantial portion of the vertical growth phase[100].

Statistical Analysis

Patient demographics were analyzed using the Student's t-test for continuous variables and the Fisher's exact test for categorical variables. CD2 count was analyzed as a continuous variable using the Student's t-test. Number of CD2 positive cells was correlated with disease recurrence and overall survival using univariable logistic regression and Cox proportional hazards models, respectively, in SPSS Statistical Analysis Software Package Version 20. The predictive power of CD2 was also examined in the context of known clinical predictors using multivariable logistic regression and Cox proportional hazards models. The relationship between CD2 and overall survival was also examined using the Kaplan-Meier method and log-rank test in GraphPad Prism Version 5.0. The relationship between the number of CD2 positive cells and the number of CD4 and CD8 positive cells was analyzed using Spearman correlation in GraphPad Prism Version 5.0. The relationship between the CD2 count and various TILs characterizations was analyzed using the Kruskal-Wallis test in GraphPad Prism Version 5.0.

Discussion

Patients with history of melanoma are at risk of recurrence and death. Current predictors used in staging do not accurately assess prognosis for individuals.[1] Although the host immune system may modulate melanoma progression, no evidence-based immune biomarkers are in clinical use.[2]

Technological developments now allow for the analysis of partially degraded RNA, facilitating analysis of FFPE melanoma. Through the use of molecular "barcodes," NanoString technology quantifies gene expression based on individual mRNA transcripts with a high level of precision and sensitivity.[3, 4]

The role of the immune system in melanoma progression is complex. Although studies of intransit metastasis (advanced stage III) have suggested that inflammation plays a protective role in disease progression, it is well established that melanoma is able to co-opt the immune system by recruiting regulatory T cells as well as myeloid cell types that promote angiogenesis.[18-22] Tumor infiltrating lymphocytes (TILs) have been reported to favorably impact prognosis in primary melanoma, particularly if the deepest portion of the tumor was studied.[23-26] TIL quantification, however, is not routinely performed due to variability in pathologic interpretation as well as a lack of consistent correlation with outcome.[27-29]

Although the immune system has been proposed to limit melanoma progression, the exact mechanisms and clinical relevance of immune activation remain to be elucidated.[30] The studies described herein sought to determine whether expression patterns of immune-associated genes correlate with tumor recurrence in patients with previously excised localized melanoma.

In order to define a biomarker for melanoma recurrence, the expression of immune-related genes from formalin-fixed, paraffin-embedded (FFPE) primary melanoma was measured using NanoString, a hybridization assay uniquely suited for quantifying gene expression in samples with partially degraded RNA.[3, 4]

This work represents the first time an immune biomarker based on gene expression measured in FFPE tissues has been proposed for early-stage malignancy in humans. FFPE tissues are easier to obtain than frozen specimens, which require careful intra-operative processing. Using NanoString technology, a 21-immune gene signature was established which was predictive of recurrence with greater accuracy than any currently established predictor.

FFPE tissue and corresponding clinical information were obtained in 44 consecutive patients who had complete resection of primary melanoma. mRNA transcripts of 446 genes were measured. Immunohistochemistry (IHC) was used to assess protein expression of the most differentially expressed gene, CD2. Findings were validated in an independent cohort of 37 patients.

Expression profiling yielded a panel of 21 immune genes predictive of melanoma recurrence using receiver operating characteristic (ROC) curves. This panel was validated in an independent patient cohort (AUC=0.794) and correlated with improved overall survival (p<0.001). CD2 expression correlated with non-recurrence (p=0.017).

The role of the immune system in tumor development is complex, with evidence to support both protective and harmful roles for a variety of immune cell types.[32, 33] Nonetheless, there is convincing pre-clinical and clinical data that tumors undergo immune-editing whereby immunogenic clones are controlled and/or eliminated.[34, 35] The role of tumor immunosurveillance in humans is best established in colon cancer where lymphocytic infiltrates and expression of genes implicated in adaptive immunity correlate closely with prognosis.[36, 37] In melanoma, evidence for immunosurveillance was found in a previous study of cutaneous metastasis in patients with stage III disease.[20]

In the study of primary tumors described herein, also led to the discovery that higher expression of immune genes is associated with lower risk of recurrence and, although genes known to have regulatory functions were tested, these genes did not confer a poor prognosis. The data discussed herein strongly implicates a protective role for the immune system during melanoma development.

Immune gene expression showed higher correlation with recurrence and death than standard clinical predictors. Notably, pathological features characterizing melanoma are subject to observer bias.[29] In the studies described herein, the presence or absence of immune infiltrate was not predictive of prognosis in either patient cohort, but more closely correlated with the institution where the melanoma was examined. In contrast, the proposed gene signature provides an objective, more accurate indicator for risk of disease recurrence than available clinical and pathologic predictors.

Due to the small volume of specimen available from primary melanoma, it was not feasible to micro-dissect stroma from tumor. Therefore, in the studies described herein, genes may be expressed by the tumor itself and/or by stromal cells. However, CD2 is expressed by T, NK, and NKT lymphocytes, and increased CD2 levels likely indicate increased anti-melanoma immunity.[38, 39] Genes identified in the panel are implicated in cutaneous T cell trafficking and activation, interferon signaling, antigen presentation, and natural killer activity. Thus, without wishing to be bound by any scientific theory, it is speculated that the observed patterns of gene expression between patients with recurrent and non-recurrent disease are the result of an interaction between the tumor and host immune system that plays a determinative role in tumor progression. Findings presented herein lead to the development of a biomarker that informs clinicians as to which patients warrant close observation and follow up, and allow for improved stratification of patients in clinical trials.

A 21-immune gene signature is predictive of recurrence and mortality in early-stage melanoma. These data provide evidence that the immune system limits progression of early-stage melanoma and demonstrate that expression analysis of FFPE specimens yield prognostic information. A novel way to identify early-stage melanoma patients at high risk of recurrence and death is established herein.

Defining the Role of CD2 in Disease Progression and Overall Survival Among Patients with Completely Resected Stage II-III Cutaneous Melanoma.

The patients in Example 6 represent a clinically high-risk primary melanoma population. Half of the population experienced some form of disease recurrence, which is consistent with estimates for patients with AJCC Stage III disease.[81, 101] Standard predictors, including depth and patient age, correlated with disease recurrence in our population as has been previously shown.

The data of Example 6 demonstrated that CD2 expression levels within the primary tumor associate with non-recurrence and prolonged survival in 90 patients with stage II-III cutaneous melanoma. CD2 has been implicated in melanoma specific anti-tumor immunity in the past. Altomante et al suggested that the interaction between immune cells and malignant cells of the melanocytic lineage was mediated in part by CD2 expressing lymphocytes[102]. More recently, Bogunovic et al described an immune response gene expression signature, including CD2, predictive of improved survival in metastatic melanoma15. Our study expands upon these findings by demonstrating that increased CD2 staining in primary melanoma tissue sections correlates with a lower recurrence rate and improved overall survival.

Characterization of TILs is complicated by heterogeneity in the composition and location of these cells. Tumor-infiltrating lymphocytes may be "helper" T-cells (CD4 positive), "cytotoxic" T cells (CD8 positive), NK-cells, B-cells or the counterproductive regulatory T-cell, which limits the host immune response[103]. The results in Example 6 demonstrate CD2 expression predominantly on T-cells, both CD4-positive and CD8-positive, but also on NK-cells. Thus, CD2 may be a specific indicator of activated or anti-tumor infiltrating lymphocytes. Additionally, TIL characterization is inconsistently reported and subject to inter-rater variability. Monshizadeh et al examined concordance between referring pathologists and pathologists reviewing cases for the Western Australia Melanoma Advisory Service (WAMAS). They found that TILs were not reported in 51% of cases referred to WAMAS, and further found only slight agreement in those that did report TILs (52.4%, κ=0.12)[88]. Similarly, a multi-site review of histopathology reports found that only 54.2% included information about lymphocytic infiltration[104]. CD2 immunohistochemistry may be a widely accessible, more objective method for TIL characterization.

Finally, while a brisk lymphocytic infiltrate has been shown to be strongly protective, this designation only applies to a minority of patients[87]. In the population of Example 6, tumor-infiltrating lymphocytes were characterized by the Department of Dermatopathology (RGP). More than 75% of patients were classified as having non-brisk TILs, an intermediate category that adds little to the clinician's estimation of risk. The Examples herein have demonstrated that CD2 immunohistochemistry may be useful to estimate prognosis in this large subpopulation.

Limitations

Due to the retrospective nature of the study in Example 6, reporting standards and follow-up guidelines were heterogeneous across the population. Further, due to the requirement of a minimum of 24-months of clinical follow-up, the study did not capture patients who had not recurred but for whom limited follow up was available. The prognostic role of CD2 should be validated prospectively in an independent cohort to address these limitations.

CONCLUSION

Accurate assessment of prognosis at an individual patient level in Stage II and Stage III primary melanoma represents a clinical challenge. Recurrence and survival estimates range widely, and treatment options span from observation alone to enrollment in clinical trials[105]. The results provided herein demonstrate that CD2 quantification by immunohistochemistry associates with non-recurrence and prolonged survival within this group of patients. Prospective studies may define a role for CD2 immunohistochemistry that helps patients and clinicians make informed decisions regarding treatment and follow-up, and may enhance stratification for studies of adjuvant therapies.

REFERENCES

1. Wolchok J D, Saenger Y M. Current topics in melanoma. Curr Opin Oncol 2007; 19:116-20.
2. Piris A, Mihm M C, Jr. Progress in melanoma histopathology and diagnosis. Hematol Oncol Clin North Am 2009; 23:467-80, viii.
3. Fortina P, Surrey S. Digital mRNA profiling. Nat Biotechnol 2008; 26:293-4.
4. Payton J E, Grieselhuber N R, Chang L W, et al. High throughput digital quantification of mRNA abundance in primary human acute myeloid leukemia samples. J Clin Invest 2009; 119:1714-26.
5. Jeffrey E, Gershenwald C M B, Seng-Jaw Soung, John F Thompson. Prognostic factors and natural history of melanoma. In: Chalres M Balch A N H, Arthur J Sober, Seng-jaw Soong, Michael B Atkins, John F Thompson, ed. Cutaneous Melanoma. Fifth ed. St Louis, Mo.: Quality Medical Publishing; 2009:35-64.
6. Balch C M, Soong S J, Gershenwald J E, et al. Prognostic factors analysis of 17,600 melanoma patients: validation of the American Joint Committee on Cancer melanoma staging system. J Clin Oncol 2001; 19:3622-34.
7. Green A C, Baade P, Coory M, Aitken J F, Smithers M. Population-based 20-year survival among people diagnosed with thin melanomas in queensland, australia. J Clin Oncol 2012; 30:1462-7.
8. Morton D L, Thompson J F, Cochran A J, et al. Sentinel-node biopsy or nodal observation in melanoma. N Engl J Med 2006; 355:1307-17.
9. Timar J, Gyorffy B, Raso E. Gene signature of the metastatic potential of cutaneous melanoma: too much for too little? Clin Exp Metastasis 2010; 27:371-87.
10. Oakman C, Santarpia L, Di Leo A. Breast cancer assessment tools and optimizing adjuvant therapy. Nat Rev Clin Oncol 2010; 7:725-32.
11. Conway C, Mitra A, Jewell R, et al. Gene expression profiling of paraffin-embedded primary melanoma using the DASL assay identifies increased osteopontin expression as predictive of reduced relapse-free survival. Clin Cancer Res 2009; 15:6939-46.
12. Winnepenninckx V, Lazar V, Michiels S, et al. Gene expression profiling of primary cutaneous melanoma and clinical outcome. J Natl Cancer Inst 2006; 98:472-82.
13. Smith A P, Hoek K, Becker D. Whole-genome expression profiling of the melanoma progression pathway reveals marked molecular differences between nevi/melanoma in situ and advanced-stage melanomas. Cancer Biol Ther 2005; 4:1018-29.
14. Koh S S, Opel M L, Wei J P, et al. Molecular classification of melanomas and nevi using gene expression microarray signatures and formalin-fixed and paraffin-embedded tissue. Mod Pathol 2009; 22:538-46.
15. Kabbarah O, Nogueira C, Feng B, et al. Integrative genome comparison of primary and metastatic melanomas. PLoS One 2010; 5:e10770.
16. Segura M F, Belitskaya-Levy I, Rose A E, et al. Melanoma MicroRNA signature predicts post-recurrence survival. Clin Cancer Res 2010; 16:1577-86.
17. Bittner M, Meltzer P, Chen Y, et al. Molecular classification of cutaneous malignant melanoma by gene expression profiling. Nature 2000; 406:536-40.
18. Taube J M, Anders R A, Young G D, et al. Colocalization of inflammatory response with B7-h1 expression in human melanocytic lesions supports an adaptive resistance mechanism of immune escape. Sci Transl Med 2012; 4:127ra37.
19. Wang E, Miller L D, Ohnmacht G A, et al. Prospective molecular profiling of melanoma metastases suggests classifiers of immune responsiveness. Cancer Res 2002; 62:3581-6.
20. Bogunovic D, O'Neill D W, Belitskaya-Levy I, et al. Immune profile and mitotic index of metastatic melanoma lesions enhance clinical staging in predicting patient survival. Proc Natl Acad Sci USA 2009; 106:20429-34.
21. Gajewski T F, Fuertes M, Spaapen R, Zheng Y, Kline J. Molecular profiling to identify relevant immune resistance mechanisms in the tumor microenvironment. Curr Opin Immunol 2011; 23:286-92.
22. Drake C G, Jaffee E, Pardoll D M. Mechanisms of immune evasion by tumors. Adv Immunol 2006; 90:51-81.
23. Tuthill R J, Unger J M, Liu P Y, Flaherty L E, Sondak V K. Risk assessment in localized primary cutaneous melanoma: a Southwest Oncology Group study evaluating nine factors and a test of the Clark logistic regression prediction model. Am J Clin Pathol 2002; 118:504-11.
24. Piras F, Colombari R, Minerba L, et al. The predictive value of CD8, CD4, CD68, and human leukocyte antigen-D-related cells in the prognosis of cutaneous malignant melanoma with vertical growth phase. Cancer 2005; 104:1246-54.
25. Day C L, Jr., Mihm M C, Jr., Sober A J, et al. Prognostic factors for melanoma patients with lesions 0.76-1.69 mm in thickness. An appraisal of "thin" level IV lesions. Ann Surg 1982; 195:30-4.
26. Clemente C G, Mihm M C, Jr., Bufalino R, Zurrida S, Collini P, Cascinelli N. Prognostic value of tumor infiltrating lymphocytes in the vertical growth phase of primary cutaneous melanoma. Cancer 1996; 77:1303-10.
27. Chao C, Wong S L, Ross M I, et al. Patterns of early recurrence after sentinel lymph node biopsy for melanoma. Am J Surg 2002; 184:520-4; discussion 5.
28. Scheri R P, Essner R, Turner R R, Ye X, Morton D L. Isolated tumor cells in the sentinel node affect long-term prognosis of patients with melanoma. Ann Surg Oncol 2007; 14:2861-6.
29. Busam K J, Antonescu C R, Marghoob A A, et al. Histologic classification of tumor-infiltrating lymphocytes in primary cutaneous malignant melanoma. A study of interobserver agreement. Am J Clin Pathol 2001; 115:856-60.
30. Parmiani G. Tumor-infiltrating T cells—friend or foe of neoplastic cells? N Engl J Med 2005; 353:2640-1.
31. Geiss G K, Bumgarner R E, Birditt B, et al. Direct multiplexed measurement of gene expression with color-coded probe pairs. Nat Biotechnol 2008; 26:317-25.
32. Colotta F, Allavena P, Sica A, Garlanda C, Mantovani A. Cancer-related inflammation, the seventh hallmark of cancer: links to genetic instability. Carcinogenesis 2009; 30:1073-81.
33. Allavena P, Sica A, Solinas G, Porta C, Mantovani A. The inflammatory micro-environment in tumor progression: the role of tumor-associated macrophages. Crit Rev Oncol Hematol 2008; 66:1-9.
34. Chow M T, Moller A, Smyth M J. Inflammation and immune surveillance in cancer. Semin Cancer Biol 2012; 22:23-32.
35. Koebel C M, Vermi W, Swann J B, et al. Adaptive immunity maintains occult cancer in an equilibrium state. Nature 2007; 450:903-7.

36. Galon J, Costes A, Sanchez-Cabo F, et al. Type, density, and location of immune cells within human colorectal tumors predict clinical outcome. Science 2006; 313:1960-4.
37. Fridman W H, Pages F, Sautes-Fridman C, Galon J. The immune contexture in human tumours: impact on clinical outcome. Nat Rev Cancer 2012; 12:298-306.
38. Altomonte M, Gloghini A, Bertola G, et al. Differential expression of cell adhesion molecules CD54/CD11a and CD58/CD2 by human melanoma cells and functional role in their interaction with cytotoxic cells. Cancer Res 1993; 53:3343-8.
39. Li Y, Hellstrom K E, Newby S A, Chen L. Costimulation by CD48 and B7-1 induces immunity against poorly immunogenic tumors. J Exp Med 1996; 183:639-44.
40. CD2 (MRQ-11) [package insert]. Tucson, Ariz.: Ventana Medical Systems; 2010.
41. Liaw A, Wiener M. Classification and regression by randomForest. R news 2002; 2(3):18-22.
42. Zou H, Hastie T. Regularization and variable selection via the elastic net. Journal of the Royal Statistical Society 2005; SeriesB:301-320.
43. Friedman J, Hastie T, Tibshirani R. Regularization paths for generalized linear models via coordinate descent. Journal of Statistical Software 2010; 33:1-22.
44. Bogunovic D, O'Neill D W, Belitskaya-Levy I, et al. Immune profile and mitotic index of metastatic melanoma lesions enhance clinical staging in predicting patient survival. Proc Natl Acad Sci USA 2009; 106:20429-34.
45. Budhu A, Forgues M, Ye Q H, et al. Prediction of venous metastases, recurrence, and prognosis in hepatocellular carcinoma based on a unique immune response signature of the liver microenvironment. Cancer Cell 2006; 10:99-111.
46. Conway C, Mitra A, Jewell R, et al. Gene expression profiling of paraffin-embedded primary melanoma using the DASL assay identifies increased osteopontin expression as predictive of reduced relapse-free survival. Clin Cancer Res 2009; 15:6939-46.
47. Desai K V, Michalowska A M, Kondaiah P, Ward J M, Shih J H, Green J E. Gene expression profiling identifies a unique androgen-mediated inflammatory/immune signature and a PTEN (phosphatase and tensin homolog deleted on chromosome 10)—mediated apoptotic response specific to the rat ventral prostate. Mol Endocrinol 2004; 18:2895-907.
48. Haass N K, Smalley K S. Melanoma biomarkers: current status and utility in diagnosis, prognosis, and response to therapy. Mol Diagn Ther 2009; 13:283-96.
49. Harlin H, Meng Y, Peterson A C, et al. Chemokine expression in melanoma metastases associated with CD8+ T-cell recruitment. Cancer Res 2009; 69:3077-85.
50. Hoek K S. Melanoma progression, gene expression and DNA microarrays. G Ital Dermatol Venereol 2009; 144:39-49.
51. Hoshida Y, Villanueva A, Kobayashi M, et al. Gene expression in fixed tissues and outcome in hepatocellular carcinoma. N Engl J Med 2008; 359:1995-2004.
52. Jaeger J, Koczan D, Thiesen H J, et al. Gene expression signatures for tumor progression, tumor subtype, and tumor thickness in laser-microdissected melanoma tissues. Clin Cancer Res 2007; 13:806-15.
53. Jonsson G, Busch C, Knappskog S, et al. Gene expression profiling-based identification of molecular subtypes in stage IV melanomas with different clinical outcome. Clin Cancer Res 2010; 16:3356-67.
54. Kannengiesser C, Spatz A, Michiels S, et al. Gene expression signature associated with BRAF mutations in human primary cutaneous melanomas. Mol Oncol 2008; 1:425-30.
55. Kashani-Sabet M, Venna S, Nosrati M, et al. A multimarker prognostic assay for primary cutaneous melanoma. Clin Cancer Res 2009; 15:6987-92.
56. Koh S S, Opel M L, Wei J P, et al. Molecular classification of melanomas and nevi using gene expression microarray signatures and formalin-fixed and paraffin-embedded tissue. Mod Pathol 2009; 22:538-46.
57. Mandruzzato S, Callegaro A, Turcatel G, et al. A gene expression signature associated with survival in metastatic melanoma. J Transl Med 2006; 4:50.
58. Riker A I, Enkemann S A, Fodstad O, et al. The gene expression profiles of primary and metastatic melanoma yields a transition point of tumor progression and metastasis. BMC Med Genomics 2008; 1:13.
59. Roepman P, Jassem J, Smit E F, et al. An immune response enriched 72-gene prognostic profile for early-stage non-small-cell lung cancer. Clin Cancer Res 2009; 15:284-90.
60. Ryu B, Kim D S, Deluca A M, Alani R M. Comprehensive expression profiling of tumor cell lines identifies molecular signatures of melanoma progression. PLoS One 2007; 2:e594.
61. Schwartzentruber D J, Hom S S, Dadmarz R, et al. In vitro predictors of therapeutic response in melanoma patients receiving tumor-infiltrating lymphocytes and interleukin-2. J Clin Oncol 1994; 12:1475-83.
62. Smith A P, Hoek K, Becker D. Whole-genome expression profiling of the melanoma progression pathway reveals marked molecular differences between nevi/melanoma in situ and advanced-stage melanomas. Cancer Biol Ther 2005; 4:1018-29.
63. Teschendorff A E, Caldas C. A robust classifier of high predictive value to identify good prognosis patients in ER-negative breast cancer. Breast Cancer Res 2008; 10:R73.
64. Timar J, Gyorffy B, Raso E. Gene signature of the metastatic potential of cutaneous melanoma: too much for too little? Clin Exp Metastasis 2010; 27:371-87.
65. Ugurel S, Utikal J, Becker J C. Tumor biomarkers in melanoma. Cancer Control 2009; 16:219-24.
66. Wang E, Miller L D, Ohnmacht G A, et al. Prospective molecular profiling of melanoma metastases suggests classifiers of immune responsiveness. Cancer Res 2002; 62:3581-6.
67. Winnepenninckx V, Lazar V, Michiels S, et al. Gene expression profiling of primary cutaneous melanoma and clinical outcome. J Natl Cancer Inst 2006; 98:472-82.
68. Geiss G K, Bumgarner R E, Birditt B, Dahl T, Dowidar N, Dunaway D L, Fell H P, Ferree S, George R D, Grogan T, James J J, Maysuria M, Mitton J D, Oliveri P, Osborn J L, Peng T, Ratcliffe A L, Webster P J, Davidson E H, Hood L, Dimitrov K. Direct multiplexed measurement of gene expression with color-coded probe pairs. Nat Biotechnol. 2008 March; 26(3):317-25. Epub 2008 Feb. 17.
69. Balch C M. Cutaneous Melanoma. 5th edition. Quality Medical Publishing, S.L., MO; 2009.
70. Korn, E. L., et al., Meta-analysis of phase II cooperative group trials in metastatic stage IV melanoma to determine progression-free and overall survival benchmarks for future phase II trials. J Clin Oncol, 2008. 26 (4): p. 527-34.

71. Rosenberg, S. A., J. C. Yang, and N. P. Restifo, Cancer immunotherapy: moving beyond current vaccines. Nat Med, 2004. 10 (9): p. 909-15.
72. Subramanian, J. and R. Simon, What should physicians look for in evaluating prognostic gene-expression signatures? Nat Rev Clin Oncol, 2010. 7 (6): p. 327-34.
73. Kauffmann, A., et al., High expression of DNA repair pathways is associated with metastasis in melanoma patients. Oncogene, 2008. 27 (5): p. 565-73.
74. Winnepenninckx, V., et al., Gene expression profiling of primary cutaneous melanoma and clinical outcome. J Natl Cancer Inst, 2006. 98 (7): p. 472-82.
75. Timar, J., B. Gyorffy, and E. Raso, Gene signature of the metastatic potential of cutaneous melanoma: too much for too little? Clin Exp Metastasis, 2010. 27 (6): p. 371-87.
76. Koh, S. S., et al., Molecular classification of melanomas and nevi using gene expression microarray signatures and formalin-fixed and paraffin-embedded tissue. Mod Pathol, 2009. 22 (4): p. 538-46.
77. Bogunovic, D., et al., Immune profile and mitotic index of metastatic melanoma lesions enhance clinical staging in predicting patient survival. Proc Natl Acad Sci USA, 2009. 106 (48): p. 20429-34.
78. Dobbin, K. and R. Simon, Sample size determination in microarray experiments for class comparison and prognostic classification. Biostatistics, 2005. 6 (1): p. 27-38.
79. Lee, W. C., Detecting Differentially Expressed Genes: Minimizing Burden of Testing and Maximizing Number of Discoveries. Ann Epidemiol, 2010.
80. Siegel R, DeSantis C, Virgo K, et al. Cancer treatment and survivorship statistics. CA Cancer J Clin 2012; 62:220-41.
81. Balch C M, Gershenwald J E, Soong S J, et al. Final version of 2009 AJCC melanoma staging and classification. Journal of clinical oncology: official journal of the American Society of Clinical Oncology 2009; 27:6199-206.
82. Ben-Porat L, Panageas K S, Hanlon C, et al. Estimates of stage-specific survival are altered by changes in the 2002 American Joint Committee on Cancer staging system for melanoma. Cancer 2006; 106:163-71.
83. Soong S J, Shaw H M, Balch C M, McCarthy W H, Urist M M, Lee J Y. Predicting survival and recurrence in localized melanoma: a multivariate approach. World J Surg 1992; 16:191-5.
84. Soong S J, Harrison R A, McCarthy W H, Urist M M, Balch C M. Factors affecting survival following local, regional, or distant recurrence from localized melanoma. J Surg Oncol 1998; 67:228-33.
85. Green A C, Baade P, Coory M, Aitken J F, Smithers M. Population-based 20-year survival among people diagnosed with thin melanomas in Queensland, Australia. Journal of clinical oncology: official journal of the American Society of Clinical Oncology 2012; 30:1462-7.
86. Aris M, Barrio M M, Mordoh J. Lessons from cancer immunoediting in cutaneous melanoma. Clin Dev Immunol 2012; 2012:192719.
87. Azimi F, Scolyer R A, Rumcheva P, et al. Tumor-infiltrating lymphocyte grade is an independent predictor of sentinel lymph node status and survival in patients with cutaneous melanoma. Journal of clinical oncology: official journal of the American Society of Clinical Oncology 2012; 30:2678-83.
88. Monshizadeh L, Hanikeri M, Beer T W, Heenan P J. A critical review of melanoma pathology reports for patients referred to the Western Australian Melanoma Advisory Service. Pathology 2012; 44:441-7.
89. Crawford K, Stark A, Kitchens B, et al. CD2 engagement induces dendritic cell activation: implications for immune surveillance and T-cell activation. Blood 2003; 102:1745-52.
90. Tibaldi E V, Salgia R, Reinherz E L. CD2 molecules redistribute to the uropod during T cell scanning: implications for cellular activation and immune surveillance. Proc Natl Acad Sci USA 2002; 99:7582-7.
91. Sabry M, Tsirogianni M, Bakhsh I A, et al. Leukemic priming of resting NK cells is killer Ig-like receptor independent but requires CD15-mediated CD2 ligation and natural cytotoxicity receptors. J Immunol 2011; 187: 6227-34.
92. Bierer B E, Peterson A, Gorga J C, Herrmann S H, Burakoff S J. Synergistic T cell activation via the physiological ligands for CD2 and the T cell receptor. J Exp Med 1988; 168:1145-56.
93. Moingeon P, Chang H C, Wallner B P, Stebbins C, Frey A Z, Reinherz E L. CD2-mediated adhesion facilitates T lymphocyte antigen recognition function. Nature 1989; 339:312-4.
94. Bogunovic D, O'Neill D W, 477 Belitskaya-Levy I, et al. Immune profile and mitotic index of metastatic melanoma lesions enhance clinical staging in predicting patient survival. Proc Natl Acad Sci USA 2009; 106:20429-34.
95. Mann G J, Pupo G M, Campain A E, et al. BRAF Mutation, NRAS Mutation, and the Absence of an Immune-Related Expressed Gene Profile Predict Poor Outcome in Patients with Stage III Melanoma. The Journal of investigative dermatology 2013; 133:509-17.
96. Sivendran S C R, Harcharik S, Hall L, Bernardo S, Moskalenko M, et al. Immune gene expression in primary melanomas to predict lower risk of recurrence and death [abstract]. In: 2013 ASCO Annual Meeting. Poster Discussion Session: Developmental Therapeutics—Immunotherapy; 2013 May 31-Jun. 4. Accepted. 2013.
97. Patarroyo M, Prieto J, Rincon J, et al. Leukocyte-cell adhesion: a molecular process fundamental in leukocyte physiology. Immunological reviews 1990; 114:67-108.
98. Wang A, Batteux F, Wakeland E K. The role of SLAM/CD2 polymorphisms in systemic autoimmunity. Current opinion in immunology 2010; 22:706-14.
99. Mihm M C, Jr., Clemente C G, Cascinelli N. Tumor infiltrating lymphocytes in lymph node melanoma metastases: a histopathologic prognostic indicator and an expression of local immune response. Lab Invest 1996; 74:43-7.
100. Rao U N, Lee S J, Luo W, Mihm M C, Jr., Kirkwood J M. Presence of tumor infiltrating lymphocytes and a dominant nodule within primary melanoma are prognostic factors for relapse-free survival of patients with thick (t4) primary melanoma: pathologic analysis of the e1690 and e1694 intergroup trials. Am J Clin Pathol; 133:646-53.
101. Leiter U, Buettner P G, Eigentler T K, et al. Hazard rates for recurrent and secondary cutaneous melanoma: an analysis of 33,384 patients in the German Central Malignant Melanoma Registry. J Am Acad Dermatol 2012; 66:37-45.
102. Altomonte M, Gloghini A, Bertola G, et al. Differential expression of cell adhesion molecules CD54/CD11a and CD58/CD2 by human melanoma cells and functional role in their interaction with cytotoxic cells. Cancer Res 1993; 53:3343-8.
103. Oble D A, Loewe R, Yu P, Mihm M C, Jr. Focus on TILs: prognostic significance of tumor infiltrating lymphocytes in human melanoma. Cancer Immun 2009; 9:3.

104. Thompson B, Austin R, Coory M, et al. Completeness of histopathology reporting of melanoma in a high-incidence geographical region. Dermatology 2009; 218:7-14.
105. Fox M C, Lao C D, Schwartz J L, Frohm M L, Bichakjian C K, Johnson T M. Management options for metastatic melanoma in the era of novel therapies: a primer for the practicing dermatologist: part I: Management of stage III disease. J Am Acad Dermatol 2013; 68:1 e-9; quiz 10-2.
106. Manolio T A, Chisholm R L, Ozenberger B, et al. Implementing genomic medicine in the clinic: the future is here. Genetics in medicine: official journal of the American College of Medical Genetics 2013; 15:258-67.
107. Balch C M, Gershenwald J E, Soong S J, Thompson J F. Update on the melanoma staging system: the importance of sentinel node staging and primary tumor mitotic rate. Journal of surgical oncology 2011; 104:379-85.
108. Pennock G K, Waterfield W, Wolchok J D. Patient responses to ipilimumab, a novel immunopotentiator for metastatic melanoma: how different are these from conventional treatment responses? American journal of clinical oncology 2012; 35:606-11.
109. Agarwala S S. An update on pegylated IFN-alpha2b for the adjuvant treatment of melanoma. Expert review of anticancer therapy 2012; 12:1449-59.
110. Eggermont A M, Suciu S, Testori A, et al. Long-term results of the randomized phase III trial EORTC 18991 of adjuvant therapy with pegylated interferon alfa-2b versus observation in resected stage III melanoma. Journal of clinical oncology: official journal of the American Society of Clinical Oncology 2012; 30:3810-8.
111. Sondak V K, Kudchadkar R. Pegylated interferon for the adjuvant treatment of melanoma: FDA approved, but what is its role? The oncologist 2012; 17:1223-4.
112. Balch C M, Gershenwald J E, Soong S J, et al. Final version of 2009 AJCC melanoma staging and classification. Journal of clinical oncology: official journal of the American Society of Clinical Oncology 2009; 27:6199-206.
113. Balch C M, Soong S J, Gershenwald J E, et al. Prognostic factors analysis of 17,600 melanoma patients: validation of the American Joint Committee on Cancer melanoma staging system. Journal of clinical oncology: official journal of the American Society of Clinical Oncology 2001; 19:3622-34.
114. Wong S L, Balch C M, Hurley P, et al. Sentinel lymph node biopsy for melanoma: American Society of Clinical Oncology and Society of Surgical Oncology joint clinical practice guideline. Journal of clinical oncology: official journal of the American Society of Clinical Oncology 2012; 30:2912-8.
115. Morton D L, Thompson J F, Cochran A J, et al. Sentinel-node biopsy or nodal observation in melanoma. The New England journal of medicine 2006; 355:1307-17.
116. Balch C M, Gershenwald J E, Soong S J, et al. Multivariate analysis of prognostic factors among 2,313 patients with stage III melanoma: comparison of nodal micrometastases versus macrometastases. Journal of clinical oncology: official journal of the American Society of Clinical Oncology 2010; 28:2452-9.
117. Bindea G, Mlecnik B, Fridman W H, Galon J. The prognostic impact of anti-cancer immune response: a novel classification of cancer patients. Semin Immunopathol 2011; 33:335-40.
118. Ott P A, Carvajal R D, Pandit-Taskar N, et al. Phase I/II study of pegylated arginine deiminase (ADI-PEG 20) in patients with advanced melanoma. Investigational new drugs 2013; 31:425-34.
119. Fridman W H, Galon J, Dieu-Nosjean M C, et al. Immune infiltration in human cancer: prognostic significance and disease control. Curr Top Microbiol Immunol 2011; 344:1-24.
120. Ascierto P A, Capone M, Urba W J, et al. The additional facet of immunoscore: immunoprofiling as a possible predictive tool for cancer treatment. Journal of translational medicine 2013; 11:54.
121. Clemente C G, Mihm M C, Jr., Bufalino R, Zurrida S, Collini P, Cascinelli N. Prognostic value of tumor infiltrating lymphocytes in the vertical growth phase of primary cutaneous melanoma. Cancer 1996; 77:1303-10.
122. Azimi F, Scolyer R A, Rumcheva P, et al. Tumor-infiltrating lymphocyte grade is an independent predictor of sentinel lymph node status and survival in patients with cutaneous melanoma. Journal of clinical oncology: official journal of the American Society of Clinical Oncology 2012; 30:2678-83.
123. Busam K J, Antonescu C R, Marghoob A A, et al. Histologic classification of tumor-infiltrating lymphocytes in primary cutaneous malignant melanoma. A study of interobserver agreement. Am J Clin Pathol 2001; 115:856-60.
124. Frishberg D P, Balch C, Balzer B L, et al. Protocol for the examination of specimens from patients with melanoma of the skin. Arch Pathol Lab Med 2009; 133:1560-7.
125. Bogunovic D, O'Neill D W, Belitskaya-Levy I, et al. Immune profile and mitotic index of metastatic melanoma lesions enhance clinical staging in predicting patient survival. Proc Natl Acad Sci USA 2009; 106:20429-34.
126. Mann G J, Pupo G M, Campain A E, et al. BRAF mutation, NRAS mutation, and the absence of an immune-related expressed gene profile predict poor outcome in patients with stage III melanoma. The Journal of investigative dermatology 2013; 133:509-17.
127. Messina J L, Fenstermacher D A, Eschrich S, et al. 12-Chemokine gene signature identifies lymph node-like structures in melanoma: potential for patient selection for immunotherapy? Scientific reports 2012; 2:765.
128. Chow M T, Moller A, Smyth M J. Inflammation and immune surveillance in cancer. Seminars in cancer biology 2012; 22:23-32.
129. Fortina P, Surrey S. Digital mRNA profiling. Nature biotechnology 2008; 26:293-4.
130. Geiss G K, Bumgarner R E, Birditt B, et al. Direct multiplexed measurement of gene expression with color-coded probe pairs. Nature biotechnology 2008; 26:317-
131. Raskin L, Fullen D R, Giordano T J, Thomas D G et al. Transcriptome Profiling Identifies HMGA2 as a Biomarker of Melanoma Progression and Prognosis. J. Invest Dermatol 2013; doi: 10.1038/jid.2013.197
132. Zhang B, and Horvath S. A General Framework for Weighted Gene Co-Expression Network Analysis. Statistical Applications in Genetics and Molecular Biology. 2005; 4:(1) Article 17
133. Hu Z, et al. VisANT 4.0: Integrative network platform to connect genes, drugs, diseases and therapies. Nucl. Acids Res. 2013; 41:W225-31.

134. Hu Z, Mellor J, Wu J and DeLisi C. VisANT: an online visualization and analysis tool for biological interaction data. BMC Bioinformatics. 2004; 5:17.
135. Huang D W, Sherman B T, Lempicki R A. Systematic and integrative analysis of large gene lists using DAVID Bioinformatics Resources. Nature Protoc. 2009; 4(1):44-57.
136. Huang D W, Sherman B T, Lempicki R A. Bioinformatics enrichment tools: paths toward the comprehensive functional analysis of large gene lists. Nucleic Acids Res. 2009; 37(1):1-13.
137. Christmas R, Avila-Campillo I, et al. Cytoscape: A Software Environment for Integrated Models of Biomolecular Interaction Networks. Am Assoc Cancer Res Educ Book. 2005; 12-16.

What is claimed is:

1. A treatment method comprising:
   a) obtaining a sample of previously removed melanoma tissue containing RNA from a patient previously afflicted with melanoma;
   b) determining by direct multiplexed measurement of gene expression with color-coded probe pairs from the RNA contained in the sample the level of expression of a plurality of genes comprising CD2, KLRK1, ITK, and HLAE;
   c) predicting that the patient has an increased risk of reoccurrence of melanoma when the level of expression of said plurality of genes in the sample is determined to be lower than a predetermined reference level of expression of said plurality of genes; and
   d) administering an anti-melanoma immunotherapy agent to the patient predicted to have an increased risk of reoccurrence of melanoma.

2. The method of claim 1, wherein the sample is a fixed, wax-embedded tissue specimen.

3. The method of claim 2, wherein the expression level of each gene of the plurality of genes is normalized relative to the expression level of one or more reference genes.

4. The method of claim 3, wherein the expression level of each of the plurality of genes is normalized relative to the expression level of at least one of the following genes: ABCF1, ACTB, ALAS1, CLTC, G6PD, GAPDH, GUSB, HPRT1, LDHA, PGK1, POLR1B, POLR2A, RPL19, RPLPO, SDHA, TBP and TUBB.

5. The method of claim 1, wherein the immunotherapy is an oncolytic immunotherapy.

6. The method of claim 5, wherein the oncolytic immunotherapy comprises a virus.

7. The method of claim 6, wherein the virus is derived from HSV-1.

8. The method of claim 5, wherein the oncolytic immunotherapy is a vaccine.

9. The method of claim 8, wherein the vaccine is talimogene laherparepvec (T-VEC).

10. A treatment method comprising:
    a) obtaining a sample of melanoma tissue containing RNA from a patient that currently has melanoma or was previously afflicted with melanoma;
    b) assaying the sample to determine from the RNA contained in the sample the level of expression of a plurality of genes, wherein the genes comprise CD2, KLRK1, ITK, and HLAE;
    c) predicting that the patient has an increased risk of melanoma progression when the level of expression of said plurality of genes in the sample is lower than a predetermined reference level of expression of said plurality of genes; and
    d) administering an anti-melanoma immunotherapy to the patient predicted to have an increased risk of melanoma progression.

11. The method of claim 10, wherein the expression level is determined from direct multiplexed measurement of gene expression with color-coded probe pairs.

12. A treatment method comprising:
    a) obtaining a sample of previously removed melanoma tissue containing RNA from a patient previously afflicted with melanoma;
    b) determining by direct multiplexed measurement of gene expression with color-coded probe pairs from the RNA contained in the sample the level of expression of a plurality of genes comprising CD2, KLRK1, ITK, HLAE, IFNAR1, LCK, CD4, LGMN, and IFI27;
    c) predicting that the patient has a reduced risk of reoccurrence of melanoma when the level of expression of said plurality of genes in the sample is higher than a predetermined reference level of expression of said plurality of genes; and
    d) administering a reduced amount or less frequent dose of anti-melanoma immunotherapy to said patient predicted to have a reduced risk of reoccurrence of melanoma.

13. A treatment method comprising:
    administering an anti-melanoma immunotherapy agent to a human patient previously afflicted with melanoma who has an increased risk of reoccurrence of melanoma because the level of expression of CD2, KLRK1, ITK, and HLAE in a sample of previously removed melanoma tissue containing RNA from said human patient as determined by direct multiplexed measurement of gene expression with color-coded probe pairs from the RNA contained in the sample is lower than a predetermined reference level of expression of CD2, KLRK1, ITK, and HLAE.

* * * * *